United States Patent [19]
Cohen et al.

[11] Patent Number: 5,434,186
[45] Date of Patent: Jul. 18, 1995

[54] CARBOXYLIC ACID LEUKOTRIENE B4 ANTAGONISTS

[75] Inventors: Noal Cohen, Montclair; Ferdinand K. Lee, Teaneck; Keith A. Yagaloff, Hohokus, all of N.J.

[73] Assignee: Hoffmann-La Roche Inc., Nutley, N.J.

[21] Appl. No.: 128,612

[22] Filed: Sep. 28, 1993

Related U.S. Application Data

[60] Division of Ser. No. 898,852, Jun. 15, 1992, Pat. No. 5,273,999, which is a continuation-in-part of Ser. No. 757,100, Sep. 10, 1991, abandoned.

[51] Int. Cl.⁶ .................. A61K 31/19; A61K 31/235; A61K 31/165; C07C 235/32; C07C 63/04; C07C 69/78; C07C 255/49
[52] U.S. Cl. .................. 514/571; 514/570; 514/569; 514/568; 514/544; 514/533; 514/532; 514/522; 514/602; 514/604; 514/616; 514/622; 514/621; 514/671; 558/415; 560/12; 560/51; 560/53; 560/54; 562/461; 562/462; 562/427; 564/169; 564/162; 564/156; 564/154
[58] Field of Search .............. 560/51, 53, 54, 12; 562/462, 461, 427; 564/169, 162, 156, 154; 558/415; 514/571, 570, 569, 568, 533, 544, 532, 522, 602, 604, 616, 671, 621, 622

[56] References Cited

U.S. PATENT DOCUMENTS

| | | | |
|---|---|---|---|
| 3,776,944 | 12/1973 | Brown et al. | 562/466 |
| 4,650,812 | 3/1987 | Cohen et al. | 514/456 |
| 4,801,616 | 1/1989 | Gapinski | 514/381 |
| 4,824,836 | 4/1989 | Regnier et al. | 514/278 |
| 4,889,871 | 12/1989 | Djuric et al. | 514/456 |
| 4,992,576 | 2/1991 | Gapinski | 560/52 |

FOREIGN PATENT DOCUMENTS

| | | |
|---|---|---|
| 0079637 | 11/1982 | European Pat. Off. |
| 0292977 | 5/1988 | European Pat. Off. |
| 0405116A2 | 1/1991 | European Pat. Off. |
| WO92/00011 | 9/1992 | WIPO |

OTHER PUBLICATIONS

Brown, F. J. et al.—Hydroxyacetophenone—Derived Antagonists of the Peptidoleukotrienes—J. Med. Chem. 1989, 32, 807–826.

Gapinski, D. M. et al—Benzophenone Dicarboxylic Acid Antagonists of Leokotriene B4—J. Med. Chem. 1990, 33, 2807–2873.

Konno, M. et al—Synthesis and Structure—Activity Relationships of A Series of Substituted—Phenylpropionic Acids—Advanced in Prostaglandin Thromboxane and Leukotriene Res. vol. 21, 411–413 (1990).

Communications-7-3-(4-acetyl-3-methoxy-2-propylphenoxy)propoxy-3,4-dihydro-8-propyl-2H-1-benzopyran-2-carboxylic acid—J. Med. Chem. 1989, vol. 32, No. 6, 1145–1147.

Primary Examiner—Nicky Chan
Attorney, Agent, or Firm—George M. Gould; George W. Johnston; Robert A. Silverman

[57] ABSTRACT

Compounds of the formula

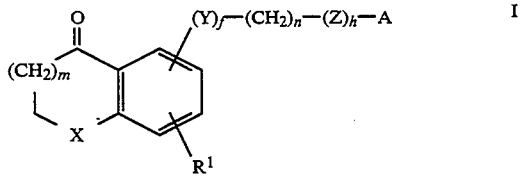

wherein X is O or $CH_2$;
Y is O, $-CH_2-CH_2-$, $-CH=CH-$, $-C\equiv C-$, or $-OCH_2C_6H_4-$;
Z is $-CH_2-CH_2-$, $-CH=CH-$ or $-C\equiv C-$;
f, h, k, m and t, independently, are 0 or 1;
n is an integer from 1 to 12;
$R^1$ is hydrogen, lower alkyl, lower alkenyl, cycloalkyl, or aralkyl; and A is B or $-O-B$, wherein B is a mono-, di- or tricyclic aromatic or heteroaromatic moiety substituted by the group $-COR^2$, $-(O)_f-(W)_s-COR^2$ or $-(CH=CH)_pCOR^2$ and which may also contain up to 4 additional substituents selected, independently, from the group consisting of halogen, cyano, lower alkyl, lower alkoxy, sulfonamido, alkanoyl, aroyl, $-(Q-)_k-(W)_s-E$ or $-(Q)_k-(W)_{s''}-C_6H_4-(W)-$ (Abstract continued on next page.)

$s'''$—E, provided that no more than one of said substituents is —$(Q)_k$—$(W)_{s'}$—E or —$(Q)_k$—$(W)_{s''}$—$C_6H_4$—$(W)_{s'''}$—E, and wherein E is $COR^2$ or $R^2$, W is —$CR^3R^4$—, Q is O or carbonyl, p is an integer from 1 to 2, s and s', independently, are an integer from 1–12, s" and s''', independently, are an integer from 0 to 12, $C_6H_4$ is a 1,2-, 1,3-, or 1,4-phenylene moiety, and $R^2$ is hydroxy, lower alkoxy or $NR^3R^4$, wherein $R^3$ and $R^4$, each occurence, independently, are hydrogen or lower alkyl, their geometric and optical isomers and, when $R^2$ is hydroxy, pharmaceutically acceptable salts thereof with bases.

The compounds of formula I are potent leukotriene $B_4$ antagonists and are therefore useful in the treatment of inflammatory diseases, such as psoriasis, inflammatory bowel disease, asthma, allergy, arthritis, dermatitis, gout, pulmonary disease, ischemia/reperfusion injury, and trauma induced inflammation, such as spinal cord injury.

16 Claims, No Drawings

CARBOXYLIC ACID LEUKOTRIENE B4 ANTAGONISTS

CROSS REFERENCE TO RELATED APPLICATION

This is a division of application Ser. No. 07/898,852, filed Jun. 15, 1992, now U.S. Pat. No. 5,273,999, which is a CIP of Ser. No. 07/757,100, filed Sep. 10, 1991 now abandoned.

BRIEF SUMMARY OF THE INVENTION

The invention relates to compounds of the formula

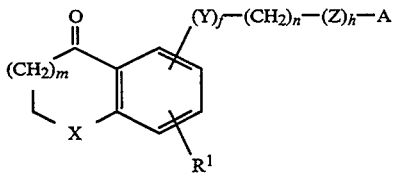

wherein X is O or $CH_2$;
Y is O, $-CH_2-CH_2-$, $-CH=CH-$, $-C\equiv C-$, or $-OCH_2C_6H_4-$;
Z is $-CH_2-CH_2-$, $-CH=CH-$ or $-C\equiv C-$;
f, h, k, m and t, independently, are 0 or 1;
n is an integer from 1 to 12;
$R^1$ is hydrogen, lower alkyl, lower alkenyl, cycloalkyl, or alkyl; and A is B or $-O-B$, wherein B is a mono, di- or tricyclic aromatic or heteroaromatic moiety substituted by the group $-COR^2$, $-(O)_t-(W)_s-COR^2$ or $-(CH=CH)_pCOR^2$ and which may also contain up to 4 additional substituents selected, independently, from the group consisting of halogen, cyano, lower alkyl, lower alkoxy, sulfonamido, alkanoyl, aroyl, $-(Q)_k-(W)_{s'}-E$ or $-(Q)_k-(W)_{s''}-C_6H_4-(W)_{s'''}-E$, provided that no more than one of said substituents is $-(Q)_k-(W)_{s'}-E$ or $-(Q)_k-(W)_{s''}-C_6H_4-(W)_{s'''}-E$, and wherein E is $-COR^2$ or $R^2$, W is $-CR^3R^4-$, Q is O or carbonyl, p is an integer from 1 to 2, s and s', independently, are an integer from 1-12, s'' and s''', independently, are an integer from 0 to 12, $C_6H_4$ is a 1,2-, 1,3-, or 1,4-phenylene moiety, and
$R^2$ is hydroxy, lower alkoxy or $NR^3R^4$, wherein $R^3$ and $R^4$, each occurence, independently, are hydrogen or lower alkyl, their geometric and optical isomers and, when $R^2$ is hydroxy, pharmaceutically acceptable salts thereof with bases.

The compounds of formula I are potent leukotriene B4 antagonists and are therefore useful in the treatment of inflammatory diseases, such as psoriasis, inflammatory bowel disease, asthma, allergy, arthritis, dermatitis, gout, pulmonary disease, ischemia/reperfusion injury, and trauma induced inflammation, such as spinal cord injury.

In another aspect, the invention relates to compositions and methods of use comprising the compounds of formula.

DETAILED DESCRIPTION OF THE INVENTION

The invention relates to compounds of the formula

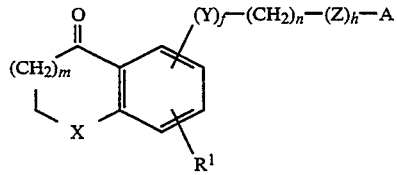

wherein X is O or $CH_2$;
Y is O, $-CH_2-CH_2-$, $-CH=CH-$, $-C\equiv C-$, or $-OCH_2C_6H_4-$;
Z is $-CH_2-CH_2-$, $-CH=CH-$ or $-C\equiv C-$;
f, h, k, m and t, independently, are 0 or 1;
n is an integer from 1 to 12;
$R^1$ is hydrogen, lower alkyl, lower alkenyl, cycloalkyl, or aralkyl; and A is B or $-O-B$, wherein B is a mono, di- or tricyclic aromatic or heteroaromatic moiety substituted by the group $-COR^2$, $-(O)_t-(W)_s-COR^2$ or $-(CH=CH)_pCOR^2$ and which may also contain up to 4 additional substituents selected, independently, from the group consisting of halogen, cyano, lower alkyl, lower alkoxy, sulfonamido, alkanoyl, aroyl, $-(Q)_k-(W)_{s'}-E$ or $-(Q)_k-(W)_{s''}-C_6H_4-(W)_{s'''}-E$, provided that no more than one of said substituents is $-(Q)_k-(W)_{s'}-E$ or $-(Q)_k-(W)_{s''}-C_6H_4-(W)_{s'''}-E$, and wherein E is $-COR^2$ or $R^2$, W is $-CR^3R^4-$, Q is O or carbonyl, p is an integer from 1 to 2, s and s', independently, are an integer from 1-12, s'' and s''', independently, are an integer from 0 to 12, $C_6H_4$ is a 1,2-, 1,3-, or 1,4-phenylene moiety, and $R^2$ is hydroxy, lower alkoxy or $NR^3R^4$, wherein $R^3$ and $R^4$, each occurence, independently, are hydrogen or lower alkyl, their geometric and optical isomers and, when $R^2$ is hydroxy, pharmaceutically acceptable salts thereof with bases.

As used herein, the term "lower alkyl", denotes a straight or branched chain saturated hydrocarbon containing 1 to 7 carbon atoms, preferably from 1 to 4 carbon atoms, for example, methyl, ethyl, propyl, isopropyl, butyl, t-butyl, neopentyl, pentyl, heptyl, and the like. The term "lower alkoxy" denotes an alkyl ether group in which the alkyl group is as described above, for example, methoxy, ethoxy, propoxy, pentoxy and the like.

The term "cycloalkyl" denotes a cyclic alkyl group of 3 to 6 carbon atoms, for example, cyclopropyl, cyclohexyl, and the like.

The term "lower alkenyl" denotes a straight or branched chain unsaturated hydrocarbon containing 2 to 7 carbon atoms, for example, vinyl, propenyl, butenyl and the like.

The term "halogen" denotes all the halogens, i.e., bromine, chlorine, fluorine, and iodine. The term "aryl" or "mono-, di- or tri cyclic aromatic" preferably denotes naphthalenyl, phenyl, anthracenyl, phenanthrenyl or the like, which may be mono-, di- or trisubstituted by halogen, trifluoromethyl, lower alkyl, phenyl, lower alkoxy, cyano or nitro.

The term "aralkyl" denotes an alkyl group substituted by an aryl group, for example, benzyl, phenethyl, or the like, which may be substituted by halogen, trifluoromethyl, lower alkyl, lower alkoxy, cyano, nitro or the like.

The term "lower alkanoyl" connotes a primary or secondary alkanoyl group containing up to 7 carbon atoms such as acetyl, propionyl, butyryl, isobutyryl and the like. The term "aroyl" preferably denotes the benzoyl group or a substituted benzoyl group, for example a nitrobenzoyl group such as p-nitrobenzoyl or a halobenzoyl group such as o-, m- or p-iodobenzoyl.

The term "heteroaromatic moiety" denotes a monocyclic 5- or 6-membered heterocyclic or a bi- or tricyclic heterocyclic radical containing one or more hetero atoms, selected from nitrogen, oxygen and sulfur, which radical may optionally be substituted by one or two lower alkyl, lower alkoxy groups, chlorines or fluorines. It is understood that heterocyclic refers to a carbocyclic moiety in which one or more of the carbons are replaced, independently, by oxygen, nitrogen or sulfur.

Exemplary of 5- or 6-membered aromatic heteromonocyclic radicals are pyridinyl, imidazolinyl, thienyl, 2-chlorothienyl, furyl, pyrimidinyl, oxazolinyl or the like.

Exemplary of hetero-bicyclic radicals are benzofuranyl, benzopyranyl, indolyl, quinolinyl, benzothienyl or the like.

Exemplary of hetero-tricyclic radicals are dibenzofuranyl, carbazolyl or the like.

Exemplary of the group —(W)—$_{s,s',s''\ or\ s'''}$, that is, —(CR$^3$R$^4$)—$_{s,s',s''\ or\ s'''}$ are 1,1-dimethylpropylenyl, 2,2-dimethylpropylenyl, 2,6-dimethylheptylenyl, 1-methyl-1-ethylpentylenyl, 1-ethyl-3-methylhexylenyl or the like.

As used herein, a leaving group, denotes halogen, preferably, bromine and iodine; lower alkylsulfonyloxy, such as, (methylsulfonyl)oxy, (trifluoromethylsulfonyl)oxy or the like; arylsulfonyloxy, such as, para-toluenesulfonyloxy or the like.

A preferred, group of compounds of formula I is one in which Y is O, R$^1$ is lower alkyl, n is 3–8, m and f are 1.

A more preferred group of compounds of formula I is one in which Y is O, R$^1$ is lower alkyl, h is 0, m and f are 1, n is 3–8 and A is —O—B, and B is a mono-, di- or tricyclic aromatic moiety.

A still more preferred group of compounds of formula I is one in which Y is O, R$^1$ is lower alkyl or aralkyl, h is 0, m and f are 1, n is 3–8, and A is B, wherein B is a monocyclic aromatic moiety substituted by —(O)$_t$—(W)$_s$—COR$^2$ and —(Q)$_k$—(W)$_{s'}$—E, wherein E is COR$^2$, Q is O, R$_2$ is hydroxy, t is 0, s is 2, k is 1 and s' is 1 to 12.

A most preferred group of compounds of formula I is one in which X and Y are O, R$^1$ is lower alkyl, h is 0, m and f are 1, n is 3–8 and A is B, wherein B is a monocyclic aromatic moiety substituted by —(O)$_t$—(W-)$_s$—COR$^2$ and —(Q)$_k$—(W)$_{s'}$—E, wherein E is COR$^2$, Q is O, R$_2$ is hydroxy, t is 0, s is 2, k is 1 and s' is 1 to 6.

Most preferred examples of this invention are:

2-[(5-Carboxypentyl)oxy]-6-[6-[(3,4-dihydro-4-oxo-8-propyl-2H-1-benzopyran-7-yl)oxy]hexyl]benzenepropanoic Acid;

2-(4-Carboxybutoxy)-6-[6-[(3,4-dihydro-4-oxo-8-propyl-2H-1-benzopyran-7-yl)oxy]hexyl]benzenepropanoic Acid;

2-[(5-Carboxypentyl)oxy]-6-[6-[[3,4-dihydro-4-oxo-8-(3-phenylpropyl)-2H-1-benzopyran-7-yl]oxy]hexyl]benzenepropanoic Acid;

2-[(4-Carboxy-4-methylpentyl)oxy]-6-[6-[(3,4-dihydro-4-oxo-8-propyl-2H-1-benzopyran-7-yl)oxy]hexyl]benzenepropanoic Acid;

5-(3-Carboxypropoxy)-2-[6-[(3,4-dihydro-4-oxo-8-propyl-2H-1-benzopyran-7-yl)oxy]hexyl]benzenepropanoic Acid;

6-(4-Carboxybutoxy)-2-[5-[(3,4-dihydro-4-oxo-8-propyl-2H-1-benzopyran-7-yl)oxy]pentyloxy]benzenepropanoic Acid;

E-3-[5-(3-Carboxypropoxy)-2-[6-[(3,4-dihydro-4-oxo-8-propyl-2H-1-benzopyran-7-yl)oxy]hexyl]phenyl]-2-propenoic Acid;

3-(2-Carboxyethyl)-4-[5-[(3,4-dihydro-4-oxo-8-propyl-2H-1-benzopyran-7-yl)oxy]pentyloxy]benzenepentanoic Acid;

2-(2-Carboxyethyl)-3-[6-[(3,4-dihydro-4-oxo-8-propyl-2H-1-benzopyran-7-yl)oxy]hexyl]benzenehexanoic Acid;

2-[6-[(3,4-Dihydro-4-oxo-8-propyl-2H-1-benzopyran-7-yl)oxy]hexyl]-6-[(5-hydroxypentyl)oxy]benzenepropanoic Acid; and 2-[(5-Carboxypentyl)oxy]-6-[6-[(5,6,7,8-tetrahydro-5-oxo-1-propyl-2-naphthalenyl)oxy]hexyl]benzenepropanoic Acid;

Preferred examples of this invention are:

5-[(3-Carboxyphenyl)carbonyl]-2-[5-[(3,4-dihydro-4-oxo-8-propyl-2H-1-benzopyran-7-yl)oxy]pentyloxy]-benzenepropanoic Acid;

5-[(3-Carboxyphenyl)carbonyl]-2-[6-[(3,4-dihydro-4-oxo-8-propyl-2H-1-benzopyran-7-yl)oxy]hexyl]benzenepropanoic Acid;

5-[(3-Carboxyphenyl)carbonyl]-2-[6-[(3,4-dihydro-4-oxo-8-propyl-2H-1-benzopyran-7-yl)oxy]hexyloxy]-benzenepropanoic Acid;

5-(3-Carboxypropoxy)-2-[5-[(3,4-dihydro-4-oxo-8-propyl-2H-1-benzopyran-7-yl)oxy]pentyloxy]benzenepropanoic Acid;

5-(4-Carboxybutoxy)-2-[5-[(3,4-dihydro-4-oxo-8-propyl-2H-1-benzopyran-7-yl)oxy]pentyloxy]benzenepropanoic Acid Hemihydrate;

5-[(3-Carboxyphenyl)carbonyl]-2-[7-[(3,4-dihydro-4-oxo-8-propyl-2H-1-benzopyran-7-yl)oxy]heptyloxy]-benzenepropanoic Acid;

5-[(3-Carboxyphenyl)carbonyl]-2-[8-[(3,4-dihydro-4-oxo-8-propyl-2H-1-benzopyran-7-yl)oxy]octyloxy]-benzenepropanoic Acid;

5-[(4-Carboxyphenyl)carbonyl]-2-[5-[(3,4-dihydro-4-oxo-8-propyl-2H-1-benzopyran-7-yl)oxy]pentyloxy]-benzenepropanoic Acid;

3-(2-Carboxyethyl)-4-[5-[(3,4-dihydro-4-oxo-8-propyl-2H-1-benzopyran-7-yl)oxy]pentyloxy]-γ-oxobenzenebutanoic Acid;

5-[2-(2-Carboxyphenyl)-1-oxoethyl]-2-[5-[(3,4-dihydro-4-oxo-8-propyl-2H-1-benzopyran-7-yl)oxy]pentyloxy]benzenepropanoic Acid;

6-(Carboxymethoxy)-2-[5-[(3,4-dihydro-4-oxo-8-propyl-2H-1-benzopyran-7-yl)oxy]pentyloxy]-1-naphthalenepropanoic Acid;

2-[[5-[[3,4-Dihydro-4-oxo-8-(3-phenylpropyl)-2H-1-benzopyran-7-yl]oxy]pentyl]oxy]benzenepropanoic Acid; and 2-[6-[(3,4-Dihydro-4-oxo-8-propyl-2H-1-benzopyran-7-yl)oxy]hexyl]benzenepropanoic Acid;

Other examples of this invention are:

rac-6-Acetyl-7-[5-[(3,4-dihydro-4-oxo-8-propyl-2H-1-benzopyran-7-yl)oxy]pentyloxy]-3,4-dihydro-2H-1-benzopyran-2-carboxylic Acid;

5-[5-[(3,4-Dihydro-4-oxo-8-propyl-2H-1-benzopyran-7-yl)oxy]pentyloxy]-2-benzofurancarboxylic Acid;
6-[[5-[(3,4-Dihydro-4-oxo-8-propyl-2H-1-benzopyran-7-yl)oxy]pentyl]oxy]-2,5-quinolinedipropanoic Acid;
2-[5-[(2,3-Dihydro-1-oxo-4-propyl-1H-inden-5-yl)oxy]pentyloxy]benzenepropanoic Acid;
(E)-3-[2-[7-(3,4-Dihydro-4-oxo-8-propyl-2H-1-benzopyran-7-yl)-1,6-heptadiynyl]phenyl]-2-propenoic Acid;
5-[6-[(3,4-Dihydro-4-oxo-8-propyl-2H-1-benzopyran-7-yl)oxy]hexyl]-2-thiophenepropanoic Acid;
4-[6-[(3,4-Dihydro-4-oxo-8-propyl-2H-1-benzopyran-7-yl)oxy]hexyl]-3-thiophenepropanoic Acid;
3-[6-[(3,4-Dihydro-4-oxo-8-propyl-2H-1-benzopyran-7-yl)oxy]hexyl]-2-thiophenepropanoic Acid;
2-[6-[(3,4-Dihydro-4-oxo-8-propyl-2H-1-benzopyran-7-yl)oxy]hexyl]-3-thiophenepropanoic Acid;
2-[5-[(5-Oxo-2-propyl-5,6,7,8-tetrahydro-1-naphthalenyl)oxy]pentyloxy]benzenepropanoic Acid;
2-[5-[(3,4-Dihydro-4-oxo-8-propyl-2H-1-benzopyran-7-yl)oxy]pentyloxy]-5-[(methylsulfonyl)amino]benzenepropanoic Acid;
(E)-3-[5-Cyano-2-[5-[(3,4-dihydro-4-oxo-8-propyl-2H-1-benzopyran-7-yl)oxypentyloxy]phenyl]-2-propenoic Acid;
2-[5-[(3,4-Dihydro-4-oxo-8-propyl-2H-1-benzopyran-7-yl)oxy]pentyloxy]-5-(3-carboxypropoxy)-3,4,6-trimethylbenzenepropanoic Acid;
(E,E)-5-[2-[5-[(3,4-Dihydro-4-oxo-8-propyl-2H-1-benzopyran-7-yl)oxy]pentyloxy]phenyl]-2,4-pentadienoic Acid;
2-[6-[(3,4-Dihydro-4-oxo-8-propyl-2H-1-benzopyran-7-yl)oxy]hexyl]-6-[(5-aminopentyl)oxy]benzenepropanoic Acid;
2-[(6-Dimethylamino-6-oxohexyl)oxy]-6-[6-[(3,4-dihydro-4-oxo-8-propyl-2H-1-benzopyran-7-yl)oxy]hexyl]benzenepropanoic Acid and the like.

The Compounds of formula I can be prepared as hereinafter described in Reaction Schemes 1–32.

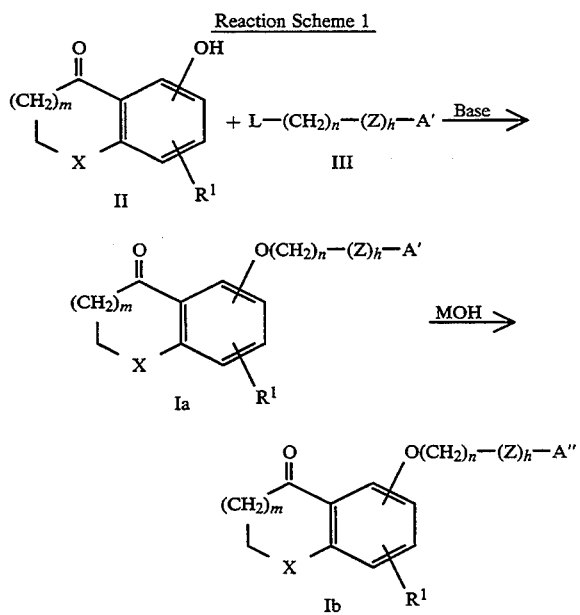

wherein A' is —B' or —O—B', wherein B'— is a mono-, di- or tricyclic aromatic or heteroaromatic moiety substituted by the group —COR$^{2'}$, —(O)$_r$(W)$_s$COR$^{2'}$ or —(CH=CH)$_p$COR$^{2'}$ and which may also contain up to 4 additional substituents selected, independently, from the group consisting of halogen, cyano, lower alkyl, lower alkoxy, sulfonamido, alkanoyl, aroyl, —(Q)$_k$—(W)$_{s'}$—E' or —(Q)$_k$—(W)$_{s''}$—C$_6$H$_4$—(W)$_{s'''}$—E', provided that no more than one of said substituents is —(Q)$_k$—(W)$_{s'}$—E', or —(Q)$_k$—(W)$_{s''}$—C$_6$H$_4$—(W)$_{s'''}$—E', E' is —COR$^{2'}$ or R$^2$ and R$^{2'}$ is lower alkoxy.

A" is —B" or —O—B", wherein B" is a mono, di- or tricyclic aromatic or heteroaromatic moiety substituted by the group —COR$^{2''}$, —(O)$_r$(W)$_s$COR$^{2''}$ or —(CH=CH)$_p$COR$^{2''}$ and which may also contain up to 4 additional substituents selected, independently, from the group consisting of halogen, cyano, lower alkyl, lower alkoxy, sulfonamido, alkanoyl, aroyl, —(Q)$_k$—(W)$_{s'}$—E" or —(Q)$_k$—(W)$_{s''}$—C$_6$H$_4$—(W)$_{s'''}$—E", provided that no more than one of said substituents is —(Q)$_k$—(W)$_{s'}$—E", or —(Q)$_k$—(W)$_{s''}$—C$_6$H$_4$—(W)$_{s'''}$—E", E" is —COR$^{2''}$ or R$^2$ and R$^{2''}$ is hydroxy.

L is a leaving group, M is an alkali metal, and h, m, n, X, Z, and R$^1$ are as previously described.

In Reaction Scheme 1, a compound of formula II, which represents known compounds or compounds which can be prepared according to known procedures or as hereinafter described, is allowed to react with a compound of formula III, which represents known compounds or compounds which can be prepared according to known procedures or as hereinafter described, in the presence of a base, for example, an alkali metal carbonate such as sodium or potassium carbonate, at a temperature in the range of from about 25° C. to about 110° C., in a polar, aprotic solvent such as acetonitrile, N,N-dimethylformamide, 2-butanone, dimethyl sulfoxide and the like.

Alternatively, the procedure of U.S. Pat. No. 4,931,574 can be utilized. In this variation, compounds of formulas II and III are allowed to react in the presence of an alkali metal carbonate, preferably potassium carbonate, and a phase transfer catalyst preferably tris[2-(2-methoxyethoxy)ethyl]amine (TDA-1), in an aromatic hydrocarbon solvent, preferably toluene, at a temperature in the range of 80° C. to 110° C.

The resulting compound of formula Ia can be recovered utilizing conventional methods such as chromatography or recrystallization and can be converted by saponification using an alkali metal hydroxide such as lithium, sodium, or potassium hydroxide, in a solvent mixture of water and a water miscible solvent such as methanol, ethanol, or tetrahydrofuran, at a temperature in the range of from about 25° C. to about 60° C., to the corresponding acid of formula Ib. The compounds of formula Ib can be purified by conventional methods such as recrystallization, chromatography and the like.

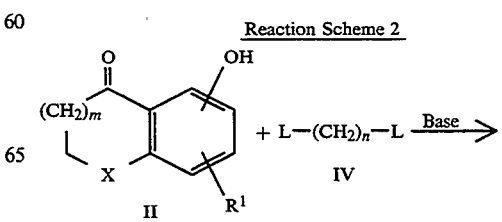

Reaction Scheme 2

Reaction Scheme 2 -continued

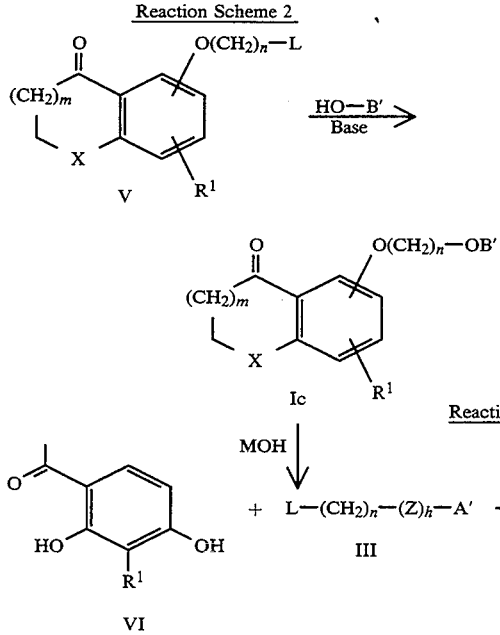

wherein B′, B″, L, X, R¹, m, and n are as previously described.

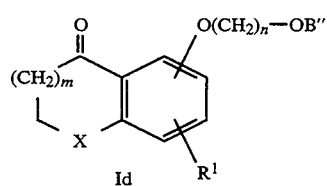

In Reaction Scheme 2, a compound of formula II is allowed to react with a compound of formula IV which represents known compounds, in the presence of a base and under conditions as described in Reaction Scheme 1. The resulting compound of formula V can be recovered by conventional techniques such as chromatography and is allowed to react with a compound of formula HO-B′, in the presence of a base and under conditions as described in Reaction Scheme 1. The resulting compound of formula Ic is purified by conventional chromatography or recrystallization methods. Saponification of compound Ic under conditions described in Reaction Scheme 1 for the conversion of Ia to Ib gives the corresponding acid of formula Id which can be purified by aforementioned conventional procedures.

Reaction Scheme 3

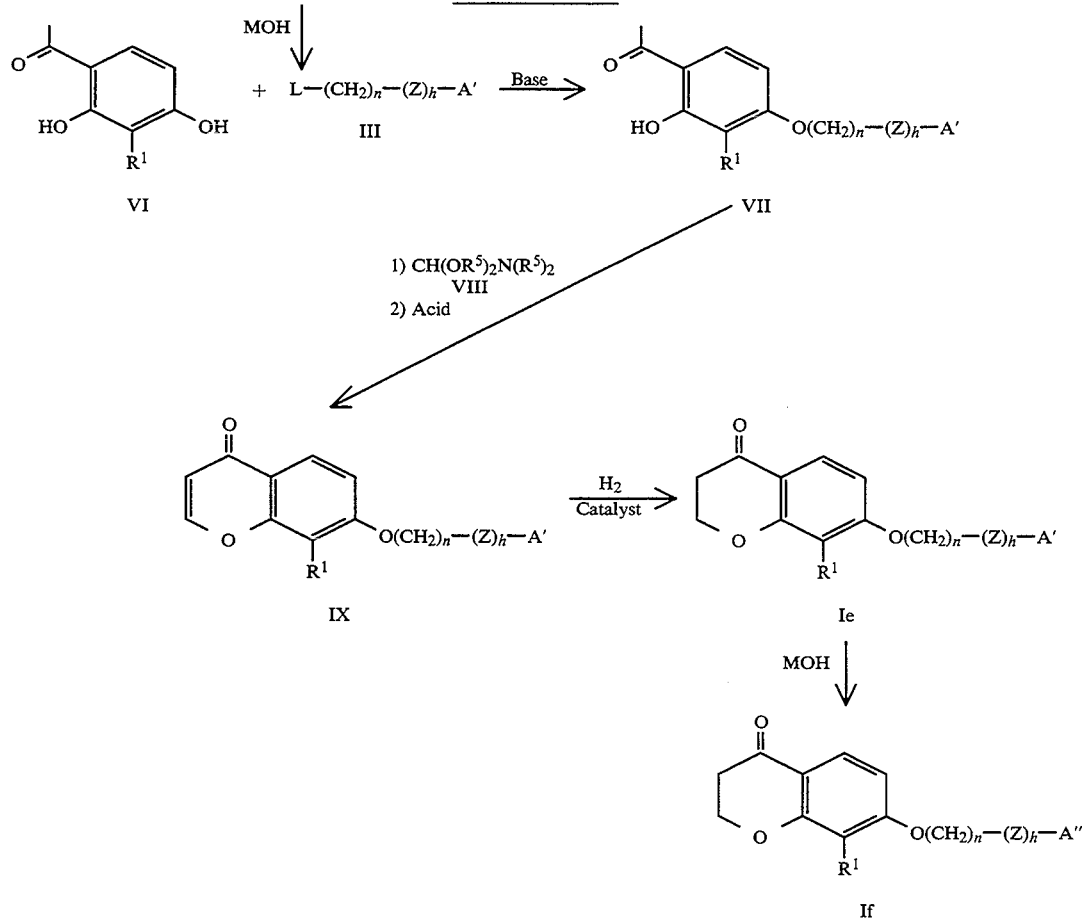

wherein $R^5$ is lower alkyl, and $R^1$, L, Z, A′, A″, h and n are as previously described.

In Reaction Scheme 3, a dihydroxyacetophenone of formula VI which represents known compounds or compounds which can be prepared according to known procedures, is allowed to react with compound of formula III under conditions described in Reaction Scheme 1 for the conversion of II to Ia, giving a compound of formula VII. Treatment of a compound of formula VII with a known formamide acetal of formula VIII, at a temperature in the range of from 120° C. to 160° C., in an aromatic hydrocarbon solvent, preferably xylene, gives a compound which is not recovered but immediately cyclized by acid treatment to the chromone product of formula IX. Preferred acids for effecting this cyclization include the organic sulfonic acids such as para-toluenesulfonic acid. Preferred solvents for carrying out this cyclization include the lower alkanols such as methanol and ethanol, at a temperature in the range of 60° C. to 80° C. The resulting chromone of formula IX is generally recovered by conventional chromatographic methods. Catalytic hydrogenation of the chromone of formula IX gives the chromanone Ie. This hydrogenation is carried out under conventional conditions. A supported transition metal catalyst such as 5% or 10% palladium metal on carbon or charcoal is preferred. It is preferred that this hydrogenation be carried out at ambient temperature and under one atmosphere of hydrogen gas pressure. Preferred solvents for effecting this hydrogenation are the lower alkanols such as methanol or ethanol, or ester solvents such as ethyl acetate. Mixtures of these solvents can also be used. The resulting compound of formula Ie can be isolated by conventional chromatographic means and saponified to the acid If using conditions described above for the saponification and recovery of esters Ia and Ic.

wherein X, $R^1$, Z, A', A'', M, h, m and n are as previously described.

In Reaction Scheme 4, a compound of formula IIa, which represents known compounds or compounds prepared as hereinafter described, is converted to the corresponding trifluoromethanesulfonate of formula X by treatment with trifluoromethanesulfonic anhydride in the presence of an amine base. Any conventional amine base may be utilized. Pyridine or triethylamine are preferred. This transformation is preferably carried out in dichloromethane solvent at a temperature in the range of 0°-25° C. The compounds of formula X can be recovered by conventional means such as chromatography. The compound of formula X is allowed to react with an acetylenic compound of formula XI in the presence of a palladium catalyst and an amine base giving the compound of formula Ig. It is preferred that this transformation be carried out using dichlorobis(triphenylphosphine)palladium II as the catalyst and triethylamine as the base, in di-methylformamide solvent, at a temperature in the range of 80°-100° C. The product of

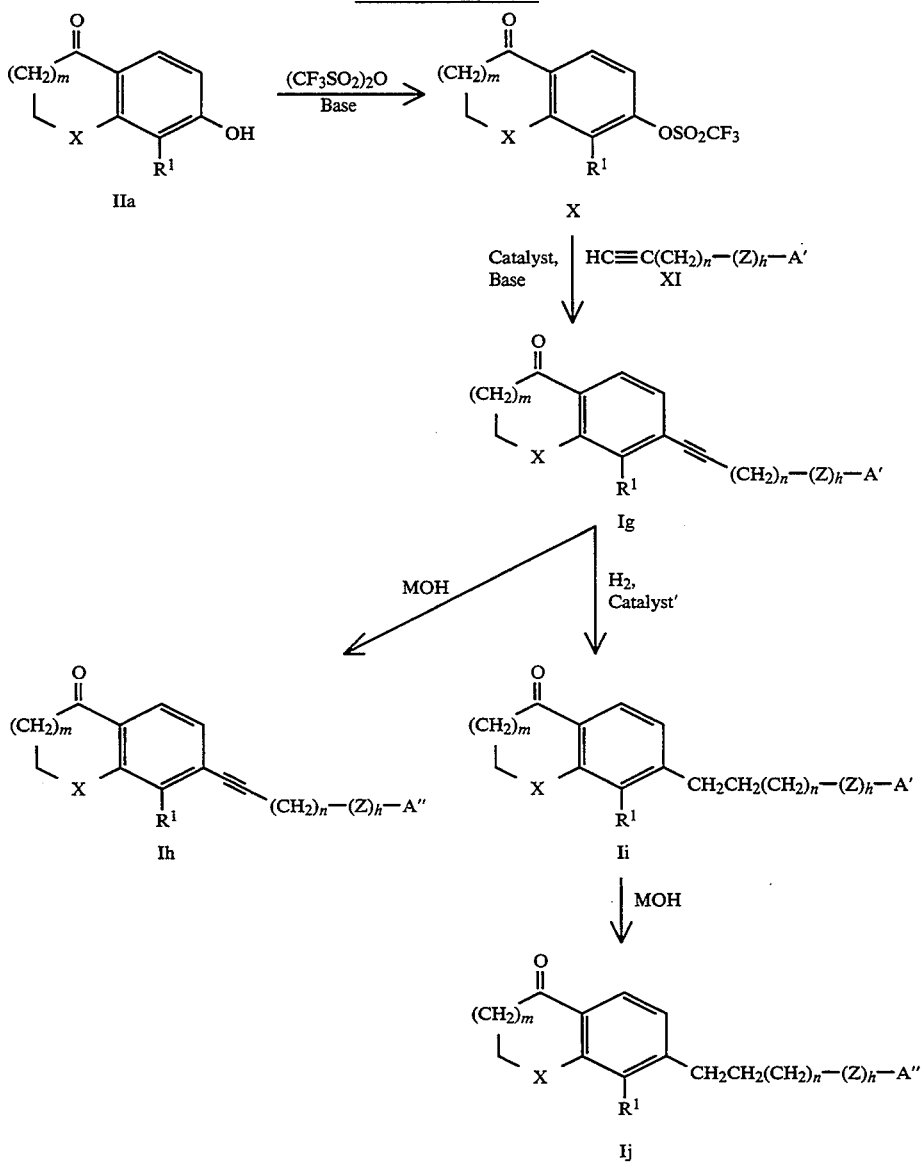

Reaction Scheme 4 formula Ig is recovered using conventional chromatographic techniques. Conventional catalytic hydrogenation of the compound of formula Ig, using conditions described in Scheme 5 gives the corresponding saturated compound of formula Ii. Saponification of the compound of formula Ii using conditions described in Reaction Scheme 1 gives the corresponding acid of formula Ij. Alternatively, the compound of formula Ig can be directly saponified using the conditions described in Reaction Scheme 1 to give the corresponding acetylenic acid of formula Ih. The compounds of formulas Ih, Ii, and Ij can be recovered by conventional chromatographic techniques or by conventional recrystallization.

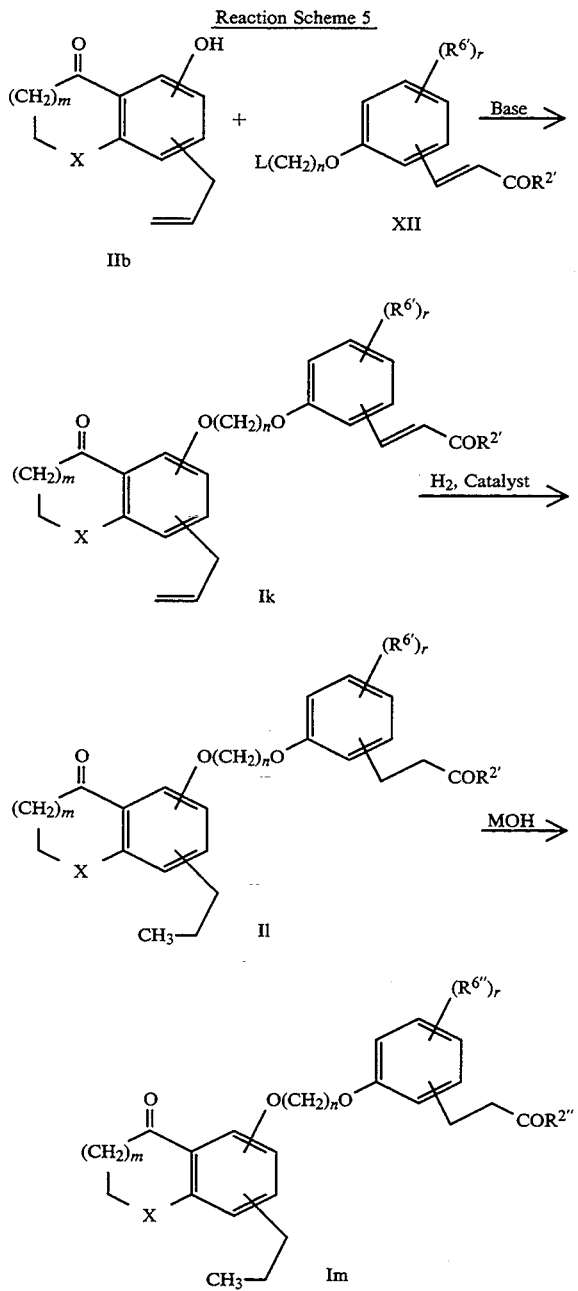

Reaction Scheme 5 wherein r is an integer from 0 to 4, $R^{6'}$, each occurence, independently, is halogen, cyano, lower alkyl, lower alkoxy, sulfonamido, alkanoyl, aroyl, —(Q-)$_k$—(W)$_{s'}$—E' or —(Q)$_k$—(W)$_{s'}$—C$_6$H$_4$—(W)$_{s'''}$—E', provided that no more than one of $R^{6'}$ is —(Q-)$_k$—(W)$_{s'}$—E' or —(Q)$_k$—(W)$_{s'}$—C$_6$H$_4$—(W)$_{s'''}$—E', and wherein $R^{6''}$, independently, is halogen, cyano, lower alkyl, lower alkoxy, sulfonamido, alkanoyl, aroyl, —(Q)$_k$—(W)$_{s'}$—E'' or —(Q)$_k$—(W)$_{s'}$—C$_6$H$_4$—(W)$_{s'''}$—E'', and provided that no more than one of $R^{6''}$ is —(Q)$_k$—(W)$_{s'}$—E'' or —(Q)$_k$—(W)$_{s'}$—C$_6$H$_4$—(W)$_{s'''}$—E'', and wherein X, E', E'', L, M, Q, C$_6$H$_4$, m, n, s, s', s'' and s''' are as previously described In Reaction Scheme 5, a compound of formula IIb, which represents known compounds or compounds which can be prepared according to known procedures or as hereinafter described, is allowed to react with a compound of formula XII which represents compounds which can be prepared as hereinafter described in Reaction Scheme 13, in the presence of a base, for example, an alkali metal carbonate, such as, sodium or potassium carbonate, at a temperature in the range of from about 25° C. to about 110° C., in a polar, aprotic solvent such as acetonitrile, N,N-dimethylformamide, 2-butanone, dimethyl sulfoxide or the like. Alternatively, the procedure of U.S. Pat. No. 4,931,574 can be utilized. In this variation, a compound of formula IIb and of formula XII are allowed to react in the presence of an alkali metal carbonate, preferably potassium carbonate, and a phase transfer catalyst preferably tris[2-(2-methoxyethoxy)ethyl]amine (TDA-1), in an aromatic hydrocarbon solvent, preferably toluene, at a temperature in the range of 80° C. to 110° C. The resulting compound of formula Ik can be recovered utilizing conventional methods, such as, chromatography or recrystallization.

Catalytic hydrogenation of the compound of formula Ik gives the corresponding saturated compound of formula Il. The hydrogenation is carried out under conventional conditions. More specifically, a supported transition metal catalyst, such as, 5% or 10% palladium metal on carbon or charcoal is preferred. It is preferred that hydrogenation be carried out at ambient temperature and under one atmosphere of hydrogen gas pressure. Preferred solvents for the hydrogenation are lower alkanols, such as, methanol or ethanol, or ester solvents, such as, ethyl acetate, or the like. Mixtures of these solvents can also be used. The resulting compound of formula Il can be isolated by conventional chromatographic means or the like.

The compound of formula Il can be converted by saponification using an alkali metal hydroxide, such as, lithium, sodium, or potassium hydroxide, in a solvent mixture of water and a water miscible solvent, such as, methanol, ethanol, or tetrahydrofuran, at a temperature in the range of from about 25° C. to about 60° C., to the corresponding acid of formula Im. The compounds of formula Im can be purified by conventional methods, such as, recrystallization or chromatography.

Reaction Scheme 6

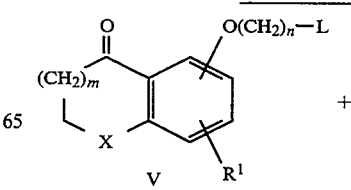

Reaction Scheme 6 (continued)

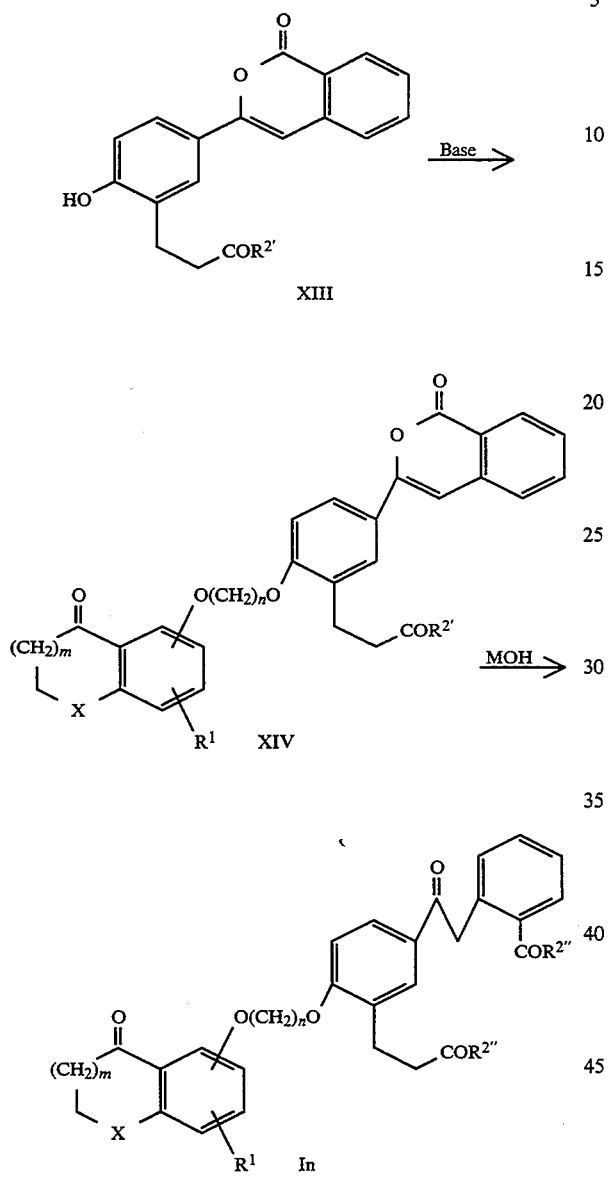

wherein $R^1$, X, L, $R^{2'}$, $R^{2''}$, m and n are as previously described.

In Reaction Scheme 6, a compound of formula V is allowed to react with a compound of formula XIII, prepared as hereinafter described in Reaction Scheme 20, in the presence of a base, and using conditions described in Scheme 1. The resulting compound of formula XIV is recovered using conventional recrystallization or chromatographic techniques. Saponification of the compound of formula XIV, using conditions as described in Reaction Scheme 1, gives the corresponding diacid of formula In which can be recovered, for example, by recrystallization.

Reaction Scheme 7

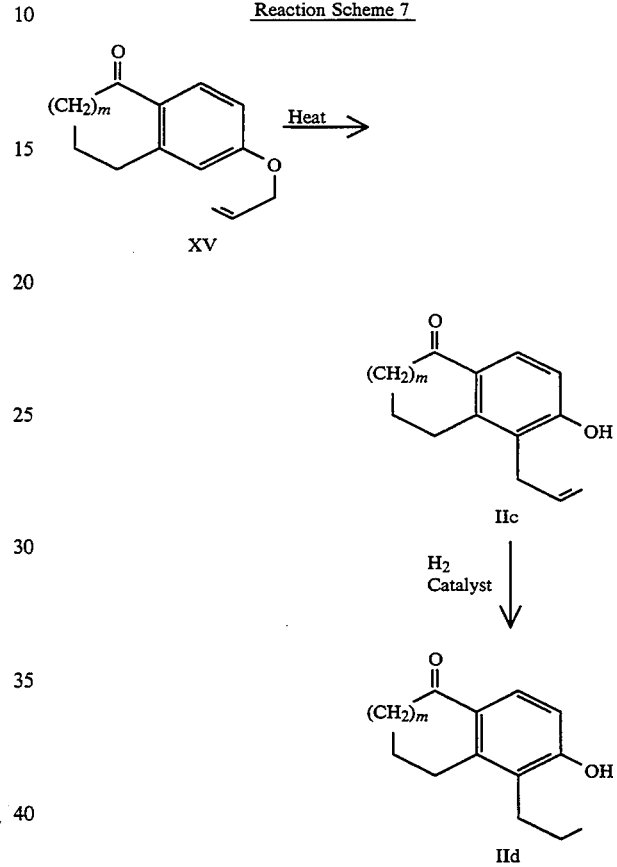

wherein m is as previously described.

In Reaction Scheme 7, an ether of formula XV, which represents known compounds, is thermolyzed in order to effect a Claisen rearrangement. It is preferred that the thermolysis be carried out at a temperature in the range of 180°–195° C. and in the presence of a solvent of sufficiently high boiling point, such as, N,N-diethylaniline or without any solvent. The desired product of this thermolysis is the corresponding compound, formula IIc, which can be recovered by recrystallization. Catalytic hydrogenation of the resulting compound of formula IIc, using the standard conditions described in Reaction Scheme 5, gives the corresponding saturated compound of formula IId, which can be recovered by conventional chromatography, recrystallization or the like.

Reaction Scheme 8

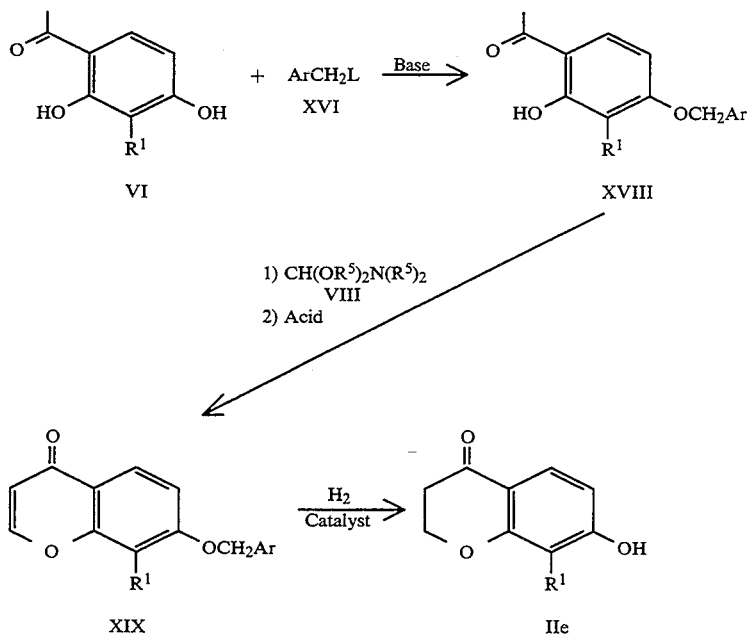

wherein Ar is aryl, $R^1$, $R^5$ and L are as previously described.

In Reaction Scheme 8, a dihydroxyacetophenone of formula VI, which represents known compounds, is allowed to react with a compound of formula XVI, which also represents known compounds, under conditions described in Reaction Scheme 1 for the conversion of II to Ia, to give the corresponding compound of formula XVIII. Among the various compounds of formula XVI which can be employed, benzyl chloride or benzyl bromide are preferred. Treatment of the compound XVIII with a known formamide acetal of formula VIII followed by acidic cyclization, as described in Reaction Scheme 3 for the conversion of VII to IX, gives the corresponding chromone of formula XIX. The chromone of formula XIX is generally recovered by conventional chromatographic methods, recrystallization or the like.

Catalytic hydrogenation of the chromone XIX, with concomitant hydrogenolytic cleavage of the arylmethyl ether moiety, gives the corresponding chromanone of formula IIe. The hydrogenation hydrogenolysis is carried out utilizing conventional conditions. A supported transition metal catalyst, such as 5% or 10% palladium metal on carbon or charcoal is preferred. It is preferred that the hydrogenation be carried out at ambient temperature and under one atmosphere of hydrogen gas pressure. Preferred solvents for effecting the hydrogenation-hydrogenolysis are the lower alkanols, such as, methanol or ethanol, or ester solvents, such as, ethyl acetate or the like. Mixtures of such solvents can also be used. The chromanone of formula IIe can be recovered by conventional chromatographic means.

Reaction Scheme 9

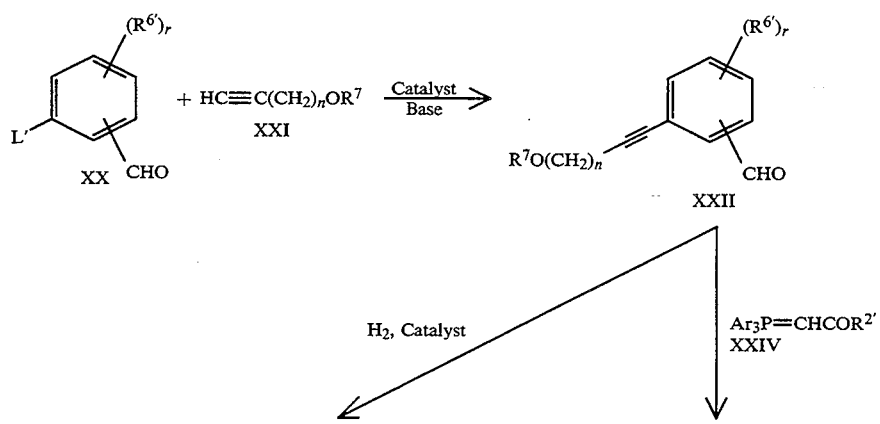

-continued

Reaction Scheme 9

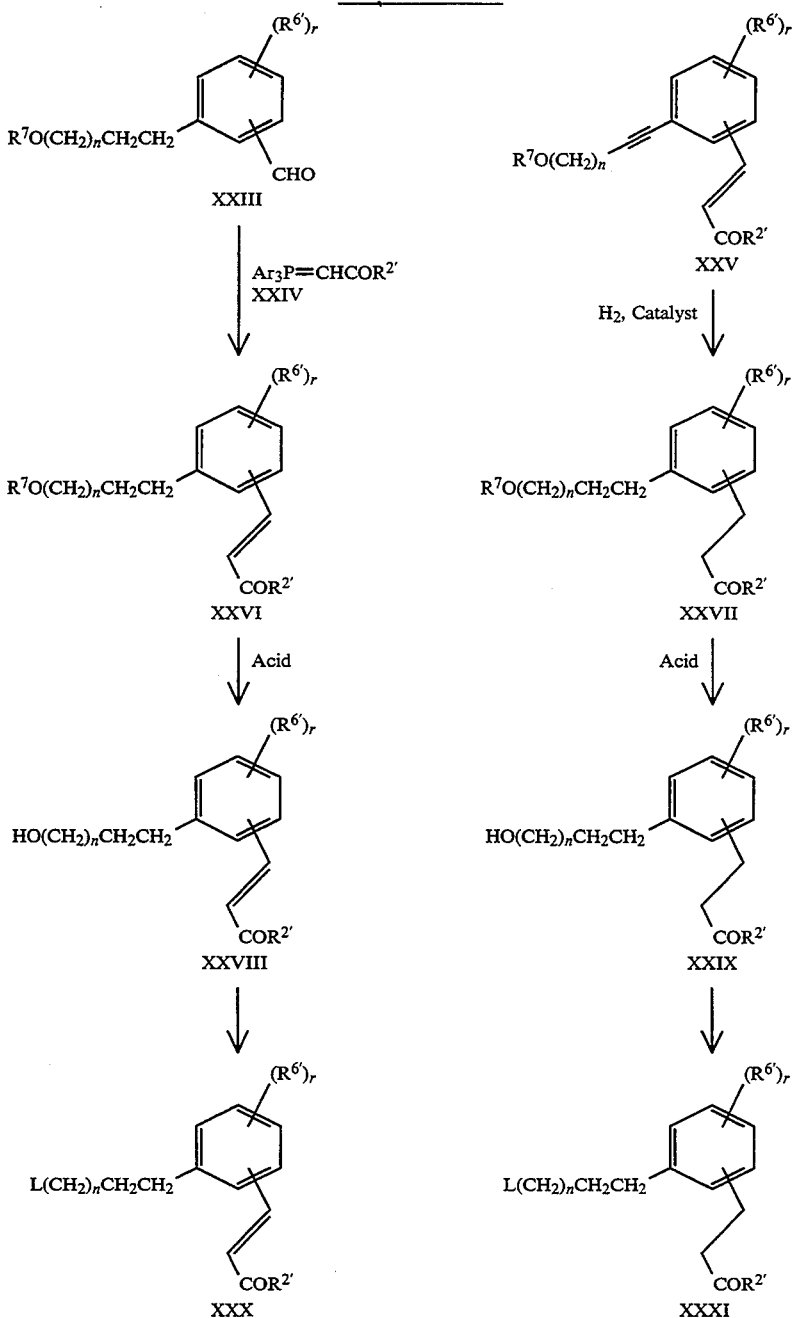

wherein $R^{2'}$, $R^{6'}$, Ar, L, r and n are as previously described, and $R^7$ is an acid labile hydroxy protecting group, such as, tetrahydropyranyl, trityl, t-butyl or the like, and L' is bromine, iodine or (trifluoromethyl)sulfonyloxy.

In Reaction Scheme 9, a benzaldehyde of formula XX, which represents known compounds or compounds which can be prepared according to known procedures or as hereinafter described, is allowed to react with an acetylene of formula XXI, which represents known compounds, in the presence of a palladium catalyst, a copper salt, and an amine base to give the corresponding compound of formula XXII. A preferred palladium catalyst is dichlorobis(triphenylphosphine)-palladium II and a preferred copper salt is cuprous iodide. A preferred amine base is triethylamine which can also be used as the solvent medium. It is preferred that this reaction be carried out at a temperature in the range of 60°-80° C. The resulting compound of formula XXII is recovered by conventional chromatography or the like. Catalytic hydrogenation of the compound of formula XXII is carried out in the manner described in Reaction Scheme 4 for the conversion of Ig to Ii, to give the corresponding reduced compound of formula XXIII which is recovered conventionally. Condensation of the resulting aldehyde of formula XXIII with a phosphorane of formula XXIV, which represents compounds known in the art, gives the corresponding compound of formula XXVI. It is preferred that the condensation be carried out at a temperature in the range of 80°–120° C., in an aromatic hydrocarbon solvent. Toluene is a preferred solvent medium. The resulting compound of formula XXVI is recovered by chromatography or the like and is converted to the corresponding alcohol of formula XXVIII by removal of the protecting group (R⁷) utilizing an acidic catalyst. It is preferred that the deprotection be carried out in a lower alkanol solvent, such as, methanol or ethanol. Useful acid catalysts for effecting the deprotection are organic sulfonic acids or amine salts thereof, at a temperature in the range of 20°–80° C. It is particularly preferred that the transformation be carried out using para-toluenesulfonic acid in methanol. The resulting compound of formula XXVIII is recovered by conventional chromatography or the like and is converted to the corresponding derivative of formula XXX using standard methods known in the art for transforming a hydroxy group into a leaving group (L). These methods include treatment with halogenating reagents, such as, N-bromosuccinimide/triphenylphosphine or N-chlorosuccinimide/triphenylphosphine in dichloromethane. Alteratively, the compound of formula XXVIII can be converted to the corresponding sulfonate of formula XXX by conventional methods, such as, treatment with an alkyl- or arylsulfonyl chloride and an organic amine. It is preferred that the compound of formula XXVIII be treated with methanesulfonyl chloride and triethylamine in dichloromethane, ether or ethyl acetate, at a temperature in the range of 0°–25° C.

Alternatively, an aldehyde of formula XXII can be converted to the corresponding compound of formula XXV by condensation with a compound of formula XXIV, as described for the conversion of XXIII to XXVI. Catalytic hydrogenation of the resulting compound of formula XXV gives the corresponding saturated compound of formula XXVII, as described for the conversion of XXII to XXIII. The resulting compound of formula XXVII is converted to the corresponding alcohol of formula XXIX, as described for the conversion of XXVI to XXVIII. The resulting compound of formula XXIX is converted to the corresponding compound of formula XXXI, as described for XXVIII to XXX.

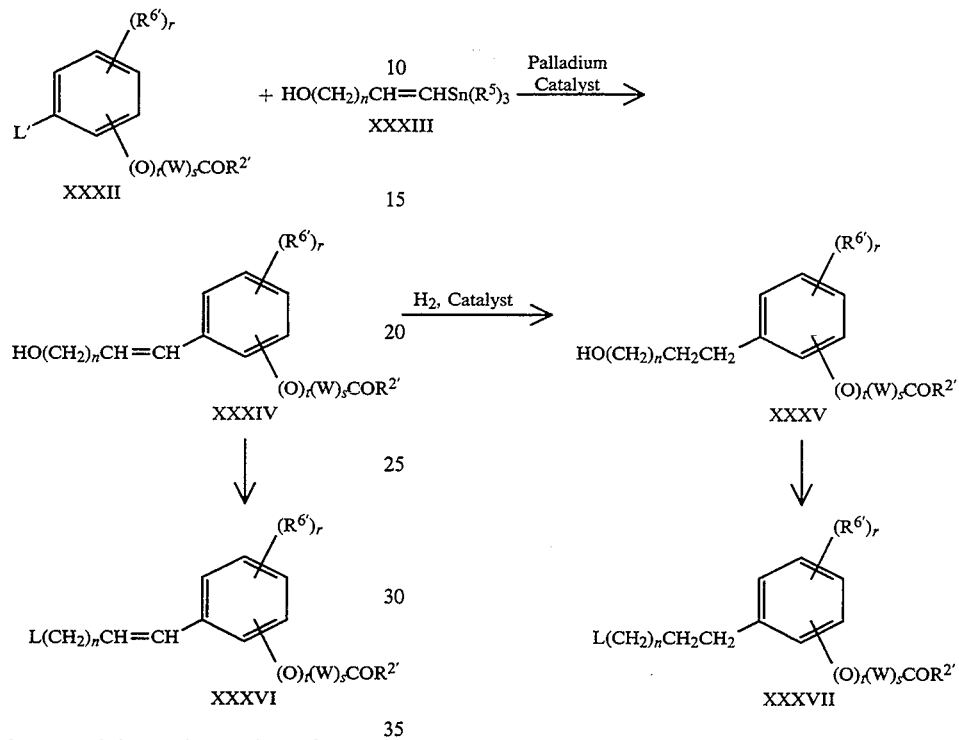

wherein R⁵, R²′, R⁶′, L, L′, W, n, s, r and t are as previously described.

In Reaction Scheme 10, a compound of the formula XXXII, which represents known compounds or compounds which can be prepared according to known procedures or as hereinafter described, is allowed to react with an alkenylstannane of formula XXXIII, which represents known compounds, in the presence of a palladium catalyst, to give the corresponding compound of formula XXXIV. The preferred palladium catalyst for effecting this transformation is a zero-valent palladium species, such as, tetrakis(triphenylphosphine)palladium. The transformation is preferably carried out in the presence of an alkali metal halide salt, such as, lithium chloride, and in an inert, ether solvent, preferably dioxane. It is preferred that this reaction be carried out at a temperature in the range of 80°–120° C. The resulting compound of formula XXXIV is recovered by standard chromatographic techniques or the like. Catalytic hydrogenation of the compound of formula XXXIV under standard conditions described previously, leads to the corresponding saturated compound of formula XXXV.

The compound of formula XXXV is recovered by conventional chromatography or the like and is converted to the corresponding derivative XXXVII using standard methods known in the art for transforming a hydroxy group into a leaving group, as described in Reaction Scheme 9 for the conversion of XXVIII to XXX. In a similar manner, the compound of formula XXXIV can be converted to the corresponding compound of formula XXXVI. Compounds XXXVI and XXXVII are recovered by standard chromatographic methods.

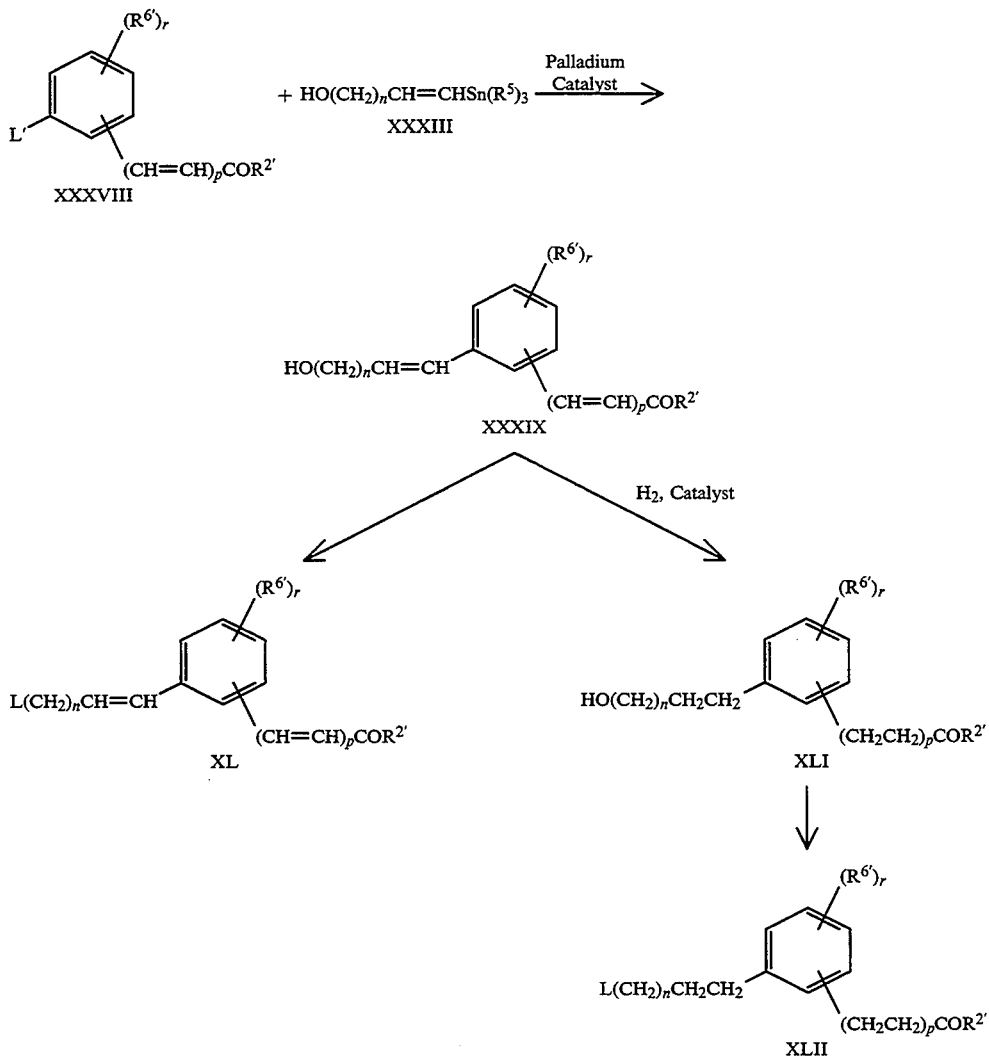

Reaction Scheme 11 wherein $R^{2'}$, $R^5$, $R^{6'}$, L, L', n, p, r and s are as previously described.

In Reaction Scheme 11, a compound of formula XXXVIII, which represents known compounds or compounds which can be prepared according to known procedures, is allowed to react with an alkenylstannane of the formula XXXIII, which represents known compounds, in the presence of a palladium catalyst, to give the corresponding compound of formula XXXIX. The preferred palladium catalyst for effecting this transformation is a zero-valent palladium species such as tetrakis(triphenylphosphine) palladium. The transformation is preferably carried out in the presence of an alkali metal halide salt, such as, lithium chloride, in an inert, ether solvent, preferably dioxane. It is preferred that this reaction be carried out at a temperature in the range of 80°–120° C. The compound of formula XXXIX is recovered by standard chromatographic techniques or the like. Catalytic hydrogenation of the compound of formula XXXIX under standard conditions described previously, leads to the corresponding saturated compound of formula XLI. The compound of formula XLI is recovered by conventional chromatography or the like and is converted to the corresponding derivative XLII using standard methods known in the art for transforming an hydroxy group into a leaving group, as described in Reaction Scheme 9 for the conversion of a compound of formula XXVIII to a compound of formula XXX. In a similar manner, the compound of formula XXXIX is converted to the corresponding compound of formula XL. Compounds XL and XLII are recovered by standard chromatographic methods.

Reaction Scheme 12

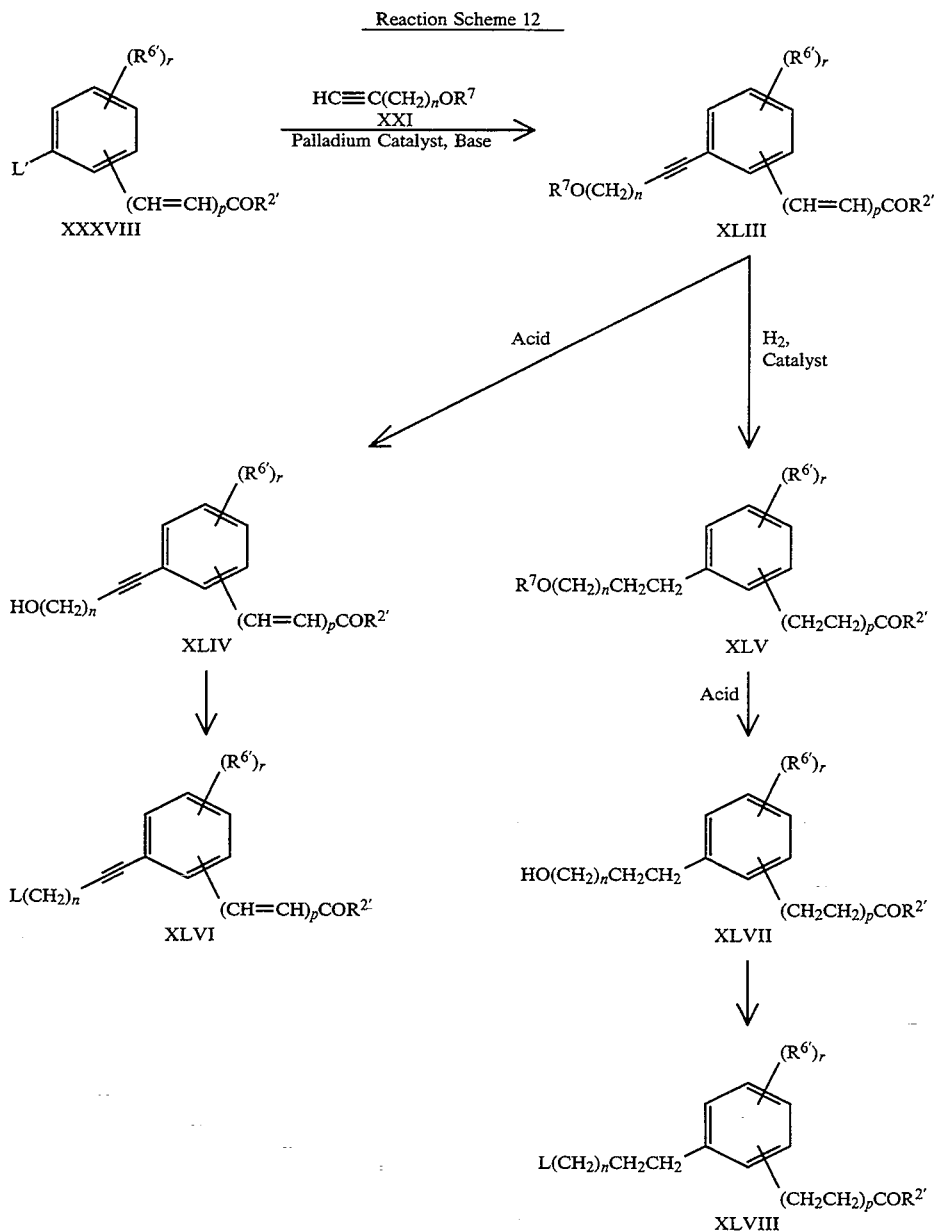

wherein $R^{2'}$, $R^{6'}$, $R^7$, L, L', n, p, r and s are as previously described.

In Reaction Scheme 12, a compound of the formula XXXVIII is allowed to react with an acetylene of formula XXI, in the presence of a palladium catalyst, a copper salt, and an amine base to give the corresponding compound of formula XLIII, using conditions described in Reaction Schemes 4 and 9 for the conversion of XX to XXII or for the conversion of X to Ig. The resulting compound of formula XLIII is recovered by conventional chromatography or the like. Catalytic hydrogenation of the compound of formula XLIII is carried out in the manner described in Reaction Scheme 4 for the conversion of Ig to Ii, giving the corresponding reduced compound of formula XLV which is recovered conventionally. The compound of formula XLV is converted to the corresponding alcohol of formula XLVII by removal of the protecting group $R^7$ utilizing an acidic catalyst, as described in Reaction Scheme 9 for the conversion of XXVI to XXVIII. The compound of formula XLVII is recovered by conventional chromatography or the like and is converted to the corresponding derivative of formula XLVIII using standard methods known in the art for transforming an hydroxy group into leaving group, as described in Reaction Scheme 9 for the conversion of XXVIII to XXX.

Alteratively, the compound of formula XLIII can be converted to the compound of formula XLIV as described for the conversion of XXVI to XXVIII. The compound of formula XLIV is converted to the compound of formula XLVI as described for the conversion of XXVIII to XXX.

Reaction Scheme 13

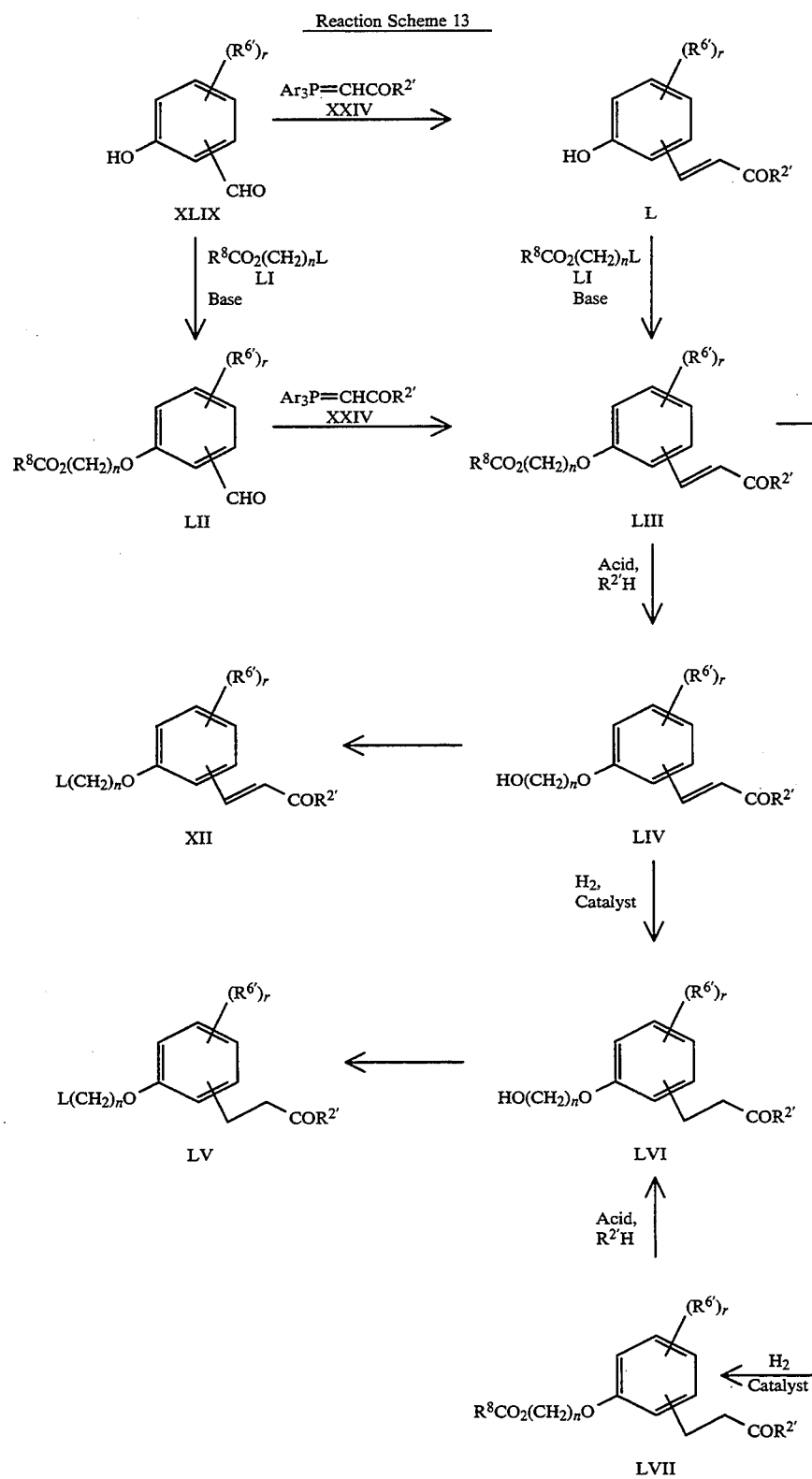

wherein $R^8$ is hydrogen, lower alkyl or aryl, and $R^{2'}$, $R^{6'}$, L, Ar, n, r and s are as previously described.

In Reaction Scheme 13, an hydroxybenzaldehyde of the formula XLIX, which represents known compounds or compounds which can be prepared according to known procedures or as hereinafter described, is allowed to react with a phosphorane of formula XXIV, using the procedure and conditions described in Reaction Scheme 9 for the conversion of XXIII to XXVI, giving the corresponding compound L. The resulting compound of formula L is recovered by conventional chromatography or the like. Alkylation of the compound of formula L with an ester of formula LI, which represents known compounds, in the presence of a base, gives the corresponding compound of formula LIII. The alkylation is carried out under standard conditions for effecting the alkylation of a phenol, such as, those described in Reaction Scheme 1 for the conversion of II to Ia. The compound of formula LIII is recovered by conventional chromatographic methods or the like. Alternatively, a compound of formula LIII can be prepared from the corresponding compound of formula XLIX by reversing this order of reactions, in other words, by first conventionally alkylating the compound of formula XLIX with the compound of formula LI to give the compound of formula LII. The compound of formula LII is then condensed with a phosphorane of formula XXIV to give the corresponding compound of formula LIII. The conditions required for effecting these transformations are as previously described.

A compound of formula LIII is converted to the corresponding alcohol of formula LIV by removal of the ester protecting group ($R^8CO$) utilizing an acidic catalyst. It is preferred that the deprotection process be carried out by transesterification in a lower alkanol solvent which is $R^{2'}H$. Useful acid catalysts for effecting the deprotection are organic sulfonic acids or amine salts thereof, at a temperature in the range of 20°–80° C. It is particularly preferred that the transformation be carried out using para-toluenesulfonic acid in methanol. The resulting alcohol of formula LIV is recovered by conventional chromatography or the like and is converted to the corresponding derivative of formula XII using standard methods for transforming an hydroxy group into a leaving group, such as those described in Reaction Scheme 9 for the conversion of XXVIII to XXX.

Alternatively, catalytic hydrogenation of a compound of formula LIV gives the corresponding saturated compound of formula LVI, as described in Reaction Scheme 9 for the conversion of XXV to XXVII. The resulting compound of formula LVI is converted to the corresponding compound of formula LV, as described in Reaction Scheme 9 for the conversion of XXVIII to XXX.

In yet another variation, conventional catalytic hydrogenation of a compound of formula LIII gives the corresponding saturated derivative of formula LVII. The resulting compound of formula LVII is then converted to the corresponding compound of formula LVI as described for the conversion LIII to LIV.

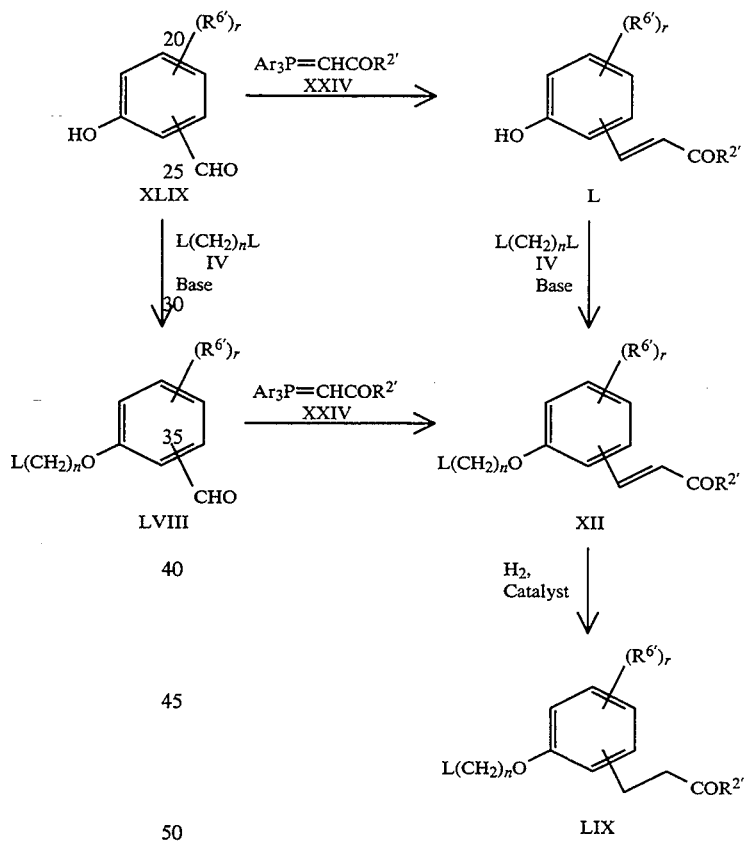

wherein $R^{2'}$, $R^{6'}$, L, Ar, n, r and s are as previously described.

In Reaction Scheme 14, an hydroxybenzaldehyde of formula XLIX, is alkylated with a compound of formula IV using the conditions described in Reaction Scheme 2 for the conversion of II to V. The resulting compound of formula LVIII is recovered by conventional chromatography or the like. The compound of formula LVIII is then condensed with a phosphorane of formula XXIV to give the corresponding compound of formula XII. The conditions required for effecting these transformations are as previously described.

Alternatively, a compound of formula L, prepared as described in Reaction Scheme 13, is alkylated with a compound of formula IV using the conditions described in Reaction Scheme 2 for the conversion of II to V, to give the corresponding compound of formula XII. Catalytic hydrogenation of a compound of formula XII gives the corresponding saturated derivative of formula LIX. It is preferred that this hydrogenation be performed using a catalyst compatible with the preservation of the leaving group "L", in an inert solvent. Preferred conditions for effecting the reduction involve the use of rhodium on alumina as the catalyst and toluene as the solvent, under one atmosphere of hydrogen pressure, at a temperature in the range of 0°–25° C.

conversion II to Ia. The resulting compound of formula LXII is recovered by conventional chromatographic methods or the like. A compound of formula LXII is converted to the corresponding alcohol of formula LXIII by removal of the ester protecting group ($R^8CO$) using an acidic catalyst. The transformation is carried out as described in Reaction Scheme 13 for the conversion of LIII to LIV. The compound of formula LXIII can be recovered by conventional chromatography or

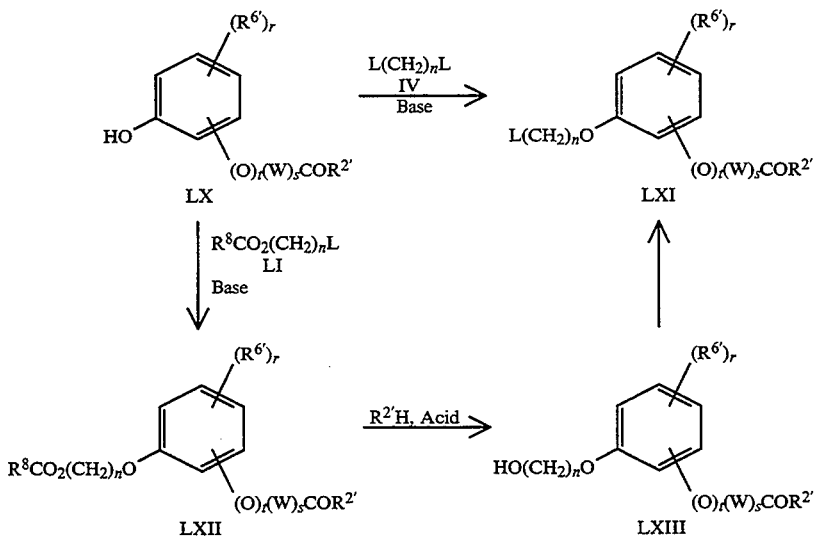

Reaction Scheme 15 wherein $R^{2'}$, $R^{6'}$, $R^8$, L, W, n, s, r and t are as previously described.

Alkylation of a phenol of formula LX, which represents known compounds or compounds which can be prepared according to known procedures or as hereinafter described, with an ester of formula LI in the presence of a base, gives the corresponding compound of formula LXII. This alkylation is carried out under standard conditions for effecting the alkylation of a phenol such as those described in Reaction Scheme 1 for the the like and is converted to the corresponding derivative LXI using standard methods for transforming an hydroxy group into a leaving group, such as those described in Reaction Scheme 9 for the conversion of XXVIII to XXX.

Alternatively, a phenol of formula LX can be alkylated with a compound of formula IV to give the corresponding compound of formula LXI. The alkylation is carried out under conditions described in Reaction Scheme 2 for the conversion of II to V.

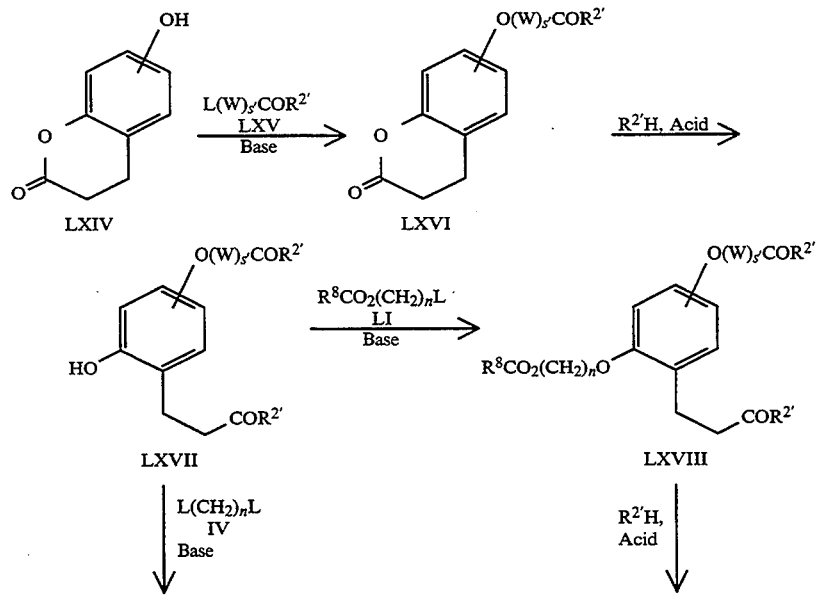

Reaction Scheme 16

Reaction Scheme 16

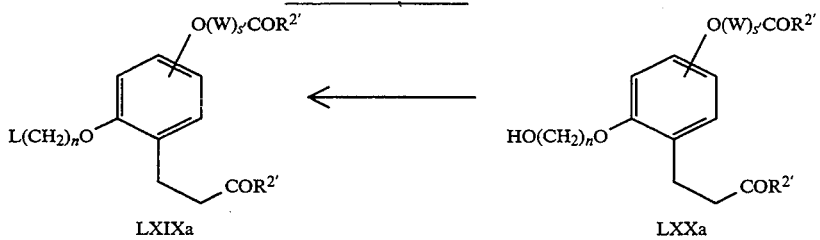

wherein $R^{2'}$, $R^8$, L, W, n and s' are as previously described.

In Reaction Scheme 16, alkylation of a dihydrocoumarin of formula LXIV, which represents known compounds, with an ester of formula LXV, which also represents known compounds in the presence of a base, gives the corresponding compound of formula LXVI. The alkylation can be carried out under standard conditions for effecting the alkylation of a phenol, such as, those described in Reaction Scheme 13 for the conversion of L to LIII. The resulting compound of formula LXVI can be recovered by conventional chromatographic methods. The compound of formula LXVI is converted to the corresponding phenol of formula LXVII by alcoholysis of the lactone ring using an acidic catalyst in a lower alkanol solvent. The transformation is carried out using any of the common acids, such as, hydrochloric or sulfuric acid, an alkyl sulfonic acid or an arylsulfonic acids. It is preferred that this transformation be carried out in methanol or ethanol with para-toluenesulfonic acid, at a temperature in the range of 60°–80° C. The compound of formula LXVII can be recovered by standard chromatographic methods or the like. Alkylation of the compound of formula LXVII with a compound of formula IV is carried out as described in Reaction Scheme 2 for the conversion of II to V, and affords the corresponding compound of formula LXIXa, which is recovered by chromatography.

Alteratively, a compound of formula LXVII is alkylated with a compound of formula LI to give the corresponding compound of formula LXVIII. This alkylation is carried out as described in Reaction Scheme 13 for the conversion of L to LIII. The compound of formula LXVIII which is recovered by conventional chromatography or the like, is converted to the corresponding alcohol of formula LXXa as described in Reaction Scheme 13 for the conversion of LIII to LIV. The compound of formula LXXa is recovered by chromatography or the like and is converted to the compound of formula LXIXa using procedures described in Reaction Scheme 9 for the conversion of XXVIII to XXX.

Reaction Scheme 17

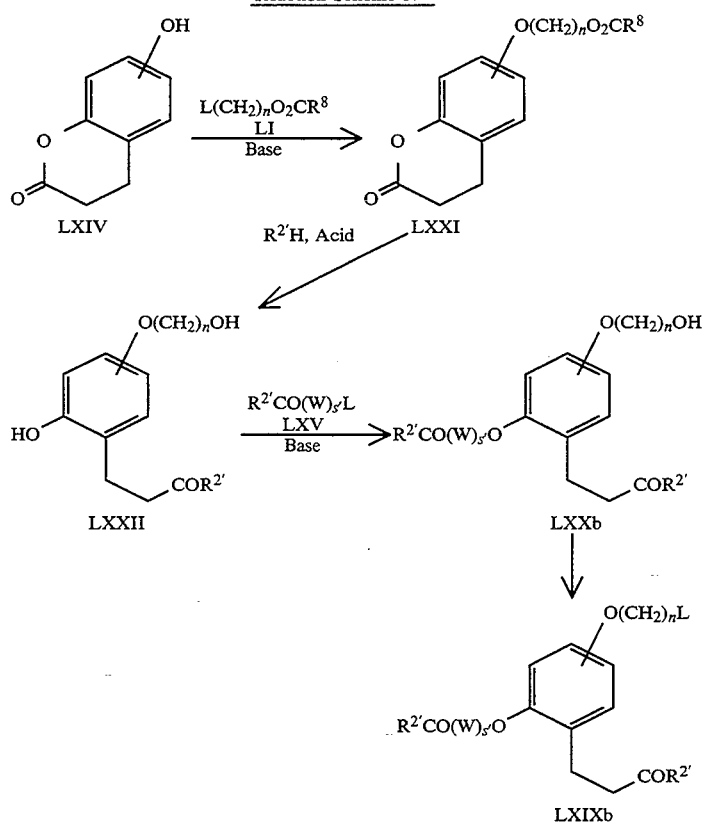

wherein $R^{2'}$, $R^8$, Z, L, W, n and s' are as previously described.

dures described in Reaction Scheme 9 for the conversion of XXVIII to XXX.

Reaction Scheme 18

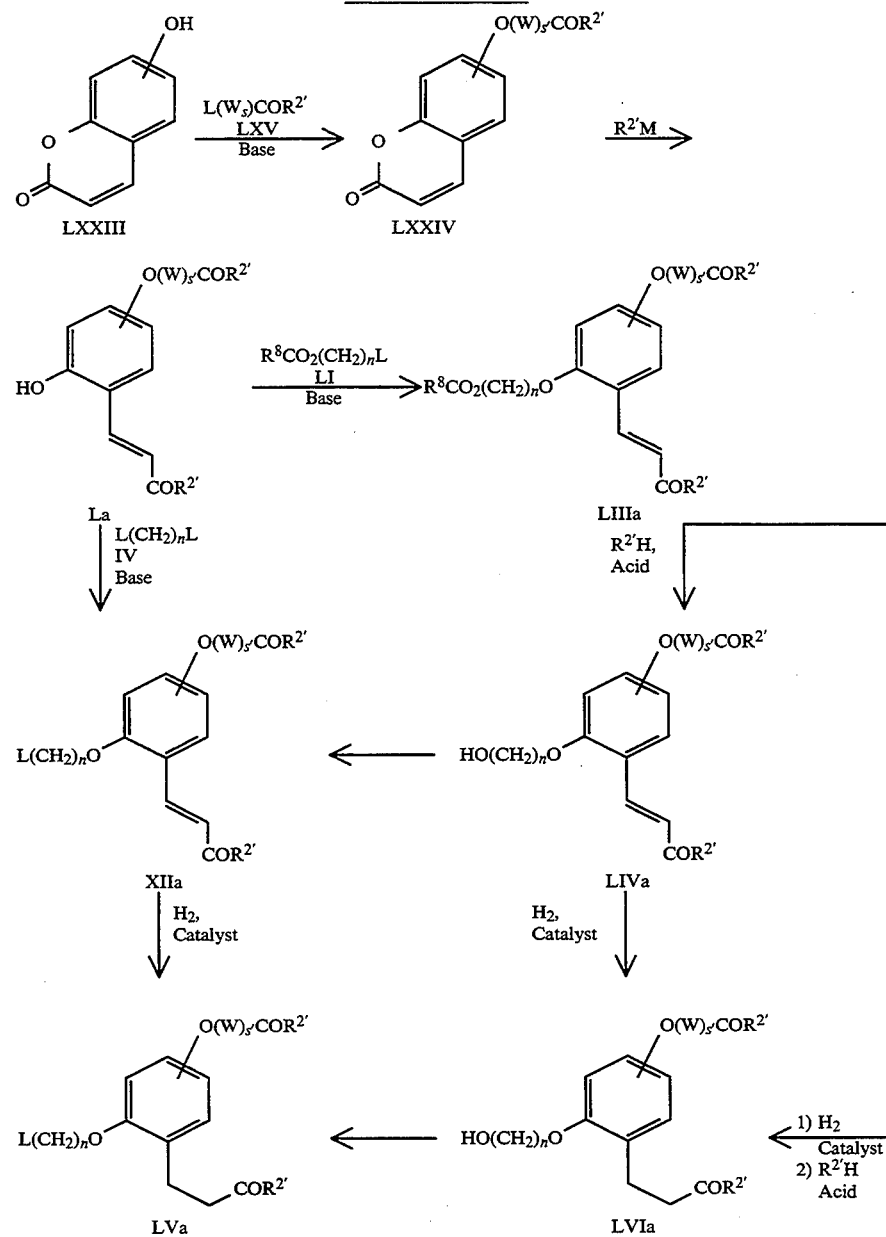

In Reaction Scheme 17, alkylation of the dihydrocoumarin of formula LXIV with an ester of formula LI, as described in Reaction Scheme 13 for the conversion of L to LIII, gives the corresponding compound of formula LXXI. The resulting compound of formula LXXI is converted to the corresponding phenol of formula LXXII as described in Reaction Scheme 16 for the conversion of LXVI to LXVII. The compound of formula LXXII is recovered by standard chromatographic methods or the like. Alkylation of a compound of formula LXXII with a compound of formula LXV can be carried out as described in Reaction Scheme 16 for the conversion of LXIV to LXVI, and gives the corresponding compound of formula LXXb which can be recovered by chromatography or the like. A compound of formula LXXb can be converted to the corresponding compound of formula LXIXb using procedures described in Reaction Scheme 9 for the conversion of XXVIII to XXX.

wherein $R^{2'}$, $R^8$, L, W, n and s' are as previously described.

In Reaction Scheme 18, alkylation of a coumarin of formula LXXIII, which represents known compounds with an ester of formula LXV in the presence of a base, gives the corresponding compound of formula LXXIV. The alkylation is carried out under standard conditions for effecting the alkylation of a phenol, such as, those described in Reaction Scheme 13 for the conversion of L to LIII. The compound of formula LXXIV is recovered by conventional chromatographic methods or the like. A compound of formula LXXIV can be converted to the corresponding phenol of formula La by alcoholysis of the lactone ring using an alkali metal lower alkoxide in a lower alkanol solvent. The transformation can be carried out using lithium, sodium, or potassium lower alkoxide. It is preferred that the transformation be carried out in methanol or ethanol with sodium methoxide or sodium ethoxide, respectfully, at a temperature in the range of 60°–80° C. The compound of formula La is recovered by standard chromatographic methods. Alkylation of a compound of formula La with a compound of formula IV is carried out as described in Reaction Scheme 2 for the conversion of II to V, and gives the corresponding compound of formula XIIa which is recovered by chromatography. Catalytic hydrogenation of a compound of formula XIIa using the procedure described in Reaction Scheme 14 for the conversion XII to LIX, gives the corresponding saturated compound of formula LVa.

Alternatively, a compound of formula La is alkylated with a compound of formula LI giving the corresponding compound of formula LIIIa. The alkylation is carried out as described in Reaction Scheme 13 for the conversion of L to LIII. A compound of formula LIIIa, which is recovered by conventional chromatography or the like, is converted to the corresponding alcohol of formula LIVa as described in Reaction Scheme 13 for the conversion of LIII to LIV. The compound of formula LIVa is recovered by chromatography and is converted to the corresponding compound of formula XIIa using procedures described in Reaction Scheme 9 for the conversion of XXVIII to XXX. Catalytic hydrogenation of a compound of formula LIVa gives the corresponding saturated compound LVIa which, in turn, can be transformed to the corresponding compound of formula LVa using the standard methodology described previously.

If desired, a compound of formula LIIIa can be first hydrogenated and the ester protecting group removed as previously described to give the corresponding saturated alcohol of formula LVIa. The resulting compound of formula LVIa can then be converted to the corresponding compound of formula LVa. All of these transformations are carried out using the standard reaction and the recovery procedures previously described.

Reaction Scheme 19

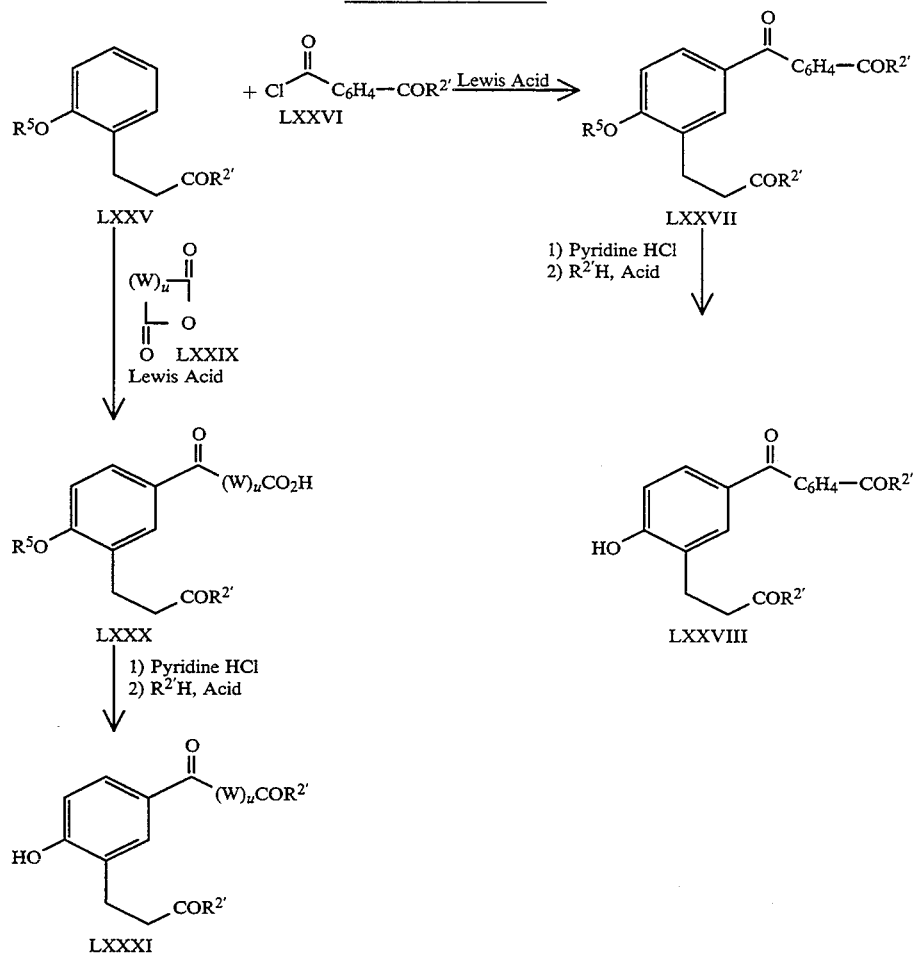

wherein $R^{2'}$, $R^5$, W, and $C_6H_4$ are as previously described, and u is an integer of 2 or 3.

In Reaction Scheme 19, an ether ester of formula LXXV, which represents known compounds, is caused to undergo Friedel-Crafts acylation with an acid chloride ester of the formula LXXVI, which also represents known compounds, in the presence of a Lewis acid, to give the corresponding keto diester compound of formula LXXVII. Any standard Lewis acids, such as, aluminum, boron, or titanium halides, can be employed in the reaction. The acylation can be carried out in an inert solvent, such as, a halogenated hydrocarbon or an aromatic hydrocarbon. It is preferred that the acylation be carried out using aluminum chloride, in dichloromethane, at a temperature in the range of 25°–120° C.

The compound of formula LXXVII can be recovered by chromatography or recrystallization. Removal of the lower alkyl ether protecting group (R⁵) in a compound of formula LXXVII can be effected using any of the known method for dealkylation of alkyl aryl ethers, for example, by treatment with a mineral acid, such as, hydrogen bromide or hydrogen iodide and the like, and amine salts thereof. Aluminum and boron halides can also be used. It is preferred that the dealkylation be carried out by heating a compound of formula LXXVII with pyridine hydrochloride, at a temperature in the range of 180°-220° C. Since this treatment also induces cleavage of the ester groups (R²'), the acid product of the dealkylation is immediately subjected to reesterification using standard Fischer esterification conditions which involve exposure of the crude reaction product to the lower alkanol of the formula R²'H and a strong acid catalyst, such as, para-toluenesulfonic acid, hydrogen chloride or thionyl chloride. The resulting keto diester phenol product of formula LXXVIII is recovered by conventional chromatography or the like.

Friedel-Crafts acylation of a compound of formula LXXV with an anhydride of formula LXXIX, which represents known compounds is carried out as described for the conversion of LXXV to LXXVII, to give the corresponding ester acid compound of the formula LXXX. A compound of formula LXXX is dealkylated and reesterified as described for the conversion of LXXVII to LXXVIII, to give the corresponding keto diester phenol compound of formula LXXXI which can be recovered by chromatography or the like.

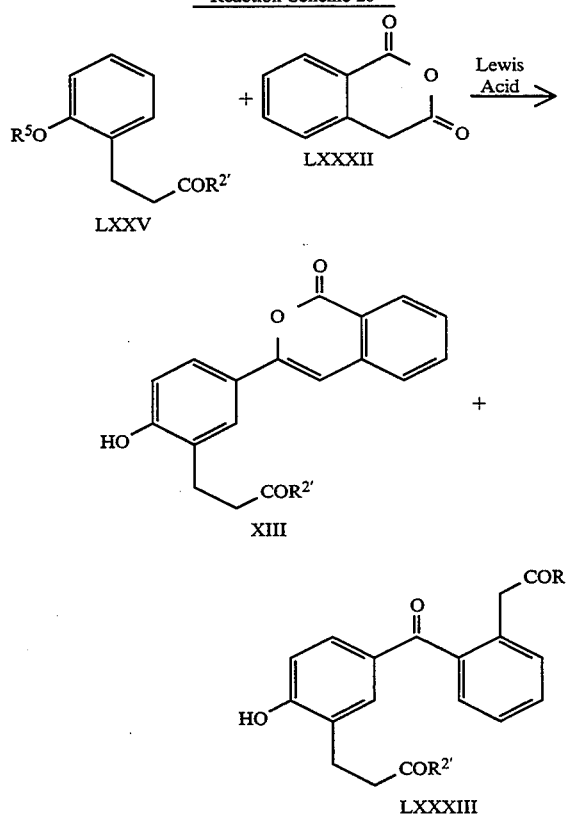

wherein R²' and R⁵ are as previously described.

In Reaction Scheme 20, an ether ester of formula LXXV is caused to undergo Friedel-Crafts acylation with the known homophthalic anhydride of the formula LXXXII, in the presence of a Lewis acid, to give a mixture of compounds which can be separated by chromatography into ether and phenol functions. The separated ether products of the mixture are dealkylated and reesterified giving the corresponding compounds of formulas XIII and LXXXIII, which can be recovered by conventional chromatography or the like. The procedures employed for carrying out the transformations are as described in Reaction Scheme 19 for the conversion of LXXV to LXXVIII. pp

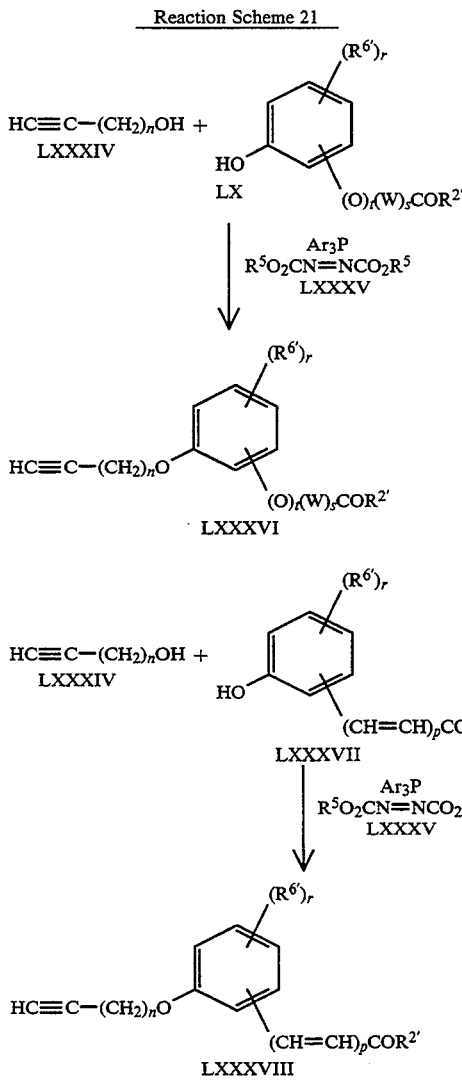

wherein R²', R⁵, R⁶', Ar, n, W, p, s, r and t are as previously described.

In Reaction Scheme 21, an alkynol of formula LXXXIV, which represents known compounds, is condensed with a phenol of formula LX, to give the corresponding ether compound of formula LXXXVI. The condensation is carried out by treatment of the reactants with a triarylphosphine and a di-lower alkyl ester of azodicarboxylic acid of the formula LXXXV, in an inert solvent. It is preferred that the condensation be carried out using triphenylphosphine and diethyl azodicarboxylate in tetrahydrofuran solution, at a temperature in the range of 25°-50° C. The resulting product of formula LXXXVI can be recovered by chromatography or the like.

In a similar manner, the alkynol of formula LXXXIV is condensed with a phenol of formula LXXXVII, prepared as herein described, to give the corresponding compound of formula LXXXVIII.

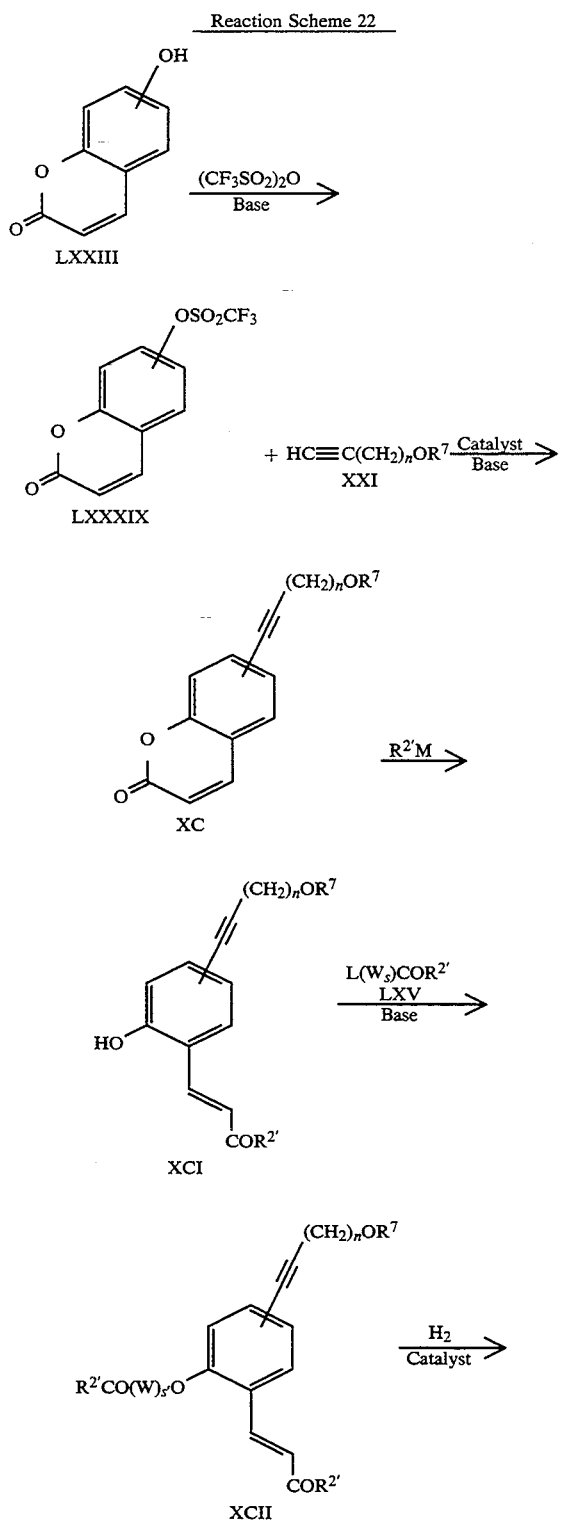

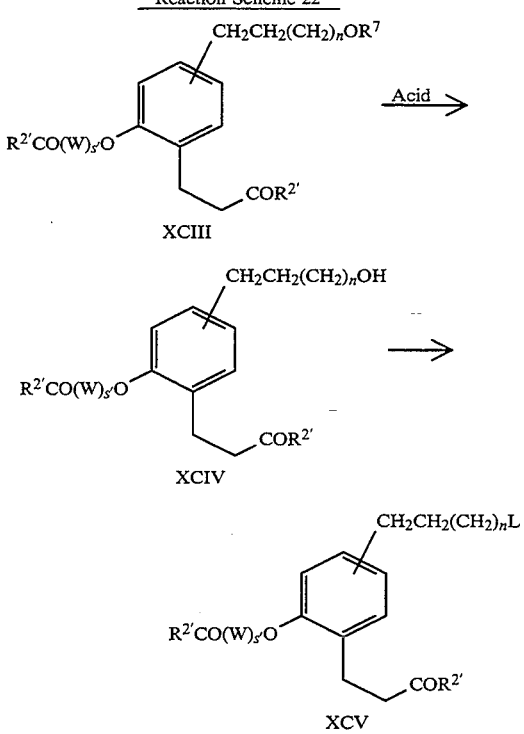

wherein $R^{2'}$, $R^7$, L, W, n and s' are as previously described.

In Reaction Scheme 22, a coumarin of formula LXXIII is converted to the corresponding trifluoromethanesulfonic ester of formula LXXXIX, as described in Reaction Scheme 4 for the conversion of IIa to X. The resulting compound of formula LXXXIX is recovered by conventional chromatographic methods, recrystallization or the like. Condensation of a sulfonate of formula LXXXIX with the acetylene of formula XXI is carried out as described in Reaction Scheme 4 for the conversion of X to Ig, to give the corresponding adduct of formula XC which can be recovered by chromatography or the like. A compound of formula XC is converted to the corresponding phenolic cinnamate of formula XCI by alcoholysis of the lactone ring using an alkali metal lower alkoxide in a lower alkanol solvent. The transformation is carried out as described in Reaction Scheme 18 for the conversion of LXXIV to La. A compound of formula XCI is recovered by standard chromatographic methods. Alkylation of a compound of formula XCI with a compound of formula LXV is carried out as described in Reaction Scheme 18 for the conversion of the compound of formula LXXIII to the compound of formula LXXIV, and affords the compound of formula XCII which is recovered by chromatography. Catalytic hydrogenation of the compound of formula XCII using the procedure described in Reaction Scheme 14 for the conversion of XII to LIX, gives the corresponding saturated compound of formula XCIII. Removal of the protecting group ($R^7$) in a compound of formula XCIII can be carried out as described in Reaction Scheme 9 for the transformation of XXVI to XXVIII, and yields the corresponding alcohol of formula XCIV. The resulting compound of formula XCIV is converted to XCV as described in Reaction Scheme 9 for the conversion of XXVIII to XXX.

Reaction Scheme 23

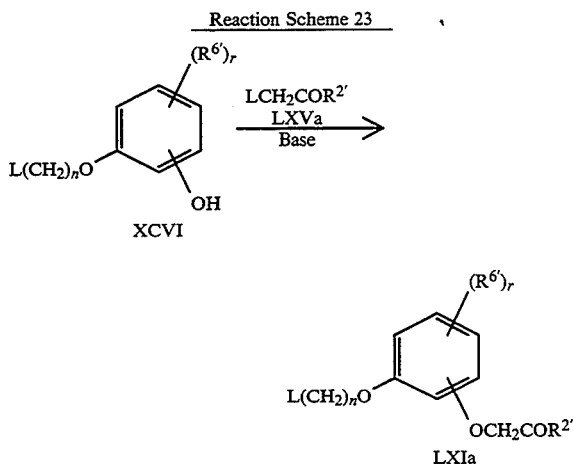

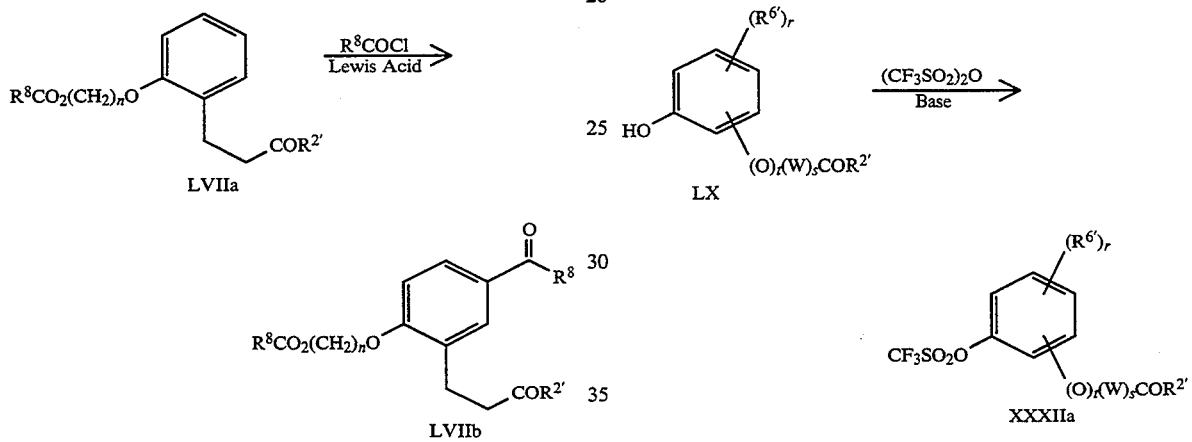

wherein $R^{2'}$, $R^{6'}$, $R^8$, L, W, n, r, s and t are as previously described.

In Reaction Scheme 23, alkylation of a phenol of formula XCVI, which represents known compounds, or compounds which can be prepared by known procedures, with an ester of formula LXVa, which also represents known compounds, in the presence of a base, gives the product of formula LXIa. This alkylation is carried out under standard conditions for effecting the alkylation of a phenol such as those described in Reaction Scheme 13 for the conversion of the compound of formula L to the compound of formula LIII. The compound of formula LXIa is recovered by conventional chromatographic methods.

Friedel-Crafts acylation of a diester of formula LVIIa with a carboxylic acid chloride $R^8COCl$ gives the corresponding product of formula LVIIb. This acylation is carried out using a Lewis acid under standard Friedel-Crafts conditions such as those described in Reaction Scheme 19 for the conversion of LXXV to LXXVII. The product LVIIb is recovered by standard chromatography.

Alkylation of a phenol of formula LX with a compound of formula XCVII, which represents known compounds, in the presence of base, gives the corresponding product of formula XCVIII, which is recovered by chromatography. This alkylation can be carried out as described in Reaction Scheme 2 for the conversion of II to V.

Reaction Scheme 24

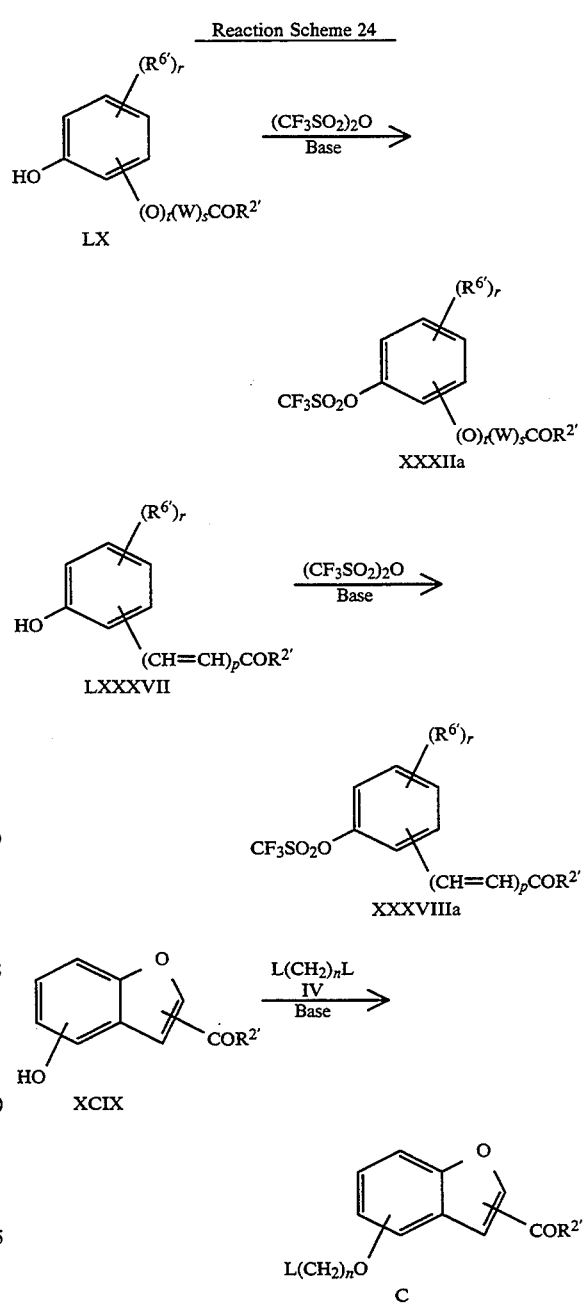

-continued
Reaction Scheme 24

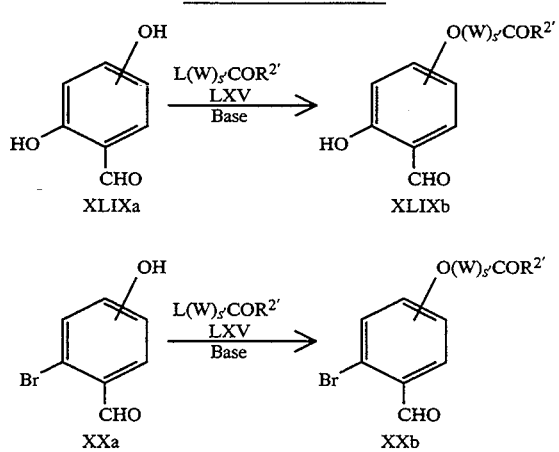

wherein R$^{2'}$, R$^{6'}$, L, W, n, p, r, s, s' and t are as previously described.

In reaction Scheme 24, a phenol of formula LX is converted to the corresponding trifluoromethanesulfonate of formula XXXIIa by treatment with trifluoromethanesulfonic anhydride in the presence of an amine base. Any conventional amine base may be utilized. Pyridine or triethylamine are preferred. This transformation is preferably carried out in dichloromethane solvent at a temperature in the range of 0°–25° C. The compound of formula XXXIIa can be recovered by conventional means such as chromatography. In a similar manner, the phenol of formula LXXXVII is converted to the corresponding trifluoromethanesulfonate of formula XXXVIIIa.

Alkylation of an hydroxybenzofurancarboxylate of formula XCIX, which represents known compounds, with a compound of formula IV, in the presence of a base, gives the corresponding product of formula C. This alkylation can be carried out under standard conditions for effecting the alkylation of a phenol, such as those described in Reaction Scheme 2 for the conversion of II to V. The product of formula C is isolated conventionally by chromatography.

Alkylation of a dihydroxybenzaldehyde of formula XLIXa, which represents known compounds, with one molar equivalent of a compound of formula LXV, in the presence of at least two molar equivalents of a base, gives the corresponding monoalkylated product of formula XLIXb. It is preferred that an alkali metal hydride base be employed in this alkylation, in a polar aprotic solvent, at a temperature in the range of 25°–80° C. It is most preferred that this alkylation be carried out using sodium hydride, in N,N-dimethylformamide, at ambient temperature. The product of formula XLIXb is recovered by chromatography.

Alkylation of a bromophenol of formula XXa, which represents known compounds, with a compound of formula LXV, in the presence of a base, gives the corresponding product of formula XXb which is recovered by chromatography. This alkylation is carried out under standard conditions for effecting the alkylation of a phenol such as those described in Reaction Scheme 1 for the conversion of II to Ia.

Reaction Scheme 25

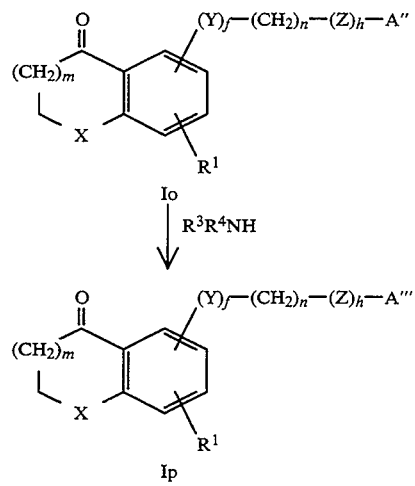

wherein A''' is —B''' or —O—B''', wherein B''' is a mono-, di- or tricyclic aromatic or heteroaromatic moiety substituted by the group —COR$^{2'''}$, —(O)$_r$—(W-)$_s$—COR$^{2'''}$ or —(CH=CH)$_p$COR$^{2'''}$ and which may also contain up to 4 additional substituents selected, independently, from the group consisting of halogen, cyano, lower alkyl, lower alkoxy, sulfonamido, alkanoyl, aroyl, —(Q)$_k$—(W)$_{s'}$—E''' or —(Q)$_k$—(W)$_{s'}$—C$_6$H$_4$—(W)$_{s'''}$—E''', provided that no more than one of said substituents is —(Q)$_k$—(W)$_{s'}$—E''' or —(Q)$_k$—(W)$_{s'}$—C$_6$H$_4$—(W)$_{s'''}$—E''', E''' is COR$^{2'''}$ and R$^{2'''}$ NR$^3$R$^4$, and wherein R$^1$, R$^3$, R$^4$, A'', Q, W, X, Y, Z, f, h, p, m, n, p, s, s', s'', and s''' are as previously described.

In Reaction Scheme 25, an acid of formula Io is converted to the corresponding amide of formula Ip by reaction with the amine R$^3$R$^4$NH. This reaction can be carried out using any of the standard methods of forming amides from acids. These include treatment of the acid with 1,1'-carbonyldiimidazole and the amine or exposure of the acid to a base, a carbodiimide and the amine. It is understood that if more than one carboxyl moiety is present in the starting acid, all such groups will be converted to the corresponding amide linkage. It is preferred that the amidation reaction be performed by treating the acid of formula Io with 1-(3-dimethylaminopropyl)-3-ethylcarbodiimide hydrochloride, 1-hydroxybenzotriazole, triethylamine, and the amine R$^3$R$^4$NH, in dichloromethane solution, at ambient temperature. The amide of formula Ip is recovered by chromatography or recrystallization.

Reaction Scheme 26

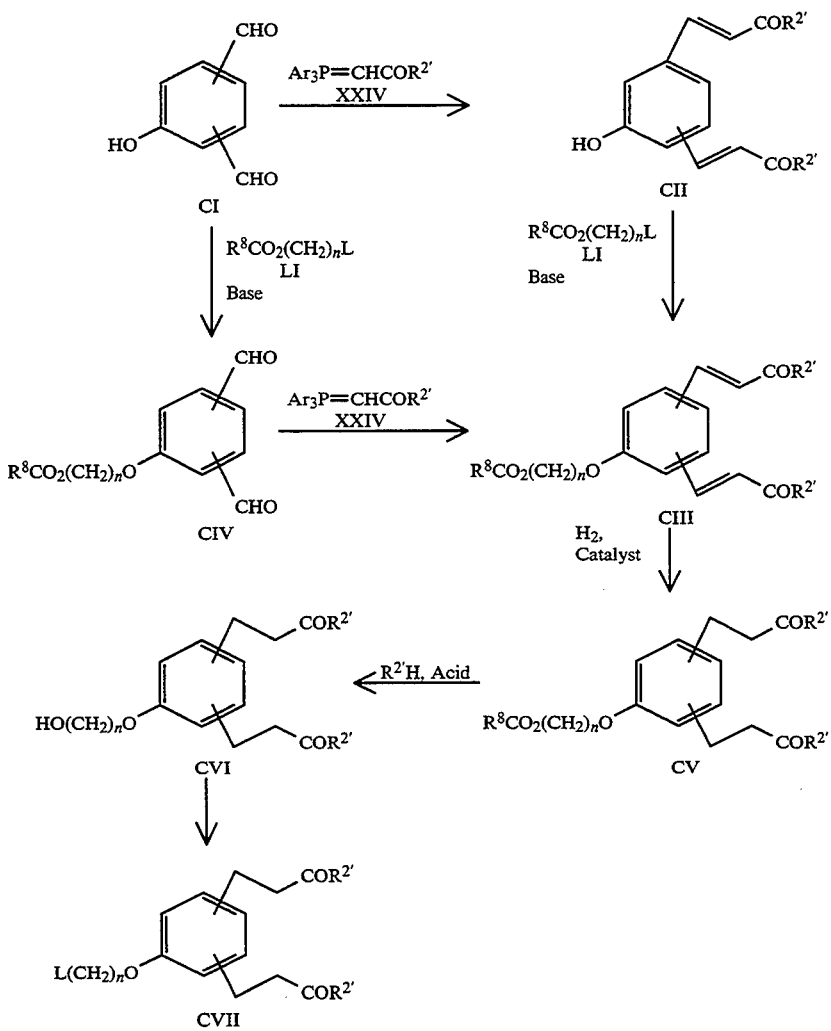

wherein Ar, $R^{2'}$, $R^8$, n, and L are as previously described.

In Reaction Scheme 26, an hydroxydialdehyde of formula CI, which represents known compounds, is condensed with a phosphorane of formula XXIV using reaction conditions previously described (Reaction Scheme 9), to give the corresponding diester product of formula CII which is recovered by conventional chromatography. Alkylation of the compound of formula CII with an ester of formula LI, in the presence of a base, gives the product of formula CIII. This alkylation is carried out under standard conditions for effecting the alkylation of a phenol such as those described previously in Reaction Scheme 13. The compound of formula CIII is recovered by conventional chromatographic methods.

Alternatively, the compound of formula CIII can be produced from the compound of formula CI by reversing this order of reactions, in other words, by first conventionally alkylating the compound of formula CI with the compound of formula LI to give the compound of formula CIV. The compound of formula CIV is then condensed with a phosphorane of formula XXIV to give the compound of formula CIII. The conditions required for effecting these transformations are as described previously. Catalytic hydrogenation of the compound of formula CIII under conditions described previously, gives the corresponding saturated triester of formula CV. The compound of formula CV is converted to the corresponding hydroxy diester of formula CVI by removal of the ester protecting group $R^8CO$ using an acidic catalyst. This transformation is carried out as described in Reaction Scheme 13 for the conversion of the compound of formula LIII to the compound of formula LIV. The compound of formula CVI is recovered by conventional chromatography and is converted to the corresponding derivative CVII using standard methods known in the art for transforming hydroxy groups into leaving groups, such as those described in Reaction Scheme 9 for the conversion of a compound of formula XXVIII to a compound of formula XXX.

Reaction Scheme 27

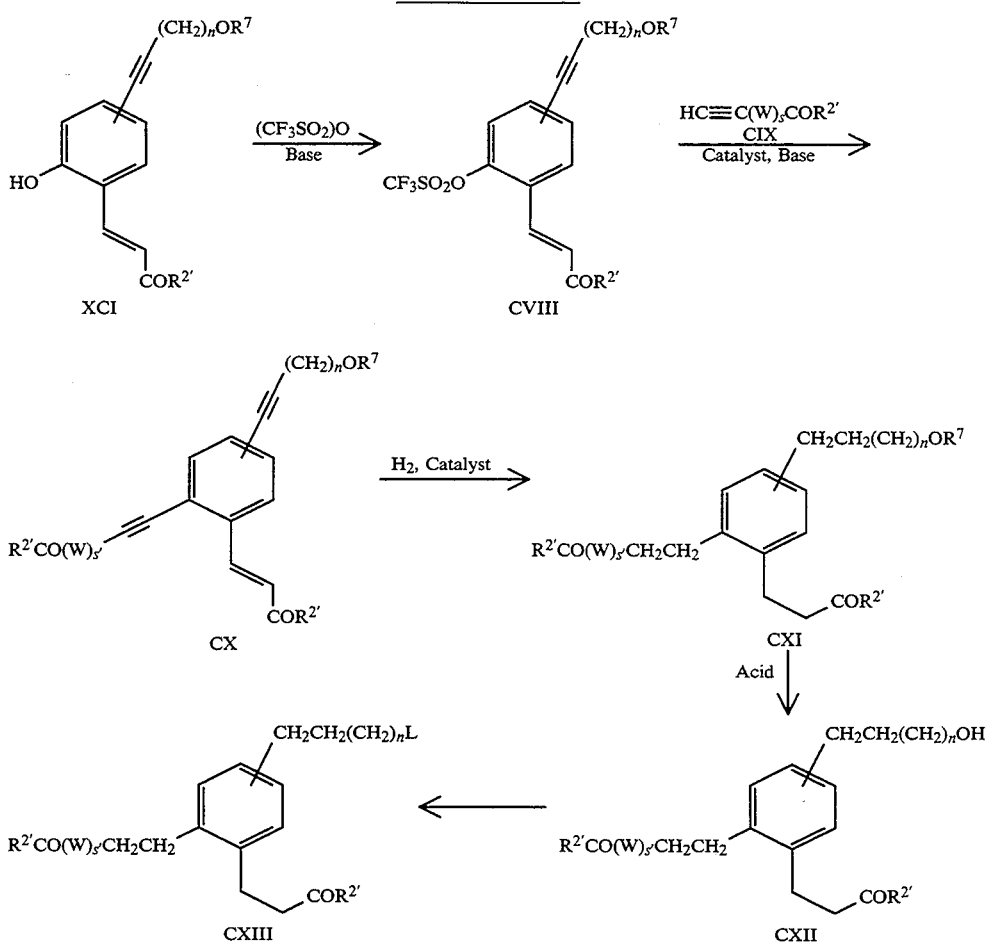

wherein $R^{2'}$, $R^7$, L, W, n, and s' are as previously described.

In Reaction Scheme 27, an hydroxy cinnamate of formula XCI (Reaction Scheme 22) is converted to the corresponding trifluoromethanesulfonic ester CVIII as described in Reaction Scheme 4 for the conversion of a compound of formula IIa to a compound of formula X. The compound of formula CVIII is recovered by conventional chromatographic methods. Condensation of the sulfonate of formula CVIII with the acetylenic ester of formula CIX, which represents known compounds, is carried out as described in Reaction Scheme 4 for the conversion of a compound of formula X to the corresponding compound of formula Ig, giving the adduct of formula CX which is recovered by chromatography. The compound of formula CX is converted to the corresponding saturated diester of formula CXI by conventional catalytic hydrogenation and is recovered by standard chromatographic methods. Removal of the protecting group $R^7$ in the compound of formula CXI is carried out as described in Reaction Scheme 9 for the transformation of a compound of formula XXVI to the corresponding compound of formula XXVIII, and affords the corresponding hydroxy diester of formula CXII. The compound of formula CXII is converted to the compound of formula CXIII as described in Reaction Scheme 9 for the conversion of the compound of formula XXVIII to the compound of formula XXX.

Reaction Scheme 28

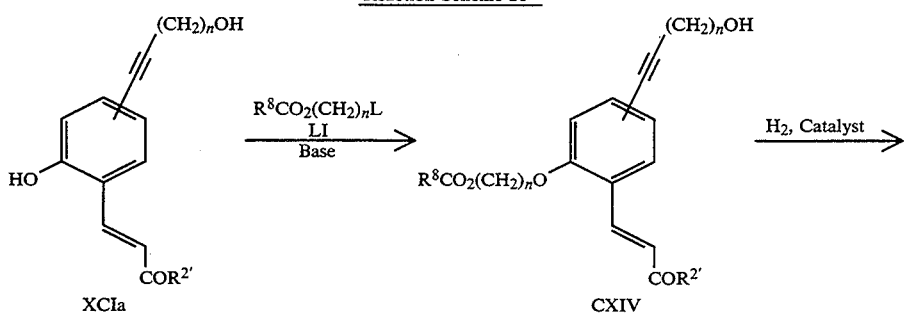

Reaction Scheme 28

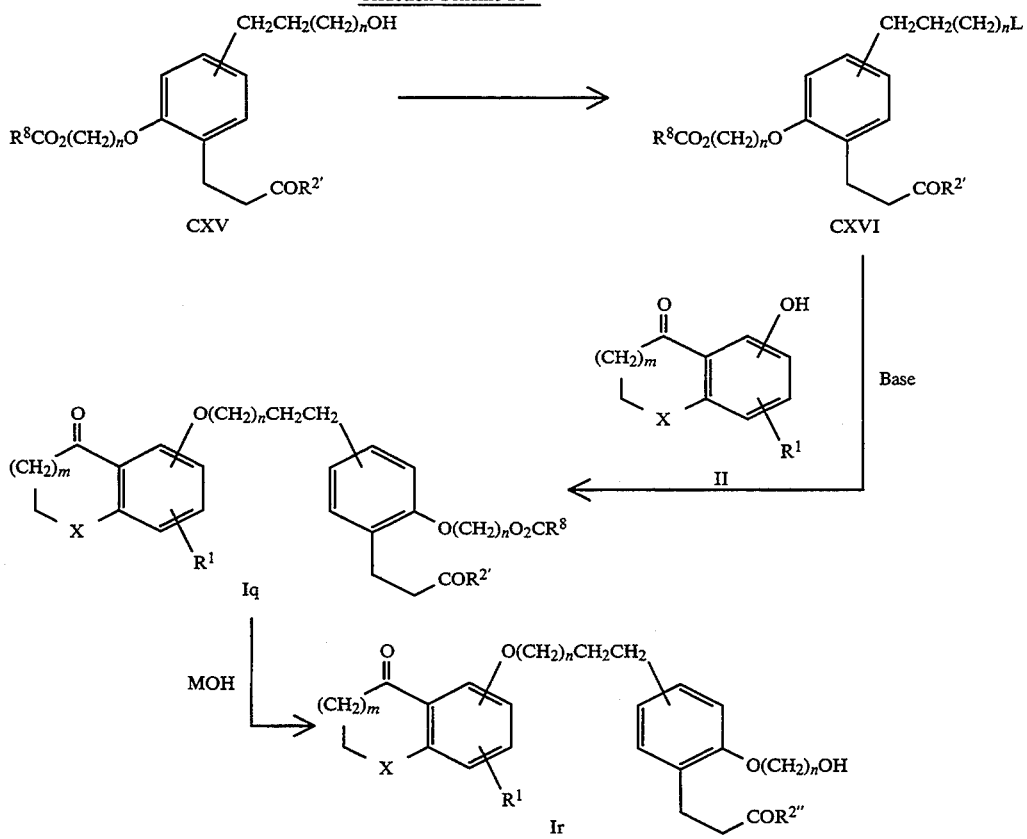

wherein $R^1$, $R^{2'}$, $R^{2''}$, $R^8$, L, M, X, m, and n are as previously described.

In Reaction Scheme 28, alkylation of a dihydroxy cinnamate of formula XCIa with the compound of formula LI gives the corresponding hydroxy diester of formula CXIV. This alkylation is carried out as described in Reaction Scheme 13 for the conversion of a compound of formula L to the corresponding compound of formula LIII. The compound of formula CXIV, which is recovered by conventional chromatography, is catalytically hydrogenated under conditions described previously, giving the corresponding saturated compound of formula CXV. The compound of formula CXV is converted to the compound of formula CXVI as described in Reaction Scheme 9 for the conversion of a compound of formula XXVIII to the corresponding compound of formula XXX. Alkylation of a compound of formula II with a corresponding compound of formula CXVI using conditions described in Reaction Scheme 1, gives the product diester of formula Iq which is recovered by conventional chromatography. Saponification of the compound of formula Iq using conditions described in Reaction Scheme 1, gives the corresponding hydroxy acid product of formula Ir which is recovered by conventional recrystallization or chromatography.

Reaction Scheme 29

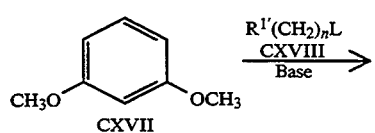

-continued
Reaction Scheme 29

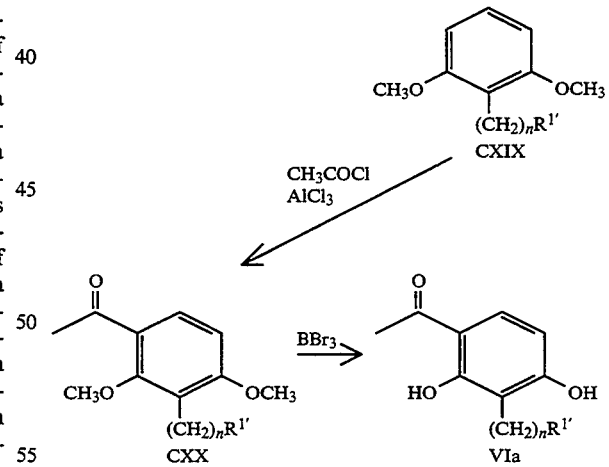

wherein $R^{1'}$ is hydrogen, lower alkenyl, cycloalkyl, or aryl, and L and n are as previously described.

In Reaction Scheme 29, 1,3-dimethoxybenzene, a known compound of formula CXVII, is converted into the product of formula CXIX by first treatment with a strong base followed by an alkylating agent of formula CXVIII which represents known compounds. It is preferred that the base used in this alkylation be an organolithium species such as methyllithium, phenyllithium, n-butyllithium and the like and that the alkylation be carried out in an inert ether solvent. It is particularly preferred that the alkylation be carried out using n-butyllithium in tetrahydrofuran, at a temperature of from −20° C. to room temperature. The product of formula CXIX is recovered by conventional chromatography.

Acetylation of the compound of formula CXIX is carried out under standard Friedel-Crafts conditions such as those described in Reaction Schemes 19 and 23, giving the corresponding acetophenone product of formula CXX which is recovered by chromatography. Treatment of the compound of formula CXX under standard demethylation conditions, such as using boron tribromide in dichloromethane solution, at from −50° C. to room temperature, gives the corresponding dihydroxyacetophenone product of formula VIa which is recovered by conventional chromatography or recrystallization.

The compound of formula CXXI is recovered by conventional chromatography.

Under similar reaction conditions, catalytic hydrogenation-hydrogenolysis of a compound of formula XXXIVa (Reaction Scheme 10) gives the corresponding compound of formula XXXVa. In this case, the olefinic function present in the starting compound is also reduced.

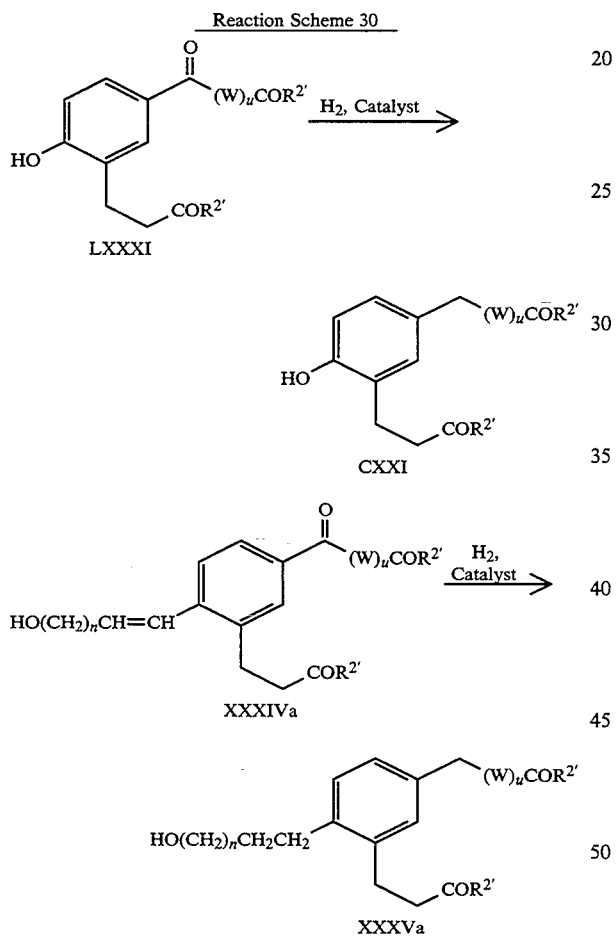

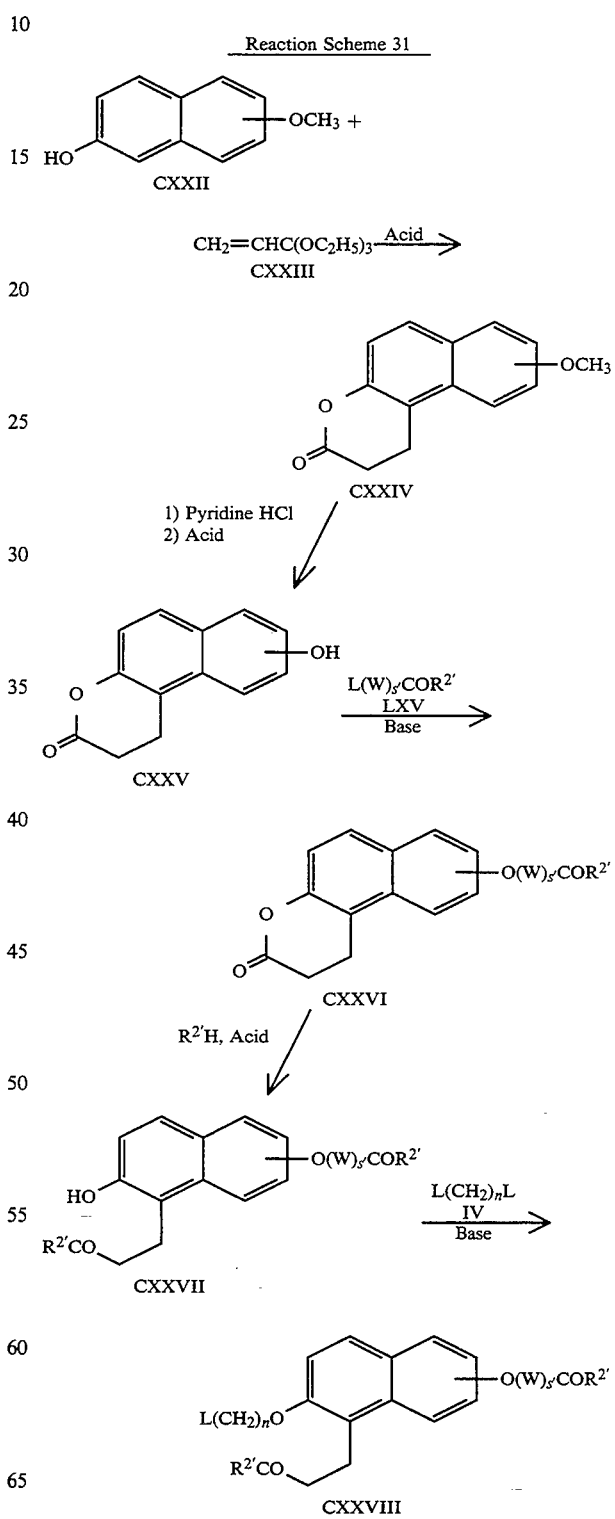

wherein $R^{2'}$, W, n, and u are as previously described.

In Reaction Scheme 30, a compound of formula LXXXI from Reaction Scheme 19, is catalytically hydrogenated to give the corresponding compound of formula CXXI. This reduction is carried out under standard conditions for effecting the hydrogenolytic removal of aromatic carbonyl groups such as reduction over a noble metal catalyst. It is preferred that this reduction be carried out using palladium on carbon as the catalyst. This hydrogenation can be carried out in conventional solvents such as ethanol, ethyl acetate, or acetic acid. It is preferred that this hydrogenation be carried out in acetic acid, under a hydrogen pressure of from 14 to 50 psi, and at room temperature to 50° C.

wherein L, W, $R^{2'}$, n, and s' are as previously described.

In Reaction Scheme 31, a methoxynaphthalenol of formula CXXII which represents known compounds, is allowed to react with triethyl orthoacrylate represented by formula CXXIII, also a known compound, in the presence of an acid catalyst, to effect a Claisen rearrangement. It is preferred that a carboxylic acid be used as the catalyst in this transformation. It is most preferred that the acid catalyst be trimethylacetic acid. This reaction can be carried out in an inert solvent such as an aromatic hydrocarbon at a temperature in the range of 100°–150° C. It is preferred that this reaction be carried out in refluxing toluene. The initial product of this reaction is an ortho ester which is not recovered but, rather, directly treated with dilute acid to give a mixture of the lactone product of formula CXXIV and the corresponding open hydroxy ethyl ester. This mixture upon exposure to a strong acid, preferably para-toluenesulfonic acid, gives pure lactone CXXIV which is recovered by conventional chromatography or recrystallization. The compound of formula CXXIV is demethylated under standard conditions for effecting such a dealkylation, preferably, by fusion with pyridine hydrochloride. It is preferred that this demethylation be carried out at a temperature in the range of 200°–250° C. Since these demethylation conditions also cause cleavage of the lactone ring, the crude product is treated with a strong acid in order to recyclize the isolated hydroxy acid. It is preferred that this cyclization be carried out by treatment of the demethylation product with para-toluenesulfonic acid in refluxing toluene. The product of formula CXXV is recovered by conventional chromatography or recrystallization.

Alkylation of the compound of formula CXXV with the compound of formula LXV is carried out as described in Reaction Scheme 16 for the conversion of a compound of formula LXIV to the corresponding compound of formula LXVI, giving the product of formula CXXVI, which is recovered by conventional chromatography.

The compound of formula CXXVI is converted to the corresponding compound of formula CXXVII as described in Reaction Scheme 16 for the conversion of a compound of formula LXVI to the corresponding compound of formula LXVII. The compound of formula CXXVII is recovered by conventional chromatography and is converted to the compound of formula CXXVIII as described in Reaction Scheme 16 for the conversion of the compound of formula LXVII to the compound of formula LXIXa. The compound of formula CXXVIII is recovered by conventional chromatography.

Reaction Scheme 32

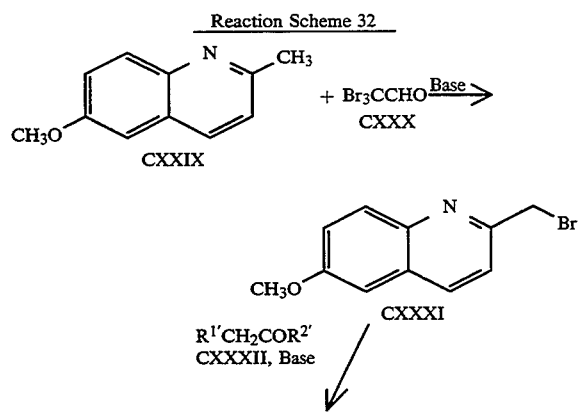

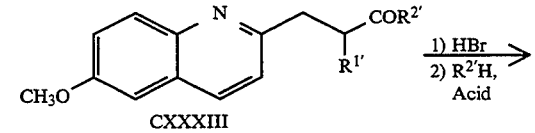

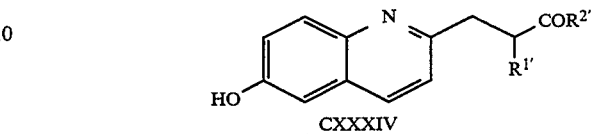

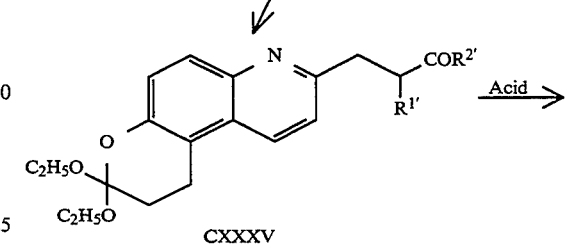

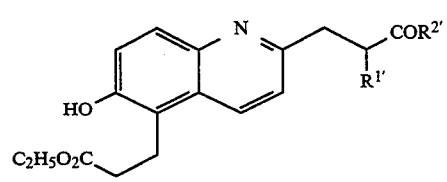

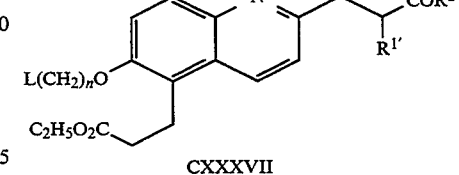

wherein $R^{1'}$, $R^{2'}$, L, and n are as previously described.

In Reaction Scheme 32, 6-methoxy-2-methylquinoline, the compound of formula CXXIX, a known compound, is allowed to react with tribromoacetaldehyde, the compound of formula CXXX, also a known compound, in the presence of a base catalyst, to give the product of formula CXXXI. It is preferred that the catalyst in this reaction be an amine base, specifically, pyridine, and that the reaction be carried out in a polar, aprotic solvent preferably N,N-dimethylformamide, at a temperature in the range of 50°–100° C. The compound of formula CXXXI is recovered by conventional chromatography or recrystallization, and is converted to a compound of formula CXXXIII by alkylation of the enolate derived from a known ester of the formula CXXXII. The required enolate is generated by treatment of the ester CXXXII with a strong base. It is preferred that this base be the alkali metal salt of a di-lower alkyl amine, specifically, lithium diisopropylamide. The alkylation reaction is carried out in an inert solvent, preferably tetrahydrofuran, at a temperature in the range of from −78° to 25° C. The product of formula CXXXIII is recovered by conventional chromatography, and is demethylated by treatment with a strong acid, preferably 48% aqueous hydrobromic acid, at reflux.

Since these conditions also induce ester hydrolysis, the crude demethylation product is reesterified by treatment with an alcohol, $R^2H$, in the presence of an acid catalyst, preferably acetyl chloride, giving the corresponding phenol product CXXXIV which is recovered by conventional chromatography or recrystallization. The compound of formula CXXXIV is allowed to react with triethyl orthoacrylate, the compound of formula CXXIII, using the procedure described in Reaction Scheme 31 for the conversion of a compound of formula CXXII to the compound of formula CXXIV. In this case, however, the ortho ester of formula CXXXV rather than the corresponding lactone is recovered. A compound of formula CXXXV is converted to the corresponding compound of formula CXXXVI by treatment with a strong acid, preferably para-toluenesulfonic acid, in a mixture of water and an organic solvent, preferably diethyl ether, at room temperature. The compound of formula CXXXVI is recovered by conventional chromatography and is converted to the compound of formula CXXXVII as described in Reaction Scheme 16 for the conversion of a compound of formula LXVII to the corresponding compound of formula LXIXa. Compound CXXXVII is recovered by conventional chromatography.

The invention also relates to salts of the compounds of formula I when they contain an acidic functionally which lends itself to salt formation with a base. Salts of compounds of formula I which have a carboxy group are prepared by the reaction with a base having a non-toxic, pharmacologically acceptable cation. In general, any base which will form a salt with a carboxylic acid and whose pharmacological properties will not cause an adverse physiological effect is within the scope of this invention.

Suitable bases thus include, for example, the alkali metal and alkaline earth metal hydroxides, carbonates or the like, for example, calcium hydroxide, sodium hydroxide, sodium carbonate, potassium carbonate or the like, ammonia, primary, secondary and tertiary amines, such as, monoalkylamines, dialkylamines, trialkylamines, for example, methylamine, diethylamine, diethylamine or the like, nitrogen containing heterocyclic amines, for example, piperidine or the like. A salt thus produced is the functional equivalent of the corresponding compound of formula I wherein $R^2$ is hydroxy and one skilled in the art will appreciate that the variety of salts embraced by the invention is limited only by the criterion that a base employed in forming the corresponding salts be both non-toxic and physiologically acceptable.

The useful activity of the compounds of formula I as leukotriene $B_4$ antagonists can be demonstrated as hereinafter set forth.

METHODOLOGY

LTB$_4$ Receptor Binding Assay

Binding assays can be performed in microtiter wells. Isolated human neutrophils in Gey's salt solution are incubated on ice for 45 minutes with 0.5 nM $^3$H-LTB$_4$ in the presence or absence of test compounds. Assays are terminated by adding 12 ml ice cold 50 mM Tris (pH 7.4) followed by rapid filtration under vacuum through GF/C filters. Radioactivity is determined by scintillation counting. Non specific binding is defined as the binding not displaced by 100 fold excess of unlabelled LTB$_4$. Specific binding is defined as the difference between total binding and non-specific binding. Non linear analysis of the binding data is performed using LIGAND (Munson and Rodbard, 1980). $K_i$ (Inhibition Constant) values were determined using the Cheng-Prusoff relationship (Cheng and Prusoff, 1973).

When representative compounds of formula I of the invention were tested, the results as set forth in Table I and expressed as inhibition of $^3$H-LTB$_4$ binding were obtained.

TABLE I

| EXAMPLE | TEST COMPOUND | HUMAN NEUTROPHIL CELLS (Ki, nM) |
|---|---|---|
| 4 | 2-[5-[(3,4-Dihydro-4-oxo-8-propyl-2H-1-benzopyran-7-yl)oxy]pentyloxy]benzenepropanoic Acid | 29 |
| 8 | 2-[5-[(3,4-Dihydro-4-oxo-8-propyl-2H-1-benzopyran-7-yl)oxy]pentyl]benzenepropanoic Acid | 63 |
| 10 | 2-[[5-(5-Oxo-1-propyl-5,6,7,8-tetrahydro-2-naphthalenyl)oxy]pentyloxy]benzenepropanoic Acid | 78 |
| 11 | rac.-6-Acetyl-7-[5-[(3,4-dihydro-4-oxo-8-propyl-2H-1-benzopyran-7-yl)oxy]pentyloxy]-3,4-dihydro-2H-1-benzopyran-2-carboxylic Acid | 105 |
| 13 | [2-[5-[(3,4-Dihydro-oxo-8-propyl-2H-1-benzopyran-7-yl)oxy]pentyloxy]phenoxy]acetic Acid | 70 |
| 17 | 5-Chloro-2-[5-[(3,4-dihydro-4-oxo-8-propyl-2H-1-benzopyran-7-yl)oxy]pentyloxy]benzenepropanoic Acid | 36 |
| 19 | 7-[5-[(3,4-Dihydro-4-oxo-8-propyl-2H-1-benzopyran-7-yl)oxy]pentyloxy]-2-benzofurancarboxylic Acid | 250 |
| 20 | 5-[(3-Carboxyphenyl)carbonyl]-2-[5-[(3,4-dihydro-4-oxo-8-propyl-2H-1-benzopyran-7-yl)oxy]-pentyloxy]benzenepropanoic Acid | 2 |
| 22 | 5-[(3-Carboxyphenyl)carbonyl]-2-[6-[(3,4-dihydro-4-oxo-8-propyl-2H-1-benzopyran-7-yl)oxy]-hexyloxy]benzenepropanoic Acid | 3 |
| 24 | 5-[(3-Carboxyphenyl)carbonyl]-2-[4-[(3,4-dihydro-4-oxo-8-propyl-2H-1-benzopyran-7-yl)oxy]-butoxy]benzenepropanoic Acid | 15 |
| 26 | 5-[5-[(3,4-Dihydro-4-oxo-8-propyl-2H-1-benzopyran-7-yl)oxy]pentyloxy]-2-benzofurancarboxylic Acid | 270 |
| 33 | 5-Acetyl-2-[5-[(3,4-dihydro-4-oxo-8-propyl-2H-1-benzopyran-7-yl)oxy]pentyloxy]benzenepropanoic Acid | 10 |
| 37 | 2-[6-[(3,4-Dihydro-4-oxo-8-propyl-2H-1-benzopyran-7-yl)oxy]hexyl]benzenepropanoic Acid | 10 |
| 39 | 2-[3-[[(3,4-Dihydro-4-oxo-8-propyl-2H-1-benzopyran-7-yl)oxy]methyl]phenylmethoxy]-benzenepropanoic Acid | 100 |
| 40 | 2-[5-[(2,3-Dihydro-3-oxo-7-propylbenzofuran-6-yl)oxy]pentyloxy]benzenepropanoic Acid | 75 |
| 47 | 5-(3-Carboxypropoxy)-2-[5-[(3,4-dihydro-4-oxo-8-propyl-2H-1-benzopyran-7-yl)oxy]-pentyloxy]benzenepropanoic Acid | 3 |

TABLE I-continued

| EXAMPLE | TEST COMPOUND | HUMAN NEUTROPHIL CELLS (Ki, nM) |
|---|---|---|
| 54 | 5-(3-Carboxypropoxy)-2-[6-[(3,4-dihydro-4-oxo-8-propyl-2H-1-benzopyran-7-yl)oxy]hexyl]-benzenepropanoic Acid | 1 |
| 58 | 5-(4-Carboxybutoxy)-2-[5-[(3,4-dihydro-4-oxo-8-propyl-2H-1-benzopyran-7-yl)oxy]pentyloxy]-benzenepropanoic Acid Hemihydrate | 4 |
| 62 | 6-(4-Carboxybutoxy)-2-[5-[(3,4-dihydro-4-oxo-8-propyl-2H-1-benzopyran-7-yl)oxy]pentyloxy]-benzenepropanoic Acid | 0.8 |
| 68 | 3-[5-[(3,4-Dihydro-4-oxo-8-propyl-2H-1-benzopyran-7-yl)oxy]pentyloxy]benzenepropanoic Acid | 60 |
| 73 | 2-[5-[(3,4-Dihydro-4-oxo-8-(phenylmethyl)-2H-1-benzopyran-7-yl)oxy]pentyloxy]benzenepropanoic Acid | 150 |
| 79 | 2-[5-[(5-Oxo-2-propyl-5,6,7,8-tetrahydro-1-naphthalenyl)oxy]pentyloxy]benzenepropanoic Acid | 1500 |
| 81 | 5-[(3-Carboxyphenyl)carbonyl-2-[7-[(3,4-dihydro-4-oxo-8-propyl-2H-1-benzopyran-7-yl)oxy]-heptyloxy]benzenepropanoic Acid | 3 |
| 83 | 5-[(3-Carboxyphenyl)carbonyl]-2-[8-[(3,4-dihydro-4-oxo-8-propyl-2H-1-benzopyran-7-yl)oxy]-octyloxy]benzenepropanoic Acid | 3 |
| 85 | 5-[(4-Carboxyphenyl)carbonyl]-2-[5-[(3,4-dihydro-4-oxo-8-propyl-2H-1-benzopyran-7-yl)oxy]-pentyloxy]benzenepropanoic Acid | 3 |
| 87 | 3-(2-Carboxyethyl)-4-[5-[(3,4-dihydro-oxo-8-propyl-2H-1-benzopyran-7-yl)oxy]pentyloxy]-δ-oxobenzenepentanoic Acid | 3 |
| 89 | 3-(2-Carboxyethyl)-4-[5-[(3,4-dihydro-4-oxo-8-propyl-2H-1-benzopyran-7-yl)oxy]pentyloxy]-γ-oxobenzenebutanoic Acid | 4 |
| 92 | 5-[2-(2-Carboxyphenyl)-1-oxoethyl]-2-[5-[(3,4-dihydro-4-oxo-8-propyl-2H-1-benzopyran-7-yl)oxy]-pentyloxy]benzenepropanoic Acid | 5 |
| 95 | 5-[[2-(Carboxymethyl)phenyl]carbonyl] -2-[5-[(3,4-dihydro-4-oxo-8-propyl-2H-1-benzopyran-7-yl)-oxy]pentyloxy]benzenepropanoic Acid | 8 |
| 99 | 5-[(3-Carboxyphenyl)carbonyl]-2-[6-[(3,4-dihydro-4-oxo-8-propyl-2H-1-benzopyran-7-yl)oxy]-hexyl]benzenepropanoic Acid | 1 |
| 101 | (E)-5-[(3-Carboxyphenyl)carbonyl]-2-[6-[(3,4-dihydro-4-oxo-8-propyl-2H-1-benzopyran-7-yl)oxy]-1-hexenyl]benzenepropanoic Acid | 4 |
| 106 | 2-[6-(3,4-Dihydro-4-oxo-8-propyl-2H-1-benzopyran-7-yl)hexyloxy]benzenepropanoic Acid | 20 |
| 107 | 2[6-(3,4-Dihydro-4-oxo-8-propyl-2H-1-benzopyran-7-yl)-5-hexynyloxy]benzenepropanoic Acid | 50 |
| 109 | (E)-3-[2-[5-[(3,4-Dihydro-4-oxo-8-propyl-2H-1-benzopyran-7-yl)oxy]pentyloxy]phenyl-2-propenoic Acid | 80 |
| 114 | (E)-4-[3-(2-Carboxyethenyl)-4-[6-[(3,4-dihydro-4-oxo-8-propyl-2H-1-benzopyran-7-yl)oxy]-hexyl]phenoxy]butanoic Acid | 1 |
| 118 | 2-[5-[(3,4-Dihydro-4-oxo-8-pentyl-2H-1-benzopyran-7-yl)oxy]pentyloxy]benzenepropanoic Acid | 607 |
| 126 | 2-(4-Carboxybutoxy)-6-[6-[(3,4-dihydro-4-oxo-8-propyl-2H-1-benzopyran-7-yl)oxy]hexyl]-benzenepropanoic Acid | 1.5 |
| 138 | 4-(3-Carboxypropoxy)-2-[5-[(3,4-dihydro-4-oxo-8-propyl-2H-1-benzopyran-7-yl)oxy]-pentyloxy]benzenepropanoic Acid | 88 |
| 145 | 2-[5-[(3,4-Dihydro-4-oxo-8-propyl-2H-1-benzopyran-7-yl)oxy]pentyloxy]benzenebutanoic Acid | 30 |
| 147 | 2-[5-[(3,4-Dihydro-4-oxo-8-propyl-2H-1-benzopyran-7-yl)oxy]pentyloxy]benzenepentanoic Acid | 200 |
| 152 | 2-(Carboxymethoxy)-6-[6-[(3,4-dihydro-4-oxo-8-propyl-2H-1-benzopyran-7-yl)oxy]-hexyl]benzenepropanoic Acid | 1 |
| 157 | 2-[(5-Carboxypentyl)oxy]-6-[6-[(3,4-dihydro-4-oxo-8-propyl-2H-1-benzopyran-7-yl)oxy]-hexyl]benzenepropanoic Acid | 1 |
| 163 | 4-[5-[(3,4-Dihydro-4-oxo-8-propyl-2H-1-benzopyran-7-yl)oxy]pentyloxy]-1,3-benzenedipropanoic Acid | 3 |
| 169 | 2-(2-Carboxyethyl)-3-[6-[(3,4-dihydro-4-oxo-8-propyl-2H-1-benzopyran-7-yl)oxy]-hexyl]benzenehexanoic Acid | 1 |
| 174 | 2-[(4-Carboxy-4-methylpentyl)oxy]-6-[6-[(3,4-dihydro-4-oxo-8-propyl-2H-1-benzopyran-7-yl)oxy]hexyl]benzenepropanoic Acid | 1 |
| 180 | 2-[6-[(3,4-Dihydro-4-oxo-8-propyl-2H-1-benzopyran-7-yl)oxy]hexyl]-6-[(5-hydroxy-pentyl)oxy]benzenepropanoic Acid | 1 |
| 184 | 2-[(7-Carboxyheptyl)oxy]-6-[6-[(3,4-dihydro-4-oxo-8-propyl-2H-1-benzopyran-7-yl)-oxy]hexyl]benzenepropanoic Acid | 1 |
| 188 | 2-[(8-Carboxyoctyl)oxy]-6-[6-[(3,4-dihydro-4-oxo-8-propyl-2H-1-benzopyran-7-yl)-oxy]hexyl]benzenepropanoic Acid | 3 |
| 195 | 2-[[5-[[3,4-Dihydro-4-oxo-8-(3-phenylpropyl)-2H-1-benzopyran-7-yl]oxy]-pentyl]oxy]benzenepropanoic Acid | 95 |
| 196 | 2-[6-[(3,4-Dihydro-4-oxo-8-propyl-2H-1-benzopyran-7-yl)oxy]hexyl]-6-[[5-(dimethylamino)-5-oxopentyl]oxy]-N,N-dimethylbenzenepropanamide | 200 |
| 200 | 2-[(5-Carboxypentyl)oxy]-6-[6-[[3,4-dihydro-4-oxo-8-(3-phenylpropyl)-2H-1-benzopyran-7-yl]oxy]hexyl]benzenepropanoic Acid | 1 |
| 205 | 2-(3-Carboxypropoxy)-6-[6-[(3,4-dihydro-4-oxo-8-propyl-2H-1-benzopyran-7-yl)-oxy]hexyl]benzenepropanoic Acid | 1 |
| 206 | 2-[(5-Carboxypentyl)oxy]-6-[6-[(5,6,7,8-tetrahydro-5-oxo-1-propyl-2-naphthalenyl)-oxy]hexyl]benzenepropanoic Acid | 3 |
| 211 | 3-(2-Carboxyethyl)4-[6-[(3,4-dihydro-4-oxo-8-propyl-2H-1-benzopyran-7-yl)oxy]-hexyl]-δ-oxobenzenepentanoic Acid | 0.8 |
| 215 | 3-(2-Carboxyethyl)-4-[[5-[(3,4-dihydro-4-oxo-8-propyl-2H-1-benzopyran-7-yl)oxy]-pentyl]oxy]benzenepentanoic Acid | 3 |
| 219 | 3-(2-Carboxyethyl)-4-[6-[(3,4-dihydro-4-oxo-8-propyl-2H-1-benzopyran-7-yl)oxy]-hexyl]benzenepentanoic Acid | 1 |
| 226 | 7-(Carboxymethoxy)-2-[[5-[(3,4-dihydro-4-oxo-8-propyl-2H-1-benzopyran-7-yl)oxy]-pentyl]oxy]-1-naphthalenepropanoic Acid | 1 |
| 231 | 6-(Carboxymethoxy)-2-[[5-[(3,4-dihydro-4-oxo-8-propyl-2H-1-benzopyran-7-yl)oxy]-pentyl]oxy]-1-naphthalenepropanoic Acid | 0.8 |
| 238 | 6-[[5-[(3,4-Dihydro-4-oxo-8-propyl-2H-1-benzopyran-7-yl)oxy]pentyl]oxy]- | 2 |

TABLE I-continued

| EXAMPLE | TEST COMPOUND | HUMAN NEUTROPHIL CELLS (Ki, nM) |
|---|---|---|
| | 2,5-quinolinedipropanoic Acid | |

Isolation of Intact Neutrophils

Human neutrophils are prepared from citrated or heparinized blood. The blood was diluted 1:1 with Hank's balanced salt solution (HBSS) minus calcium and magnesium and underlayed with 10 ml lymphocyte separation medium (Organon Teknika), followed by centrifugation at 500× g for 30 min., at room temperature. Supernatants are removed down to the red blood cell pellet. HBSS minus calcium and magnesium are added to give 25 ml. To this are added 25 ml 6% dextran in 0.85% NaCl. Samples are mixed and allowed to stand 20 min at room temperature. Supernatants are removed and centrifuged at 500× g for 5 min at 4° C. Pellets are resuspended with 20 ml 0.2% saline for 20 sec followed by the addition of 20 ml 1.6% saline. Samples are centrifuged at 500× g for 5 min at 4° C. The lysis is repeated and the cells (90–95% neutrophils) are resuspended at $2 \times 10^6$ cell/ml in GEY's salt solution.

Calcium Flux Assay

LTB$_4$ induced changes in intracellular calcium concentration are measured using Fura2 labelled human neutrophils. Cells at a concentration of $2-5 \times 10^6$/ml are labelled with 5 µM Fura2 for 30 minutes in Hank's balanced salt solution without calcium and magnesium. The cells are washed and resuspended at a final concentration of $1-2 \times 10^7$ cells/ml in Gey's solution. Calcium fluxes are initiated by the addition of 2.4 nM LTB$_4$. Test compounds at appropriate concentrations are added to the cells just prior to the addition of LTB$_4$. IC$_{50}$ values are determined as the concentration of compound required to give 50% inhibition of the LTB$_4$-induced calcium flux. Fluorescence measurements are made in a Perkin Elmer model LS-5B spectrofluorimeter at a temperature setting of 37° C. Calcium concentrations are determined using the ratio method (ratio of cell fluorescence to media fluorescence).

When representative compounds of formula I of the invention were tested, the results set forth in Table H and expressed as inhibition of LTB$_4$ mediated calcium fluxes in human neutrophils, were obtained.

TABLE II

| TEST COMPOUND | CALCIUM FLUX (IC$_{50}$, nM) |
|---|---|
| 2-[5-[(3,4-Dihydro-4-oxo-8-propyl-2H-1-benzopyran-7-yl)oxy]pentyloxy]benzenepropanoic Acid | 26 |
| rac.-6-Acetyl-7-[5-[(3,4-dihydro-4-oxo-8-propyl-2H-1-benzopyran-7-yl)oxy]pentyloxy]-3,4-dihydro-2H-1-benzopyran-2-carboxylic Acid | 300 |
| 5-Chloro-2-[5-[(3,4-dihydro-4-oxo-8-propyl-2H-1-benzopyran-7-yl)oxy]pentyloxy]benzenepropanoic Acid | 70 |
| 5-[(3-Carboxyphenyl)carbonyl]-2-[5-[(3,4-dihydro-4-oxo-8-propyl-2H-1-benzopyran-7-yl)oxy]pentyloxy]-benzenepropanoic Acid | 1 |
| 5-[(3-Carboxyphenyl)carbonyl]-2-[6-[(3,4-dihydro-4-oxo-8-propyl-2H-1-benzopyran-7-yl)oxy]hexyloxy]-benzenepropanoic Acid | 1 |
| 5-[(3-Carboxyphenyl)carbonyl]-2-[4-[(3,4-dihydro-4-oxo-8-propyl-2H-1-benzopyran-7-yl)oxy]butoxy]-benzenepropanoic Acid | 11 |
| 5-(3-Carboxypropoxy)-2-[6-[(3,4-dihydro-4-oxo-8-propyl-2H-1-benzopyran-7-yl)oxy]hexyl]-benzenepropanoic Acid | 2 |
| 2-(4-Carboxybutoxy)-6-[6-[(3,4-dihydro-4-oxo-8-propyl-2H-1-benzopyran-7-yl)oxy]hexyl]-benzenepropanoic Acid | 2 |
| 2-[(5-Carboxypentyl)oxy]-6-[6-[(3,4-dihydro-4-oxo-8-propyl-2H-1-benzopyran-7-yl)oxy]hexyl]-benzenepropanoic Acid | 1 |
| 2-(Carboxymethoxy)-6-[6-[(3,4-dihydro-4-oxo-8-propyl-2H-1-benzopyran-7-yl)oxy]hexyl]-benzenepropanoic Acid | 3 |
| 2-(2-Carboxyethyl)-3-[6-[(3,4-dihydro-4-oxo-8-propyl-2H-1-benzopyran-7-yl)oxy]hexyl]benzenehexanoic Acid | 1 |
| 2-[6-[(3,4-Dihydro-4-oxo-8-propyl-2H-1-benzopyran-7-yl)-oxy]hexyl]-6-[(5-hydroxypentyl)oxy]-benzenepropanoic Acid | 1 |

LTB$_4$ Induced Skin Inflammation

Skin inflammation is induced in the hairless guinea pig by the intradermal injection of 50 µl Gey's salt solution/10% DMSO containing 120 ng LTB$_4$. Injections are performed along the dorsal skin of the animals. Test compounds are administered at various times by co-injection, intravenous or oral administration. The test animals are euthanized four to six hours after the LTB$_4$ injection and uniform skin punches are prepared from the injection sites. Punches are homogenized in 0.5% hexadecyltrimethyl ammonium bromide for one minute and centrifuged for 20 minutes at 14,000× g. Leukocyte accumulation is measured by assaying for myeloperoxidase activity in a kinetic assay using dimethoxybenzidine as the substrate. Normal skin shows myeloperoxidase levels of 0.02–0.04 U/punch. Skin injected with 120 ng LTB$_4$ can show myeloperoxidase levels of 0.30–0.40 U/punch. LTB$_4$ induced leukocyte accumulation is confirmed histologically in hematoxylin/eosin stained sections. ID$_{50}$ values are determined as the dose of test compound required to give 50% inhibition of the LTB$_4$-induced skin inflammation.

5-[(3-Carboxyphenyl)carbonyl]-2-[5-[(3,4-dihydro-4-oxo-8-propyl-2H-1-benzopyran-7-yl)oxy]pentyloxy]-benzenepropanoic Acid (Example 20) gave ID$_{50}$'s of 100 ng by coinjection with LTB$_4$, 6 mg/kg by intravenous administration at the time of the intradermal LTB$_4$ injection, and 30 mg/kg by the oral route.

5-(3-Carboxypropoxy)-2-[6-[(3,4-dihydro-4-oxo-8-propyl-2H-1-benzopyran-7-yl)oxy]hexyl]benzenepropanoic Acid (Example 54) gave ID$_{50}$'s of 10 ng by coinjection with LTB$_4$ and 5 mg/kg by the oral route.

3-(2-Carboxyethyl)-4-[5-[(3,4-dihydro-4-oxo-8-propyl-2H-1-benzopyran-7-yl)oxy]pentyloxy]-δ-oxobenzenepentanoic Acid (Example 87) gave an ID$_{50}$ of 20 ng by co-injection.

6-(4-Carboxybutoxy)-2-[5-[(3,4-dihydro-4-oxo-8-propyl-2H-1-benzopyran-7-yl)oxy]pentyloxy]benzenepropanoic Acid (Example 62) gave an $ID_{50}$ of 35 ng by co-injection.

5-[(3-Carboxyphenyl)carbonyl]-2-[6-[(3,4-dihydro-4-oxo-8-propyl-2H-1-benzopyran-7-yl)oxy]hexyl]benzenepropanoic Acid (Example 99) gave an $ID_{50}$ of 20 ng by co-injection.

Guinea Pig Bronchoconstriction. In Vivo

Male guinea pigs (Hartley strain) weighing 300 to 500 g are anesthetized with urethane (2 g/kg) intraperitoneally and a polyethylene cannula is inserted into the jugular vein for drug administration. Tracheal pressure is recorded from a cannula inserted into the trachea and connected to a Gould P23ID pressure transducer. After surgical preparation of the animals, a period of time is allowed for pulmonary functions to stabilize. The test compound is administered intravenously five minutes prior to leukotriene $B_4$ administration according to the following protocol: Animals are paralyzed with succinylcholine (1.2 mg/kg i.v.) and mechanically respirated (Harvard rodent respirator) at 40 breaths/minute and 2.5 cc tidal volume. Propranolol (0.1 mg/kg) is then administered intravenously one minute prior to leukotriene $B_4$ administration. Animals are then challenged with an intermediate constrictory dose of leukotriene $B_4$ (1 μg/kg) delivered intravenously.

The change (cm $H_2O$) between pre and peak ventilatory pressure readings is averaged for five control and five drug treated animals. The percent inhibition is calculated from the formula:

$$((Control - Drug\ Treated)/Control) \times 100$$

When various drug concentrations are tested, the percent inhibition at each concentration is plotted as log concentration (abscissa) versus percent inhibition (ordinate) and the $ID_{50}$ is determined from linear regression analysis as the dose of test compound causing 50% inhibition of $LTB_4$-induced bronchoconstriction.

When representative compounds of formula I of the invention were utilized as the test compounds the following results were obtained:

TABLE III

| EXAMPLE | NAME | $ID_{50}$ (mg/kg), i.v. | $ID_{50}$ (mg/kg), p.o. |
|---|---|---|---|
| 4 | 2-[5-[(3,4-Dihydro-4-oxo-8-propyl-2H-1-benzopyran-7-yl)oxy]pentyloxy]-benzenepropanoic Acid | 0.66 | >10 |
| 10 | 2-[[5-(5-Oxo-1-propyl-5,6,7,8-tetrahydro-2-naphthalenyl)oxy]-pentyloxy]benzenepropanoic Acid | 2.08 | |
| 13 | [2-[5-[(3,4-Dihydro-4-oxo-8-propyl-2H-1-benzopyran-7-yl)oxy]-pentyloxy]phenoxy]acetic Acid | 1.85 | |
| 17 | 5-Chloro-2-[5-[(3,4-dihydro-4-oxo-8-propyl-2H-1-benzopyran-7-yl)-oxy]pentyloxy]benzenepropanoic Acid | 2.02 | |
| 20 | 5-[(3-Carboxyphenyl)carbonyl]-2-[5-[(3,4-dihydro-4-oxo-8-propyl-2H-1-benzopyran-7-yl)oxy]pentyloxy]-benzenepropanoic Acid | 1.46 | |
| 33 | 5-Acetyl-2-[5-[(3,4-dihydro-4-oxo-8-propyl-2H-1-benzopyran-7-yl)-oxy]pentyloxy]benzenepropanoic Acid | 1.80 | |
| 37 | 2-[6-[(3,4-Dihydro-4-oxo-8-propyl-2H-1-benzopyran-7-yl)oxy]hexyl]-benzenepropanoic Acid | 0.45 | >10 |
| 39 | 2-[3-[[(3,4-Dihydro-4-oxo-8-propyl-2H-1-benzopyran-7-yl)oxy]methyl]-phenylmethoxy]benzenepropanoic Acid | 5.40 | |

TABLE III-continued

| EXAMPLE | NAME | $ID_{50}$ (mg/kg), i.v. | $ID_{50}$ (mg/kg), p.o. |
|---|---|---|---|
| 47 | 5-(3-Carboxypropoxy)-2-[5-[(3,4-dihydro-4-oxo-8-propyl-2H-1-benzopyran-7-yl)oxy]pentyloxy]-benzenepropanoic Acid | 3.66 | |
| 54 | 5-(3-Carboxypropoxy)-2-[6-[(3,4-dihydro-4-oxo-8-propyl-2H-1-benzopyran-7-yl)oxy]hexyl]-benzenepropanoic Acid | 0.01 | 8.70 |
| 58 | 5-(4-Carboxybutoxy)-2-[5-[(3,4-dihydro-4-oxo-8-propyl-2H-1-benzopyran-7-yl)oxy]pentyloxy]-benzenepropanoic Acid Hemihydrate | 5.09 | |
| 62 | 6-(4-Carboxybutoxy)-2-[5-[(3,4-dihydro-4-oxo-8-propyl-2H-1-benzopyran-7-yl)oxy]pentyloxy]-benzenepropanoic Acid | 2.06 | |
| 68 | 3-[5-[(3,4-Dihydro-4-oxo-8-propyl-2H-1-benzopyran-7-yl)oxy]pentyloxy]-benzenepropanoic Acid | 3.56 | |
| 73 | 2-[5-[[3,4-Dihydro-4-oxo-8-(phenylmethyl)-2H-1-benzopyran-7-yl]-oxy]pentyloxy]benzenepropanoic Acid | 0.13 | >10 |
| 85 | 5-[(4-Carboxyphenyl)carbonyl]-2-[5-[(3,4-dihydro-4-oxo-8-propyl-2H-1-benzopyran-7-yl)oxy]pentyloxy]-benzenepropanoic Acid | 6.23 | |
| 87 | 3-(2-Carboxyethyl)-4-[5-[(3,4-dihydro-4-oxo-8-propyl-2H-1-benzopyran-7-yl)oxy]pentyloxy]-δ-oxobenzenepentanoic Acid | 4.41 | >10 |
| 89 | 3-(2-Carboxyethyl)-4-[5-[(3,4-dihydro-4-oxo-8-propyl-2H-1-benzopyran-7-yl)oxy]pentyloxy]-γ-oxobenzenebutanoic Acid | 4.33 | |
| 118 | 2-[5-[(3,4-Dihydro-4-oxo-8-pentyl-2H-1-benzopyran-7-yl)oxy]pentyloxy]-benzenepropanoic Acid | 0.18 | >10 |
| 126 | 2-(4-Carboxybutoxy)-6-[6-[(3,4-dihydro-4-oxo-8-propyl-2H-1-benzopyran-7-yl)oxy]hexyl]-benzenepropanoic Acid | 0.12 | 0.54 |
| 145 | 2-[5-[(3,4-Dihydro-4-oxo-8-propyl-2H-1-benzopyran-7-yl)oxy]pentyloxy]-benzenebutanoic Acid | 0.56 | >10 |
| 147 | 2-[5-[(3,4-Dihydro-4-oxo-8-propyl-2H-1-benzopyran-7-yl)oxy]pentyloxy]-benzenepentanoic Acid | 1.18 | |
| 152 | 2-(Carboxymethoxy)-6-[6-[(3,4-dihydro-4-oxo-8-propyl-2H-1-benzopyran-7-yl)oxy]hexyl]-benzenepropanoic Acid | 2.00 | |
| 157 | 2-[(5-Carboxypentyl)oxy]-6-[6-[(3,4-dihydro-4-oxo-8-propyl-2H-1-benzopyran-7-yl)oxy]hexyl]-benzenepropanoic Acid | 0.07 | 0.27 |
| 163 | 4-[5-[(3,4-Dihydro-4-oxo-8-propyl-2H-1-benzopyran-7-yl)oxy]pentyloxy]-1,3-benzenedipropanoic Acid | 3.11 | |
| 169 | 2-(2-Carboxyethyl)-3-[6-[(3,4-dihydro-4-oxo-8-propyl-2H-1-benzopyran-7-yl)oxy]hexyl]-benzenehexanoic Acid | 0.13 | 4.40 |
| 174 | 2-[(4-Carboxy-4-methylpentyl)oxy]-6-[6-[(3,4-dihydro-4-oxo-8-propyl-2H-1-benzopyran-7-yl)oxy]hexyl]-benzenepropanoic Acid | 0.22 | 1.10 |
| 180 | 2-[6-[(3,4-Dihydro-4-oxo-8-propyl-2H-1-benzopyran-7-yl)oxy]hexyl]-6-[(5-hydroxypentyl)oxy]-benzenepropanoic Acid | 0.14 | 4.80 |
| 184 | 2-[(7-Carboxyheptyl)oxy]-6-[6-[(3,4-dihydro-4-oxo-8-propyl-2H-1-benzopyran-7-yl)oxy]hexyl]-benzenepropanoic Acid | 0.17 | |
| 188 | 2-[(8-Carboxyoctyl)oxy]-6-[6-[(3,4-dihydro-4-oxo-8-propyl-2H-1-benzopyran-7-yl)oxy]hexyl]-benzenepropanoic Acid | 0.90 | |
| 195 | 2-[[5-[[3,4-Dihydro-4-oxo-8-(3- | 0.04 | 5.80 |

TABLE III-continued

| EX-AM-PLE | NAME | ID$_{50}$ (mg/kg), i.v. | ID$_{50}$ (mg/kg), p.o. |
|---|---|---|---|
| | phenylpropyl)-2H-1-benzopyran-7-yl]oxy]pentyl]oxy]-benzenepropanoic Acid | | |
| 196 | 2-[6-[(3,4-Dihydro-4-oxo-8-propyl-2H-1-benzopyran-7-yl)oxy]hexyl]-6-[[5-(dimethylamino)-5-oxopentyl]oxy]-N,N-dimethylbenzenepropanamide | 0.62 | |
| 200 | 2-[(5-Carboxypentyl)oxy]-6-[6-[[3,4-dihydro-4-oxo-8-(3-phenylpropyl)-2H-1-benzopyran-7-yl]oxy]-hexyl]benzenepropanoic Acid | 0.06 | 0.16 |
| 205 | 2-(3-Carboxypropoxy)-6-[6-[(3,4-dihydro-4-oxo-8-propyl-2H-1-benzopyran-7-yl)oxy]hexyl]-benzenepropanoic Acid | 0.26 | |
| 206 | 2-[(5-Carboxypentyl)oxy]-6-[6-[(5,6,7,8-tetrahydro-5-oxo-1-propyl-2-naphthalenyl)-oxy]hexyl]benzenepropanoic Acid | 0.12 | |
| 211 | 3-(2-Carboxyethyl)-4-[6-[(3,4-dihydro-4-oxo-8-propyl-2H-1-benzopyran-7-yl)oxy]hexyl]-δ-oxobenzenepentanoic Acid | 2.39 | |
| 215 | 3-(2-Carboxyethyl)-4-[[5-[(3,4-dihydro-4-oxo-8-propyl-2H-1-benzopyran-7-yl)oxy]pentyl]oxy]-benzenepentanoic Acid | 0.24 | 4.65 |
| 219 | 3-(2-Carboxyethyl)-4-[6-[(3,4-dihydro-4-oxo-8-propyl-2H-1-benzopyran-7-yl)oxy]hexyl]-benzenepentanoic Acid | 0.08 | >10 |
| 226 | 7-(Carboxymethoxy)-2-[[5-[(3,4-dihydro-4-oxo-8-propyl-2H-1-benzopyran-7-yl)oxy]-pentyl]oxy]-1-naphthalenepropanoic Acid | 4.40 | |
| 231 | 6-(Carboxymethoxy)-2-[[5-[(3,4-dihydro-4-oxo-8-propyl-2H-1-benzopyran-7-yl)oxy]pentyl]-oxy]-1-naphthalenepropanoic Acid | 1.36 | |
| 238 | 6-[[5-[(3,4-Dihydro-4-oxo-8-propyl-2H-1-benzopyran-7-yl)oxy]-pentyl]oxy]-2,5-quinoline-dipropanoic Acid | 1.24 | |

Acetic acid colitis

Male Wistar rats, weighing 175–225 g, are pretreated with test compound at 10 mg/kg, twice daily for 3 days (72 hours) prior to the evaluation of colitis. Colitis is induced after 2 days (48 hours) with an enema of 2 ml of 3.5% acetic acid; the acetic acid is neutralized after 10 seconds by 3 ml of phosphate-buffered saline, pH 7.4. After 3 days (72 hours), animals are sacrificed and myeloperoxidase activity in mucosal scrapings is determined as described in the skin inflammation model. Myeloperoxidase levels are presented as Units/gm mucosa.

Results obtained in this test are set forth below.

Acetic Acid 46.8+/−7.4 N=10
control 6.8+/−0.9 N=10

5-(3-Carboxypropoxy)-2-[6-[(3,4-dihydro-4-oxo-8-propyl-2H-1-benzopyran-7-yl)oxy]hexyl]benzenepropanoic Acid (Example 54)

19.5+/=3.9$N$=10 (68% inhibition).

References

Cheng, Y. and Prusoff, W. H. (1973) Relationship between the inhibition constant (K$_i$) and the concentration of inhibitor which causes 50% inhibition (I$_{50}$) of an enzymatic reaction, Biochem. Pharmacol., 22, 3099–3108.

Munson, P. J. and Rodbard, D. (1980) LIGAND: A versatile computerized approach for the characterization of ligand binding systems, Anal. Biochem., 107,220–239.

In the practice of the invention, the dose of a compound of formula I or a salt thereof to be administered and the frequency of administration will be dependent on the potency and duration of activity of the particular compound of formula I or salt to be administered and on the route of administration, as well as the severity and nature of the condition and age of the mammal to be treated and the like. Oral doses of a compound of formula I or a salt thereof contemplated for use in practicing the invention can be in the range of from 2 mg to about 2 g per day, preferably about 2 mg to about 1 gm per day, either as a single dose or in divided doses.

The examples which follow further illustrate the invention.

A compound of formula I, or a salt or a composition containing a therapeutically effective amount of a compound of formula I, an enantiomer or a racemate or a salt thereof can be administered by methods well known in the art. Thus, a compound of formula I, or a salt thereof can be administered either singly or with other pharmaceutical agents, for example, antihistamines, mediator release inhibitors, methyl xanthines, beta agonists or antiasthmatic steroids such as prednisone and prednisolone, orally, parenterally, rectally, or by inhalation, for example in the form of an aerosol, micropulverized powder or nebulized solution. For oral administration they can be administered in the form of tablets, capsules, for example, in admixture with talc, starch, milk sugar or other inert ingredients, that is, pharmaceutically acceptable carriers, or in the form of aqueous solutions, suspensions, elixirs or aqueous alcoholic solutions, for example, in admixture with sugar or other sweetening agents, flavoring agents, colorants, thickeners and other conventional pharmaceutical excipients. For parenteral administration, they can be administered as solutions or suspension, for example, as an aqueous or peanut oil solution or suspension using excipients and carriers conventional for this mode of administration. For administration as aerosols, they can be dissolved in a suitable pharmaceutically acceptable solvent, for example, ethyl alcohol or combinations of miscible solvents, and mixed with a pharmaceutically acceptable propellant. Such aerosol compositions are packaged for use in pressurized container fitted with an aerosol valve suitable for release of the pressurized composition. Preferably, the aerosol valve is a metered valve, that is one which on activation releases a predetermined effective dose of the aerosol composition.

It is to be understood that formula I as used herein, includes geometric isomers when Y and/or Z are —CH=CH—. The geometric isomers can be separated into the respective E- and Z-isomers utilizing known procedures as further examplified herein.

Furthermore, since compounds of formula I of the invention may possess an asymmetric carbon atom, they are ordinarily obtained as racemic mixtures. It is to be understood the enantiomers and diastereomers also form part of this invention. The resolution of such racemates into the optically active isomers can be carried out by known procedures. Some racemic mixtures can be precipitated as eutectics and can thereafter be separated. Chemical resolution is, however, preferred. By this method, diastereomers are formed from the racemic mixture of a compound of formula I, with an optically active resolving agent. The formed diastereomers are separated by selective crystallization or chromatography and converted to the corresponding optical isomer. Thus, the invention covers the racemates of the compounds of formula I as well as their optically active isomers (enantiomers).

In the following examples, the "usual work-up" procedure involves three extractions with the specified solvent. The organic extracts were combined, washed with water and saturated brine, dried over anhydrous magnesium sulfate, filtered, and concentrated under water aspirator pressure. The residue was dried to constant weight at 45° C./high vacuum. All reactions except hydrogenations were carried out under an inert atmosphere of nitrogen or argon.

EXAMPLE 1

Preparation of
7-(Phenylmethoxy)-8-propyl-4H-1-benzopyran-4-one

A mixture of 3.09 g (10.88 mmol) of 1-[2-hydroxy-4-(phenylmethoxy)-3-propylphenyl]ethanone, 1.55 g (13 mmol) of dimethylformamide dimethyl acetal, and 2.7 mL of xylene was stirred and heated in a 120°–130° C. oil-bath as methanol was distilled out using a 3 in. Vigreux column, over a 2 hr period. The bath temperature was then raised to 150°–160° C. and the reaction mixture was stirred at this temperature for an additional 30 min. The mixture was cooled and concentrated at 60° C./high vacuum. To the viscous, red-brown, oily residue was added 2.48 g (13 mmol) of p-toluenesulfonic acid monohydrate and 25 mL of ethanol. The resulting solution was stirred and refluxed for 1.5 hr, then cooled and diluted with 100 mL of water. Work-up with ether in the usual manner gave a crude product which was purified by flash chromatography on silica gel, eluting with 1:1 hexane-ether. There was obtained 2.8 g (87.5%) of 7-(phenylmethoxy)-8-propyl-4H-1-benzopyran-4-one as a beige solid. An analytical specimen was obtained from another experiment by recrystallization from ethyl acetate-hexane, as a colorless solid, mp 87.5°–89° C.

Anal. Calcd for $C_{19}H_{18}O_3$: C, 77.53; H, 6.16. Found: C, 77.34; H, 6.06.

EXAMPLE 2

Preparation of
2,3-Dihydro-7-hydroxy-8-propyl-4H-1-benzopyran-4-one

A mixture of 3.99 g (13.57 mmol) of 7-(phenylmethoxy)-8-propyl-4H-1-benzopyran-4-one, 0.8 g of 10% palladium on carbon, and 300 mL of 1:1 methanol-ethyl acetate was stirred in an atmosphere of hydrogen. The progress of the hydrogenation was monitored by TLC. The mixture was filtered with suction through a Celite pad and the filter cake was washed with ethyl acetate. Concentration of the combined filtrate and washes in vacuo gave 2.78 g of a beige solid. Flash chromatography on silica gel, eluting with 1:1 hexane-ether afforded 1.7 g (60.8%) of 2,3-dihydro-7-hydroxy-8-propyl-4H-1-benzopyran-4-one. A sample was recrystallized from hexane-ethyl acetate giving a colorless solid, mp 126°–129° C.

Anal. Calcd for $C_{12}H_{14}O_3$: C, 69.89; H, 6.84. Found: C, 69.69; H, 6.92.

EXAMPLE 3

Preparation of
2-[(5-Bromopentyl)oxy]benzenepropanoic Acid Methyl Ester

A mixture of 3.6 g (20 mmol) of 2-hydroxybenzenepropanoic acid methyl ester, 22 mL (160 mmol) of 1,5-dibromopentane, 8.73 g (63.3 mmol) of anhydrous granular potassium carbonate, and 145 mL of acetonitrile was stirred and refluxed for 24 hr. The resulting slurry was cooled and diluted with 300 mL of ether. The solids were removed by suction filtration and the filter cake was washed well with ether. The filtrate and washes were combined and concentrated in vacuo giving 38.59 g of a brown oil which was chromatographed on 200 g of silica gel, eluting with 49:1 and 19:1 hexane-ether. The fractions containing the desired product were combined and concentrated giving 5.86 g of an oil which was dissolved in 50 mL of methanol containing 0.2 g of p-toluenesulfonic acid monohydrate. The solution was stirred at room temperature for 17 hr and refluxed for 5 hr before being cooled and concentrated in vacuo. The residue was dissolved in ether and the solution was washed with saturated sodium bicarbonate solution and worked-up in the usual manner. The oily residue was chromatographed on 100 g of silica gel. Elution with 19:1 hexane-ether afforded 4.85 g (73.7%) of 2-[(5-bromopentyl)oxy]benzenepropanoic acid methyl ester as a colorless oil.

EXAMPLE 4

Preparation of
2-[5-[(3,4-Dihydro-4-oxo-8-propyl-2H-1-benzopyran-7-yl)oxy]pentyloxy]benzenepropanoic Acid A mixture of 0.43 g (2.1 mmol) of 2,3-dihydro-7-hydroxy-8-propyl-4H-1-benzopyran-4-one, 0.66 g (2.0 mmol) of 2-[(5-bromopentyl)oxy]benzenepropanoic acid methyl ester, 1.0 g (7.25 mmol) of anhydrous granular potassium carbonate, 8.4 mL of anhydrous N,N-dimethylformamide, and 16.8 mL of acetone was stirred and refluxed for 5 hr. The resulting slurry was filtered with suction and the solids were washed well with acetone. The filtrate and washes were concentrated in vacuo and the residue was dissolved in ether and worked-up in the usual manner giving 0.9 g of a yellow oil. This material was purified first by flash chomatography on silica gel, eluting with 1:1 hexane-ether, and then by conventional chromatography on 150 g of silica gel, eluting with 9:1 toluene-ethyl acetate giving 0.63 g (69.4%) of 2-[5-[(3,4-dihydro-4-oxo-8-propyl-2H-1-benzopyran-7-yl)oxy]pentyloxy]benzenepropanoic acid methyl ester as a viscous oil. This material was dissolved in 15 mL of tetrahydrofuran and 1.4 mL of 3N aqueous lithium hydroxide was added. The mixture was stirred at room temperature for 60 hr then diluted with water and extracted twice with ether (ether extracts discarded). The aqueous, alkaline solution was acidified with 3N aqueous hydrochloric acid and worked-up with ether in the usual manner giving a viscous oil which crystallized. Recrystallization from hexane-ethyl acetate gave 0.32 g (52.4%) of 2-[5-[(3,4-dihydro-4-oxo-8-propyl-2H-1-benzopyran-7-yl)oxy]pentyloxy]benzenepropanoic acid as a colorless solid, mp 82°–85° C.

Anal. Calcd for $C_{26}H_{32}O_6$: C, 70.89; H, 7.32. Found: C, 70.65; H, 7.28.

EXAMPLE 5

Preparation of 2-(5-Hydroxy-1-pentynyl)benzaldehyde

Argon was bubbled through a stirred mixture of 11.1 g (60 mmol) of 2-bromobenzaldehyde, 6.5 g (77 mmol) of 4-pentyn-1-ol, 450 mg of anhydrous cuprous iodide, and 240 mL of dry triethylamine and 840 mg of dichlorobis(triphenylphosphine) palladium (II) was added. The mixture was heated to 90° C. and stirred at this temperature for 3 hr during which time a dense precipitate and a black color developed. The reaction mixture was cooled and poured into a mixture of ice and 3N hydrochloric acid. Extractive work-up with dichloromethane was carried out in the usual manner giving 12.7 g of a red-brown oil. This material was purified by flash chromatography on silica gel, eluting with 2:1 hexane-ethyl acetate. There was obtained 5.4 g (48%) of 2-(5-hydroxy-1-pentynyl)benzaldehyde as an oil.

EXAMPLE 6

Preparation of 2-(5-Hydroxypentyl)benzenepropanoic Acid Methyl Ester

A mixture of 2.4 g (12.7 mmol) of 2-(5-hydroxy-1-pentynyl)benzaldehyde, 5.0 g (15 mmol) of methyl (triphenylphosphoranylidene)acetate, and 200 mL of toluene was stirred and refluxed for 4 hr and then kept overnight at room temperature. The resulting solution was concentrated in vacuo. The residue (9.2 g) was combined with 9.9 g of similarly prepared crude material from a separate experiment, and flash chromatographed on silica gel, eluting with 2:1 toluene-ethyl acetate. There was obtained 4.9 g of a pale-yellow oil. This material was dissolved in 200 mL of methanol and the solution was treated with 1 g of 10% palladium on carbon. The mixture was then stirred in an atmosphere of hydrogen, at room temperature, for 5.5 hr during which time the theoretical volume of hydrogen was absorbed. The catalyst was removed by suction filtration and the filtrate was concentrated in vacuo giving 4.87 g (75.8%) of 2-(5-hydroxypentyl)benzenepropanoic acid methyl ester as a colorless oil.

EXAMPLE 7

Preparation of 2-(5-Iodopentyl)benzenepropanoic Acid Methyl Ester

A solution of 4.87 g (19.48 mmol) of 2-(5-hydroxypentyl)benzenepropanoic acid methyl ester from example 7, 4.15 mL of pyridine, and 18 mL of chloroform was stirred with ice-bath cooling as 5.07 g (26.6 mmol) of p-toluenesulfonyl chloride was added in one portion. The mixture was stirred at 0°-5° C. for 1 hr and then kept at this temperature overnight before being poured into saturated sodium bicarbonate solution. Work-up with dichloromethane in the usual manner gave a colorless oily tosylate which was treated with 4.5 g (30 mmol) of sodium iodide and 50 mL of acetone. The resulting mixture was stirred at room temperature for 2 hr, kept at 0°-5° C. overnight, and, finally, refluxed for 5 hr after the addition of 100 mL of acetone. The mixture was poured into water and worked-up with ether in the usual manner (the ether solution was additionally washed with aqueous sodium thiosulfate solution) giving a yellow oil. Flash chromatography on silica gel, eluting with 10:1 hexane-ethyl acetate afforded 5.75 g (82%) of 2-(5-iodopentyl) benzenepropanoic acid methyl ester as a colorless oil.

EXAMPLE 8

Preparation of 2-[5-[(3,4-Dihydro-4-oxo-8-propyl-2H-1-benzopyran-7-yl)oxy]pentyl]benzenepropanoic Acid Using the procedure of example 4, 2-[5-[(3,4-dihydro-4-oxo-8-propyl-2H-1-benzopyran-7-yl)oxy]pentyl]benzenepropanoic acid methyl ester was prepared, in 67.5% yield, starting from 0.35 g (1.69 mmol) of 2,3-dihydro-7-hydroxy-8-propyl-4H-1-benzopyran-4-one and 0.54 g (1.5 mmol) of 2-(5-iodopentyl)benzenepropanoic acid methyl ester. A 0.5 g (1.14 mmol) sample of this ester was treated with 20 mL of methanol and 3 mL of aqueous 1N sodium hydroxide. The mixture was stirred and refluxed for 2.5 hr and then the solvent was removed in vacuo. The residue was diluted with water, acidified, and worked-up with ether in the usual manner. The product was recrystallized from hexane-ethyl acetate giving 2-[5-[(3,4-dihydro-4-oxo-8-propyl-2H-1-benzopyran-7-yl)oxy]pentyl]benzenepropanoic acid as a colorless solid, mp 94°–96° C., in 58.2% overall yield.

Anal. Calcd for $C_{26}H_{32}O_5$: C, 73.56; H, 7.60. Found: C, 73.21; H, 7.66.

EXAMPLE 9

Preparation of 6-Hydroxy-5-propyl-1,2,3,4-tetrahydronaphthalen-1-one

A 1.78 g (8.81 mmol) sample of 6-(2-propenyloxy)-1,2,3,4-tetrahydronaphthalen-1-one was heated at 180°–195° C. for 1.5 hr and at 215° C. for 1.5 hr. The resulting dark-brown oil was cooled and dissolved in warm ethyl acetate. The warm solution was treated with Norit-A and the mixture was filtered with suction through a Celite pad. The filter cake was washed well with ethyl acetate and then the filtrate and washes were combined and concentrated under reduced pressure. The residue was dried at 45° C./high vacuum giving 1.6 g of a tan solid which by TLC and NMR analysis was a mixture of 5- and 7-allyl isomers. This material was recrystallized twice from ethyl acetate giving 0.9 g (50.5%) of the pure, desired 5-allyl isomer, mp 147°–149° C. This material was dissolved in 45 mL of ethanol and treated with 0.1 g of 10% palladium on carbon. The mixture was stirred in an atmosphere of hydrogen, at room temperature, for 25 min during which time one equivalent of hydrogen gas was absorbed. The catalyst was removed by suction filtration over Celite and the filtrate was concentrated in vacuo giving 0.9 g (ca. 100%) of 6-hydroxy-5-propyl-1,2,3,4-tetrahydronaphthalen-1-one as an off-white solid, mp 159°–160° C.

Anal. Calcd for $C_{13}H_{16}O_2$: C, 76.44; H, 7.90. Found: C, 76.13; H, 7.83.

EXAMPLE 10

Preparation of 2-[[5-(5-Oxo-1-propyl-5,6,7,8-tetrahydro-2-naphthalenyl)oxy]pentyloxy]benzenepropanoic Acid Using the procedure of example 4, 2-[[5-(5-oxo-1-propyl-5,6,7,8-tetrahydro-2-naphthalenyl)oxy]pentyloxy]benzenepropanoic acid methyl ester, an oil, was prepared in 80.7% yield starting from 0.38 g (1.86 mmol) of 6-hydroxy-5-propyl-1,2,3,4-tetrahydronaphthalen-1-one and 0.66 g (2.0 mmol) of 2-(5-bromopentyloxy)benzenepropanoic acid methyl ester. Saponification of this ester using the procedure of example 4 gave 2-[[5-(5-oxo-1-propyl-5,6,7,8-tetrahydro-2-naphthalenyl)oxy]pentyloxy]benzenepropanoic acid in 77% yield, as a colorless solid, mp 90°–92° C., after recrystallization from hexane-ethyl acetate.

Anal. Calcd for $C_{27}H_{34}O_5$: C, 73.95; H, 7.81. Found: C, 73.89; H, 7.92.

EXAMPLE 11

Preparation of rac-6-Acetyl-7-[5-[(3,4-dihydro-4-oxo-8-propyl-2H-1-benzopyran-7-yl)oxy]pentyloxy]-3,4-dihydro-2H-1-benzopyran-2-carboxylic Acid A mixture of 0.8 g (3.88 mmol) of 2,3-dihydro-7-hydroxy-8-propyl-4H-1-benzopyran-4-one, 1.6 g (3.88 mmol) of rac-6-acetyl-7-[[5-[(methylsulfonyl)oxy]pentyl]oxy]-3,4-dihydro-2H-1-benzopyran-2-carboxylic acid methyl ester, 0.78 g (5.65 mmol) of anhydrous potassium carbonate, 0.082 g of tris[2-(2-methoxyethoxy)ethyl]amine (TDA-1), and 20 mL of toluene was stirred and refluxed for 6 hr. After being cooled, the reaction mixture was diluted with ether and toluene and filtered with suction. The solids were washed with more toluene and ether and then the filtrate and washes were combined and concentrated in vacuo. The residue was dissolved in 1:1 ether-dichloromethane and washed with water and brine. Completion of the usual work-up afforded a solid residue which was purified by flash chromatography, eluting with 1:1 hexane-ethyl acetate. There was obtained 1.85 g (91%) of rac-6-acetyl-7-[5-[(3,4-dihydro-4-oxo-8-propyl-2H-1-benzopyran-7-yl)oxy]pentyloxy]-3,4-dihydro-2H-1-benzopyran-2-carboxylic acid methyl ester as a solid, mp 131°–133° C. This material was saponified using the procedure described in example 8 giving rac-6-acetyl-7-[5-[(3,4-dihydro-4-oxo-8-propyl-2H-1-benzopyran-7-yl)oxy]pentyloxy]-3,4-dihydro-2H-1-benzopyran-2-carboxylic acid as an off-white solid, mp 148°–151° C., in 38.4% yield, after recrystallization from hexane-ethyl acetate.

Anal. Calcd for $C_{29}H_{34}O_8$: C, 68.22; H, 6.71. Found: C, 67.87; H, 6.92.

EXAMPLE 12

Preparation of [2-[(5-Bromopentyl)oxy]phenoxy]acetic Acid Methyl Ester

A mixture of 2.6 g (10 mmol) of 2-[(5-bromopentyl)oxy]phenol, 1.8 g (12 mmol) of methyl bromoacetate, 4.4 g (32 mmol) of anhydrous granular potassium carbonate, and 60 mL of dry acetonitrile was stirred and refluxed for 20 hr. The mixture was cooled and filtered with suction. The solids were washed with ether and the filtrate and washes were combined and concentrated in vacuo. The oily residue was purified by flash chromatography on silica gel, eluting with 3:1 hexane-ether. There was obtained 2.2 g (66.5%) of [2-[(5-bromopentyl)oxy]phenoxy]acetic acid methyl ester as an oil.

EXAMPLE 13

Preparation of [2-[5-[(3,4-Dihydro-4-oxo-8-propyl-2H-1-benzopyran-7-yl)oxy]pentyloxy]phenoxy]acetic Acid Using the procedure of example 4, [2-[5-[(3,4-dihydro-4-oxo-8-propyl-2H-1-benzopyran-7-yl)oxy]pentyloxy]phenoxy]acetic acid was prepared in 72.3% overall yield starting from 0.31 g (1.5 mmol) of 2,3-dihydro-7-hydroxy-8-propyl-4H-1-benzopyran-4-one and 0.53 g (1.6 mmol) of [2-[(5-bromopentyl)oxy]phenoxy]acetic acid methyl ester, as a colorless solid, mp 98°–99° C., recrystallized from hexane-ethyl acetate.

Anal. Calcd for $C_{25}H_{30}O_7$: C, 67.86; H, 6.83. Found: C, 67.90; H, 6.87.

EXAMPLE 14

Preparation of 2-[(5-Bromopentyl)oxy]-5-chlorobenzaldehyde

A mixture of 7.82 g (50 mmol) of 5-chlorosalicylaldehyde, 92.1 g (0.4 mol) of 1,5-dibromopentane, 22.1 g (0.15 mol) of anhydrous granular potassium carbonate, and 360 mL of acetonitrile was stirred and refluxed for 20 hr. The resulting slurry was cooled and diluted with 300 mL of ether. The solids were removed by suction filtration and washed thoroughly with ether. The filtrate and washes were combined and concentrated under water aspirator pressure. The excess 1,5-dibromopentane was removed by distillation under high vacuum. Flash chromatography of the residue on silica gel (eluting with 4:1 hexane-ether) afforded 12.5 g (81.8%) of 2-[(5-bromopentyl)oxy]-5-chlorobenzaldehyde as a yellow oil.

EXAMPLE 15

Preparation of (E/Z)-3-[2-[(5-Bromopentyl)oxy]-5-chlorophenyl]-2-propenoic Acid Methyl Ester A mixture of 2 g (6.54 mmol) of 2-[(5-bromopentyl)oxy]-5-chlorobenzaldehyde, 2.4 g (7.17 mmol) of methyl (triphenylphosphoranylidene)acetate, and 100 mL of toluene was stirred and refluxed for 4 hr and then stirred overnight at room temperature. The mixture was filtered with suction and the filtrate was concentrated in vacuo. The oily residue was triturated with hexane leading to the formation of a slurry which was filtered with suction. The solid (triphenylphosphine oxide) was washed thoroughly with hexane. The filtrate and washes were combined and concentrated in vacuo giving 2.57 g of a yellow oil which was chromatographed on 50 g of silica gel. Elution with 9:1 hexane-ether afforded 2.02 g (85.4%) of (E/Z)-3-[2-[(5-bromopentyl)oxy]-5-chlorophenyl]-2-propenoic acid methyl ester as a colorless oil.

EXAMPLE 16

Preparation of 2-[(5-Bromopentyl)oxy]-5-chlorobenzenepropanoic Acid Methyl Ester A mixture of 2.02 g (5.59 mmol) of 3-[2-[(5-bromopentyl)oxy]-5-chlorophenyl]-2-propenoic acid methyl ester (mixture of E/Z-isomers), 90 mL of tetrahydrofuran, 190 mL of toluene, and 1.26 g of 5% rhodium on alumina was stirred at room temperature, in an atmosphere of hydrogen, until reduction was complete. The catalyst was removed by suction filtration and the filtrate was concentrated in vacuo giving 2.05 g (ca. 100%) of 2-[(5-bromopentyl)oxy]-5-chlorobenzenepropanoic acid methyl ester as a pale-yellow oil which was used without further purification.

EXAMPLE 17

Preparation of
5-Chloro-2-[5-[(3,4-dihydro-4-oxo-8-propyl-2H-1-benzopyran-7-yl)oxy]pentyloxy]benzenepropanoic Acid Using the procedure of example 4,5-chloro-2-[5-[(3,4-dihydro-4-oxo-8-propyl-2H-1-benzopyran-7-yl)oxy]pentyloxy]benzenepropanoic acid methyl ester, a pale-yellow oil, was prepared in quantitative yield starting from 0.62 g (3 mmol) of 2,3-dihydro-7-hydroxy-8-propyl-4H-1-benzopyran-4-one and 1.21 g (3.33 mmol) of 2-[(5-bromopentyl)oxy]-5-chlorobenzenepropanoic acid methyl ester. Saponification using the procedure of example 4 afforded 1.01 g (71%) of 5-chloro-2-[5-[(3,4-dihydro-4-oxo-8-propyl-2H-1-benzopyran-7-yl)oxy]pentyloxy]benzenepropanoic acid as a colorless solid, mp 101°–103° C.

Anal. Calcd for $C_{26}H_{31}ClO_6$: C, 65.75; H, 6.58; Cl, 7.46. Found: C, 65.91; H, 6.61; Cl, 7.44.

EXAMPLE 18

Preparation of
7-[(5-Bromopentyl)oxy]-2,3-dihydro-8-propyl-4H-1-benzopyran-4-one A mixture of 0.413 g (2.00 mmol) of 2,3-dihydro-7-hydroxy-8-propyl-4H-1-benzopyran-4-one, 3.0 g (13.05 mmol) of 1,5-dibromopentane, 1.4 g (10.13 mmol) of anhydrous granular potassium carbonate and 31 mL of 2-butanone was stirred and refluxed for 18 hr. The resulting slurry was filtered with suction and the solids were washed thoroughly with ethyl acetate. The filtrate and washes were combined and concentrated in vacuo and the residue was purified by flash chromatography on 75 g of silica gel, eluting with 4:1 hexane-ethyl acetate giving 0.627 g (88%) of the title compound as a white solid, mp 47°–48° C.

Anal. Calcd for $C_{17}H_{23}BrO_3$: C, 57.47; H, 6.53; Br, 22.49. Found: C, 57.24; H, 6.49; Br, 22.69.

EXAMPLE 19

Preparation of
7-[5-[(3,4-Dihydro-4-oxo-8-propyl-2H-1-benzopyran-7-yl)oxy]pentyloxy]-2-benzofurancarboxylic Acid A mixture of 0.556 g (1.57 mmol) of 7-[(5-bromopentyl)oxy]-2,3-dihydro-8-propyl-4H-1-benzopyran-4-one, 0.323 g (1.57 mmol) of 7-hydroxy-2-benzofurancarboxylic acid ethyl ester, 0.866 g (6.26 mmol) of anhydrous granular potassium carbonate and 16 mL of 2-butanone was stirred and refluxed for 16.5 hrs. The resulting slurry was filtered with suction and the solids were washed thoroughly with ethyl acetate. The filtrate and washes were combined and concentrated in vacuo and the residue was purified by flash chromatography on 70 g of silica gel, eluting with 4:1 hexane-ethyl acetate giving 0.527 g (70%) of 7-[5-[(3,4-dihydro-4-oxo-8-propyl-2H-1-benzopyran-7-yl)oxy]pentyloxy]-2-benzofurancarboxylic acid ethyl ester as a white solid, mp 79.5°–81° C. A mixture of 0.262 g (0.55 mmol) of this ester in 3.5 mL of THF and 3.5 mL of water was treated with 35.1 mg (0.84 mmol) of lithium hydroxide monohydrate and the mixture was stirred for 17.5 hr. After being acidified with 16 mL of 3N aqueous sulfuric acid, the resulting mixture was worked-up with ether and ethyl acetate in the usual manner. The crude product was recrystallized from hexane-ethyl acetate to give 0.185 g (74.9%) of the title compound as a white solid, mp 152°–153.5° C.

Anal. Calcd for $C_{26}H_{28}O_7$: C, 69.01; H, 6.24. Found: C, 68.84; H, 6.39.

EXAMPLE 20

Preparation of
5-[(3-Carboxyphenyl)carbonyl]-2-[5-[(3,4-dihydro-4-oxo-8-propyl-2H-1-benzopyran-7-yl)oxy]pentyloxy]benzenepropanoic Acid Starting with 0.275 g (0.78 mmol) of 7-[(5-bromopentyl)oxy]-2,3-dihydro-8-propyl-4H-1-benzopyran-4-one, and 0.286 g (0.77 mmol) of 5-[[3-(ethoxycarbonyl)phenyl]carbonyl]-2-hydroxybenzenepropanoic acid ethyl ester, 5-[(3-carboxyphenyl)carbonyl]-2-[5-[(3,4-dihydro-4-oxo-8-propyl-2H-1-benzopyran-7-yl)oxy]pentyloxy]benzenepropanoic acid (0.163 g; 52% overall yield) was obtained, as a white solid, mp 122°–128° C. (recrystallized from hexane-ethyl acetate), using the procedure of example 19.

Anal. Calcd for $C_{34}H_{36}O_9$: C, 69.37; H, 6.17. Found: C, 69.86; H, 6.58.

EXAMPLE 21

Preparation of
2-[(6-Bromohexyl)oxy]-5-[[3-(ethoxycarbonyl)phenyl]carbonyl]benzenepropanoic Acid Ethyl Ester A mixture of 0.393 g (1.06 mmol) of 5-[[3-(ethoxycarbonyl)phenyl]carbonyl]-2-hydroxybenzenepropanoic acid ethyl ester, 2.06 g (8.44 mmol) of 1,6-dibromohexane, 0.882 g (6.39 mmol) of anhydrous granular potassium carbonate and 15 mL of 2-butanone was stirred and refluxed for 18.5 hrs. The resulting slurry was filtered with suction and the solids were washed thoroughly with ethyl acetate. The filtrate and washes were combined and concentrated in vacuo and the residue was purified by flash chromatography on 75 g of silica gel, eluting with 5:1 hexane-ethyl acetate, giving 0.43 g (75.8%) of the title compound as a colorless oil.

Anal. Calcd for $C_{27}H_{33}BrO_6$: C, 60.79; H, 6.24; Br, 14.98. Found: C, 60.41; H, 6.27; Br, 15.30.

EXAMPLE 22

Preparation of
5-[(3-Carboxyphenyl)carbonyl]-2-[6-[(3,4-dihydro-4-oxo-8-propyl-2H-1-benzopyran-7-yl)oxy]hexyloxy]benzenepropanoic Acid A mixture of 0.144 g (0.70 mmol) of 2,3-dihydro-7-hydroxy-8-propyl-4H-1-benzopyran-4-one, 0.371 g (0.70 mmol) of 2-[(6-bromohexyl)oxy]-5-[[3-(ethoxycarbonyl)phenyl]carbonyl]benzenepropanoic acid ethyl ester, 0.479 g (3.47 mmol) of anhydrous granular potassium carbonate and 13.1 mL of 2-butanone was stirred and refluxed for 18 hr. The resulting slurry was filtered with suction and the solids washed thoroughly with ethyl acetate. The filtrate and washes were combined and concentrated in vacuo and the residue was purified by flash chromatography on 75 g of silica gel, eluting with 3:1 hexane-ethyl acetate, giving 0.37 g (80.6%) of 2-[6-[(2,3-dihydro-4-oxo-8-propyl-4H-1-benzopyran-7-yl)oxy]hexyloxy]-5-[[3-(ethoxycarbonyl)phenyl]carbonyl]benzenepropanoic acid ethyl ester as a white solid, mp 58°–59.5° C. A mixture of 0.331 g (0.50 mmol) of this ester in 6 mL of THF and 6 mL of water was treated with 64.7 mg (1.54 mmol) of lithium hydroxide monohydrate and the resulting mixture was stirred for 25.5 hr at room temperature, before being acidified with 17 mL of 3N aqueous sulfuric acid. Work-up with ethyl acetate in the usual manner gave a crude product which was recrystallized from hexane-ethyl acetate affording 0.242 g (79.7%) of the title compound as a white solid, mp 169°–172° C.

Anal. Calcd for $C_{35}H_{38}O_9$: C, 69.75; H, 6.36. Found: C, 69.57; H, 6.36.

EXAMPLE 23

Preparation of 2-(4-Bromobutoxy)-5-[[3-(ethoxycarbonyl)phenyl]carbonyl]benzenepropanoic Acid Ethyl Ester Starting with 0.388 g (1.05 mmol) of 5-[[3-(ethoxycarbonyl)phenyl]carbonyl]-2-hydroxybenzenepropanoic acid ethyl ester, and 1.81 g (8.38 mmol) of 1,4-dibromobutane, the title compound was obtained as a colorless oil, in 81.2% yield, using the procedure of example 21.

Anal. Calcd for $C_{25}H_{29}BrO_6$: C, 59.41; H, 5.78; Br, 15.81. Found: C, 59.19; H, 5.75; Br, 15.51.

EXAMPLE 24

Preparation of 5-[(3-Carboxyphenyl)carbonyl]-2-[4-[(3,4-dihydro-4-oxo-8-propyl-2H-1-benzopyran-7-yl)oxy]butoxy]benzenepropanoic Acid Starting with 0.144 g (0.70 mmol) of 2,3-dihydro-7-hydroxy-8-propyl-4H-1-benzopyran-4-one, and 0.35 g (0.69 mmol) of 2-(4-bromobutoxy)-5-[[3-(ethoxycarbonyl)phenyl]carbonyl]benzenepropanoic acid ethyl ester, the title compound (0.202 g; 63.4% overall yield) was obtained as a white solid, mp 177°–180° C. (recrystallized from hexane-ethyl acetate), using the procedure of example 22.

Anal. Calcd for $C_{33}H_{34}O_9$: C, 68.98; H, 5.96. Found: C, 68.98; H, 6.06.

EXAMPLE 25

Preparation of 5-[(5-Bromopentyl)oxy]-2-benzofurancarboxylic Acid Ethyl Ester

Starting with 2.41 g (11.69 mmol) of 5-hydroxy-2-benzofurancarboxylic acid ethyl ester, and 8.06 g (35.06 mmol) of 1,5-dibromopentane, the title compound (3.03 g; 73%) was obtained as a white solid, mp 31° C., using the procedure of example 21.

Anal. Calcd for $C_{16}H_{19}BrO_4$: C, 54.10; H, 5.39; Br, 22.50. Found: C, 54.03; H, 5.28; Br, 22.36.

EXAMPLE 26

Preparation of 5-[5-[(3,4-Dihydro-4-oxo-8-propyl-2H-1-benzopyran-7-yl)oxy]pentyloxy]-2-benzofurancarboxylic Acid Starting with 0.207 g (1.00 mmol) of 2,3-dihydro-7-hydroxy-8-propyl-4H-1-benzopyran-4-one, and 0.355 g (1.00 mmol) of 5-[(5-bromopentyl)oxy]-2-benzofurancarboxylic acid ethyl ester, there was obtained 0.093 g (20.5%) of the title compound as an off-white solid, mp 192°–195° C. (recrystallized from hexane-ethyl acetate), using the procedure of example 22.

Anal. Calcd for $C_{26}H_{28}O_7$: C, 69.01; H, 6.24. Found: C, 68.63; H, 6.25.

EXAMPLE 27

Preparation of 2-[[5-(Acetyloxy)pentyl]oxy]benzaldehyde

A mixture of 12.2 g (0.1 mol) of salicylaldehyde, 23 g (0.11 mol) of 5-bromopentyl acetate, 44.2 g (0.3 mol) of anhydrous, granular potassium carbonate, and 700 mL of acetonitrile was stirred and refluxed for 20 hr. After being cooled, the resulting mixture was filtered with suction and the solids were washed well with ether. The filtrate and washes were combined and concentrated in vacuo giving a yellow oil which was purified by flash chromatography on silica gel, eluting with 4:1 hexane-ether. There was obtained 10.9 g (43.6%) of 2-[[5-(acetyloxy)pentyl]oxy]benzaldehyde as an oil.

EXAMPLE 28

Preparation of (E/Z)-3-[2-[[5-(Acetyloxy)pentyl]oxy]phenyl]-2-propenoic Acid Methyl Ester A mixture of 3.75 g (15 mmol) of 2-[[5-(acetyloxy)pentyl]oxy]benzaldehyde, 6.02 g (18 mmol) of methyl (triphenylphosphoranylidene)acetate, and 200 mL of toluene was stirred and refluxed for 4 hr and then stirred overnight at room temperature. The solvent was removed under reduced pressure and the oily residue was flash chromatographed on silica gel, eluting with 2:1 hexane-ether. There was obtained 4.4 g (96%) of (E/Z)-3-[2-[[5-(acetyloxy)pentyl]oxy]phenyl]-2-propenoic acid methyl ester as an oil.

EXAMPLE 29

Preparation of 2-[[5-(Acetyloxy)pentyl]oxy]benzenepropanoic Acid Methyl Ester

A mixture of 4.4 g of (E/Z)3-[2-[[5-(acetyloxy)pentyl]oxy]phenyl]-2-propenoic acid methyl ester and 0.5 g of 10% palladium on carbon, in 200 mL of ethyl acetate was stirred in an atmosphere of hydrogen until hydrogen uptake ceased. The catalyst was removed by suction filtration and the filtrate was concentrated in vacuo giving 4.3 g (97%) of 2-[[5-(acetyloxy)pentyl]oxy]benzenepropanoic acid methyl ester as a colorless oil.

EXAMPLE 30

Preparation of 2-[[5-(Acetyloxy)pentyl]oxy]-5-acetylbenzenepropanoic Acid Methyl Ester A solution of 4.3 g (13.96 mmol) of 2-[[5-(acetyloxy)pentyl]oxy]benzenepropanoic acid methyl ester and 2.18 g (27.8 mmol) of freshly distilled acetyl chloride in 250 mL of dry dichloromethane was stirred with ice-bath cooling while 7.5 g (56.7 mmol) of anhydrous aluminum chloride was added in one portion. The resulting mixture was stirred at 0°–5° C. for 2 hr before being treated with ice. Work-up with dichloromethane in the usual manner gave an oil which was chromatographed on 100 g of silica gel. Elution with 1:1 hexane-ether afforded 4.22 g (86.4%) of 2-[[5-(acetyloxy)pentyl]oxy]-5-acetylbenzenepropanoic acid methyl ester as an almost colorless oil.

EXAMPLE 31

Preparation of
2-[(5-Hydroxypentyl)oxy]-5-acetylbenzenepropanoic
Acid Methyl Ester A solution of 4.22 g (12.06 mmol) of 2-[[5-(acetyloxy)pentyl]oxy]-5-acetylbenzenepropanoic acid methyl ester and 0.1 g of p-toluenesulfonic acid monohydrate in 50 mL of methanol was stirred and refluxed for 3.5 hr and stirred at room temperature for 21 hr. Most of the methanol was removed in vacuo and the residue was diluted with water and worked-up with ether in the usual manner (the combined ether extracts were additionally washed with saturated aqueous sodium bicarbonate). The product was purified by flash chromatography on silica gel, eluting with 1:2 hexane-ethyl acetate. There was obtained 3.6 g (97%) of 2-[(5-hydroxypentyl)oxy]-5-acetylbenzenepropanoic acid methyl ester as a viscous oil.

EXAMPLE 32

Preparation of
2-[[5-[(Methylsulfonyl)oxy]pentyl]oxy]-5-acetylbenzenepropanoic Acid Methyl Ester A solution of 0.62 g (2 mmol) of 2-[(5-hydroxypentyl)oxy]-5-acetylbenzenepropanoic acid methyl ester and 2 mL of triethylamine, in 6 mL of ethyl acetate was stirred with ice-bath cooling while 0.6 mL of methanesulfonyl chloride was added dropwise. The resulting mixture was stirred at 0°–5° C. for 1.33 hr and then poured into ice—3N HCl. Work-up with ethyl acetate in the usual manner gave 0.96 g of 2-[[5-(methylsulfonyl)oxy]pentyl]oxy]-5-acetylbenzenepropanoic acid methyl ester as an oil which was used without further purification.

EXAMPLE 33

Preparation of
5-Acetyl-2-[5-[(3,4-dihydro-4-oxo-8-propyl-2H-1-benzopyran-7-yl)oxy]pentyloxy]benzenepropanoic Acid Using the procedure of example 11 and starting with 0.2 g (1 mmol) of 2,3-dihydro-7-hydroxy-8-propyl-4H-1-benzopyran-4-one and 0.39 g (1 mmol) of 2-[[5-[(methylsulfonyl)oxy]pentyl]oxy]-5-acetylbenzenepropanoic acid methyl ester (from example 32), 5-acetyl-2-[5-[(3,4-dihydro-4-oxo-8-propyl-2H-1-benzopyran-7-yl)oxy]pentyloxy]benzenepropanoic acid was obtained in 64.3% overall yield, as a colorless solid, mp 115°–118° C. (recrystallized from hexane-ethyl acetate).

Anal. Calcd for $C_{28}H_{34}O_7$: C, 69.69; H, 7.10. Found: C, 69.47; H, 7.22.

EXAMPLE 34

Preparation of 2-(6-Hydroxy-1-hexynyl)benzaldehyde

Using the procedure of example 5 and starting with 11.1 g (60 mmol) of 2-bromobenzaldehyde and 7.62 g (77 mol) of 5-hexyn-1-ol, 2-(6-hydroxy-1-hexynyl)benzaldehyde was obtained in 59.4% yield, as a yellow oil.

EXAMPLE 35

Preparation of 2-(6-Hydroxyhexyl)benzenepropanoic Acid Methyl Ester

Using the procedure of example 6, 7.2 g (35.6 mmol) of 2-(6-hydroxy-1-hexynyl)benzaldehyde was converted, in 78% overall yield, into 2-(6-hydroxyhexyl)benzenepropanoic acid methyl ester, as a colorless oil.

EXAMPLE 36

Preparation of
2-[6-[(Methylsulfonyl)oxy]hexyl]benzenepropanoic
Acid Methyl Ester Using the procedure of example 32, 2-(6-hydroxyhexyl)benzenepropanoic acid methyl ester (2 mmol) was converted into 2-[6-[(methylsulfonyl)oxy]hexyl]benzenepropanoic acid methyl ester, a yellow oil, in quantitative yield.

EXAMPLE 37

Preparation of
2-[6-[(3,4-Dihydro-4-oxo-8-propyl-2H-1-benzopyran-7-yl)oxy]hexyl]benzenepropanoic Acid Using the procedure of example 11 and starting with 0.2 g (1 mmol) of 2,3-dihydro-7-hydroxy-8-propyl-4H-1-benzopyran-4-one and 0.32 g (1 mmol) of 2-[6-[(methylsulfonyl)oxy]hexyl]benzenepropanoic acid methyl ester (from example 36), 2-[6-[(3,4-dihydro-4-oxo-8-propyl-2H-1-benzopyran-7-yl)oxy]hexyl]benzenepropanoic acid was obtained in 45.6% overall yield, as a colorless solid, mp 98°–99° C. (recrystallized from hexane-ethyl acetate).

Anal. Calcd for $C_{27}H_{34}O_5$: C, 73.95; H, 7.81. Found: C, 73.89; H, 7.89.

EXAMPLE 38

Preparation of
2-[3-(Chloromethyl)phenylmethoxy]benzenepropanoic
Acid Methyl Ester A mixture of 1.8 g (10 mmol) of 2-hydroxybenzenepropanoic acid methyl ester, 14 g (80 mmol) of α,α'-dichloro-m-xylene, 4.25 g (30.8 mmol) of anhydrous, granular potassium carbonate, and 70 mL of acetonitrile was stirred and refluxed for 4 hr. After being cooled, the resulting mixture was diluted with 200 mL of ether and filtered with suction. The solids were washed thoroughly with ether and then the filtrate and washes were combined and concentrated in vacuo. The oily residue was chromatographed on 100 g of silica gel. Elution with 19:1 hexane-ether afforded 1.74 g (54.6%) of 2-[3-(chloromethyl)phenylmethoxy]benzenepropanoic acid methyl ester as a colorless oil.

EXAMPLE 39

Preparation of
2-[3-[[(3,4-Dihydro-4-oxo-8-propyl-2H-1-benzopyran-7-yl)oxy]methyl]phenylmethoxy]benzenepropanoic
Acid Using the procedure of example 4, and starting with 0.62 g (3 mmol) of 2,3-dihydro-7-hydroxy-8-propyl-4H-1-benzopyran-4-one and 1.05 g (3.3 mmol) of 2-[3-(chloromethyl)phenylmethoxy]benzenepropanoic acid methyl ester, 2-[3-[[(3,4-dihydro-4-oxo-8-propyl-2H-1-benzopyran-7-yl)oxy]methyl]phenylmethoxy]benzenepropanoic acid was prepared, in 52% overall yield, as an off-white solid, mp 132°–135° C. (recrystallized from acetonitrile).

Anal. Calcd for $C_{29}H_{30}O_6$: C, 73.40; H, 6.37. Found: C, 73.19; H, 6.31.

EXAMPLE 40

Preparation of
2-[5-[(2,3-Dihydro-3-oxo-7-propylbenzofuran-6-yl)oxy]pentyloxy]benzenepropanoic Acid A mixture of 0.154 g (0.8 mmol) of 6-hydroxy-7-propyl-2H-benzofuran-3-one, 0.27 g (0.82 mmol) of 2-[(5-bromopentyl)oxy]benzenepropanoic acid methyl ester, 0.382 g (2.77 mmol) of anhydrous granular potassium carbonate, and 6 mL of anhydrous N,N-dimethylformamide was stirred at 60°–65° C. for 3 hr. The resulting slurry was cooled and the solvent was removed in vacuo. The residue was purified by flash chomatography on silica gel, eluting with 7:3 and 6:4 hexane-ethyl acetate. There was obtained 0.24 g (68%) of 2-[5-[(2,3-dihydro-3-oxo-7-propylbenzofuran-6-yl)oxy]pentyloxy]benzenepropanoic acid methyl ester as a pale-yellow oil. A 0.1 g (0.227 mmol) sample of this material was dissolved in 10 mL of tetrahydrofuran and 1 mL of 3N aqueous HCl was added. The mixture was stirred at room temperature for 2.5 hr then heated at 60°–65° C. for 28 hr. After being stirred overnight at room temperature, the solution was diluted with water and worked-up with dichloromethane in the usual manner giving a viscous oil. Flash chromatography on silica gel, eluting with ethyl acetate and 9:1 ethyl acetate-methanol gave 0.04 g (41.5%) of 2-[5-[(2,3-dihydro-3-oxo-7-propylbenzofuran-6-yl)oxy]pentyloxy]benzenepropanoic acid as a pale-yellow gum which crystallized. Trituration of a sample with ether-hexane gave a pale-yellow solid, mp 101°–102.5° C.

EXAMPLE 41

Preparation of
4-(3-Formyl-4-hydroxyphenoxy)butanoic Acid Ethyl Ester

A 1.86 g (46.4 mmol) sample of 60% sodium hydride-mineral oil dispersion was washed free of the oil with heptane and suspended in 100 mL of dimethyl sulfoxide. The slurry was stirred at room temperature while a solution of 2.76 g (20 mmol) of 2,5-dihydroxybenzaldehyde in 10 mL of dimethyl sulfoxide was added dropwise over a 5 min period. The resulting mixture was stirred at room temperature for 45 min during which time hydrogen gas was evolved and a dark red-orange coloration developed. To the stirring mixture was added dropwise 4.3 g (22 mmol) of ethyl 4-bromobutyrate washed in with 5 mL of dimethyl sulfoxide. The reaction mixture was stirred at room temperature for 1.5 hr and at 70° C. for 18 hr. After being cooled, the jet-black mixture was poured into 200 mL of cold 0.75N HCl. Work-up with ether in the usual manner gave 3.84 g of a dark-brown oil which was chromatographed on 100 g of silica gel. Elution with 4:1 hexane-ether afforded 0.79 g (15.7%) of 4-(3-formyl-4-hydroxyphenoxy)butanoic acid ethyl ester as a yellow oil.

EXAMPLE 42

Preparation of
4-[[5-(Acetyloxy)pentyl]oxy]-3-formylphenoxy]-butanoic Acid Ethyl Ester A mixture of 4-(3-formyl-4-hydroxyphenoxy)butanoic acid ethyl ester from the preceding example (0.79 g; 3.13 mmol), 0.72 g (3.44 mmol) of 5-bromopentyl acetate, 1.37 g (9.93 mmol) of anhydrous granular potassium carbonate, and 23 mL of acetonitrile was stirred and refluxed for 18 hr. The resulting tan slurry was cooled, diluted with 75 mL of ether, and filtered with suction. The solids were washed thoroughly with ether. The filtrate and washes were combined and concentrated in vacuo giving 1.22 g of 4-[[5-(acetyloxy)pentyl]oxy]-3-formylphenoxy]butanoic acid ethyl ester as an amber oil which was used without further purification.

EXAMPLE 43

Preparation of
(E/Z)-4-[4-[[5-(Acetyloxy)pentyl]oxy]-3-(3-ethoxy-3-oxo-1-propenyl)phenoxy]butanoic Acid Ethyl Ester A mixture of the crude 4-[[5-(acetyloxy)pentyl]oxy]-3-formylphenoxy]butanoic acid ethyl ester from the preceding example (1.22 g; ca. 3.13 mmol), 1.63 g (4.68 mmol) of (carbethoxymethylene)triphenylphosphorane, and 10 mL of toluene was stirred and refluxed for 4.5 hr and then stirred overnight at room temperature. The solvent was removed under reduced pressure and the oily residue was triturated with 1:1 hexane-ether. The resulting solid was filtered with suction and washed with 1:1 hexane-ether. The filtrate and washes were combined and concentrated in vacuo giving 2.3 g of an oil which was flash chromatographed on silica gel, eluting with 1:1 hexane-ether. There was obtained 1.1 g (78%) of (E/Z)-4-[4-[[5-(acetyloxy)pentyl]oxy]-3-(3-ethoxy-3-oxo-1-propenyl)phenoxy]butanoic acid ethyl ester as an oil.

EXAMPLE 44

Preparation of
2-[[5-(Acetyloxy)pentyl]oxy]-5-(4-ethoxy-4-oxobutoxy)benzenepropanoic Acid Ethyl Ester A mixture of 1.1 g (2.4 mmol) of (E/Z)-4-[4-[[5-(acetyloxy)pentyl]oxy]-3-(3-ethoxy-3-oxo-1-propenyl)-phenoxy]butanoic acid ethyl ester from the preceding example and 0.15 g of 10% palladium on carbon, in 50 mL of ethyl acetate and 10 mL of ethanol was stirred in an atmosphere of hydrogen until hydrogen uptake ceased. The catalyst was removed by suction filtration and the filtrate was concentrated in vacuo giving 1.0 g (91%) of 2-[[5-(acetyloxy)pentyl]oxy]-5-(4-ethoxy-4-oxobutoxy)benzenepropanoic acid ethyl ester as a colorless oil.

EXAMPLE 45

Preparation of
2-[(5-Hydroxypentyl)oxy]-5-(4-ethoxy-4-oxobutoxy)-benzenepropanoic Acid Ethyl Ester A solution of 1.0 g (2.2 mmol) of 2-[[5-(acetyloxy)pentyl]oxy]-5-(4-ethoxy-4-oxobutoxy)benzenepropanoic acid ethyl ester from the preceding example, and 0.018 g of p-toluenesulfonic acid monohydrate in 10 mL of ethanol was stirred and refluxed for 30 hr and stirred at room temperature for 21 hr. Most of the ethanol was removed in vacuo and the residue was diluted with water and worked-up with ether in the usual manner (the combined ether extracts were additionally washed with saturated aqueous sodium bicarbonate). The product was purified by flash chromatography on silica gel, eluting with 1:1 hexane-ethyl acetate. There was obtained 0.6 g (66.5%) of 2-[(5-hydroxypentyl)oxy]-5-(4-ethoxy-4-oxobutoxy)benzenepropanoic acid ethyl ester as a viscous oil.

EXAMPLE 46

Preparation of
2-[[5-[(Methylsulfonyl)oxy]pentyl]oxy]-5-(4-ethoxy-4-oxobutoxy)benzenepropanoic Acid Ethyl Ester Using the procedure of example 32, the 2-[(5-hydroxypentyl)oxy]-5-(4-ethoxy-4-oxobutoxy)benzenepropanoic acid ethyl ester from the preceding example (0.6 g; 1.46 mmol) was converted into 2-[[5-[(methylsulfonyl)oxy]pentyl]oxy]-5-(4-ethoxy-4 -oxobutoxy)benzenepropanoic acid ethyl ester in essentially quantitative yield and was used without further purification.

EXAMPLE 47

Preparation of
5-(3-Carboxypropoxy)-2-[5-[(3,4-dihydro-4-oxo-8-propyl-2H-1-benzopyran-7-yl)oxy]pentyloxy]benzenepropanoic Acid Using the procedure of example 11 and starting with 0.28 g (1.4 mmol) of 2,3-dihydro-7-hydroxy-8-propyl-4H-1-benzopyran-4-one and 0.7 g (1.4 mmol) of 2-[5-(methylsulfonyl)oxypentyloxy]-5-(3-ethoxycarbonylpropoxy)benzenepropanoic acid ethyl ester (from example 46), 5-(3-ethoxycarbonylpropoxy)-2-[5-[(3,4-dihydro-4-oxo-8-propyl-2H-1-benzopyran-7-yl)oxy]pentyloxy]benzenepropanoic acid ethyl ester was obtained in 83.6% yield (0.7 g) as a solid. This diester (1.17 mmol) was saponified with 3 mL of 3N aqueous lithium hydroxide in 25 mL of tetrahydrofuran, at room temperature, for 37 hr. Work-up as in example 4 gave a light-brown oily acid which was flash-chromatographed on silica gel, eluting with 95:5:1 chloroform-methanol-acetic acid. There was obtained 0.39 g (61.5%) of pure 5-(3-carboxypropoxy)-2-[5-[(3,4-dihydro-4-oxo-8-propyl-2H-1-benzopyran-7-yl)oxy]pentyloxy]benzenepropanoic acid. Recrystallization from hexane-ethyl acetate gave a colorless solid, mp 119°–124° C.

Anal. Calcd for $C_{30}H_{38}O_9$: C, 66.40; H, 7.06. Found: C, 66.21; H, 7.10.

EXAMPLE 48

Preparation of 4-(4-Bromo-3-formylphenoxy)butanoic Acid Ethyl Ester

A mixture of 3.5 g (17.4 mmol) of 2-bromo-5-hydroxybenzaldehyde, 3.7 g (19 mmol) of ethyl 4-bromobutyrate, 5.5 g (40 mmol) of anhydrous, granular potassium carbonate, and 40 mL of dry dimethyl sulfoxide was stirred at room temperature for 5 hr and then kept at room temperature overnight. The resulting slurry was poured into ice-water and worked-up with ether in the usual manner giving an oily product which was flash-chromatographed on silica gel. Elution with 2:1 hexane-ether afforded 4.4 g (80.3%) of 4-(4-bromo-3-formylphenoxy)butanoic acid ethyl ester as an oil.

EXAMPLE 49

Preparation of
rac-4-[3-Formyl-4-[6-[(tetrahydro-2H-pyran-2-yl)oxy]-1-hexynyl]phenoxy]butanoic Acid Ethyl Ester Using the procedure of example 5 and starting with 3.15 g (10 mmol) of 4-(4-bromo-3-formylphenoxy)butanoic acid ethyl ester and 2.34 g (12.8 mmol) of rac-6-[(tetrahydro-2H-pyran-2-yl)oxy]-1-hexyne, rac-4-[3-formyl-4-[6-[(tetrahydro-2H-pyran-2-yl)oxy]-1-hexynyl]phenoxy]butanoic acid ethyl ester was prepared in 93.7% yield, as an oil.

EXAMPLE 50

Preparation of
rac-(E)-4-[3-(3-methoxy-3-oxo-1-propenyl)-4-[6-(tetrahydro-2H-pyran-2-yl)oxy]-1-hexynyl]phenoxy]butanoic Acid Ethyl Ester Using the procedure of example 28 and starting with 3.9 g (9.37 mmol) of rac-4-[3-formyl-4-[6-[(tetrahydro-2H-pyran-2-yl)oxy]-1-hexynyl]phenoxy]butanoic acid ethyl ester and 3.69 g (11 mmol) of methyl (triphenylphosphoranylidene)acetate, rac-(E)-4-[3-(3-methoxy-3-oxo-1-propenyl)-4-[6-(tetrahydro-2H-pyran-2-yl)oxy]-1-hexynyl]phenoxy]butanoic acid ethyl ester was prepared, in 98% yield, as an oil.

EXAMPLE 51

Preparation of
rac-2-[6-[(Tetrahydro-2H-pyran-2-yl)oxy]hexyl]-5-(4-ethoxy-4-oxobutoxy)benzenepropanoic Acid Methyl Ester A 4.3 g (9.1 mmol) sample of rac-(E)-4-[3-(3-methoxy-3-oxo-1-propenyl)-4-[6-(tetrahydro-2H-pyran-2-yl)oxy]-1-hexynyl]phenoxy]butanoic acid ethyl ester was hydrogenated in 300 mL of methanol, over 0.5 g of 10% palladium on carbon, at room temperature and atmospheric pressure, until hydrogen uptake ceased. The catalyst was filtered with suction and washed with ethyl acetate. Concentration of the combined filtrate and washes gave 4.26 g (97.8%) of rac-2-[6-[(tetrahydro-2H-pyran-2-yl)oxy]hexyl]-5-(4-ethoxy-4-oxobutoxy)benzenepropanoic acid methyl ester as an oil.

EXAMPLE 52

Preparation of
2-(6-Hydroxyhexyl)-5-(4-methoxy-4-oxobutoxy)benzenepropanoic Acid Methyl Ester A solution of 4.26 g (8.91 mmol) of rac-2-[6-[(3,4,5,6-tetrahydro-2H-pyran-2-yl)oxy]hexyl]-5-(4-ethoxy-4-oxobutoxy)benzenepropanoic acid methyl ester, 0.16 g of p-toluenesulfonic acid monohydrate, and 75 mL of methanol was stirred and refluxed for 24 hr. The solvent was removed in vacuo and the residue was dissolved in ether. The ether solution was washed with saturated sodium bicarbonate solution and processed in the usual manner giving an oil. This material was flash-chromatographed on silica gel, eluting with 1:1 hexane-ethyl acetate. There was obtained 2.0 g (59%) of 2-(6-hydroxyhexyl)-5-(4-methoxy-4-oxobutoxy)benzenepropanoic acid methyl ester as a colorless oil.

EXAMPLE 53

Preparation of
2-[6-[(Methylsulfonyl)oxy]hexyl]-5-(4-methoxy-4-oxobutoxy)benzenepropanoic Acid Methyl Ester Using the procedure of example 32, 2-(6-hydroxyhexyl)-5-(4-methoxy-4-oxobutoxy)benzenepropanoic acid methyl ester was converted into 2-[6-[(methylsulfonyl)oxy]hexyl]-5-(4-methoxy-4-oxobutoxy)benzenepropanoic acid methyl ester, an oil, in essentially quantitative yield.

EXAMPLE 54

Preparation of
5-(3-Carboxypropoxy)-2-[6-[(3,4-dihydro-4-oxo-8-propyl-2H-1-benzopyran-7-yl)oxy]hexyl]benzenepropanoic Acid Using the procedure of example 11 and starting with 0.28 g (1.4 mmol) of 2,3-dihydro-7-hydroxy-8-propyl-4H-1-benzopyran-4-one and 0.64 g (1.4 mmol) of 2-[6-[(methylsulfonyl)oxy]hexyl]-5-(4-methoxy-4-oxobutoxy)benzenepropanoic acid methyl ester (from example 53), 5-(4-methoxy-4-oxobutoxy)-2-[6-[(3,4-dihydro-4-oxo-8-propyl-2H-1-benzopyran-7-yl)oxy]hexyl]benzenepropanoic acid methyl ester was obtained in 86.7% yield (0.69 g) as an oil. This diester (1.21 mmol) was saponified with 2 mL of 3N aqueous lithium hydroxide in 20 mL of tetrahydrofuran, at room temperature, for 24 hr. Work-up as in example 4 gave a light-brown oily acid which was flash-chromatographed on silica gel, eluting with 95:5:1 chloroform-methanol-acetic acid. There was obtained 0.6 g (91.8%) of pure 5-(3-carboxypropoxy)-2-[6-[(3,4-dihydro-4-oxo-8-propyl-2H-1-benzopyran-7-yl)oxy]hexyl]benzenepropanoic acid. Recrystallization from hexane-ethyl acetate gave 0.49 g (75%) of a colorless solid, mp 119°–120° C.

Anal. Calcd for $C_{31}H_{40}O_8$: C, 68.87; H, 7.46. Found: C, 68.69; H, 7.30.

EXAMPLE 55

Preparation of
5-(5-Ethoxy-5-oxopentyloxy)-2-hydroxybenzenepropanoic Acid Ethyl Ester A mixture of 1.5 g (9.15 mmol) of 6-hydroxy-3,4-dihydrocoumarin, 2.1 g (10 mmol) of ethyl 5-bromovalerate, 4.16 g (30 mmol) of anhydrous, granular potassium carbonate, and 15 mL of N,N-dimethylformamide was stirred at room temperature, for 23 hr. The resulting dark-brown slurry was diluted with ether and washed with water and brine. Completion of the usual work-up gave 2.32 g of a red-orange oil which was chromatographed on 50 g of silica gel. Elution with 1:1 hexane-ether gave 2.03 g of a yellow oil which was a mixture of the desired 5-[(3,4-dihydro-2-oxo-2H-1-benzopyran-6-yl)oxy]pentanoic acid ethyl ester and an impurity. This material was dissolved in 25 mL of ethanol and 52 mg of p-toluenesulfonic acid monohydrate was added. The resulting solution was stirred and refluxed for 22.5 hr and then concentrated in vacuo. The residue was dissolved in ether and the ether solution was processed in the usual manner giving an amber oil. This material was chromatographed on 50 g of silica gel. Elution with 1:1 hexane-ether afforded 1.90 g (61.4%) of 5-(5-ethoxy-5-oxopentyloxy)-2-hydroxybenzenepropanoic acid ethyl ester as a pale-yellow oil.

EXAMPLE 56

Preparation of
2-[(5-Hydroxypentyl)oxy]-5-(5-methoxy-5-oxopentyloxy)benzenepropanoic Acid Methyl Ester A mixture of 1.9 g (5.62 mmol) of 5-(5-ethoxy-5-oxopentyloxy)-2-hydroxybenzenepropanoic acid ethyl ester from the preceding example, 1.29 g (6.18 mmol) of 5-bromopentyl acetate, 2.15 g (15.6 mmol) of anhydrous, granular potassium carbonate, and 15 mL of dimethyl sulfoxide was stirred at room temperature for 18.5 hr. The resulting slurry was diluted with ether and washed with water and brine. The ether solution was processed in the usual manner giving 2.64 g of a pale-yellow oil. This material was dissolved in 50 mL of methanol and 0.1 g of p-toluenesulfonic acid monhydrate was added. The solution was stirred and refluxed for 23 hr and then concentrated in vacuo. The residue was dissolved in ether and the ether solution was washed with saturated aqueous sodium bicarbonate solution before being processed in the usual manner to give 2.18 g of an oil. This material was chromatographed on 50 g of silica gel. Elution with 1:1 hexane-ethyl acetate afforded 1.46 g (65.6%) of 2-[(5-hydroxypentyl)oxy]-5-(5-methoxy-5-oxopentyloxy)benzenepropanoic acid methyl ester as an almost colorless oil.

EXAMPLE 57

Preparation of
2-[[5-[(Methylsulfonyl)oxy]pentyl]oxy]-5-(5-methoxy-5-oxopentyloxy)benzenepropanoic acid Methyl Ester Using the procedure of example 32, the 2-[(5-hydroxypentyl)oxy]-5-(5-methoxy-5-oxopentyloxy)benzenepropanoic acid methyl ester from the preceding example (1.46 g; 3.7 mmol) was converted into 2-[5-(methylsulfonyl)oxypentyloxy]-5-(5-methoxy-5-oxopentyloxy)benzenepropanoic acid methyl ester, an oil, in essentially quantitative yield.

EXAMPLE 58

Preparation of
5-(4-Carboxybutoxy)-2-[5-[(3,4-dihydro-4-oxo-8-propyl-2H-1-benzopyran-7-yl)oxy]pentyloxy]benzenepropanoic Acid Hemihydrate Using the procedure of example 11 and starting with 0.28 g (1.4 mmol) of 2,3-dihydro-7-hydroxy-8-propyl-4H-1-benzopyran-4-one and 0.66 g (1.4 mmol) of 2-[[5-[(methylsulfonyl)oxy]pentyl]oxy]-5-(5-methoxy-5-oxopentyloxy)benzenepropanoic acid methyl ester (from example 57), 5-(5-methoxy-5-oxopentyloxy)-2-[5-[(3,4-dihydro-4-oxo-8-propyl-2H-1-benzopyran-7-yl)oxy]pentyloxy]benzenepropanoic acid methyl ester was obtained in 61% yield (0.5 g) as a colorless solid. This diester (0.85 mmol) was saponified with 3 mL of 3N aqueous lithium hydroxide in 20 mL of tetrahydrofuran, at room temperature, for 24 hr. Work-up as in example 4 gave a crystalline acid which was flash-chromatographed on silica gel, eluting with 95:5:1 chloroform-methanol-acetic acid. There was obtained 0.44 g (93%) of pure 5-(4-carboxybutoxy)-2-[5-[(3,4-dihydro-4-oxo-8-propyl-2H-1-benzopyran-7-yl)oxy]pentyloxy]benzenepropanoic acid. Recrystallization from ethyl acetate gave 0.35 g (74%) of a colorless solid, mp 138°–139° C.

Anal. Calcd for $C_{31}H_{40}O_9 \cdot 0.5H_2O$: C, 65.83; H, 7.13. Found: C, 66.19; H, 7.21.

EXAMPLE 59

Preparation of
2-Hydroxy-6-[(5-hydroxypentyl)oxy]benzenepropanoic Acid Methyl Ester A mixture of 1.17 g (7.13 mmol) of 5-hydroxy-3,4-dihydrocoumarin, 1.64 g (7.85 mmol) of 5-bromopentyl acetate, 2.72 g (19.74 mmol) of anhydrous, granular potassium carbonate, and 18 mL of dimethyl sulfoxide was stirred at room temperature for 18 hr. The resulting pink slurry was diluted with ether and washed three times with water and once with saturated brine. Completion of the usual work-up gave 0.76 g of a yellow oil. The aqueous washes were combined and acidified with 6N HCl. Work-up with ether in the usual manner gave 1.43 g of a viscous, red oil. These neutral and acidic products were combined, dissolved in 60 mL of methanol containing 0.11 g of p-toluenesulfonic acid, and the solution was stirred and refluxed for 20.5 hr. Removal of the methanol under reduced pressure left an oil which was dissolved in ether. The ether solution was washed with dilute sodium bicarbonate solution and then processed in the usual manner giving a yellow oil. This material was purified by flash chromatography on silica gel, eluting with 1:2 hexane-ethyl acetate. There was obtained 1.4 g (69.6%) of 2-hydroxy-6-[(5-hydroxypentyl)oxy]benzenepropanoic acid methyl ester as a yellow, viscous oil.

EXAMPLE 60

Preparation of
6-[(5-Hydroxypentyl)oxy]-2-(5-ethoxy-5-oxopentyloxy)benzenepropanoic Acid Methyl Ester A mixture of the 2-hydroxy-6-[(5-hydroxypentyl)oxy]benzenepropanoic acid methyl ester from the preceding example (1.4 g; 4.96 mmol), 1.13 g (5.4 mmol) of ethyl 5-bromovalerate, 1.57 g (11.4 mmol) of anhydrous, granular potassium carbonate, and 12 mL of dimethyl sulfoxide was stirred at room temperature for 6 hr. The resulting slurry was filtered with suction and the solids were washed well with ethyl acetate. The filtrate and washed were combined and treated with water. Work-up with ether in the usual manner gave an oily product which was purified by chromatography on silica gel. Elution with 1:3 hexane-ether afforded 1.0 g (49.3%) of 6-[(5-hydroxypentyl)oxy]-2-(5-ethoxy-5-oxopentyloxy)benzenepropanoic acid methyl ester as an oil.

EXAMPLE 61

Preparation of
6-(5-Ethoxy-5-oxopentyloxy)-2-[[5-[(methylsulfonyl)oxy]pentyl]oxy]benzenepropanoic Acid Methyl Ester Using the procedure of example 32, the 6-[(5-hydroxypentyl)oxy]-2-(5-ethoxy-5-oxopentyloxy)benzenepropanoic acid methyl ester from the preceding example (1.0 g; 2.43 mmol) was converted into 6-(5-ethoxy-5-oxopentyloxy)-2-[[5-[(methylsulfonyl)oxy]pentyl]oxy)benzenepropanoic acid methyl ester, an oil, in 84% yield.

EXAMPLE 62

Preparation of
6-(4-Carboxybutoxy)-2-[5-[(3,4-dihydro-4-oxo-8-propyl-2H-1-benzopyran-7-yl)oxy]pentyloxy]benzenepropanoic Acid Using the procedure of example 11 and starting with 0.2 g (1.0 mmol) of 2,3-dihydro-7-hydroxy-8-propyl-4H-1-benzopyran-4-one and 0.49 g (1.0 mmol) of 6-(5-ethoxy-5-oxopentyloxy)-2-[[5-[(methylsulfonyl)oxy]pentyl]oxy)benzenepropanoic acid methyl ester, (from example 61), 6-(5-ethoxy-5-oxopentyloxy)-2-[5-[(3,4-dihydro-4-oxo-8-propyl-2H-1-benzopyran-7-yl)oxy]pentyloxy]benzenepropanoic acid methyl ester was obtained in 72% yield (0.43 g) as a colorless solid. This diester (0.72 mmol) was saponified with 2 mL of 3N aqueous lithium hydroxide in 20 mL of tetrahydrofuran, at room temperature, for 24 hr. Work-up as in example 4 gave a crystalline acid which was flash-chromatographed on silica gel, eluting with 95:5:1 chloroform-methanol-acetic acid. There was obtained 0.35 g of pure 6-(4-carboxybutoxy)-2-[5-[(3,4-dihydro-4-oxo-8-propyl-2H-1-benzopyran-7-yl)oxy]pentyloxy]benzenepropanoic acid. Recrystallization from ethyl acetate-hexane gave 0.22 g (55%) of a colorless solid, mp 85°–87° C.

Anal. Calcd for $C_{31}H_{40}O_9$: C, 66.89; H, 7.24. Found: C, 67.06; H, 7.35.

EXAMPLE 63

Preparation of
3-[[5-(Acetyloxy)pentyl]oxy]benzaldehyde

A mixture of 1.22 g (10 mmol) of 3-hydroxybenzaldehyde, 2.3 g (11 mmol) of 5-bromopentyl acetate, 3.82 g (27.7 mmol) of anhydrous, granular potassium carbonate, and 25 mL of dimethyl sulfoxide was stirred at room temperature for 20 hr. The resulting brown slurry was diluted with ether and washed with water and saturated brine. Completion of the usual work-up gave 2.59 g (100%) of 3-[[5-(acetyloxy)pentyl]oxy]benzaldehyde as a yellow oil which was used without further purification.

EXAMPLE 64

Preparation of
(E)-3-[3-[[5-(Acetyloxy)pentyl]oxy]phenyl]-2-propenoic Acid Methyl Ester Using the procedure of example 28, the title compound was prepared in 80% yield, from 2.6 g (10.4 mmol) of 3-[[5-(acetyloxy)pentyl]oxy]benzaldehyde and 4.0 g (12 mmol) of methyl (triphenylphosphoranylidene)acetate, as a colorless solid, mp 65°–67° C.

EXAMPLE 65

Preparation of
3-[[5-(Acetyloxy)pentyl]oxy]benzenepropanoic Acid Methyl Ester

Using the procedure of example 29, except that methanol was used as the solvent, (E)-3-[3-[[5-(acetyloxy)pentyl]oxy]phenyl]-2-propenoic acid methyl ester was hydrogenated giving 3-[[5-(acetyloxy)pentyl]oxy]benzenepropanoic acid methyl ester as a pale-yellow oil, in 97% yield.

EXAMPLE 66

Preparation of
3-[(5-Hydroxypentyl)oxy]benzenepropanoic Acid Methyl Ester

Using the procedure of example 31, 3-[[5-(acetyloxy)pentyl]oxy]benzenepropanoic acid methyl ester was converted into 3-[(5-hydroxypentyl)oxy]benzenepropanoic acid methyl ester, a colorless oil, in 61% yield.

EXAMPLE 67

Preparation of
3-[[5-[(Methylsulfonyl)oxy]pentyl]oxy]benzenepropanoic Acid Methyl Ester Using the procedure of example 32, the 3-[(5-hydroxypentyl)oxy]benzenepropanoic acid methyl ester from the preceding example was converted into 3-[[5 -[(methylsulfonyl)oxy]pentyl]oxy)benzenepropanoic acid methyl ester, an oil, in quantitative yield.

EXAMPLE 68

Preparation of
3-[5-[(3,4-Dihydro-4-oxo-8-propyl-2H-1-benzopyran-7-yl)oxy]pentyloxy]benzenepropanoic Acid Using the procedure of example 11 and starting with 0.28 g (1.4 mmol) of 2,3-dihydro-7-hydroxy-8-propyl-4H-1-benzopyran-4-one and 0.48 g (1.4 mmol) of 3-[[5-[(methylsulfonyl)oxy]pentyl]oxy]benzenepropanoic acid methyl ester (from example 67), 3-[5-[(3,4-dihydro-4-oxo-8-propyl-2H-1-benzopyran-7-yl)oxy]pentyloxy]-benzenepropanoic acid methyl ester was obtained in 57% yield (0.36 g) as a yellow oil. This diester (0.79 mmol) was saponified with 2 mL of 3N aqueous lithium hydroxide in 20 mL of tetrahydrofuran, at room temperature, for 22 hr. Work-up as in example 4 gave crystalline 3-[5-[(3,4-dihydro-4-oxo-8-propyl-2H-1-benzopyran-7-yl)oxy]pentyloxy]benzenepropanoic acid. Recrystallization from ethyl acetate-hexane gave 0.30 g (86%) of a colorless solid, mp 124°–125° C.

Anal. Calcd for $C_{26}H_{32}O_6$: C, 70.89; H, 7.32. Found: C, 70.94; H, 7.32.

EXAMPLE 69

Preparation of
7-(Phenylmethoxy)-8-(phenylmethyl)-4H-1-benzopyran-4-one

Using the procedure of example 1, 14.02 g (42.3 mmol) of 1-[2-hydroxy-4-(phenylmethoxy)-3-(phenylmethyl)phenyl]ethanone was converted into 7-(phenylmethoxy)-8-(phenylmethyl)-4H-1-benzopyran-4-one as a beige solid, in 59% yield. An analytical specimen was obtained from another experiment by recrystallization from ether, as a colorless solid, mp 108.5°–109.5° C.

Anal. Calcd for $C_{23}H_{18}O_3$: C, 80.67; H, 5.30. Found: C, 80.52; H, 5.46.

EXAMPLE 70

Preparation of
2,3-Dihydro-7-hydroxy-8-(phenylmethyl)-4H-1-benzopyran-4-one

Using the procedure of example 2, 5.7 g (16.6 mmol) of 7-(phenylmethoxy)-8-(phenylmethyl)-4H-1-benzopyran-4-one was catalytically hydrogenated giving 2,3-dihydro-7-hydroxy-8-(phenylmethyl)-4H-1-benzopyran-4-one, as a solid, in 45% yield. A sample was recrystallized from acetonitrile giving a colorless solid, mp 176°–176.5° C.

Anal. Calcd for $C_{16}H_{14}O_3$: C, 75.58; H, 5.55. Found: C, 75.34; H, 5.58.

EXAMPLE 71

Preparation of
2-[(5-Hydroxypentyl)oxy]benzenepropanoic Acid Methyl Ester

Using the procedure of example 31, 2-[[5-(acetyloxy)pentyl]oxy]benzenepropanoic acid methyl ester (from example 29) was converted into 2-[(5-hydroxypentyl)oxy]benzenepropanoic acid methyl ester as a colorless, viscous oil, in 91.5% yield.

EXAMPLE 72

Preparation of
2-[[5-[(Methylsulfonyl)oxy]pentyl]oxy]benzenepropanoic Acid Methyl Ester Using the procedure of example 32, 2-[(5-hydroxypentyl)oxy]benzenepropanoic acid methyl ester was converted into 2-[[5-[(methylsulfonyl)oxy]pentyl]oxy]benzenepropanoic acid methyl ester in quantitative yield, as a colorless oil which was used without further purification.

EXAMPLE 73

Preparation of
2-[5-[[3,4-Dihydro-4-oxo-8-(phenylmethyl)-2H-1-benzopyran-7-yl]oxy]pentyloxy]benzenepropanoic Acid Using the procedure of example 11 and starting with 1.2 g (4.72 mmol) of 2,3-dihydro-7-hydroxy-8-(phenylmethyl)-4H-1-benzopyran-4-one (from example 70) and 1.64 g (4.76 mmol) of 2-[[5-[(methylsulfonyl)oxy]pentyl]oxy]benzenepropanoic acid methyl ester (from example 72), 2-[5-[(3,4-dihydro-4-oxo-8-(phenylmethyl)-2H-1-benzopyran-7-yl)oxy]pentyloxy]benzenepropanoic acid methyl ester was obtained in 91.5% yield (2.17 g) as a yellow oil. This diester (4.32 mmol) was saponified with 6.5 mL of 3N aqueous lithium hydroxide in 21 mL of tetrahydrofuran, at room temperature, for 48 hr. Work-up as in example 4 gave 2-[5-[(3,4-dihydro-4-oxo-8-(phenylmethyl)-2H-1-benzopyran-7-yl)oxy]pentyloxy]benzenepropanoic acid as an oil. This material was flash chromatographed on silica gel eluting with ethyl acetate-hexane mixtures giving 1.0 g (47.6%) of pure acid as a solid. Recrystallization from ethyl acetate-ether gave a colorless solid, mp 117°–118° C.

Anal. Calcd for $C_{30}H_{32}O_6$: C, 73.75; H, 6.60. Found: C, 74.00; H, 6.61.

EXAMPLE 74

Preparation of
(E)-3-[2-[[5-(Acetyloxy)pentyl]oxy]phenyl]-2-propenoic Acid Methyl Ester Using the procedure of example 63, 1.78 g (10 mmol) of methyl 2-hydroxycinnamate was alkylated with 2.3 g (11 mmol) of 5-bromopentyl acetate giving (E)-3-[2-[[5-(acetyloxy)pentyl]oxy]phenyl]-2-propenoic acid methyl ester, as a pale-yellow oil, in quantitative yield. The crude product was used without further purification.

EXAMPLE 75

Preparation of
(E)-3-[2-[(5-Hydroxypentyl)oxy]phenyl]-2-propenoic Acid Methyl Ester Using the procedure of example 31, 3.22 g (ca. 10 mmol) of crude (E)-3-[2-[[5-(acetyloxy)pentyl]oxy]phenyl]-2-propenoic acid methyl ester was converted into 2.27 g (86%) of (E)-3-[2-[(5-hydroxypentyl)oxy]phenyl]-2-propenoic acid methyl ester, as a colorless oil.

EXAMPLE 76

Preparation of
(E)-3-[2-[[5-[(Methylsulfonyl)oxy]pentyl]oxy]phenyl]-2-propenoic Acid Methyl Ester Using the procedure of example 32, 1.09 g (4.13 mmol) of (E)-3-[2-[(5-hydroxypentyl)oxy]phenyl]-2-propenoic acid methyl ester was converted into 1.37 g (97%) of (E)-3-[2-[[5-[(methylsulfonyl)oxy]pentyl]oxy]-phenyl]-2-propenoic acid methyl ester, as a yellow oil.

EXAMPLE 77

Preparation of
(E)-3-[2-[5-[(5-Oxo-2-(2-propenyl)-5,6,7,8-tetrahydro-1-naphthalenyl)oxy]pentyloxy]phenyl]-2-propenoic Acid Methyl Ester A mixture of 1.37 g (4 mmol) of (E)-3-[2-[[5-[(methylsulfonyl)oxy]pentyl]oxy]phenyl]-2-propenoic acid methyl ester from example 76, 0.81 g (4 mmol) of 5-oxo-2-(2-propenyl)-5,6,7,8-tetrahydro-1-naphthalenol, 0.8 g (5.8 mmol) of anhydrous, granular potassium carbonate, 0.08 mL of TDA-1, and 25 mL of toluene was stirred under reflux for 5.5 hr and at room temperature for 12 hr. After being treated with 0.3 g of additional potassium carbonate, the mixture was stirred and refluxed for a further 24 hr. The mixture was cooled and diluted with ether. The organic phase was washed with water and saturated brine and work-up was completed in the usual manner giving a brown oil. This material was chomatographed on 50 g of silica gel. Elution with 1:1 hexane-ether afforded 1.72 g (96%) of (E)-3-[2-[5-[(5-oxo-2-(2-propenyl)-5,6,7,8-tetrahydro-1-naphthalenyl)oxy]pentyloxy]phenyl]-2-propenoic acid methyl ester as a yellow-orange oil.

EXAMPLE 78

Preparation of
2-[5-[(5-Oxo-2-propyl-5,6,7,8-tetrahydro-1-naphthalenyl)oxy]pentyloxy]benzenepropanoic Acid Methyl Ester A mixture of 1.72 g (3.84 mmol) of (E)-3-[2-[5-[(5-oxo-2-(2-propenyl)-5,6,7,8-tetrahydro-1-naphthalenyl)oxy]pentyloxy]phenyl]-2-propenoic acid methyl ester from the preceding experiment, 0.1 g of 10% palladium of carbon, and 50 mL of ethyl acetate was stirred in an atmosphere of hydrogen until gas uptake ceased. The catalyst was filtered with suction on a pad of Celite and the filter cake was washed thoroughly with ethyl acetate. Concentration of the combined filtrate and washes under reduced pressure gave a yellow oil which was chromatographed on 50 g of silica gel. Elution with 4:1 hexane-ether afforded 1.35 g (78%) of 2-[5-[(5-oxo-2-propyl-5,6,7,8-tetrahydro-1-naphthalenyl)oxy]pentyloxy]benzenepropanoic acid methyl ester as a pale-yellow oil.

EXAMPLE 79

Preparation of
2-[5-[(5-Oxo-2-propyl-5,6,7,8-tetrahydro-1-naphthalenyl)oxy]pentyloxy]benzenepropanoic Acid The 2-[5-[(5-oxo-2-propyl-5,6,7,8-tetrahydro-1-naphthalenyl)oxy]pentyloxy]benzenepropanoic acid methyl ester from the preceding example (1.35 g; 2.99 mmol) and 8 mL of 1N aqueous sodium hydroxide in 15 mL of methanol was stirred and refluxed for 1.5 hr. After being cooled, the resulting solution was diluted with water and acidified with 3N HCl. Work-up with ether in the usual manner gave 1.3 g (100%) 2-[5-[(5-oxo-2-propyl-5,6,7,8-tetrahydro-1-naphthalenyl)oxy]pentyloxy]benzenepropanoic acid as an orange oil.

EXAMPLE 80

Preparation of
2-[(7-Bromoheptyl)oxy]-5-[[3-(ethoxycarbonyl)-phenyl]carbonyl]benzenepropanoic Acid Ethyl Ester Starting with 0.381 g (1.03 mmol) of 5-[[3-(ethoxycarbonyl)phenyl]carbonyl]-2-hydroxybenzenepropanoic acid ethyl ester, and 2.13 g (8.26 mmol) of 1,7-dibromoheptane, the title compound was obtained as a colorless oil, in 81.6% yield, using the procedure of example 21.

Anal. Calcd for $C_{28}H_{35}BrO_6$: C, 61.43; H, 6.44; Br, 14.60. Found: C, 61.82; H, 6.45; Br, 14.89.

EXAMPLE 81

Preparation of
5-[(3-Carboxyphenyl)carbonyl]-2-[7-[(3,4-dihydro-4-oxo-8-propyl-2H-1-benzopyran-7-yl)oxy]heptyloxy]-benzenepropanoic Acid Starting with 0.153 g (0.74 mmol) of 2,3-dihydro-7-hydroxy-8-propyl-4H-1-benzopyran-4-one, and 0.41 g (0.74 mmol) of 2-[(7-bromoheptyl)oxy]-5-[[3-(ethoxycarbonyl)phenyl]carbonyl]benzenepropanoic acid ethyl ester, the title compound (0.286 g; 77.8% overall yield) was obtained as a white solid, mp 152°–153° C. (recrystallized from hexane-ethyl acetate), using the procedure of example 22.

Anal. Calcd for $C_{36}H_{40}O_9$: C, 70.11; H, 6.54. Found: C, 70.28; H, 6.84.

EXAMPLE 82

Preparation of
2-[(8-Bromooctyl)oxy]-5-[[3-(ethoxycarbonyl)phenyl]-carbonyl]benzenepropanoic Acid Ethyl Ester Starting with 0.370 g (1.0 mmol) of 5-[[3-(ethoxycarbonyl)phenyl]carbonyl]-2-hydroxybenzenepropanoic acid ethyl ester, and 2.17 g (7.98 mmol) of 1,8-dibromooctane, the title compound was obtained as a colorless oil, in 72.6% yield, using the procedure of example 21.

Anal. Calcd for $C_{29}H_{37}BrO_6$: C, 62.03; H, 6.64; Br, 14.23. Found: C, 62.06; H, 6.59; Br, 14.38.

EXAMPLE 83

Preparation of
5-[(3-Carboxyphenyl)carbonyl]-2-[8-[(3,4-dihydro-4-oxo-8-propyl-2H-1-benzopyran-7-yl)oxy]octyloxy]benzenepropanoic Acid Starting with 0.128 g (0.62 mmol) of 2,3-dihydro-7-hydroxy-8-propyl-4H-1-benzopyran-4-one, and 0.349 g (0.62 mmol) of 2-[(8-bromooctyl)oxy]-5-[[3-(ethoxycarbonyl)phenyl]carbonyl]benzenepropanoic acid ethyl ester, the title compound (0.232 g; 76.3% overall yield) was obtained as a white solid, mp 112°–117° C. (recrystallized from hexane-ethyl acetate), using the procedure of example 22.

Anal. Calcd for $C_{37}H_{42}O_9$: C, 70.46; H, 6.71. Found: C, 69.94; H, 6.98.

EXAMPLE 84

Preparation of
2-[(5-Bromopentyl)oxy]-5-[[4-(ethoxycarbonyl)phenyl]-carbonyl]benzenepropanoic Acid Ethyl Ester Starting with 0.484 g (1.31 mmol) of 5-[[4-(ethoxycarbonyl)phenyl]carbonyl]-2-hydroxybenzenepropanoic acid ethyl ester, and 2.4 g (10.44 mmol) of 1,5-dibromopentane, the title compound was obtained in 72.6% yield as a white solid, mp 76.5°–78° C., using the procedure of example 21.

Anal. Calcd for $C_{26}H_{31}BrO_6$: C, 60.12; H, 6.02; Br, 15.38. Found: C, 60.28; H, 6.00; Br, 15.56.

EXAMPLE 85

Preparation of
5-[(4-Carboxyphenyl)carbonyl]-2-[5-[(3,4-dihydro-4-oxo-8-propyl-2H-1-benzopyran-7-yl)oxy]pentyloxy]-benzenepropanoic Acid Starting with 0.157 g (0.76 mmol) of 2,3-dihydro-7-hydroxy-8-propyl-4H-1-benzopyran-4-one, and 0.391 g (0.75 mmol) of 2-[(5-bromopentyl)oxy]-5-[[4-(ethoxycarbonyl)phenyl]carbonyl]benzenepropanoic acid ethyl ester, the title compound (0.240 g; 63.6% overall yield) was obtained as a white solid, mp 175°–177° C. (recrystallized from hexane-ethyl acetate), using the procedure of example 22.

Anal. Calcd for $C_{34}H_{36}O_9$: C, 69.37; H, 6.17. Found: C, 69.36; H, 6.26.

EXAMPLE 86

Preparation of
4-[(5-Bromopentyl)oxy]-3-(3-ethoxy-3-oxopropyl)-δ-oxobenzenepentanoic Acid Ethyl Ester Starting with 0.332 g (0.99 mmol) of 3-(3-ethoxy-3-oxopropyl)-4-hydroxy-δ-oxobenzenepentanoic acid ethyl ester, and 1.16 g (5.04 mmol) of 1,5-dibromopentane, the title compound was obtained in 85.7% yield as a white solid, mp 48°–49° C., using the procedure of example 21.

Anal. Calcd for $C_{23}H_{33}BrO_6$: C, 56.91; H, 6.85; Br, 16.64. Found: C, 56.59; H, 6.83; Br, 16.76.

EXAMPLE 87

Preparation of
3-(2-Carboxyethyl)-4-[5-[(3,4-dihydro-4-oxo-8-propyl-2H-1-benzopyran-7-yl)oxy]pentyloxy]-δ-oxobenzenepentanoic Acid Starting with 0.135 g (0.66 mmol) of 2,3-dihydro-7-hydroxy-8-propyl-4H-1-benzopyran-4-one, and 0.31 g (0.64 mmol) of 4-[(5-bromopentyl)oxy]-3-(3-ethoxy-3-oxopropyl)-δ-oxobenzenepentanoic acid ethyl ester, the title compound (0.190 g; 62.8% overall yield) was obtained as a white solid, mp 151°–153.5° C. (recrystallized from hexane-ethyl acetate), using the procedure of example 22.

Anal. Calcd for $C_{31}H_{38}O_9$: C, 67.13; H, 6.91. Found: C, 66.81; H, 6.99.

EXAMPLE 88

Preparation of
4-[(5-Bromopentyl)oxy]-3-(3-ethoxy-3-oxopropyl)-γ-oxobenzenebutanoic Acid Ethyl Ester Starting with 0.458 g (1.42 mmol) of 3-(3-ethoxy-3-oxopropyl)-4-hydroxy-γ-oxobenzenebutanoic acid ethyl ester, and 1.65 g (7.29 mmol) of 1,5-dibromopentane, the title compound was obtained in 80.6% yield as a white solid, mp 40°–41° C., using the procedure of example 21.

Anal. Calcd for $C_{22}H_{31}BrO_6$: C, 56.06; H, 6.63; Br, 16.95. Found: C, 55.78; H, 6.60; Br, 17.05.

EXAMPLE 89

Preparation of
3-(2-Carboxyethyl)-4-[5-[(3,4-dihydro-4-oxo-8-propyl-2H-1-benzopyran-7-yl)oxy]pentyloxy]-γ-oxobenzenebutanoic Acid Starting with 0.156 g (0.76 mmol) of 2,3-dihydro-7-hydroxy-8-propyl-4H-1-benzopyran-4-one, and 0.357 g (0.76 mmol) of 4-[(5-bromopentyl)oxy]-3-(3-ethoxy-3-oxopropyl)-γ-oxobenzenebutanoic acid ethyl ester, the title compound (0.237 g; 63.8% overall yield) was obtained as a white solid, mp 181.5°–184° C. (recrystallized from ethanol-ethyl acetate), using the procedure of example 22.

Anal. Calcd for $C_{30}H_{36}O_9$: C, 66.65; H, 6.71. Found: C, 66.69; H, 6.76.

EXAMPLE 90

Preparation of
2-Methoxy-5-(1-oxo-1H-2-benzopyran-3-yl)benzenepropanoic Acid Ethyl Ester (Ro 25-2105/000),
2-Hydroxy-5-(1-oxo-1H-2-benzopyran-3-yl)benzenepropanoic Acid Ethyl Ester (Ro 25-2106/000), and
5-[[2-(2-Ethoxy-2-oxoethyl)phenyl]carbonyl]-2-methoxybenzenepropanoic Acid Ethyl Ester A mixture of 6.41 g (39.53 mmol) homophthalic anhydride, 8.21 g (39.42 mmol) of 2-methoxybenzenepropanoic acid ethyl ester, 21.03 g (0.158 mol) of aluminum chloride, and 75 mL of dry methylene chloride was stirred and heated in an oil bath kept at ca. 45° C. for 21 hr. The mixture was cooled to room temperature and then poured onto crushed ice. Aqueous sulfuric acid (3N, 150 ml) was added and the mixture was extracted three times with ether. The combined ethereal solution was washed twice with water and three times with saturated sodium bicarbonate solution (the organic phase was discarded). After being cooled in an ice bath, the aqueous alkaline phase was acidified with concentrated hydrochloric acid and the resulting solution was extracted once with ether and twice with ethyl acetate. The organic extracts were combined and processed in the usual manner to give 12.61 g of a white solid residue. This material was dissolved in 500 ml of ethanol and concentrated sulfuric acid (8 ml) was added. The resulting mixture was heated at reflux for 5.7 hr, and then cooled to room temperature. Most of the solvent was removed under aspirator pressure. The residue was taken up in ethyl acetate and processed in the usual manner (the organic solution was additionally washed with saturated sodium bicarbonate solution). The crude product was purified by flash chromatography on 500 g of silica gel, eluting with hexane-ethyl acetate (4:1 then 2:1) to give a less polar fraction (6.55 g) and a more polar fraction (2.34 g). Crystallization of the less polar fraction from ethanol afforded 2.42 g of 2-methoxy-5-(1-oxo-1H-2-benzopyran-3-yl)benzenepropanoic acid ethyl ester as colorless needles, mp 105°–105.5° C.

Anal. Calcd for $C_{21}H_{20}O_5$: C, 71.58; H, 5.72. Found: C, 71.59; H, 5.71.

From the remaining mother liquor (4.13 g), 1.3 g was purified further by flash chromatography on 100 g of silica gel, eluting with 4:1 hexane-ethyl acetate gave 1.26 g of 5-[[2-(2-ethoxy-2-oxoethyl)phenyl]carbonyl]-2-methoxybenzenepropanoic acid ethyl ester as a colorless oil.

Anal. Calcd for $C_{23}H_{26}O_6$: C, 69.33; H, 6.58. Found: C, 69.29; H, 6.55.

Similarly, crystallization of the more polar fraction from ethanol afforded 0.56 g of 2-hydroxy-5-(1-oxo-1H-2-benzopyran-3-yl)benzenepropanoic acid ethyl ester as an off-white solid, mp 179°–180° C.

Anal. Calcd for $C_{20}H_{18}O_5$: C, 71.00; H, 5.36. Found: C, 70.78; H, 5.33.

EXAMPLE 91

Preparation of 2-[5-[(3,4-Dihydro-4-oxo-8-propyl-2H-1-benzopyran-7-yl)oxy]pentyloxy]-5-(1-oxo-1H-2-benzopyran-3-yl)benzenepropanoic Acid Ethyl Ester A mixture of 0.352 g (0.99 mmol) of 7-[(5-bromopentyl)oxy]-2,3-dihydro-8-propyl-4H-1-benzopyran-4-one, 0.346 g (1.02 mmol) of 2-hydroxy-5-(1-oxo-1H-2-benzopyran-3-yl)benzenepropanoic acid ethyl ester, 0.574 g (4.15 mmol) of anhydrous granular potassium carbonate and 20.9 mL of 2-butanone was stirred and refluxed for 45 hrs. The resulting slurry was filtered with suction and the solids were washed thoroughly with ethyl acetate. The filtrate and washes were combined and concentrated in vacuo and the residue was purified by flash chromatography on 75 g of silica gel, eluting with 3:1 hexane-ethyl acetate, affording 0.352 g (58.1%) of the title compound as a white solid, mp 143.5°–144° C.

Anal. Calcd for $C_{37}H_{40}O_8$: C, 72.53; H, 6.58. Found: C, 72.68; H, 6.47.

EXAMPLE 92

Preparation of 5-[2-(2-Carboxyphenyl)-1-oxoethyl]-2-[5-[(3,4-dihydro-4-oxo-8-propyl-2H-1-benzopyran-7-yl)oxy]pentyloxy]-benzenepropanoic Acid A mixture of 0.145 g (0.24 mmol) of 2-[5-[(3,4-dihydro-4-oxo-8-propyl-2H-1-benzopyran-7-yl)oxy]pentyloxy]-5-(1-oxo-1H-2-benzopyran-3-yl)benzenepropanoic acid ethyl ester in 5 mL of THF and 5 mL of water was treated with 29.8 mg (0.71 mmol) of lithium hydroxide monohydrate and the mixture was stirred for 47 hrs. After being acidified with 16 mL of 3N aqueous sulfuric acid, the resulting mixture was worked up in the usual manner. The crude product was crystallized from hexane-ethyl acetate to give 0.114 g (79.6%) of the title compound as a white solid, mp 178°–182° C.

Anal. Calcd for $C_{35}H_{38}O_9$: C, 69.75; H, 6.36. Found: C, 69.66; H, 6.25.

EXAMPLE 93

Preparation of 5-[[2-(2-Ethoxy-2-oxoethyl)phenyl]carbonyl]-2-hydroxybenzenepropanoic Acid Ethyl Ester A mixture of 1.07 g (2.69 mmol) of 5-[[2-(2-ethoxy-2-oxoethyl)phenyl]carbonyl]-2-methoxybenzenepropanoic acid ethyl ester and 3.63 g (31.41 mmol) of pyridine hydrochloride was heated at 220°–260° C. for 40 min and then cooled to room temperature. Aqueous 3N sulfuric acid (40 mL) was added, and the mixture was worked-up with ethyl acetate in the usual manner. The crude product was dissolved in 150 mL of ethanol. To this solution was added 3 mL of thionyl chloride and the resulting solution was heated at reflux for 16 hr. The solvent was removed in vacuo and the crude product was purified by flash chromatography on 120 g of silica gel, eluting with 3:1 hexane-ethyl acetate. This afforded 0.469 g (45.4%) of the title compound as a pale yellow oil.

EXAMPLE 94

Preparation of 2-[(5-Bromopentyl)oxy]-5-[[2-(2-ethoxy-2-oxoethyl)-phenyl]carbonyl]benzenepropanoic Acid Ethyl Ester Starting with 0.436 g (1.13 mmol) of 5-[[2-(2-ethoxy-2-oxoethyl)phenyl]carbonyl]-2-hydroxybenzenepropanoic acid ethyl ester, and 6.80 g (29.57 mmol) of 1,5-dibromopentane, the title compound was obtained as a pale yellow oil, in 74% yield, using the procedure of example 21.

Anal. Calcd for $C_{27}H_{33}BrO_6$: C, 60.79; H, 6.24; Br, 14.98. Found: C, 60.38; H, 6.21; Br, 15.14.

EXAMPLE 95

Preparation of 5-[[2-(Carboxymethyl)phenyl]carbonyl]-2-[5-[(3,4-dihydro-4-oxo-8-propyl-2H-1-benzopyran-7-yl)oxy]pentyloxy]benzenepropanoic Acid Starting with 0.153 g (0.74 mmol) of 2,3-dihydro-7-hydroxy-8-propyl-4H-1-benzopyran-4-one, and 0.394 g (0.74 mmol) of 2-[(5-bromopentyl)oxy]-5-[[2-(2-ethoxy-2-oxoethyl)phenyl]carbonyl]benzenepropanoic acid ethyl ester, the title compound (0.103 g, 26.7% overall yield) was obtained as a white solid, mp 105°–108.5° C. (recrystallized from hexane-ethyl acetate), using the procedure of example 22.

Anal. Calcd for $C_{35}H_{38}O_9$: C, 69.75; H, 6.36. Found: C, 69.60; H, 6.45.

EXAMPLE 96

Preparation of 5-[[3-(Ethoxycarbonyl)phenyl]carbonyl]-2-[[(trifluoromethyl)sulfonyl]oxy]benzenepropanoic Acid Ethyl Ester To a solution of 8.50 g (22.95 mmol) of 5-[[3-(ethoxycarbonyl)phenyl]carbonyl]-2-hydroxybenzenepropanoic acid ethyl ester in 20 mL of pyridine cooled in an ice bath was added slowly 4.2 mL (24.97 mmol) of trifluoromethanesulfonic anhydride. After being stirred for 43 hr, the reaction mixture was treated with 100 mL of water and worked-up with ether in the usual manner. The crude product obtained was purified by flash chromatography on 600 g of silica gel, eluting with 4:1 hexane-ethyl acetate. This afforded 10.09 g (87.5%) of the title compound as a colorless oil.

Anal. Calcd for $C_{22}H_{21}F_3O_8S$: C, 52.59; H, 4.21; F, 11.34; S, 6.38. Found: C, 52.55; H, 4.20; F, 11.10; S, 6.68.

EXAMPLE 97

Preparation of (Z)-5-[[3-(Ethoxycarbonyl)phenyl]carbonyl]-2-(6-hydroxy-1-hexenyl)benzenepropanoic Acid Ethyl Ester and (E)-5-[[3-(Ethoxycarbonyl)phenyl]carbonyl]-2-(6-hydroxy-1-hexenyl)benzenepropanoic Acid Ethyl Ester A mixture of 1.78 g (3.55 mmol) of 5-[[3-(ethoxycarbonyl)phenyl]carbonyl]-2-[[(trifluoromethyl)sulfonyl]oxy]benzenepropanoic acid ethyl ester, 1.476 g (3.73 mmol) of (E/Z)-tri-n-butyl-(6-hydroxy-1-hexenyl)stannane, 0.456 g (10.76 mmol) of lithium chloride, 0.24 g (0.21 mmol) of tetrakis(triphenylphosphine)palladium, a few crystals of 2,6-di-tert-butyl-4-methylphenol and 20 mL of dioxane was stirred and heated at reflux for a total of 2.75 hr. After being cooled to room temperature, the reaction mixture was treated with 2 mL of pyridine and 4 mL of a solution of HF in pyridine/THF (ca. 1.2N) and stirring was continued overnight. The mixture was taken up in 200 mL of ether, filtered through Celite, and worked up in the usual manner. The crude product was purified by flash chromatography on 200 g of silica gel, eluting with 2:1 hexane-ethyl acetate. This afforded 0.17 g (10.6%) of (Z)-5-[[3-(ethoxycarbonyl)phenyl]carbonyl]-2-(6-hydroxy-1-hexenyl)benzenepropanoic acid ethyl ester as a colorless oil. Further elution gave 0.516 g (32.2%) of mixed fractions followed by 0.789 g (49.2%) of (E)-5-[[3-(ethoxycarbonyl)phenyl]carbonyl]-2-(6-hydroxy-1-hexenyl)benzenepropanoic acid ethyl ester as a white solid, mp 48°–50° C.

Anal. Calcd for $C_{27}H_{32}O_6$: C, 71.66; H, 7.13. Found: C, 71.48; H, 7.11.

EXAMPLE 98

Preparation of 2-(6-Bromohexyl)-5-[[3-(ethoxycarbonyl)phenyl]carbonyl]benzenepropanoic Acid Ethyl Ester To a solution of 0.686 g (1.52 mmol) of a mixture of (E/Z)-5-[[3-(ethoxycarbonyl)phenyl]carbonyl]-2-(6-hydroxy-1-hexenyl)benzenepropanoic acid ethyl ester in 5 mL of ethanol and 5 mL of ethyl acetate was added 110 mg of 10% Pd/C catalyst, and the mixture was hydrogenated at atmospheric pressure until no further hydrogen uptake could be observed. The mixture was filtered through Celite, the filter cake was washed thoroughly with ethyl acetate, and the filtrate and washes were combined and concentrated in vacuo to give 0.563 g of the saturated product. To this was added 0.822 g (2.48 mmol) of carbon tetrabromide, 0.65 g (2.48 mmol) of triphenylphosphine and 10 mL of ether, and the mixture was stirred overnight. The mixture was filtered through Celite, the filter cake was washed thoroughly with ether, and the combined filtrate and washes concentrated in vacuo. The crude product was purified by flash chromatography on 50 g of silica gel, eluting with 6:1 hexane-ethyl acetate affording 0.486 g (61.9% overall yield) of the title compound as a colorless oil.

Anal. Calcd for $C_{27}H_{33}BrO_5$: C, 62.67; H, 6.43; Br, 15.42. Found: C, 62.43; H, 6.43; Br, 15.18.

EXAMPLE 99

Preparation of 5-[(3-Carboxyphenyl)carbonyl]-2-[6-[(3,4-dihydro-4-oxo-8-propyl-2H-1-benzopyran-7-yl)oxy]hexyl]benzenepropanoic Acid Starting with 0.169 g (0.82 mmol) of 2,3-dihydro-7-hydroxy-8-propyl-4H-1-benzopyran-4-one and 0.425 g (0.82 mmol) of 2-(6-bromohexyl)-5-[[3-(ethoxycarbonyl)phenyl]carbonyl]benzenepropanoic acid ethyl ester, the title compound (0.157 g; 34.7% overall yield) was obtained as a white solid, mp 137°–139° C. (recrystallized from hexane-ethyl acetate), using the procedure of example 22.

Anal. Calcd for $C_{35}H_{38}O_8$: C, 71.66; H, 6.53. Found: C, 71.25; H, 6.89.

EXAMPLE 100

Preparation of (E)-2-(6-Bromo-1-hexenyl)-5-[[3-(ethoxycarbonyl)phenyl]carbonyl]benzenepropanoic Acid Ethyl Ester Starting with 0.660 g (1.46 mmol) of (E)-5-[[3-(ethoxycarbonyl)phenyl]carbonyl]-2-(6-hydroxy-1-hexenyl)benzenepropanoic acid ethyl ester, the title compound (0.667 g; 88.8%) was obtained as a colorless oil, using the procedure of example 98 but omitting the hydrogenation step.

EXAMPLE 101

Preparation of (E)-5-[(3-Carboxyphenyl)carbonyl]-2-[6-[(3,4-dihydro-4-oxo-8-propyl-2H-1-benzopyran-7-yl)oxy]-1-hexenyl]benzenepropanoic Acid Starting with 0.242 g (1.17 mmol) of 2,3-dihydro-7-hydroxy-8-propyl-4H-1-benzopyran-4-one and 0.604 g (1.17 mmol) of (E)-2-(6-bromo-1-hexenyl)-5-[[3-(ethoxycarbonyl)phenyl]carbonyl]benzenepropanoic acid ethyl ester, the title compound was obtained (97 mg; 15.8% overall yield) as a white solid, mp 105°–109° C. (recrystallized from hexane-ethyl acetate), using the procedure of example 22.

Anal. Calcd for $C_{35}H_{36}O_8$: C, 71.90; H, 6.21. Found: C, 71.61; H, 6.16.

EXAMPLE 102

Preparation of 2-[(5-Hexynyl)oxy]benzenepropanoic Acid Methyl Ester

A mixture of 0.98 g (10 mmol) of 5-hexyn-1-ol, 1.98 g (11 mmol) of 2-hydroxybenzenepropanoic acid methyl ester, 2.88 g (11 mmol) of triphenylphosphine, 1.91 g (11 mmol) of diethyl azodicarboxylate, and 220 mL of dry tetrahydrofuran was stirred at room temperature for 100 hr and then concentrated under reduced pressure. The residue was triturated with 9:1 hexane-ether. The solid was filtered with suction and washed with the same solvent mixture. The filtrate and washes were combined and concentrated in vacuo. Flash chromatography of the residue on silica gel, eluting with 9:1 hexane-ether gave 2 g (77%) of 2-[(5-hexynyl)oxy]benzenepropanoic acid methyl ester as a colorless oil.

EXAMPLE 103

Preparation of 2,3-Dihydro-8-propyl-7-[[(trifluoromethyl)sulfonyl]oxy]-4H-1-benzopyran-4-one A solution of 0.824 g (4 mmol) of 2,3-dihydro-7-hydroxy-8-propyl-4H-1-benzopyran-4-one and 4 mL of dry pyridine in 20 mL of dichloromethane was stirred with cooling to 0° C. while 1.69 g (6 mmol) of trifluoromethanesulfonic anhydride was added dropwise. The solution was stirred at 0° C. for 1 hr and at room temperature for 2 hr. After being recooled, the reaction mixture was treated with an additional 0.5 mL (3 mmol) of trifluoromethanesulfonic anhydride and stirring was continued at 0° C. for 1 hr and at room temperature for 2 hr. The reaction mixture was stored at 0°–5° C. overnight before being poured into cold 3N HCl. Work-up with ether in the usual manner (the organic extract was additionally washed with saturated sodium bicarbonate solution) gave an oily product which was flash chromatographed on silica gel. Elution with 1:1 hexane-ether gave 1.14 g (84%) of 2,3-dihydro-8-propyl-7-[[(tri-

EXAMPLE 104

Preparation of
2-[6-(3,4-Dihydro-4-oxo-8-propyl-2H-1-benzopyran-7-yl)-5-hexynyloxy]benzenepropanoic Acid Methyl Ester A mixture of 1.14 g (3.37 mmol) of 2,3-dihydro-8-propyl-7-[[(trifluoromethyl)sulfonyl]oxy]-4H-1-benzopyran-4-one, 0.94 g (3.62 mmol) of 2-[(5-hexynyl)oxy]benzenepropanoic acid methyl ester, 4.9 mL of dry triethylamine, 0.197 g (0.28 mmol) of dichlorobis(triphenylphosphine)palladium (II), and 21 mL of dry dimethylformamide was stirred and heated at 100° C. for 3 hr. The mixture was cooled, poured into ice-water, and worked-up with ether in the usual manner. The orange-red, oily residue was flash chromatographed on silica gel. Elution with 1:1 hexane-ether gave 1.25 g (83%) of 2-[6-(3,4-dihydro-4-oxo-8-propyl-2H-1-benzopyran-7-yl)-5-hexynyloxy]benzenepropanoic acid methyl ester as a yellow oil.

EXAMPLE 105

Preparation of
2-[6-(3,4-Dihydro-4-oxo-8-propyl-2H-1-benzopyran-7-yl)hexyloxy]benzenepropanoic Acid Methyl Ester Catalytic hydrogenation of 2-[6-(3,4-dihydro-4-oxo-8-propyl-2H-1-benzopyran-7-yl)-5-hexynyloxy]benzenepropanoic acid methyl ester in methanol was carried out using the procedure of example 51. 2-[6-(3,4-Dihydro-4-oxo-8-propyl-2H-1-benzopyran-7-yl)hexyloxy]benzenepropanoic acid methyl ester was obtained as a colorless oil, in 86% yield.

EXAMPLE 106

Preparation of
2-[6-(3,4-Dihydro-4-oxo-8-propyl-2H-1-benzopyran-7-yl)hexyloxy]benzenepropanoic Acid A mixture of 0.65 g (1.44 mmol) of 2-[6-(3,4-dihydro-4-oxo-8-propyl-2H-1-benzopyran-7-yl)hexyloxy]benzenepropanoic acid methyl ester, 2 mL of 3N aqueous lithium hydroxide, and 30 mL of tetrahydrofuran was stirred at room temperature for 24 hr and then concentrated in vacuo. The residue was diluted with water and extracted 3 times with ether (the ether extracts were discarded). The aqueous alkaline solution was acidified with 3N HCl and worked-up with ether in the usual manner. The oily residue was chromatographed on silica gel. Elution with 2:1 toluene-ethyl acetate containing acetic acid afforded 0.5 g (79.3%) of 2-[6-(3,4-dihydro-4-oxo-8-propyl-2H-1-benzopyran-7-yl)hexyloxy]benzenepropanoic acid as viscous, colorless oil.

Anal. Calcd for $C_{27}H_{34}O_5$: C, 73.94; H, 7.81. Found: C, 73.83; H, 7.69.

EXAMPLE 107

Preparation of
2-[6-(3,4-Dihydro-4-oxo-8-propyl-2H-1-benzopyran-7-yl)-5-hexynyloxy]benzenepropanoic Acid A 0.5 g (1.12 mmol) sample of 2-[6-(3,4-dihydro-4-oxo-8-propyl-2H-1-benzopyran-7-yl)-5-hexynyloxy]benzenepropanoic acid methyl ester from example 104 was saponified using the procedure of example 106. The crude acid product was purified by flash chromatography on silica gel eluting with toluene-ethyl acetate mixtures containing 2% acetic acid, and recrystallization from acetonitrile giving 2-[6-(3,4-dihydro-4-oxo-8-propyl-2H-1-benzopyran-7-yl)-5-hexynyloxy]benzenepropanoic acid as a colorless solid, mp 88°–92° C.

EXAMPLE 108

Preparation of
(E)-3-[2-[(5-Bromopentyl)oxy]phenyl]-2-propenoic Acid Methyl Ester A mixture of 0.64 g (3.59 mmol) of methyl 2-hydroxycinnamate, 6.6. g (28.7 mmol) of 1,5-dibromopentane, 2 g (14.5 mmol) of anhydrous, granular potassium carbonate, and 25 mL of acetonitrile was stirred and refluxed for 24 hr. The resulting slurry was cooled, diluted with ether, and filtered with suction. The solids were washed well with ether. The filtrate and washes were combined and concentrated under reduced pressure. The oily residue was flash chromatographed on silica gel, eluting with 5:1 hexane-ether giving 1 g (85%) of (E)-3-[2-[(5-bromopentyl)oxy]phenyl]-2-propenoic acid methyl ester as a solid.

EXAMPLE 109

Preparation of
(E)-3-[2-[5-[(3,4-Dihydro-4-oxo-8-propyl-2H-1-benzopyran-7-yl)oxy]pentyloxy]phenyl]-2-propenoic Acid Using the procedure of example 4, and starting with 0.5 g (1.5 mmol) of (E)-3-[2-[(5-bromopentyl)oxy]phenyl]-2-propenoic acid methyl ester and 0.3 g (1.45 mmol) of 2,3-dihydro-7-hydroxy-8-propyl-4H-1-benzopyran-4-one, (E)-3-[2-[5-[(3,4-dihydro-4-oxo-8-propyl-2H-1-benzopyran-7-yl)oxy]pentyloxy]phenyl]-2-propenoic acid was obtained in 24% overall yield after purification by flash chromatography (silica gel, chloroform-methanol-acetic acid) and recrystallization from acetonitrile as a colorless solid, mp 123°–126° C.

Anal. Calcd for $C_{26}H_{30}O_6$: C, 71.23; H, 6.84. Found: C, 71.01; H, 6.97.

EXAMPLE 110

Preparation of
rac-4-[3-Formyl-4-[6-[(tetrahydro-2H-pyran-2-yl)oxy]-hexyl]phenoxy]butanoic Acid Ethyl Ester A 1.2 g (2.88 mmol) sample of rac-4-[3-formyl-4-[6-[(tetrahydro-2H-pyran-2-yl)oxy]-1-hexyn-1-yl]phenoxy]butanoic acid ethyl ester from example 49 was hydrogenated in ethyl acetate using 80 mg of 10% palladium on carbon, at room temperature, under 1 atmosphere of hydrogen. When the reduction was complete, the catalyst was filtered with suction and the filtrate concentrated under reduced pressure giving rac-4-[3-formyl-4-[6-[(tetrahydro-2H-pyran-2-yl)oxy]hexyl]phenoxy]butanoic acid ethyl ester as a pale-yellow oil, in quantitative yield.

EXAMPLE 111

Preparation of
rac-(E)-4-[3-(3-Methoxy-3-oxo-1-propenyl)-4-[6-[(tetrahydro-2H-pyran-2-yl)oxy]hexyl]phenoxy]butanoic Acid Ethyl Ester Using the procedure of example 28 and starting with 1.2 g (2.88 mmol) of rac-4-[3-formyl-4-[6-[(tetrahydro-2H-pyran-2-yl)oxy]hexyl]phenoxy]butanoic acid ethyl ester from the preceding example, and 1.12 g (3.36 mmol) of methyl (triphenylphosphoranylidene)-acetate, rac-(E)-4-[3-(3-methoxy-3-oxo-1-propenyl)-4-[6-[(tetrahydro-2H-pyran-2-yl)oxy]hexyl]phenoxy]butanoic acid ethyl ester was prepared, in 66% yield (0.9 g), as a colorless oil.

EXAMPLE 112

Preparation of
(E)-4-[4-(6-Hydroxyhexyl)-3-(3-methoxy-3-oxo-1-propenyl)phenoxy]butanoic Acid Methyl Ester Using the procedure of example 52, rac-(E)-4-[3-(3-methoxy-3-oxo-1-propenyl)-4-[6-[(tetrahydro-2H-pyran-2-yl)oxy]hexyl]phenoxy]butanoic acid ethyl ester (0.9 g; 1.89 mmol) was converted into (E)-4-[4-(6-hydroxyhexyl)-3-(3-methoxy-3-oxo-1-propenyl)-phenoxy]butanoic acid methyl ester as a pale-yellow oil, in 92% yield (0.66 g).

EXAMPLE 113

Preparation of
(E)-4-[3-(3-Methoxy-3-oxo-1-propenyl)-4-[6-[(methylsulfonyl)oxy]hexyl]phenoxy]butanoic Acid Methyl Ester Using the procedure of example 32, (E)-4-[4-(6-hydroxyhexyl)-3-(3-methoxy-3-oxo-1-propenyl)-phenoxy]butanoic acid methyl ester (0.66 g; 1.74 mmol) was converted into (E)-4-[3-(3-methoxy-3-oxo-1-propenyl)-4-[6-[(methylsulfonyl)oxy]hexyl]phenoxy]-butanoic acid methyl ester, a pale-yellow oil, in 96% yield (0.76 g).

EXAMPLE 114

Preparation of
(E)-4-[3-(2-Carboxyethenyl)-4-[6-[(3,4-dihydro-4-oxo-8propyl-2H-1-benzopyran-7-yl)oxy]hexyl]phenoxy]-butanoic Acid Using the procedure of example 11 and starting with 0.26 g (1.3 mmol) of 2,3-dihydro-7-hydroxy-8-propyl-4H-1-benzopyran-4-one and 0.76 g (1.3 mmol) of (E)-4-[3-(3-methoxy-3-oxo-1-propenyl)-4-[6-[(methylsulfonyl)oxy]hexyl]phenoxy]butanoic acid methyl ester (from example 113), (E)-4-[3-(2-carboxyethenyl)-4-[6-[(3,4-dihydro-4-oxo-8-propyl-2H-1-benzopyran-7-yl)oxy]-hexyl]phenoxy]butanoic acid methyl ester was obtained in 95% yield (0.36 g) as a colorless oil which crystallized on standing. Recrystallization from ethyl acetate-hexane gave 0.51 g (69%) of a colorless solid, mp 65°–66° C. A 0.2 g (0.35 mmol) sample of diester prepared in this way was saponified with 2 mL of 3N aqueous lithium hydroxide in 10 mL of tetrahydrofuran, at room temperature, for 22 hr. Work-up as in example 4 gave a crude acid product which was purified by chromatography on silica gel (toluene-ethyl acetate containing 2% acetic acid) and recrystallization from acetonitrile. There was obtained 0.1 g (53%) of (E)-4-[3-(2-carboxyethenyl)-4-[6-[(3,4-dihydro-4-oxo-8-propyl-2H-1-benzopyran-7-yl)oxy]hexyl]phenoxy]-butanoic acid as an off-white solid mp 140°–143° C.

Anal. Calcd for $C_{31}H_{38}O_8$: C, 69.14; H, 7.06. Found: C, 68.83; H, 7.11.

EXAMPLE 115

Preparation of
1-[2-Hydroxy-4-(phenylmethoxy)-3-pentylphenyl]ethanone

A mixture of 3.11 g (14 mmol) of 2,4-dihydroxy-3-pentylacetophenone, 1.67 mL (14 mmol) of benzyl bromide, 7.73 g (56 mmol) of anhydrous, granular potassium carbonate and 31 mL of N,N-dimethylformamide was stirred at room temperature for 3 days and then concentrated in vacuo. The residue was flash chromatographed on silica gel, eluting with hexane-ether mixtures. There was obtained 1.42 g (32.5%) of 1-[2-hydroxy-4-(phenylmethoxy)-3-pentylphenyl]ethanone as a solid. A sample was recrystallized from ether-hexane giving a colorless solid, mp 61°–62° C.

Anal. Calcd for $C_{20}H_{24}O_3$: C, 76.90; H, 7.74. Found: C, 76.73; H, 7.76.

EXAMPLE 116

Preparation of
7-(Phenylmethoxy)-8-pentyl-4H-1-benzopyran-4-one

Using the procedure of example 1, 1.4 g (4.48 mmol) of 1-[2-hydroxy-4-(phenylmethoxy)-3-pentylphenyl]ethanone was converted into 7-(phenylmethoxy)-8-pentyl-4H-1-benzopyran-4-one as a beige solid, in 55% yield. An analytical specimen was obtained by recrystallization from ether, as a colorless solid, mp 65.5°–67° C.

Anal. Calcd for $C_{21}H_{22}O_3$: C, 78.26; H, 6.83. Found: C, 77.99; H, 6.92.

EXAMPLE 117

Preparation of
2,3-Dihydro-7-hydroxy-8-pentyl-4H-1-benzopyran-4-one

Using the procedure of example 2, 3.22 g (10 mmol) of 7-(phenylmethoxy)-8-pentyl-4H-1-benzopyran-4-one was catalytically hydrogenated giving 2,3-dihydro-7-hydroxy-8-pentyl-4H-1-benzopyran-4-one, as a solid, in 66% yield. A sample was recrystallized from acetonitrile giving a colorless solid, mp 132°–133.5° C.

Anal. Calcd for $C_{14}H_{18}O_3$: C, 71.77; H, 7.24. Found: C, 71.71; H, 7.67.

EXAMPLE 118

Preparation of
2-[5-[(3,4-Dihydro-4-oxo-8-pentyl-2H-1-benzopyran-7-yl)oxy]pentyloxy]benzenepropanoic Acid Using the procedure of example 11 and starting with 1.25 g (5.34 mmol) of 2,3-dihydro-7-hydroxy-8-pentyl-4H-1-benzopyran-4-one (from example 117) and 1.64 g (4.76 mmol) of 2-[[5-[(methylsulfonyl)oxy]pentyl]oxy]-benzenepropanoic acid methyl ester (from example 72), 2-[5-[(3,4-dihydro-4-oxo-8-pentyl-2H-1-benzopyran-7-yl)oxy]pentyloxy]benzenepropanoic acid methyl ester was obtained in 98% yield (2.52 g) as a pale-yellow oil. This diester (5.18 mmol) was saponified with 7.8 mL of 3N aqueous lithium hydroxide in 25 mL of tetrahydrofuran, at room temperature, for 48 hr. Work-up as in example 4 gave 2-[5-[(3,4-dihydro-4-oxo-8-pentyl-2H-1-benzopyran-7-yl)oxy]pentyloxy]benzenepropanoic acid as an oil. This material was flash chromatographed on silica gel eluting with ethyl acetate-hexane mixtures giving 0.69 g (28.5%) of pure acid as a solid. Recrystallization from acetonitrile gave a colorless solid, mp 86°–87° C.

Anal. Calcd for $C_{28}H_{36}O_6$: C, 71.70; H, 7.68. Found: C, 71.30; H, 7.64.

EXAMPLE 119

Preparation of Trifluoromethanesulfonic Acid 2-Oxo-2H-1-benzopyran-5-yl Ester

A mixture of 1.62 g (10 mmol) of 5-hydroxycoumarin and 10 mL of dry pyridine in 25 mL of dichloromethane was stirred with ice-bath cooling while 4.5 g (16 mmol) of trifluoromethanesulfonic anhydride was added dropwise. The mixture was stirred in the cold for 30 min and then allowed to warm to room temperature and stirred for an additional 30 min before being poured into 3N hydrochloric acid. Work-up with ether in the usual manner gave a yellow solid. Flash chromatography on silica gel, eluting with 2:1 hexane-ethyl acetate afforded 2.6 g (88.4%) of trifluoromethanesulfonic acid 2-oxo-2H-1-benzopyran-5-yl ester as an off-white solid mp 104°–105° C.

Anal. Calcd for $C_{10}H_5F_3O_5S$: C, 40.83; H, 1.71. Found: C, 40.65; H, 1.59.

EXAMPLE 120

Preparation of rac-5-[6-[(Tetrahydro-2H-pyran-2-yl)oxy]-1-hexynyl]-2H-1-benzopyran-2-one A mixture of 1.47 g (5 mmol) of trifluoromethanesulfonic acid 2-oxo-2H-1-benzopyran-5-yl ester, 1.0 g (5.5 mmol) of rac-6-[(tetrahydro-2H-pyran-2-yl)oxy]-1-hexyne, 75 mg of cuprous iodide, 0.3 g (0.428 mmol) of dichlorobis(triphenylphosphine)palladium (II), 7.5 mL of triethylamine, and 35 mL of dry N,N-dimethylformamide was stirred and heated at 100° C. for 24 hr. The reaction mixture was cooled, poured into water, and worked-up with ether in the usual manner. The darkbrown, oily residue was flash chromatographed on silica gel. Elution with 2:1 hexane-ethyl acetate gave 1.09 g (67%) of rac-5-[6-[(tetrahydro-2H-pyran-2-yl)oxy]-1-hexynyl]-2H-1-benzopyran-2-one as an orange oil.

EXAMPLE 121

Preparation of rac-(E)-3-[2-Hydroxy-6-[6-[(tetrahydro-2H-pyran-2-yl)oxy]-1-hexynyl]phenyl]-2-propenoic Acid Methyl Ester A solution of 1.09 g (3.3 mmol) of rac-5-[6-[(tetrahydro-2H-pyran-2-yl)oxy]-1-hexynyl]-2H-1-benzopyran-2-one and 1.8 mL (7.9 mmol) of 25% methanolic sodium methoxide in 5 mL of methanol was stirred and refluxed for 24 hr and then concentrated under reduced pressure. The residue was treated with 1N hydrochloric acid and worked-up with ethyl acetate in the usual manner (the organic extracts were additionally washed with saturated aqueous sodium bicarbonate). The residue was purified by flash chromatography on silica gel, eluting with 2:1 hexane-ether. There was obtained 0.7 g (59%) of rac-(E)-3-[2-hydroxy-6-[6-[(tetrahydro-2H-pyran-2-yl)oxy]-1-hexynyl]phenyl]-2-propenoic acid methyl ester as a yellow oil. Trituration of a sample prepared in this way with hexane gave a colorless solid, mp 66°–67.5° C.

Anal. Calcd for $C_{21}H_{26}O_5$: C, 70.37; H, 7.31. Found: C, 70.24; H, 7.33.

EXAMPLE 122

Preparation of rac-(E)-5-[2-(3-Methoxy-3-oxo-1-propenyl)-3-[6-[(tetrahydro-2H-pyran-2-yl)oxy]-1-hexynyl]phenoxy]pentanoic Acid Ethyl Ester A mixture of 0.7 g (1.95 mmol) of rac-(E)-3-[2-hydroxy-6-[6-[(tetrahydro-2H-pyran-2-yl)oxy]-1-hexynyl]phenyl]-2-propenoic acid methyl ester, 0.45 g (2.14 mmol) of ethyl 5-bromovalerate, 0.75 g (5.4 mmol) of anhydrous, granular potassium carbonate, and 8 mL of dimethyl sulfoxide was stirred at room temperature for 24 hr. The resulting mixture was poured into water and worked-up with ether in the usual manner. The crude product was flash chromatographed on silica gel, eluting with 2:1 hexane-ethyl acetate, affording 0.86 g (90%) of rac-(E)-5-[2-(3-methoxy-3-oxo-1-propenyl)-3-[6-[(tetrahydro-2H-pyran-2-yl)oxy]-1-hexynyl]phenoxy]pentanoic acid ethyl ester as a colorless oil.

EXAMPLE 123

Preparation of rac-2-(5-Ethoxy-5-oxopentyloxy)-6-[6-[(tetrahydro-2H-pyran-2-yl)oxy]hexyl]benzenepropanoic Acid Methyl Ester A 0.86 g (1.76 mmol) sample of rac-(E)-5-[2-(3-methoxy-3-oxo-1-propenyl)-3-[6-[(tetrahydro-2H-pyran-2-yl)oxy]-1-hexynyl]phenoxy]pentanoic acid ethyl ester was hydrogenated in 50 mL of methanol, over 50 mg of 10% palladium on carbon, at room temperature and 1 atmosphere. Rac-2-(5-ethoxy-5-oxopentyloxy)-6-[6-[(tetrahydro-2H-pyran-2-yl)oxy]hexyl]benzenepropanoic acid methyl ester, an oil, was isolated by filtration of the catalyst and concentration of the filtrate, in quantitative yield.

EXAMPLE 124

Preparation of 2-(6-Hydroxyhexyl)-6-(5-methoxy-5-oxopentyloxy)benzenepropanoic Acid Methyl Ester Using the procedure of example 52, rac-2-(5-ethoxy-5-oxopentyloxy)-6-[6-[(tetrahydro-2H-pyran-2-yl)oxy]hexyl]benzenepropanoic acid methyl ester (0.87 g; 1.76 mmol) was converted into 2-(6-hydroxyhexyl)-6-(5-methoxy-5-oxopentyloxy)benzenepropanoic acid methyl ester, a colorless oil, in 53% yield.

EXAMPLE 125

Preparation of 2-(5-Methoxy-5-oxopentyloxy)-6-[6-[(methylsulfonyl)oxy]hexyl]benzenepropanoic Acid Methyl Ester Using the procedure of example 32, 2-(6-hydroxyhexyl)-6-(5-methoxy-5-oxopentyloxy)benzenepropanoic acid methyl ester was converted into 6-[6-[(methylsulfonyl)oxy]hexyl]-2-(5-methoxy-5-oxopentyloxy)benzenepropanoic acid methyl ester, an oil, in quantitative yield.

EXAMPLE 126

Preparation of 2-(4-Carboxybutoxy)-6-[6-[(3,4-dihydro-4-oxo-8-propyl-2H-1-benzopyran-7-yl)oxy]hexyl]benzenepropanoic Acid Using the procedure of example 11 and starting with 0.412 g (2.0 mmol) of 2,3-dihydro-7-hydroxy-8-propyl-4H-1-benzopyran-4-one and 1.0 g (2.1 mmol) of 6-[6-[(methylsulfonyl)oxy]hexyl]-2-(5-methoxy-5-oxopentyloxy)benzenepropanoic acid methyl ester, 6-(5-methoxy-5-oxopentyloxy)-2-[6-[(3,4-dihydro-4-oxo-8-propyl-2H-1-benzopyran-7-yl)oxy]hexyl]benzenepropanoic acid methyl ester was obtained in 83% yield (0.97 g) as a colorless oil. This diester (1.7 mmol) was saponified with 5 mL of 3N aqueous lithium hydroxide in 40 mL of tetrahydrofuran, at room temperature, for 20 hr. Work-up as in example 4 gave an oily acid which was flash-chromatographed on silica gel, eluting with 95:5:1 chloroform-methanol-acetic acid. There was obtained 0.76 g (81%) of pure 2-(4-carboxybutoxy)-6-[6-[(3,4-dihydro-4-oxo-8-propyl-2H-1-benzopyran-7-yl)oxy]hexyl]benzenepropanoic acid. Recrystallization from hexane-ethyl acetate (2:1) gave 0.64 g (68%) of a colorless solid, mp 103°–104° C.

Anal. Calcd for $C_{32}H_{42}O_8$: C, 69.29; H, 7.63. Found: C, 69.22; H, 7.58.

EXAMPLE 127

Preparation of 5-[(2-Oxo-2H-1-benzopyran-5-yl)oxy]pentanoic Acid Ethyl Ester A mixture of 2.25 g (18.6 mmol) of 5-hydroxycoumarin, 4.2 g (20 mmol) of ethyl 5-bromovalerate, 7.0 g (50 mmol) of anhydrous, granular potassium carbonate, and 10 mL of dimethyl sulfoxide was stirred at room temperature for 24 hr. The resulting slurry was filtered with suction and the solids washed well with ethyl acetate. The filtrate and washes were combined and poured into water and the mixture was worked-up with ethyl acetate in the usual manner. The semi-solid residue was triturated and washed with hexane giving 2.36 g (44%) of 5-[(2-oxo-2H-1-benzopyran-5-yl)oxy]pentanoic acid ethyl ester as a tan solid.

EXAMPLE 128

Preparation of (E)-5-[3-Hydroxy-2-(3-methoxy-3-oxo-1-propenyl)-phenoxy]pentanoic Acid Methyl Ester A solution of 2.36 g (8.15 mmol) of 5-[(2-oxo-2H-1-benzopyran-5-yl)oxy]pentanoic acid ethyl ester, 4.46 mL of 25% methanolic sodium methoxide, and 15 mL of methanol was stirred and refluxed for 2 days and then concentrated under reduced pressure. The residue was treated with 1N hydrochloric acid and extracted with ethyl acetate. The combined ethyl acetate extracts were washed twice with saturated aqueous sodium bicarbonate and work-up was completed in the usual manner giving 1.1 g of a beige solid. This material was chromatographed on silica gel affording 0.93 g of (E)-5-[3-hydroxy-2-(3-methoxy-3-oxo-1-propenyl)phenoxy]pentanoic acid methyl ester as a colorless solid, mp 97°–98° C. The aqueous alkaline washes were combined, acidified to pH 1, and worked-up with ethyl acetate in the usual manner to give 1.4 g of brown, oily acidic material. This acid fraction was reesterified by refluxing in 30 mL of methanol containing 0.1 g of p-toluenesulfonic acid monohydrate, for 24 hr. After concentration, usual work-up with ethyl acetate, and chromatography, an additional 0.9 g of the desired product was obtained (total yield: 1.83 g, 73%).

EXAMPLE 129

Preparation of (E)-5-[3-[[(Trifluoromethyl)sulfonyl]oxy]-2-(3-methoxy-3-oxo-1-propenyl)phenoxy]pentanoic Acid Methyl Ester Using the procedure of example 119, (E)-5-[3-hydroxy-2-(3-methoxy-3-oxo-1-propenyl)phenoxy]pentanoic acid methyl ester (1.8 g; 5.83 mmol) was converted into (E)-5-[[3-[(trifluoromethyl)sulfonyl]oxy]-2-(3-methoxy-3-oxo-1-propenyl)phenoxy]pentanoic acid methyl ester, a yellow oil, in 89% yield.

EXAMPLE 130

Preparation of rac-(E)-5-[2-(3-Methoxy-3-oxo-1-propenyl)-3-[6-[(tetrahydro-2H-pyran-2-yl)oxy]-1-hexynyl]phenoxy]pentanoic Acid Methyl Ester A mixture of 2.27 g (5 mmol) of (E)-5-[3-[[(trifluoromethyl)sulfonyl]oxy]-2-(3-methoxy-3-oxo-1-propenyl)phenoxy]pentanoic acid methyl ester, 1.0 g (5.5 mmol) of rac-6-[(tetrahydro-2H-pyran-2-yl)oxy]-1-hexyne, 0.3 g (0.428 mmol) of dichlorobis(triphenylphosphine)palladium (II), 0.075 g of cuprous iodide, 7.5 mL of dry triethylamine, and 35 mL of dry N,N-dimethylformamide was stirred and heated at 100° C. for 3.5 hr. An additional 0.25 g of the acetylene was added and heating was continued for 24 hr at which point 0.75 g of the acetylene was added and heating was continued for 6 hr. The resulting mixture was cooled, poured into water and worked-up with ethyl acetate in the usual manner. The crude, oily product was chromatographed on silica gel. Elution with 10:1 toluene-ethyl acetate afforded 0.9 g (38%) of rac-(E)-5-[2-(3-methoxy-3-oxo-1-propenyl)-3-[6-[(tetrahydro-2H-pyran-2-yl)oxy]-1-hexynyl]phenoxy]pentanoic acid methyl ester as a yellow oil.

EXAMPLE 131

Preparation of rac-2-(5-Methoxy-5-oxopentyloxy)-6-[6-[(tetrahydro-2H-pyran-2-yl)oxy]hexyl]benzenepropanoic Acid Methyl Ester A 0.9 g (1.9 mmol) sample of rac-5-[2-(3-methoxy-3-oxo-1-propenyl)-3-[6-[(tetrahydro-2H-pyran-2-yl)oxy]-1-hexyn-1-yl]phenoxy]pentanoic acid methyl ester was hydrogenated in 60 mL of 1:1 methanol-ethyl acetate, over 70 mg of 10% palladium on carbon, at room temperature and 1 atmosphere. rac-2-(5-Methoxy-5-oxopentyloxy)-6-[6-[(tetrahydro-2H-pyran-2-yl)oxy]hexyl]benzenepropanoic acid methyl ester, an oil, was isolated by filtration of the catalyst and concentration of the filtrate, in quantitative yield.

EXAMPLE 132

Preparation of 2-(6-Hydroxyhexyl)-6-(5-Methoxy-5-oxopentyloxy)-benzenepropanoic Acid Methyl Ester Using the procedure of example 52, rac-2-(5-methoxy-5-oxopentyloxy)-6-[6-[(tetrahydro-2H-pyran-2-yl)oxy]hexyl]benzenepropanoic acid methyl ester (0.98 g; 2.0 mmol) was converted into 2-(6-hydroxyhexyl)-6-(5-methoxy-5-oxopentyloxy)benzenepropanoic acid methyl ester, a colorless oil, in 83% yield. This material was identical to that produced as described in example 124.

EXAMPLE 133

Preparation of (E)-4-[3-Hydroxy-4-(3-methoxy-3-oxo-1-propenyl)-phenoxy]butanoic Acid Methyl Ester Using the procedure of example 121, 4-[(2-oxo-2H-1-benzopyran-7-yl)oxy]butanoic acid ethyl ester was converted into (E)-4-[3-hydroxy-4-(3-methoxy-3-oxo-1-propenyl)phenoxy]butanoic acid methyl ester, a beige solid, mp 108°–112° C., in 83% yield.

EXAMPLE 134

Preparation of
(E)-4-[3-[[5-(Acetyloxy)pentyl]oxy]-4-(3-methoxy-3-oxo-1-propenyl)phenoxy]butanoic Acid Methyl Ester Using the procedure of example 63, and starting with 2.01 g (6.84 mmol) of (E)-4-[3-hydroxy-4-(3-methoxy-3-oxo-1-propenyl)phenoxy]butanoic acid methyl ester and 1.57 g (7.51 mmol) of 5-bromopentyl acetate, (E)-4-[3-[[(5-(acetyloxy)pentyl]oxy]-4-(3-methoxy-3-oxo-1-propenyl)phenoxy]butanoic acid methyl ester was obtained, in quantitative yield, as a pale-yellow oil.

EXAMPLE 135

Preparation of
(E)-4-[3-[(5-Hydroxypentyl)oxy]-4-(3-methoxy-3-oxo-1-propenyl)phenoxy]butanoic Acid Methyl Ester A solution of 2.91 g (6.8 mmol) of (E)-4-[3-[[(5-acetyloxy)pentyl]oxy]-4-(3-methoxy-3-oxo-1-propenyl)phenoxy]butanoic acid methyl ester and 0.11 g of p-toluenesulfonic acid monohydrate in 60 mL of methanol was stirred and refluxed for 5 hr and then concentrated under reduced pressure. Treatment of the residue with water gave a solid which was filtered with suction, washed with water, and dried under high vacuum giving 2.54 g of a solid. This material was chromatographed on 50 g of silica gel. Elution with 1:1 hexane-ethyl acetate afforded 2.04 g (78.5%) of (E)-4-[3-[(5-hydroxypentyl)oxy]-4-(3-methoxy-3-oxo-1-propenyl)phenoxy]butanoic acid methyl ester as a colorless solid.

EXAMPLE 136

Preparation of
2-[(5-Hydroxypentyl)oxy]-4-(4-methoxy-4-oxobutoxy)-benzenepropanoic Acid Methyl Ester A 2.0 g (5.26 mmol) sample of (E)-4-[3-[(5-hydroxypentyl)oxy]-4-(3-methoxy-3-oxo-1-propenyl)phenoxy]butanoic acid methyl ester was hydrogenated in 100 mL of 1:1 methanol-ethyl acetate, over 0.1 g of 10% palladium on carbon, at room temperature and 1 atmosphere. 2-[(5-Hydroxypentyl)oxy]-4-(4-methoxy-4-oxobutoxy)benzenepropanoic acid methyl ester, an oil, was isolated by filtration of the catalyst and concentration of the filtrate, in quantitative yield.

EXAMPLE 137

Preparation of
2-[[5-[(Methylsulfonyl)oxy]pentyl]oxy]-4-(4-methoxy-4-oxobutoxy)benzenepropanoic Acid Methyl Ester Using the procedure of example 32, the 2-[(5-hydroxypentyl)oxy]-4-(4-methoxy-4-oxobutoxy)benzenepropanoic acid methyl ester from the preceding example (2.0 g; 5.23 mmol) was convered into 2-[[5-[(methylsulfonyl)oxy]pentyl]oxy]-4-(4-methoxy-4-oxobutoxy)-benzenepropan acid methyl ester in essentially quantitative yield and was used without further purification.

EXAMPLE 138

Preparation of
4-(3-Carboxypropoxy)-2-[5-[(3,4-dihydro-4-oxo-8-propyl-2H-1-benzopyran-7-yl)oxy]pentyloxy]benzenepropanoic Acid Using the procedure of example 11 and starting with 0.28 g (1.4 mmol) of 2,3-dihydro-7-hydroxy-8-propyl-4H-1-benzopyran-4-one and 0.65 g (1.41 mmol) of 2-[[5-[(methylsulfonyl)oxy]pentyl]oxy]-4-(4-methoxy-4-oxobutoxy)benzenepropanoic acid methyl ester (from example 137), 4-(4-methoxy-4-oxobutoxy)-2-[5-[(3,4-dihydro-4-oxo-8-propyl-2H-1-benzopyran-7-yl)oxy]-pentyloxy]benzenepropanoic acid methyl ester was obtained in 75% yield (0.6 g) as a solid, mp 58°–59° C. This diester (1.05 mmol) was saponified with 3 mL of 3N aqueous lithium hydroxide in 30 mL of tetrahydrofuran, at room temperature, for 16 hr. Work-up as in example 4 but using dichloromethane rather than ether gave a solid acid which was flash-chromatographed on silica gel, eluting with 95:5:1 chloroform-methanol-acetic acid. Recrystallization from ethyl acetate gave 0.44 g (78%) of pure 4-(3-carboxypropoxy)-2-[5-[(3,4-dihydro-4-oxo-8-propyl-2H-1-benzopyran-7-yl)oxy]-pentyloxy]benzenepropanoic acid as a colorless solid, mp 163°–164° C.

Anal. Calcd for $C_{30}H_{38}O_9$: C, 66.40; H, 7.06. Found: C, 66.63; H, 7.05.

EXAMPLE 139

Preparation of
3-(3-Ethoxy-3-oxopropyl)-4-methoxy-δ-oxobenzenepentanoic Acid

A mixture of 10.61 g (50.95 mmol) of 2-methoxybenzenepropanoic acid ethyl ester, 9.30 g (81.51 mmol) of glutaric anhydride, 20.89 g (0.157 mol) of aluminum chloride and 100 mL of anhydrous methylene chloride was stirred and heated in an oil bath kept at 46° C., for 16.5 hr. The temperature of the oil bath was raised to 80° C. and stirring was continued for another 3 hr. After being cooled to room temperature, the mixture was poured onto crushed ice. To this was added 200 mL of water and 200 mL of 6N HCl solution and most of the organic solvents were removed under aspirator pressure. The residue was extracted 3 times with ethyl acetate and the combined ethyl acetate extract was washed once with 3N sulfuric acid solution, once with water, and finally, 3 times with saturated sodium carbonate solution. The combined sodium carbonate solution was back extracted once with ether (which was discarded) and then cooled in an ice bath. To this cold, alkaline solution was slowly added concentrated hydrochloric acid solution. The precipitate was collected by filtration to give 12.14 g (73.9%) of a light-beige solid. An analytical sample was obtained by recrystallization from ethanol to give the title compound as colorless needles, mp 124°–126° C.

Anal. Calcd for $C_{17}H_{22}O_6$: C, 63.34; H, 6.88. Found: C, 63.66; H, 6.96.

EXAMPLE 140

Preparation of
3-(3-Ethoxy-3-oxopropyl)-4-hydroxy-δ-oxobenzenepentanoic Acid Ethyl Ester A mixture of 1.61 g (5.0 mmol) of 3-(3-ethoxy-3-oxopropyl)-4-methoxy-δ-oxobenzenepentanoic acid and 11.56 g (0.1 mol) of pyridine hydrochloride was heated at ca. 240° C. for 1.33 hr. After being cooled to room temperature, the reaction mixture was treated with 100 mL of water and extracted twice with ether and once with ethyl acetate. The organic extracts were processed in the usual manner to give 1.30 g of a tan solid which was dissolved in 120 mL of ethanol. To this solution was slowly added 30 drops of thionyl chloride. The resulting solution was heated at reflux for 7 hr and then kept at room temperature for ca. 65 hr. The solvent was removed in vacuo and the residue was purified by flash chromatography on 100 g of silica gel, eluting with 3:1 hexane-ethyl acetate, to give 1.44 g (85.6%) of the title compound as a light-tan solid, mp 68°–69° C.

Anal. Calcd for $C_{18}H_{24}O_6$: C, 64.27; H, 7.19. Found: C, 64.39; H, 7.31.

EXAMPLE 141

Preparation of 3-(3-Ethoxy-3-oxopropyl)-4-methoxy-γ-oxobenzenebutanoic Acid

Starting with a mixture of 3.12 g (15.0 mmol) of 2-methoxybenzenepropanoic acid ethyl ester, 1.53 g (15.3 mmol) of succinic anhydride, 4.46 g (33.5 mmol) of aluminum chloride and 20 mL of methylene chloride, the title compound (3.59 g, 77.7%) was obtained as a white solid, mp 128°–129° C. (recrystallized from ethanol), using the procedure of example 139.

Anal. Calcd for $C_{16}H_{20}O_6$: C, 62.33; H, 6.54. Found: C, 62.50; H, 6.61.

EXAMPLE 142

Preparation of 3-(3-Ethoxy-3-oxopropyl)-4-hydroxy-γ-oxobenzenebutanoic Acid Ethyl Ester Starting with a mixture of 6.48 g (21.0 mmol) of 3-(3-ethoxy-3-oxopropyl)-4-methoxy-γ-oxobenzenebutanoic acid and 24.4 g (0.211 mol) of pyridine hydrochloride, the title compound (2.87 g, 42.4%) was obtained as a light-tan oil, using the procedure of example 140.

Anal. Calcd for $C_{17}H_{22}O_6$: C, 63.34; H, 6.88. Found: C, 63.03; H, 6.84.

EXAMPLE 143

Preparation of 5-[[4-(Ethoxycarbonyl)phenyl]carbonyl]-2-hydroxybenzenepropanoic Acid Ethyl Ester A mixture of 3.6 g (20 mmol) of 4-carboxybenzoic acid methyl ester, 25 mL of toluene and 6 mL of thionyl chloride was heated in an oil bath kept at ca. 90° C. Another 25 mL of toluene was added after 1 hr, an additional 6 mL quantity of thionyl chloride was added after 2.3 hr, and heating was continued for an additional 25 hr. The solvent and excess thionyl chloride were removed in vacuo. To the residue was added 25 mL of toluene and 6 mL of thionyl chloride and the mixture was again heated at 95° C. for 0.5 hr and then at 45° C. for 64 hr and finally at 90° C. for 3 hr. The solvent and excess thionyl chloride were again removed in vacuo. This crude acid chloride was mixed with 4.16 g (20 mmol) of 2-methoxybenzenepropanoic acid ethyl ester and 45 ml of methylene chloride. Aluminum chloride 10.7 g (80 mmol) was added in one portion and the resulting mixture was heated in an oil bath kept at 45° C. for 18 hr and then at 75° C. for 3.5 hr. After being cooled to room temperature, the mixture was poured onto crushed ice and 75 mL of 3N sulfuric acid solution was added. The resulting mixture was worked-up with ether in the usual manner. The residue was dissolved in 200 mL of ethanol. Concentrated sulfuric acid (5 mL) was added and the solution was heated under reflux for 5.8 hr. Most ethanol was removed under aspirator pressure and the residue was worked-up with ethyl acetate as usual. The crude product was purified by flash chromatography on 700 g of silica gel, eluting with 3:1 hexane-ethyl acetate, affording 2.0 g (27.1%) of the title compound as an off-white solid, mp 70°–71° C.

Anal. Calcd for $C_{21}H_{22}O_6$: C, 68.10; H, 5.99. Found: C, 68.07; H, 6.16.

Further elution gave 1.325 g of a mixture of the title compound and 5-[[4-(methoxycarbonyl)phenyl]carbonyl]-2-hydroxybenzenepropanoic acid ethyl ester.

EXAMPLE 144

Preparation of 2-[(5-Bromopentyl)oxy]benzenebutanoic Acid Methyl Ester

Using the procedure of example 108, 2-hydroxybenzenebutanoic acid methyl ester was converted into the title compound by alkylation with 1,5-dibromopentane, in 81% yield, as a colorless oil.

EXAMPLE 145

Preparation of 2-[5-[(3,4-Dihydro-4-oxo-8-propyl-2H-1-benzopyran-7-yl)oxy]pentyloxy]benzenebutanoic Acid Using the procedure of example 4, 2,3-dihydro-7-hydroxy-8-propyl-4H-1-benzopyran-4-one was converted into the title compound by alkylation with 2-[(5-bromopentyl)oxy]benzenebutanoic acid methyl ester from the preceding example, followed by saponification, in 46.5% overall yield. The product was an off-white solid, mp 116°–118° C., recrystallized from acetonitrile.

Anal. Calcd for $C_{27}H_{34}O_6$: C, 71.34; H, 7.54. Found: C, 71.23; H, 7.62.

EXAMPLE 146

Preparation of 2-[(5-Bromopentyl)oxy]benzenepentanoic Acid Methyl Ester

Using the procedure of example 108, 2-hydroxybenzenepentanoic acid methyl ester was converted into the title compound in 78% yield, as a colorless oil.

EXAMPLE 147

Preparation of 2-[5-[(3,4-Dihydro-4-oxo-8-propyl-2H-1-benzopyran-7-yl)oxy]pentyloxy]benzenepentanoic Acid Using the procedure of example 4, 2,3-dihydro-7-hydroxy-8-propyl-4H-1-benzopyran-4-one was converted into the title compound by alkylation with 2-[(5-bromopentyl)oxy]benzenepentanoic acid methyl ester from the preceding example, followed by saponification, in 46.5% overall yield. The product was an off-white solid, mp 75°–76° C., recrystallized from hexane-ethyl acetate.

Anal. Calcd for $C_{28}H_{36}O_6$: C, 71.77; H, 7.74. Found: C, 71.83; H, 7.93.

EXAMPLE 148

Preparation of rac-(E)-3-[2-(2-Methoxy-2-oxoethoxy)]-6-[6-[(tetrahydro-2H-pyran-2-yl)oxy]-1-hexynyl]phenyl]-2-propenoic Acid Methyl Ester Using the procedure of example 122, rac-(E)-3-[2-hydroxy-6-[6-[(tetrahydro-2H-pyran-2-yl)oxy]-1-hexynyl]phenyl]-2-propenoic acid methyl ester (example 121) was alkylated with methyl bromoacetate giving the title compound, in 75% yield, as a colorless oil.

EXAMPLE 149

Preparation of
rac-2-(2-Methoxy-2-oxoethoxy)-6-[6-[(tetrahydro-2H-pyran-2-yl)oxy]hexyl]benzenepropanoic Acid Methyl Ester Using the procedure of example 123, rac-(E)-3-[2-(2-methoxy-2-oxoethoxy)]-6-[6-[(tetrahydro-2H-pyran-2-yl)oxy]-1-hexynyl]phenyl]-2-propenoic acid methyl ester from the preceding example was catalytically hydrogenated giving the title compound in quantitative yield, as a colorless oil.

EXAMPLE 150

Preparation of
2-(6-Hydroxyhexyl)-6-(2-methoxy-2-oxoethoxy)benzenepropanoic Acid Methyl Ester Using the procedure of example 52, rac-2-(2-methoxy-2-oxoethoxy)-6-[6-[(tetrahydro-2H-pyran-2-yl)oxy]hexyl]benzenepropanoic acid methyl ester from the preceding example was converted to the title compound in 41.3% yield, as a colorless oil.

EXAMPLE 151

Preparation of
2-(2-Methoxy-2-oxoethoxy)-6-[6-[(methylsulfonyl)oxy]hexyl]benzenepropanoic Acid Methyl Ester Using the procedure of example 32, 2-(6-hydroxyhexyl)-6-(2-methoxy-2-oxoethoxy)benzenepropanoic acid methyl ester from the preceding experiment was converted into the title compound, a yellow oil, in 91% yield.

EXAMPLE 152

Preparation of
2-(Carboxymethoxy)-6-[6-[(3,4-dihydro-4-oxo-8-propyl-2H-1-benzopyran-7-yl)oxy]hexyl]benzenepropanoic Acid Using the procedure of example 126, 2,3-dihydro-7-hydroxy-8-propyl-4H-1-benzopyran-4-one was converted into the title compound by alkylation with 2-(2-methoxy-2-oxoethoxy)-6-[6-[(methylsulfonyl)oxy]hexyl]benzenepropanoic acid methyl ester from the preceding example, followed by saponification, in 64.4% overall yield. The product was an off-white solid, mp 127°–129° C., recrystallized from hexane-ethyl acetate.

Anal. Calcd for $C_{29}H_{36}O_8$: C, 67.95; H, 7.08. Found: C, 67.75; H, 7.18.

EXAMPLE 153

Preparation of
rac-(E)-6-[2-(3-Methoxy-3-oxo-1-propenyl)-3-[6-[(tetrahydro-2H-pyran-2-yl)oxy]-1-hexynyl]phenoxy]hexanoic Acid Ethyl Ester Using the procedure of example 122, rac-(E)-3-[2-hydroxy-6-[6-[(tetrahydro-2H-pyran-2-yl)oxy]-1-hexynyl]phenyl]-2-propenoic acid methyl ester (example 121), was alkylated with ethyl 6-bromohexanoate giving the title compound as a pale-yellow oil, in 93.3% yield.

EXAMPLE 154

Preparation of
rac-2-[(6-Ethoxy-6-oxohexyl)oxy]-6-[6-[(tetrahydro-2H-pyran-2-yl)oxy]hexyl]benzenepropanoic Acid Methyl Ester Using the procedure of example 123, rac-E-6-[2-(3-methoxy-3-oxo-1-propenyl)-3-[6-[(tetrahydro-2H-pyran-2-yl)oxy]-1-hexynyl]phenoxy]hexanoic acid ethyl ester from the preceding example, was catalytically hydrogenated, giving the title compound as an oil, in quantitative yield.

EXAMPLE 155

Preparation of
2-(6-Hydroxyhexyl)-6-[(6-methoxy-6-oxohexyl)oxy]benzenepropanoic Acid Methyl Ester Using the procedure of example 52, rac-2-[(6-ethoxy-6-oxohexyl)oxy]-6-[6-[(tetrahydro-2H-pyran-2-yl)oxy]hexyl]benzenepropanoic acid methyl ester was converted to the title compound, a colorless oil, in 90% yield.

EXAMPLE 156

Preparation of
2-[(6-Methoxy-6-oxohexyl)oxy]-6-[6-[(methylsulfonyl)oxy]hexyl]benzenepropanoic Acid Methyl Ester Using the procedure of example 32, 2-(6-hydroxyhexyl)-6-[(6-methoxy-6-oxohexyl)oxy]benzenepropanoic acid methyl ester from the preceding example, was converted into the title compound, an oil, in quantitative yield.

EXAMPLE 157

Preparation of
2-[(5-Carboxypentyl)oxy]-6-[6-[(3,4-dihydro-4-oxo-8-propyl-2H-1-benzopyran-7-yl)oxy]hexyl]benzenepropanoic Acid Using the procedure of example 126, 2,3-dihydro-7-hydroxy-8-propyl-4H-1-benzopyran-4-one was converted into the title compound by alkylation with 2-[(6-methoxy-6-oxohexyl)oxy]-6-[6-(methylsulfonyl)oxyhexyl]benzenepropanoic acid methyl ester from the preceding example, followed by saponification, in 79% overall yield. The product was a colorless solid, mp 86°–88° C., recrystallized from hexane-ethyl acetate.

Anal. Calcd for $C_{33}H_{44}O_8$: C, 69.70; H, 7.80. Found: C, 69.78; H, 7.83.

EXAMPLE 158

Preparation of
(E,E)-3,3'-(4-Hydroxy-1,3-phenylene)bis-2-propenoic Acid Dimethyl Ester A mixture of 5.0 g (33.3 mmol) of 5-formyl-salicylaldehyde and 24.5 g (73.3 mmol) of methyl (triphenylphosphoranylidene)acetate, in 150 mL of toluene was stirred and refluxed for 2.5 hr and then kept at room temperature overnight. The solvent was removed in vacuo and the solid residue was flash-chromatographed on silica gel. There was obtained 8.07 g (92.5%) of the title compound as a colorless solid.

EXAMPLE 159

Preparation of
(E,E)-3,3'-[4-[[5-(Acetyloxy)pentyl]oxy]-1,3-phenylene]-bis-2-propenoic Acid Dimethyl Ester Using the procedure of example 63, (E,E)-3,3'-(4-hydroxy-1,3-phenylene)bis-2-propenoic acid dimethyl ester from the preceding example was converted into the title compound, a solid, in 85% yield.

EXAMPLE 160

Preparation of
4-[[5-(Acetyloxy)pentyl]oxy]-1,3-benzenedipropanoic Acid Dimethyl Ester Catalytic hydrogenation of 10.17 g (26.04 mmol) of (E,E)-3,3'-[4-[[5-(acetyloxy)pentyl]oxy]-1,3-phenylene]bis-2-propenoic acid dimethyl ester from the preceding example was carried out using 2.03 g of 10% palladium on carbon, in 125 mL of dry tetrahydrofuran, at room temperature and 1 atmosphere. After filtration of the catalyst and concentration of the filtrate, the title compound was obtained in quantitative yield, as a pale-yellow oil.

EXAMPLE 161

Preparation of
4-[(5-Hydroxypentyl)oxy]-1,3-benzenedipropanoic Acid Dimethyl Ester Using the procedure of example 135, 4-[[5-(acetyloxy)pentyl]oxy]-1,3-benzenedipropanoic acid dimethyl ester from the preceding example was converted into the title compound, a pale-yellow oil, in 93.5% yield.

EXAMPLE 162

Preparation of
4-[[5-[(Methylsulfonyl)oxy]pentyl]oxy]-1,3-benzenedipropanoic Acid Dimethyl Ester Using the procedure of example 32, 4-[(5-hydroxypentyl)oxy]-1,3-benzenedipropanoic acid dimethyl ester from the preceding example was converted into the title compound, a light-tan oil, in quantitative yield.

EXAMPLE 163

Preparation of
4-[5-[(3,4-Dihydro-4-oxo-8-propyl-2H-1-benzopyran-7-yl)oxy]pentyloxy]-1,3-benzenedipropanoic Acid Using the procedure of example 126, 2,3-dihydro-7-hydroxy-8-propyl-4H-1-benzopyran-4-one was converted into the title compound by alkylation with 4-[5-(methylsulfonyl)oxypentyloxy]-1,3-benzenedipropanoic acid methyl ester from the preceding example, followed by saponification, in 8% overall yield. The product was a colorless solid, mp 108°–109° C., recrystallized from hexane-ethyl acetate.

Anal. Calcd for $C_{29}H_{36}O_8$: C, 66.72; H, 6.97. Found: C, 66.49; H, 7.05.

EXAMPLE 164

Preparation of
rac-(E)-3-[2-[6-[(Tetrahydro-2H-pyran-2-yl)oxy]-1-hexynyl]-6-[[(trifluoromethyl)sulfonyl]oxy]phenyl]-2-propenoic Acid Methyl Ester Using the procedure of example 119, rac-(E)-3-[2-hydroxy-6-[6-[(tetrahydro-2H-pyran-2-yl)oxy]-1-hexynyl]phenyl]-2-propenoic acid methyl ester from example 121 was converted into the title compound, a tan oil, in quantitative yield.

EXAMPLE 165

Preparation of
rac-(E)-6-[2-(3-Methoxy-3-oxo-1-propenyl)-3-[6-[(tetrahydro-2H-pyran-2-yl)oxy]-1-hexynyl]phenyl]-5-hexynoic Acid Methyl Ester Using the procedure of example 130, rac-(E)-3-[2-[6-[(tetrahydro-2H-pyran-2-yl)oxy]-1-hexynyl]-6-[[(trifluoromethyl)sulfonyl]oxy]phenyl]-2-propenoic acid methyl ester from the preceding example was converted into the title compound, a tan oil, by reaction with methyl 5-hexynoate, in 68.3% yield.

EXAMPLE 166

Preparation of
rac-2-(3-Methoxy-3-oxopropyl)-3-[6-[(tetrahydro-2H-pyran-2-yl)oxy]hexyl]benzenehexanoic Acid Methyl Ester Rac-(E)-6-[2-(3-methoxy-3-oxo-1-propenyl)-3-[6-[(tetrahydro-2H-pyran-2-yl)oxy]-1-hexynyl]phenyl]-5-hexynoic acid methyl ester from the preceding example was catalytically hydrogenated over 10% palladium on carbon, in methanol, at room temperature and 1 atmosphere. The title compound was obtained, in 97% yield, as a pale-yellow oil.

EXAMPLE 167

Preparation of
3-(6-Hydroxyhexyl)-2-(3-methoxy-3-oxopropyl)benzenehexanoic Acid Methyl Ester Using the procedure of example 52, rac-2-(3-methoxy-3-oxopropyl)-3-[6-[(tetrahydro-2H-pyran-2-yl)oxy]hexyl]benzenehexanoic acid methyl ester from the preceding example was converted into the title compound, a pale-yellow oil, in 88.4% yield.

EXAMPLE 168

Preparation of
2-(3-Methoxy-3-oxopropyl)-3-[6-[(methylsulfonyl)oxy]hexyl]benzenehexanoic Acid Methyl Ester Using the procedure of example 32, 3-(6-hydroxyhexyl)-2-(3-methoxy-3-oxopropyl)benzenehexanoic acid methyl ester from the preceding example was converted to the title compound, an oil, in quantitative yield.

EXAMPLE 169

Preparation of
2-(2-Carboxyethyl)-3-[6-[(3,4-dihydro-4-oxo-8-propyl-2H-1-benzopyran-7-yl)oxy]hexyl]benzenehexanoic Acid Using the procedure of example 126, 2,3-dihydro-7-hydroxy-8-propyl-4H-1-benzopyran-4-one was converted into the title compound by alkylation with 2-(3-methoxy-3-oxopropyl)-3-[6-[(methylsulfonyl)oxy]hexyl]benzenehexanoic acid methyl ester from the preceding example, followed by saponification, in 16.8% overall yield. The product was a colorless solid, mp 109°–110° C., recrystallized from acetonitrile.

Anal. Calcd for $C_{33}H_{44}O_7$: C, 71.71; H, 8.02. Found: C, 71.80; H, 7.84.

EXAMPLE 170

Preparation of rac-(E)-5-[2-(3-Methoxy-3-oxo-1-propenyl)-3-[6-[(tetrahydro-2H-pyran-2-yl)oxy]-1-hexynyl]phenoxy]-2,2-dimethylpentanoic Acid Methyl Ester Using the procedure of example 122, rac-(E)-3-[2-hydroxy-6-[6-[(tetrahydro-2H-pyran-2-yl)oxy]-1-hexynyl]phenyl]-2-propenoic acid methyl ester (example 121) was alkylated with methyl 5-bromo-2,2-dimethylpentanoate giving the title compound, in 92% yield, as a colorless oil.

EXAMPLE 171

Preparation of rac-2-[(5-Methoxy-4,4-dimethyl-5-oxopentyl)oxy]-6-[6-[(tetrahydro-2H-pyran-2-yl)oxy]hexyl]benzenepropanoic Acid Methyl Ester Using the procedure of example 123, rac-(E)-5-[2-(3-methoxy-3-oxo-1-propenyl)-3-[6-[(tetrahydro-2H-pyran-2-yl)oxy]-1-hexynyl]phenoxy]-2,2-dimethylpentanoic acid methyl ester from the preceding example, was catalytically hydrogenated, giving the title compound as an oil, in quantitative yield.

EXAMPLE 172

Preparation of 2-(6-Hydroxyhexyl)-6-[(5-methoxy-4,4-dimethyl-5-oxopentyl)oxy]benzenepropanoic Acid Methyl Ester Using the procedure of example 52, rac-2-[(5-methoxy-4,4-dimethyl-5-oxopentyl)oxy]-6-[6-[(tetrahydro-2H-pyran-2-yl)oxy]hexyl]benzenepropanoic acid methyl ester from the preceding example was converted into the title compound, a colorless oil, in 88% yield.

EXAMPLE 173

Preparation of 2-[(5-Methoxy-4,4-dimethyl-5-oxopentyl)oxy]-6-[6-[(methylsulfonyl)oxy]hexyl]benzenepropanoic Acid Methyl Ester Using the procedure of example 32, 2-(6-hydroxyhexyl)-6-[(5-methoxy-4,4-dimethyl-5-oxopentyl)oxy]benzenepropanoic acid methyl ester from the preceding example, was converted into the title compound, a colorless oil, in 95% yield.

EXAMPLE 174

Preparation of 2-[(4-Carboxy-4-methylpentyl)oxy]-6-[6-[(3,4-dihydro-4-oxo-8-propyl-2H-1-benzopyran-7-yl)oxy]hexyl]benzenepropanoic Acid Using the procedure of example 126, 2,3-dihydro-7-hydroxy-8-propyl-4H-1-benzopyran-4-one was converted into the title compound by alkylation with 2-[(5-methoxy- 4,4-dimethyl-5-oxopentyl)oxy]-6-[6-[(methylsulfonyl)oxy]hexyl]benzenepropanoic acid methyl ester from the preceding example, followed by saponification, in 33.9% overall yield. The product was a colorless solid, mp 85°–87° C., recrystallized from hexane-ethyl acetate.

Anal. Calcd for $C_{34}H_{46}O_8$: C, 70.08; H, 7.96. Found: C, 70.07; H, 8.03.

EXAMPLE 175

Preparation of 5-[6-[[(1,1-Dimethylethyl)dimethylsilyl]oxy]-1-hexynyl]-2H-1-benzopyran-2-one Using the procedure of example 120, trifluoromethanesulfonic acid 2-oxo-2H-1-benzopyran-5-yl ester from example 119 was converted to the title compound by reaction with (1,1-dimethylethyl)(5-hexynyloxy)dimethylsilane. The product was a solid, obtained in 87% yield.

EXAMPLE 176

Preparation of (E)-3-[2-Hydroxy-6-(6-hydroxy-1-hexynyl)phenyl]-2-propenoic Acid Methyl Ester Using the procedure of example 121, 5-[6-[[(1,1-dimethylethyl)dimethylsilyl]oxy]-1-hexynyl]-2H-1-benzopyran-2-one from the preceding example was converted into the title compound, a solid, in 56% yield.

EXAMPLE 177

Preparation of (E)-3-[2-[[5-(Acetyloxy)pentyl]oxy]-6-(6-hydroxy-1-hexynyl)phenyl]-2-propenoic Acid Methyl Ester Using the procedure of example 63, (E)-3-[2-hydroxy-6-(6-hydroxy-1-hexynyl)phenyl]-2-propenoic acid methyl ester from the preceding example was converted into the title compound by alkylation with 5-bromopentylacetate. The product was obtained as a colorless oil in 77% yield.

EXAMPLE 178

Preparation of 2-[[5-(Acetyloxy)pentyl]oxy]-6-(6-hydroxyhexyl)benzenepropanoic Acid Methyl Ester Using the procedure of example 123, (E)-3-[2-[[5-(acetyloxy)pentyl]oxy]-6-(6-hydroxy-1-hexynyl)phenyl]-2-propenoic acid methyl ester from the preceding example was converted into the title compound by catalytic hydrogenation. The product was obtained in quantitative yield as a colorless oil.

EXAMPLE 179

Preparation of 2-[[5-(Acetyloxy)pentyl]oxy]-6-[6-[(methylsulfonyl)oxy]hexyl]benzenepropanoic Acid Methyl Ester Using the procedure of example 32, 2-[5-[(acetyloxy)pentyl]oxy]-6-(6-hydroxyhexyl)benzenepropanoic acid methyl ester from the preceding example was converted into the title compound, an oil, in 62% yield, after flash-chromatographic purification.

EXAMPLE 180

Preparation of 2-[6-[(3,4-Dihydro-4-oxo-8-propyl-2H-1-benzopyran-7-yl)oxy]hexyl]-6-[(5-hydroxypentyl)oxy]benzenepropanoic Acid Using the procedure of example 126, 2,3-dihydro-7-hydroxy-8-propyl-4H-1-benzopyran-4-one was converted into the title compound by alkylation with 2-[5-[(acetyloxy)pentyl]oxy]-6-[6-[(methylsulfonyl)oxy]hexyl]benzenepropanoic acid methyl ester from the preceding example, followed by saponification, in 57.4% overall yield. The product was a colorless solid, mp 102°–103° C., recrystallized from hexane-ethyl acetate.

Anal. Calcd for $C_{32}H_{44}O_7$: C, 71.08; H, 8.20. Found: C, 70.92; H, 8.26.

EXAMPLE 181

Preparation of
(E)-8-[2-(3-Methoxy-3-oxo-1-propenyl)-3-(6-hydroxy-1-hexynyl)phenoxy]octanoic Acid Methyl Ester Using the procedure of example 122, (E)-3-[2-hydroxy-6-(6-hydroxy-1-hexynyl)phenyl]-2-propenoic acid methyl ester (example 176) was alkylated with methyl 8-bromooctanoate giving the title compound, in 67% yield, as a colorless oil.

EXAMPLE 182

Preparation of
2-(6-Hydroxyhexyl)-6-[(8-methoxy-8-oxooctyl)oxy]benzenepropanoic Acid Methyl Ester Using the procedure of example 123, (E)-8-[2-(3-methoxy-3-oxo-1-propenyl)-3-(6-hydroxy-1-hexynyl)-phenoxy]octanoic acid methyl ester from the preceding example was converted into the title compound by catalytic hydrogenation. The product was obtained in quantitative yield as a colorless oil.

EXAMPLE 183

Preparation of
2-[(8-Methoxy-8-oxooctyl)oxy]-6-[6-[(methylsulfonyl)oxy]hexyl]benzenepropanoic Acid Methyl Ester Using the procedure of example 32, 2-(6-hydroxyhexyl)-6-[(8-methoxy-8-oxooctyl)oxy]benzenepropanoic acid methyl ester from the preceding example was converted into the title compound, a pale-yellow oil, in quantitative yield.

EXAMPLE 184

Preparation of
2-[(7-Carboxyheptyl)oxy]-6-[6-[(3,4-dihydro-4-oxo-8-propyl-2H-1-benzopyran-7-yl)oxy]hexyl]benzenepropanoic Acid A mixture of 0.68 g (1.3 mmol) of 2-[(8-methoxy-8-oxooctyl)oxy]-6-[6-[(methylsulfonyl)oxy]hexyl]benzenepropanoic acid methyl ester from the preceding example, 0.24 g (1.17 mmol) of 2,3-dihydro-7-hydroxy-8-propyl-4H-1-benzopyran-4-one, 0.26 g (1.88 mmol) of anhydrous granular potassium carbonate, 0.215 g (1.43 mmol) of anhydrous sodium iodide, and 10 mL of dry acetonitrile was stirred and refluxed for 24 hr. After being cooled, the reaction mixture was poured onto ice-water and worked-up with ether in the usual manner. The crude product was flash-chromatographed on silica gel, eluting with 2:1 hexane-ethyl acetate. There was obtained 0.69 g (94.5%) of 2-[(8-methoxy-8-oxooctyl)oxy]-6-[6-[(3,4-dihydro-4-oxo-8-propyl-2H-1-benzopyran-7-yl)-oxy]hexyl]benzenepropanoic acid methyl ester as a colorless oil. A solution of this diester and 2.5 mL of 3N aqueous lithium hydroxide in 15 mL of tetrahydrofuran was stirred at room temperature for 24 hr. The solvent was removed under reduced pressure and the residue was dissolved in water. The resulting solution was extracted with ether (the extracts were discarded) and then acidified with 3N aqueous hydrochloric acid. Work-up with ether in the usual manner gave an oily acid product which was flash-chromatographed on silica gel, eluting with 90:10:1 chloroform-methanol-acetic acid. Recrystallization of the pure acid from hexane-ethyl acetate afforded 0.5 g (76%) of the title compound as a colorless solid, mp 79°–81° C.

Anal. Calcd for $C_{35}H_{48}O_8$: C, 70.44; H, 8.11. Found: C, 70.33; H, 8.20.

EXAMPLE 185

Preparation of
(E)-9-[3-(6-Hydroxy-1-hexynyl)-2-(3-methoxy-3-oxo-1-propenyl)phenoxy]nonanoic Acid Methyl Ester Using the procedure of example 122, (E)-3-[2-hydroxy-6-(6-hydroxy-1-hexynyl)phenyl]-2-propenoic acid methyl ester (example 176) was alkylated with methyl 9-bromononanoate giving the title compound, in 71% yield, as a colorless oil.

EXAMPLE 186

Preparation of
2-(6-Hydroxyhexyl)-6-[(9-methoxy-9-oxononyl)oxy]benzenepropanoic Acid Methyl Ester Using the procedure of example 123, (E)-9-[3-(6-hydroxy-1-hexynyl)-2-(3-methoxy-3-oxo-1-propenyl)-phenoxy]nonanoic acid methyl ester from the preceding example was converted into the title compound by catalytic hydrogenation. The product was obtained in quantitative yield as a colorless oil.

EXAMPLE 187

Preparation of
2-[(9-Methoxy-9-oxononyl)oxy]-6-[6-[(methylsulfonyl)oxy]hexyl]benzenepropanoic Acid Methyl Ester Using the procedure of example 32, 2-(6-hydroxyhexyl)-6-[(9-methoxy-9-oxononyl)oxy]benzenepropanoic acid methyl ester from the preceding example was converted into the title compound, a pale-yellow oil, in quantitative yield.

EXAMPLE 188

Preparation of
2-[(8-Carboxyoctyl)oxy]-6-[6-[(3,4-dihydro-4-oxo-8-propyl-2H-1-benzopyran-7-yl)oxy]hexyl]benzenepropanoic Acid Using the procedure of example 184, the title compound was prepared in 47% overall yield by alkylation of 2,3-dihydro-7-hydroxy-8-propyl-4H-1-benzopyran-4-one with 2-[(9-methoxy-9-oxononyl)oxy]-6-[6-[(methylsulfonyl)oxy]hexyl]benzenepropanoic acid methyl ester from the preceding example followed by saponification. The diacid product was a colorless solid, mp 63°–65° C., recrystallized from hexane-ethyl acetate.

Anal. Calcd for $C_{36}H_{50}O_8$: C, 70.79; H, 8.25. Found: C, 71.02; H, 8.40.

EXAMPLE 189

Preparation of
1,3-Dimethoxy-2-(3-phenylpropyl)benzene

A solution of 8.70 g (63 mmol) of 1,3-dimethoxybenzene in 164 mL of anhydrous tetrahydrofuran was stirred at −20° C. while 1.6M n-butyllithium in hexane (42.1 mL; 67.2 mmol) was added dropwise, over 20 min. The solution was stirred at −20° C. for 3 hr and then allowed to warm to −5° C. whereupon 15.66 g (63.6 mmol) of 1-iodo-3-phenylpropane was added over 15 min. The reaction mixture was stirred at −5° C. for 1 hr and then at room temperature for 3 d. After being recooled to −5° C., the reaction mixture was decomposed by the addition of 1.5N aqueous sulfuric acid. Water was added and the mixture was worked-up with ether in the usual manner. The residue was treated with 100 mL of hexane and the mixture was filtered. Removal of the solvent in vacuo gave 15.28 g (94.7%) of the title compound as a yellow oil.

EXAMPLE 190

Preparation of
1-[2,4-Dimethoxy-3-(3-phenylpropyl)phenyl]ethanone

A solution of 15.28 g (59.6 mmol) of 1,3-dimethoxy-2-(3-phenylpropyl)benzene from the preceding example, and 4.68 g (59.6 mmol) of acetyl chloride, in 306 mL of dichloromethane was stirred at −5° to 0° C. and 7.95 g (59.6 mmol) of aluminum chloride was added. The resulting mixture was stirred at −5° to 0° C. for 2 hr and then allowed to warm to room temperature before being poured onto ice. Work-up with ether in the usual manner gave a product which was chromatographed on silica gel. Elution with 7:3 hexane-ether afforded 10.0 g (56.3%) of the title compound as a pale-yellow oil.

EXAMPLE 191

Preparation of
1-[2,4-Dihydroxy-3-(3-phenylpropyl)phenyl]ethanone

A solution of 10.0 g (33.5 mmol) of 1-[2,4-dimethoxy-3-(3-phenylpropyl)phenyl]ethanone from the preceding example in 250 mL of dichloromethane was stirred at −50° C. while 67 mL (67 mmol) of 1M boron tribromide in dichloromethane was added over a 15 min period. The reaction mixture was stirred at −50° C. for 1 hr and at room temperature for 3 days before being poured onto ice. Work-up with 9:1 dichloromethanemethanol in the usual manner gave a product which was chromatographed on silica gel. Elution with hexane-ether mixtures gave 6.69 g (74%) of the title compound as a solid. Recrystallization of a sample from ether-hexane gave colorless solid, mp 120°–122° C.

Anal. Calcd for $C_{17}H_{18}O_3$: C, 75.53; H, 6.71. Found: C, 75.31; H, 6.73.

EXAMPLE 192

Preparation of
1-[2-Hydroxy-4-(phenylmethoxy)-3-(3-phenylpropyl)-phenyl]ethanone A mixture of 6.69 g (24.7 mmol) of 1-[2,4-dihydroxy-3-(3-phenylpropyl)phenyl]ethanone, from the preceding example, 5.35 g (31.3 mmol) of benzyl bromide, 14.9 g (0.108 mol) of anhydrous potassium carbonate, 115 mL of dry N,N-dimethylformamide, and 230 mL of acetone was stirred and refluxed for 8 hr. After being cooled, the slurry was filtered with suction and the solids washed well with acetone. The filtrate and washes were combined and concentrated under reduced pressure to give a yellow oil which was chromatographed on silica gel. There was obtained 5.57 g (62.6%) of the desired monoether as a pale-yellow solid. Recrystallization of a sample from hexane-ethyl acetate gave the title compound as colorless needles, mp 115°–116° C.

Anal. Calcd for $C_{24}H_{24}O_3$: C, 79.97; H, 6.71. Found: C, 79.97; H, 6.80.

EXAMPLE 193

Preparation of
7-(Phenylmethoxy)-8-(3-phenylpropyl)-4H-1-benzopyran-4-one

Using the procedure of example 1, 1-[2-hydroxy-4-(phenylmethoxy)-3-(3-phenylpropyl)phenyl]ethanone from the preceding example, was converted into the title compound, a colorless solid, mp 106°–107.5° C. (recrystallized from hexane-ethyl acetate), in 56.7% yield.

Anal. Calcd for $C_{25}H_{22}O_3$: C, 81.05; H, 5.99. Found: C, 81.20; H, 5.99.

EXAMPLE 194

Preparation of
2,3-Dihydro-7-hydroxy-8-(3-phenylpropyl)-4H-1-benzopyran-4-one

Catalytic hydrogenation of 7-(phenylmethoxy)-8-(3-phenylpropyl)-4H-1-benzopyran-4-one, from the preceding example, using the procedure of example 2, gave the title compound, a colorless solid, mp 110°–112° C. (recrystallized from hexane-ether), in 44.9% yield.

Anal. Calcd for $C_{18}H_{18}O_3$: C, 76.57; H, 6.43. Found: C, 76.42; H, 6.43.

EXAMPLE 195

Preparation of
2-[[5-[[3,4-Dihydro-4-oxo-8-(3-phenylpropyl)-2H-1-benzopyran-7-yl]oxy]pentyl]oxy]benzenepropanoic Acid Using the procedure of example 11 and starting with 1.13 g (4 mmol) of 2,3-dihydro-7-hydroxy-8-(3-phenylpropyl)-4H-1-benzopyran-4-one (from example 194) and 1.38 g (4 mmol) of 2-[[5-[(methylsulfonyl)oxy]pentyl]oxy]benzenepropanoic acid methyl ester (from example 72), 2-[[5-[[3,4-dihydro-4-oxo-8-(3-phenylpropyl)-2H-1-benzopyran-7-yl]oxy]pentyl]oxy]benzenepropanoic acid methyl ester was obtained in 75.5% yield (1.6 g) as a pale-yellow oil. This diester (3 mmol) was saponified with 13.6 mL of 3N aqueous lithium hydroxide in 80 mL of tetrahydrofuran, at room temperature, for 96 hr. Work-up as in example 4 and recrystallization from ethyl acetate gave 0.6 g (38.5%) of the title acid, a colorless solid, mp 98°–99° C.

Anal. Calcd for $C_{32}H_{36}O_6$: C, 74.40; H, 7.02. Found: C, 74.47; H, 6.86.

EXAMPLE 196

Preparation of
2-[6-[(3,4-Dihydro-4-oxo-8-propyl-2H-1-benzopyran-7-yl)oxy]hexyl]-6-[[5-(dimethylamino)-5-oxopentyl]oxy]-N,N-dimethylbenzenepropanamide A solution of 0.555 g (1.0 mmol) of 2-(4-carboxybutoxy)-6-[6-[(3,4-dihydro-4-oxo-8-propyl-2H-1-benzopyran-7-yl)oxy]hexyl]benzenepropanoic acid from example 126, 0.196 g (2.4 mmol) of dimethylamine hydrochloride, 0.334 g (2.4 mmol) of 1-hydroxybenzotriazole, 0.48 g (2.5 mmol) of N-(3-dimethylaminopropyl)-N'-ethylcarbodiimide hydrochloride, 0.34 mL (2.4 mmol) of triethylamine, and 10 mL of dichloromethane was stirred overnight at room temperature. The reaction mixture was poured into 1N hydrochloric acid and worked-up with dichloromethane in the usual manner. The crude product was flash-chromatographed on silica gel, eluting with 98:1:1 chloroform-methanol-acetic acid. There was obtained 0.3 g (49%) of the title diamide as a colorless, viscous oil.

Anal. Calcd for $C_{36}H_{52}N_2O_6$: C, 71.02; H, 8.61; N, 4.60. Found: C, 70.89; H, 8.67; N, 4.50.

EXAMPLE 197

Preparation of 2-[6-[4-Acetyl-3-hydroxy-2-(3-phenylpropyl)phenoxy]hexyl]-6-[(6-methoxy-6-oxohexyl)oxy]benzenepropanoic Acid Methyl Ester A mixture of 0.81 g (3 mmol) of 1-[2,4-dihydroxy-3-(3-phenylpropyl)phenyl]ethanone from example 191, 1.6 g (3.29 mmol) of 2-[(6-methoxy-6-oxohexyl)oxy]-6-[6-[(methylsulfonyl)oxy]hexyl]benzenepropanoic acid methyl ester from example 156, 0.66 g (4.78 mmol) of anhydrous, granular potassium carbonate, 0.55 g (3.67 mmol) of sodium iodide, and 25 mL of acetonitrile was stirred and refluxed for 18.5 hr. The resulting thick slurry was cooled, diluted with ether, washed with water, 12% aqueous sodium bisulfite, and brine, and work-up was completed in the usual manner. Thin layer chromatographic analysis of the oily product revealed that alkylation was incomplete. Therefore, the product was dissolved in 5 mL of acetonitrile and 0.69 g (5 mmol) of anhydrous, granular potassium carbonate was added. The resulting mixture was stirred and refluxed for 24 hr before being worked-up as described above. The oily product (2.01 g) was chromatographed on 50 g of silica gel. Elution with 1:1 hexane-ether afforded 1.80 g (90.9%) of the title compound as an almost colorless oil.

EXAMPLE 198

Preparation of 2-[(6-Methoxy-6-oxohexyl)oxy]-6-[6-[[4-oxo-8-(3-phenylpropyl)-4H-1-benzopyran-7-yl]oxy]hexyl]benzenepropanoic Acid Methyl Ester Using the procedure of example 1 with the modification that methanol was used in place of ethanol, 2-[6-[4-acetyl-3-hydroxy-2-(3-phenylpropyl)phenoxy]hexyl]-6-[(6-methoxy-6-oxohexyl)oxy]benzenepropanoic acid methyl ester from the preceding example was converted into the title compound, a pale-yellow oil purified by flash-chromatography on silica gel (eluting with 3:1 toluene-ethyl acetate), in 57.4% yield.

EXAMPLE 199

Preparation of 2-[6-[[3,4-Dihydro-4-oxo-8-(3-phenylpropyl)-2H-1-benzopyran-7-yl]oxy]hexyl]-6-[(6-methoxy-6-oxohexyl)oxy]benzenepropanoic Acid Methyl Ester A 1.0 g (1.49 mmol) sample of 2-[(6-methoxy-6-oxohexyl)oxy]-6-[6-[[4-oxo-8-(3-phenylpropyl)-4H-1-benzopyran-7-yl]oxy]hexyl]benzenepropanoic acid methyl ester from the preceding example was catalytically hydrogenated over 10% palladium on carbon, in 30 mL of 1:1 methanol-ethyl acetate, at room temperature and 1 atmosphere, using thin-layer chromatography to monitor the reduction of the starting chromone. The catalyst was filtered and the filtrate was concentrated in vacuo giving an oily product which was purified by flash-chromatography. There was obtained 0.38 g (38%) of the title chromanone as a colorless oil.

EXAMPLE 200

Preparation of 2-[(5-Carboxypentyl)oxy]-6-[6-[[3,4-dihydro-4-oxo-8-(3-phenylpropyl)-2H-1-benzopyran-7-yl]oxy]hexyl]benzenepropanoic Acid The 2-[6-[[3,4-dihydro-4-oxo-8-(3-phenylpropyl)-2H-1-benzopyran-7-yl]oxy]hexyl]-6-[(6-methoxy-6-oxohexyl)oxy]benzenepropanoic acid methyl ester from the preceding example (0.38 g; 0.565 mmol) was saponified by stirring with 2 mL of 3N aqueous lithium hydroxide, in 15 mL of tetrahydrofuran for 24 hr, at room temperature. Work-up as in example 4 followed by flash-chromatography on silica gel (eluting with 96:3:1 chloroform-methanol-acetic acid) and recrystallization from hexane-ethyl acetate gave 0.36 g (98%) of the title compound as a colorless solid, mp 97°–98° C.

Anal. Calcd for $C_{39}H_{48}O_8$: C, 72.65; H, 7.50. Found: C, 72.49; H, 7.42.

EXAMPLE 201

Preparation of rac-(E)-4-[2-(3-Methoxy-3-oxo-1-propenyl)-3-[6-[(tetrahydro-2H-pyran-2-yl)oxy]-1-hexynyl]phenoxy]butanoic Acid Ethyl Ester Using the procedure of example 122, rac-(E)-3-[2-hydroxy-6-[6-[(tetrahydro-2H-pyran-2-yl)oxy]-1-hexynyl]phenyl]-2-propenoic acid methyl ester (example 121), was alkylated with ethyl 4-bromobutyrate giving the title compound as a pale-yellow oil, in quantitative yield.

EXAMPLE 202

Preparation of rac-2-(4-Ethoxy-4-oxobutoxy)-6-[6-[(tetrahydro-2H-pyran-2-yl)oxy]hexyl]benzenepropanoic Acid Methyl Ester Using the procedure of example 123, rac-(E)-4-[2-(3-methoxy-3-oxo-1-propenyl)-3-[6-[(tetrahydro-2H-pyran-2-yl)oxy]-1-hexynyl]phenoxy]butanoic acid ethyl ester from the preceding example, was catalytically hydrogenated, giving the title compound as an oil, in 90.8% yield.

EXAMPLE 203

Preparation of 2-(6-Hydroxyhexyl)-6-(4-methoxy-4-oxobutoxy)benzenepropanoic Acid Methyl Ester Using the procedure of example 52, rac-2-(4-ethoxy-4-oxobutoxy)-6-[6-[(tetrahydro-2H-pyran-2-yl)oxy]hexyl]benzenepropanoic acid methyl ester from the preceding example, was converted into the title compound, a colorless oil, in 72.5% yield.

EXAMPLE 204

Preparation of 2-(4-Methoxy-4-oxobutoxy)-6-[6-[(methylsulfonyl)oxy]hexyl]benzenepropanoic Acid Methyl Ester Using the procedure of example 32, 2-(6-hydroxyhexyl)-6-(4-methoxy-4-oxobutoxy)benzenepropanoic acid methyl ester from the preceding example, was converted into the title compound, an oil, in quantitative yield.

EXAMPLE 205

Preparation of
2-(3-Carboxypropoxy)-6-[6-[(3,4-dihydro-4-oxo-8-propyl-2H-1-benzopyran-7-yl)oxy]hexyl]benzenepropanoic Acid Using the procedure of example 184, 2,3-dihydro-7-hydroxy-8-propyl-4H-1-benzopyran-4-one was converted into the title compound by alkylation with 2-(4-methoxy-4-oxobutoxy)-6-[6-(methylsulfonyl)oxyhexyl]-benzenepropanoic acid methyl ester from the preceding example, followed by saponification, in 40% overall yield. The product was a colorless solid, mp 116°–117.5° C., recrystallized from acetonitrile.

Anal. Calcd for $C_{31}H_{40}O_8$: C, 68.87; H, 7.46. Found: C, 68.84; H, 7.53.

EXAMPLE 206

Preparation of
2-[(5-Carboxypentyl)oxy]-6-[6-[(5,6,7,8-tetrahydro-5-oxo-1-propyl-2-naphthalenyl)oxy]hexyl]benzenepropanoic Acid Using the procedure of example 184, 6-hydroxy-5-propyl-1,2,3,4-tetrahydronaphthalen-1-one from example 9 was converted into the title compound by alkylation with 2-[(6-methoxy-6-oxohexyl)oxy]-6-[6-[(methylsulfonyl)oxy]hexyl]benzenepropanoic acid methyl ester from example 156, followed by saponification, in 68% overall yield. The diacid product was a colorless solid, mp 100°–101° C., recrystallized from hexane-ethyl acetate.

Anal. Calcd for $C_{34}H_{46}O_7$: C, 72.06; H, 8.18. Found: C, 71.95; H, 8.28.

EXAMPLE 207

Preparation of
3-(3-Ethoxy-3-oxopropyl)-4-[[(trifluoromethyl)sulfonyl]oxy]-δ-oxobenzenepentanoic Acid Ethyl Ester To a solution of 5.80 g (17.2 mmol) of 3-(3-ethoxy-3-oxopropyl)-4-hydroxy-δ-oxobenzenepentanoic acid ethyl ester from example 140, in 20 mL of pyridine, cooled in an ice bath, was added trifluoromethanesulfonic anhydride (4 mL, 23.8 mmol) and the mixture was stirred at room temperature for 24.5 hr. The solution was cooled again in an ice bath, a second portion of trifluoromethanesulfonic anhydride (4 mL, 23.8 mmol) was added, and the reaction was stirred for an additional 90.5 hr. Water was added and the mixture was worked-up with ether in the usual manner (the combined organic extracts were additionally washed three times with 3N sulfuric acid solution). The crude product was purified by flash chromatography on 900 g of silica gel, eluting with hexane-ethyl acetate (6:1) to give 3.28 g (40.6%) of the title compound as a pale-yellow oil.

Anal. Calcd for $C_{19}H_{23}F_3O_8S$: C, 48.72; H, 4.95; F, 12.17; S, 6.85. Found: C, 48.75; H, 4.88; F, 12.06; S, 6.64.

EXAMPLE 208

Preparation of
(E/Z)-3-(3-Ethoxy-3-oxopropyl)-4-(6-hydroxy-1-hexenyl)-δ-oxobenzenepentanoic Acid Ethyl Ester A mixture of 2.23 g (4.76 mmol) of 3-(3-ethoxy-3-oxopropyl)-4-[[(trifluoromethyl)sulfonyl]oxy]-δ-oxobenzenepentanoic acid ethyl ester from the preceding example, 2.01 g (5.18 mmol) of (E/Z)-tri-n-butyl-(6-hydroxy-1-hexenyl)stannane, 0.643 g (15.2 mmol) of lithium chloride, 0.363 g (0.31 mmol) of tetrakis(triphenylphosphine)palladium and 3 crystals of 2,6-di-t-butyl-4-methylphenol in 25 mL of dioxane was stirred at reflux for 3 hr. A second portion of tetrakis(triphenylphosphine)palladium (0.20 g, 0.173 mmol) was added and stirring and refluxing were continued for another 1 hr. Pyridine (3.1 mL) was added followed by 6.2 mL of a solution of 1.2N HF in pyridine-tetrahydrofuran, and the resulting mixture was stirred at room temperature overnight. The mixture was diluted with 300 mL of ether and filtered through Celite. The filtrate was washed once with 75 mL of 10% aqueous hydrochloric acid and work up was completed in the usual manner. The crude product was combined with that obtained from a similar experiment starting from 2.59 g (5.53 mmol) of the triflate and purified by flash chromatography on 750 g of silica gel. Elution with hexane-ethyl acetate (2:1) afforded 3.08 g (71.4%) of the title compound as a pale-yellow oil.

EXAMPLE 209

Preparation of
4-(6-Bromohexyl)-3-(3-ethoxy-3-oxopropyl)-δ-oxobenzenepentanoic Acid Ethyl Ester To a solution of 0.69 g (1.65 mmol) of (E/Z)-3-(3-ethoxy-3-oxopropyl)-4-(6-hydroxy-1-hexenyl)-δ-oxobenzenepentanoic acid ethyl ester from the preceding example in 10 mL of ethanol and 10 mL of ethyl acetate was added 0.17 g of 10% palladium on carbon, and the resulting mixture was stirred under 1 atmosphere of hydrogen overnight. The catalyst was filtered with suction on a Celite pad, and the filtrate was concentrated in vacuo to give 0.685 g of an oil. To this crude product was added 1.08 g (3.26 mmol) of carbon tetrabromide, 0.855 g (3.26 mmol) of triphenylphosphine and 25 mL of ether, and the resulting mixture was stirred at room temperature for 23.5 hr. Additional portions of carbon tetrabromide (0.6 g, 1.81 mmol) and triphenylphosphine (0.5 g, 1.91 mmol) were added and the stirring was continued for an additional 26.3 hr. The mixture was diluted with 250 mL of ether and worked-up in the usual manner. The crude product was purified by flash chromatography on 80 g of silica gel, eluting with hexane-ethyl acetate (10:1) affording 0.496 g (62.2%) of the title compound as a pale-yellow oil.

Anal. Calcd for $C_{24}H_{35}BrO_5$: C, 59.63; H, 7.30; Br, 16.53. Found: C, 59.20; H, 7.23; Br, 16.82.

EXAMPLE 210

Preparation of
4-[6-[(3,4-Dihydro-4-oxo-8-propyl-2H-1-benzopyran-7-yl)oxy]hexyl]-3-(3-ethoxy-3-oxopropyl)-δ-oxobenzenepentanoic Acid Ethyl Ester A mixture of 0.43 g (0.89 mmol) of 4-(6-bromohexyl)-3-(3-ethoxy-3-oxopropyl)-δ-oxobenzenepentanoic acid ethyl ester from the preceding example, 0.188 g (0.91 mmol) of 2,3-dihydro-7-hydroxy-8-propyl-4H-1-benzopyran-4-one and 0.398 g (2.88 mmol) of anhydrous granular potassium carbonate in 10 mL of 2-butanone was stirred and heated at 89° C. for 19.3 hr. The mixture was filtered with suction and the solid was washed with ether and ethyl acetate. The filtrate was concentrated in vacuo and the crude product was flash chromatographed on 80 g of silica gel, eluting with hexane-ethyl acetate (5:2). There was obtained 0.496 g (91.5%) of the title compound as a colorless oil.

EXAMPLE 211

Preparation of
3-(2-Carboxyethyl)-4-[6-[(3,4-dihydro-4-oxo-8-propyl-2H-1-benzopyran-7-yl)oxy]hexyl]-δ-oxobenzenepentanoic Acid To a mixture of 0.442 g (0.73 mmol) of 4-[6-[(3,4-dihydro-4-oxo-8-propyl-2H-1-benzopyran-7-yl)oxy]hexyl]-3-(3-ethoxy-3-oxopropyl)-δ-oxobenzenepentanoic acid ethyl ester from the preceding example, in 7 mL of tetrahydrofuran and 7 mL of water was added 91.7 mg (2.19 mmol) of lithium hydroxide monohydrate and the reaction was stirred at room temperature for 19.3 hr. After being acidified with 16 mL of 3N aqueous sulfuric acid, the mixture was worked-up with ethyl acetate in the usual manner. The crude product thus obtained was recrystallized from hexane-ethyl acetate to give 0.309 g (77%) of the title compound as a white solid, mp 136°–139° C.

Anal. Calcd for $C_{32}H_{40}O_8$: C, 69.55; H, 7.30. Found: C, 69.35; H, 7.42.

EXAMPLE 212

Preparation of
3-(3-Ethoxy-3-oxopropyl)-4-hydroxybenzenepentanoic Acid Ethyl Ester To a solution of 3.91 g (11.6 mmol) of 3-(3-ethoxy-3-oxopropyl)-4-hydroxy-δ-oxobenzenepentanoic acid ethyl ester (from example 140) in 50 mL of acetic acid was added 0.5 g of 10% palladium on carbon, and the resulting mixture was shaken at room temperature and 45 p.s.i. in a Parr shaker for 18.5 hr. The mixture was filtered with suction through a Celite pad and the solids washed with ethyl acetate. The filtrate and washes were combined and concentrated in vacuo. The residue was dissolved in 200 mL of ethanol and treated with 5 mL of concentrated sulfuric acid. The resulting mixture was refluxed for 4 hr and then stirred at room temperature overnight. Most of ethanol was removed in vacuo and the residue was worked-up with ether in the usual manner (the combined ether extracts were additionally washed with saturated aqueous sodium bicarbonate solution). The crude product was purified by flash chromatography on 350 g of silica gel, eluting with hexane-ethyl acetate (4:1) to give 2.13 g (56.7%) of the title compound as a colorless oil.

Anal. Calcd for $C_{18}H_{26}O_5$: C, 67.06; H, 8.13. Found: C, 66.94; H, 8.20.

EXAMPLE 213

Preparation of
4-(5-Bromopentyloxy)-3-(3-ethoxy-3-oxopropyl)benzenepentanoic Acid Ethyl Ester A mixture of 0.655 g (2.03 mmol) of 3-(3-ethoxy-3-oxopropyl)-4-hydroxybenzenepentanoic acid ethyl ester from the preceding example, 2.80 g (12.2 mmol) of 1,5-dibromopentane, 1.12 g (8.12 mmol) of anhydrous granular potassium carbonate, and 35 mL of 2-butanone was stirred at 92° C. for 22 hr. After being cooled to room temperature, the mixture was filtered through anhydrous magnesium sulfate and the solids were washed thoroughly with ethyl acetate and ether. The filtrate and washes were combined and concentrated in vacuo and the crude product was purified by flash chromatography on 80 g of silica gel, eluting with hexane-ethyl acetate (4:1). There was obtained 0.804 g (83.9%) of the title compound as a colorless oil.

EXAMPLE 214

Preparation of
4-[[5-[(3,4-Dihydro-4-oxo-8-propyl-2H-1-benzopyran-7-yl)oxy]pentyl]oxy]-3-(3-ethoxy-3-oxopropyl)benzenepentanoic Acid Ethyl Ester A mixture of 1.69 g (3.58 mmol) of 4-(5-bromopentyloxy)-3-(3-ethoxy-3-oxopropyl)benzenepentanoic acid ethyl ester from the preceding example, 0.738 g (3.58 mmol) of 2,3-dihydro-7-hydroxy-8-propyl-4H-1-benzopyran-4-one, 2.07 g (14.98 mmol) of anhydrous potassium carbonate, and 37.5 mL of 2-butanone was stirred and refluxed for 18.5 hr. After being cooled to room temperature, the mixture was filtered through anhydrous magnesium sulfate and the solids were washed thoroughly with ethyl acetate. The filtrate and washes were combined and concentrated in vacuo and the crude product was purified by flash chromatography on 250 g of silica gel, eluting with hexane-ethyl acetate (4:1). There was obtained 1.93 g (90.1%) of the title compound as a colorless oil.

Anal. Calcd for $C_{35}H_{48}O_8$: C, 70.44; H, 8.11. Found: C, 70.16; H, 8.18.

EXAMPLE 215

Preparation of
3-(2-Carboxyethyl)-4-[[5-[(3,4-dihydro-4-oxo-8-propyl-2H-1-benzopyran-7-yl)oxy]pentyl]oxy]benzenepentanoic Acid To a solution of 1.93 g (3.23 mmol) of 4-[[5-[(3,4-dihydro-4-oxo-8-propyl-2H-1-benzopyran-7-yl)oxy]pentyl]oxy]-3-(3-ethoxy-3-oxopropyl)benzenepentanoic acid ethyl ester from the preceding example, in 30 mL of tetrahydrofuran and 30 mL of water, was added 0.407 g (9.71 mmol) of lithium hydroxide monohydrate and the resulting solution was stirred at room temperature for 46 hr. The reaction mixture was acidified with 60 mL of 3N aqueous sulfuric acid, and worked-up with ethyl acetate in the usual manner. The crude product was purified by flash chromatagraphy on 500 g of silica gel, eluting with hexane-ethyl acetate (1:1) affording 1.07 g (61.0%) of the title compound as a white solid, mp 101°–104° C.

Anal. Calcd for $C_{31}H_{40}O_8$: C, 68.87; H, 7.46. Found: C, 68.77; H, 7.52.

EXAMPLE 216

Preparation of
3-(3-Ethoxy-3-oxopropyl)-4-(6-hydroxyhexyl)benzenepentanoic Acid Ethyl Ester To a solution of 2.31 g (5.51 mmol) of (E/Z)-3-(3-ethoxy-3-oxopropyl)-4-(6-hydroxy-1-hexenyl)-δ-oxobenzenepentanoic acid ethyl ester from example 208, in 100 mL of acetic acid, was added 0.5 g of 10% palladium on carbon and the resulting mixture was shaken (Parr apparatus) under 50 p.s.i. of hydrogen, for 89 hr. The catalyst and solvent were removed as described in previous examples and the residue was dissolved in 50 mL of acetic acid, 25 mL of ethyl acetate, and 25 mL of ethanol. To this solution was added 1 g of 10% palladium on carbon, and the mixture was hydrogenated as before, for 44 hr. The mixture was filtered with suction through Celite, the filter cake washed with ethyl acetate, and the filtrate and washes combined and concentrated in vacuo. The residue was dissolved in 100 mL of ethanol, 5 mL of concentrated sulfuric acid was added, and the resulting solution was stirred at reflux for 20.5 hr. Most of ethanol was removed under reduced pressure and the residue was worked-up with ether in the usual manner (the combined ether extracts were additionally washed with saturated aqueous sodium bicarbonate solution). The residue was dissolved in 50 mL of toluene and 50 mL of tetrahydrofuran, 1.25 g of 5% rhodium on alumina was added, and the resulting mixture was hydrogenated at atmospheric pressure until hydrogen uptake had ceased. The mixture was worked up as described above and the crude product was purified by flash chromatography on 100 g of silica gel, eluting with hexane-ethyl acetate (3:1). There was obtained 0.673 g (30%) of the title compound as a colorless oil.

Anal. Calcd for $C_{24}H_{38}O_5$: C, 70.90; H, 9.42. Found: C, 70.88; H, 9.25.

EXAMPLE 217

Preparation of 4-(6-Bromohexyl)-3-(3-ethoxy-3-oxopropyl)benzenepentanoic Acid Ethyl Ester A mixture of 0.673 g (1.65 mmol) of 3-(3-ethoxy-3-oxopropyl)-4-(6-hydroxyhexyl)benzenepentanoic acid ethyl ester from the preceding example, 1.1 g (3.3 mmol) of carbon tetrabromide, and 0.9 g (3.3 mmol) of triphenylphosphine in 25 mL of ether was stirred at room temperature for 23 hr. The mixture was diluted with 250 mL of ether, and the solution worked-up in the usual manner. The crude product was purified by flash chromatography on 80 g of silica gel, eluting with hexane-ethyl acetate (10:1). There was obtained 0.588 g (75.7%) of the title compound as a colorless oil.

Anal. Calcd for $C_{24}H_{37}BrO_4$: C, 61.40; H, 7.94; Br, 17.02. Found: C, 61.64; H, 8.07; Br, 16.94.

EXAMPLE 218

Preparation of 4-[6-[(3,4-Dihydro-4-oxo-8-propyl-2H-1-benzopyran-7-yl)oxy]hexyl]-3-(3-ethoxy-3-oxopropyl)benzenepentanoic Acid Ethyl Ester Starting with 0.505 g (1.08 mmol) of 4-(6-bromohexyl)-3-(3-ethoxy-3-oxopropyl)benzenepentanoic acid ethyl ester from the preceding example, and 0.226 g (1.09 mmol) of 2,3-dihydro-7-hydroxy-8-propyl-4H-1-benzopyran-4-one, the title compound (0.636 g; 99.3%) was obtained as a colorless oil, using the procedure of example 214.

Anal. Calcd for $C_{36}H_{50}O_7$: C, 72.70; H, 8.47. Found: C, 72.57; H, 8.39.

EXAMPLE 219

Preparation of 3-(2-Carboxyethyl)-4-[6-[(3,4-dihydro-4-oxo-8-propyl-2H-1-benzopyran-7-yl)oxy]hexyl]benzenepentanoic Acid Starting with 0.574 g (0.96 mmol) of 4-[6-[(3,4-dihydro-4-oxo-8-propyl-2H-1-benzopyran-7-yl)oxy]hexyl]-3-(3-ethoxy-3-oxopropyl)benzenepentanoic acid ethyl ester from the preceding example, the title compound (0.328 g; 63.2%) was obtained as a white solid, mp 107.5°–109° C., using the saponification procedure of example 215.

Anal. Calcd for $C_{32}H_{42}O_7$: C, 71.35; H, 7.86. Found: C, 71.33; H, 7.94.

EXAMPLE 220

Preparation of 1,2-Dihydro-9-methoxy-3H-naphtho[2,1-b]pyran-3-one

A solution of 2.64 g (15.2 mmol) of 7-methoxy-2-naphthalenol, 5.27 g (30.2 mmol) of triethyl orthoacrylate, and 0.77 g (7.6 mmol) of trimethylacetic acid in 30 mL of toluene was stirred and refluxed for 22.5 hr. A second run was carried out starting with 2.09 g (12 mmol) of 7-methoxy-2-naphthalenol, 4.17 g (23.9 mmol) of triethyl orthoacrylate and 0.61 g (6 mmol) of trimethylacetic acid in 15 mL of toluene, refluxing for 18.7 hr. After being cooled to room temperature, the solutions from these two runs were combined and diluted with 50 mL of ether. The resulting solution was washed with 5% sodium hydroxide solution and work-up was completed in the usual manner to give 10.98 g of a crude product. To this material was added 100 mL of ether and 100 mL of 10% aqueous hydrochloric acid, and the mixture was stirred at room temperature for 2 hr. Work-up with ether in the usual manner gave 9.51 g of an oily residue. This product was dissolved in 200 mL of toluene, 1.0 g (5.26 mmol) of p-toluenesulfonic acid monohydrate was added, and the resulting solution was stirred and refluxed with removal of water using a Dean-Stark trap, for 21.5 hr. After being cooled to room temperature, the solution was washed with 100 mL of saturated sodium bicarbonate solution and worked-up as usual. The crude product (7.97 g) was purified on 500 g of silica gel, eluting with hexane-chloroform (2:1 and 1:1) to give 5.38 g (86.8%) of the title compound as a white solid. mp 100°–101° C.

Anal. Calcd for $C_{14}H_{12}O_3$: C, 73.67; H, 5.30. Found: C, 73.59; H, 5.33.

EXAMPLE 221

Preparation of 1,2-Dihydro-9-hydroxy-3H-naphtho[2,1-b]pyran-3-one

A mixture of 2.57 g (11.3 mmol) of 1,2-dihydro-9-methoxy-3H-naphtho[2,1-b]pyran-3-one from the preceding example and 7.86 g (68.0 mol) of pyridine hydrochloride was heated at 200°–230° C. for 2.5 hr. After being cooled to room temperature, the reaction mixture was treated with 100 mL of water and worked-up with ethyl acetate in the usual manner. The crude product (2.52 g) was dissolved in 150 mL of toluene, treated with 0.31 g (1.63 mmol) of p-toluenesulfonic acid monohydrate, and the resulting solution was stirred at reflux for 3.5 hr, with removal of water using a Dean-Stark trap. The solution was diluted with 300 mL of ethyl acetate, washed three times with saturated sodium bicarbonate solution, and work-up was completed in the usual manner. The crude product was purified by flash chromatography on 300 g of silica gel, eluting with hexane-ethyl acetate (3:1) to give 2.06 g (85.3%) of the title compound as a light-brown solid, mp 194°–202° C. (recrystallized from ethyl acetate).

Anal. Calcd for $C_{13}H_{10}O_3$; C, 72.89; H, 4.71. Found: C, 72.69; H, 4.73.

EXAMPLE 222

Preparation of
[(2,3-Dihydro-3-oxo-1H-naphtho[2,1-b]pyran-9-yl)oxy]acetic Acid 1,1-Dimethylethyl Ester A mixture of 2.73 g (12.7 mmol) of 1,2-dihydro-9-hydroxy-3H-naphtho[2,1-b]pyran-3-one from the preceding example, 6.2 g (31.8 mmol) of t-butyl bromoacetate, 7.04 g (51.0 mmol) of anhydrous granular potassium carbonate, and 70 mL of 2-butanone was stirred at 60° C. for 17 hr. After being cooled to room temperature, the mixture was filtered and the solids washed thoroughly with ether and ethyl acetate. The filtrate and washes were combined and concentrated in vacuo. The crude product was purified by flash chromatography on 200 g of silica gel, eluting with hexane-ethyl acetate (4:1) to give 1.23 g of 2,7-bis[2-(1,1-dimethylethoxy)-2-oxoethoxy]-1-naphthalenepropanoic acid 2-(1,1-dimethylethoxy)-2-oxoethyl ester. Further elution then afforded 2.97 g (71.0%) of the title compound as a pale-yellow solid, mp 117.5°-118.5° C. (recrystallized from hexane-ethyl acetate).

Anal. Calcd for $C_{19}H_{20}O_5$: C, 69.50; H, 6.14. Found: C, 69.50; H, 6.02.

EXAMPLE 223

Preparation of
7-(2-Ethoxy-2-oxoethoxy)-2-hydroxy-1-naphthalenepropanoic Acid Ethyl Ester To a solution of 2.97 g (9.0 mmol) of [(2,3-dihydro-3-oxo-1H-naphtho[2,1-b]pyran-9-yl)oxy]acetic acid 1,1-dimethylethyl ester from the preceding example, in 120 mL of ethanol, was added 2 mL of concentrated sulfuric acid and the resulting solution was allowed to stir at room temperature for 13 days. Most of ethanol was removed under reduced pressure and the residue was dissolved in ether. The solution was washed with saturated aqueous sodium bicarbonate solution and work-up was completed in the usual manner. The crude product was purified by flash chromatography on 150 g silica gel, eluting with hexane-ethyl acetate (4:1). There was obtained 2.69 g (86.0%) of the title compound as a white solid, mp 112°-113° C.

Anal. Calcd for $C_{19}H_{22}O_6$: C, 65.88; H, 6.40. Found: C, 65.72; H, 6.36.

EXAMPLE 224

Preparation of
2-[(5-Bromopentyl)oxy]-7-(2-ethoxy-2-oxoethoxy)-1-naphthalenepropanoic Acid Ethyl Ester A mixture of 1.08 g (3.12 mmol) of 7-(2-ethoxy-2-oxoethoxy)-2-hydroxy-1-naphthalenepropanoic acid ethyl ester from the preceding example, 4.31 g (18.7 mmol) of 1,5-dibromopentane, 2.59 g (18.7 mmol) of anhydrous granular potassium carbonate, and 70 mL of 2-butanone was heated at 65° C. for 24 hr. After being cooled to room temperature, the mixture was filtered through anhydrous magnesium sulfate. The solids were washed thoroughly with ethyl acetate and the filtrate and washes were combined and concentrated in vacuo. To the residue was added 60 mL of ethanol and 1 mL of concentrated sulfuric acid and the resulting solution was stirred at room temperature for 17.5 hr. Most of the ethanol was removed under reduced pressure and the residue was flash chromatographed on 110 g of silica gel, eluting with hexane-ethyl acetate (6:1) to give 1.15 g (74.4%) of the title compound as an off-white, waxy solid, mp 29.5°-32° C.

Anal. Calcd for $C_{24}H_{31}BrO_6$: C, 58.19; H, 6.31; Br, 16.13. Found: C, 57.92; H, 6.28; Br, 16.22.

EXAMPLE 225

Preparation of
2-[[5-[(3,4-Dihydro-4-oxo-8-propyl-2H-1-benzopyran-7-yl)oxy]pentyl]oxy]-7-(2-ethoxy-2-oxoethoxy)-1-naphthalenepropanoic Acid Ethyl Ester A mixture of 0.454 g (2.2 mmol) of 2,3-dihydro-7-hydroxy-8-propyl-4H-1-benzopyran-4-one, 1.09 g (2.2 mmol) of 2-[(5-bromopentyl)oxy]-7-(2-ethoxy-2-oxoethoxy)-1-naphthalenepropanoic acid ethyl ester from the preceding example, 1.23 g (8.9 mmol) of anhydrous granular potassium carbonate and 32.5 mL of 2-butanone was heated at 94° C. for 22 hr. After being cooled to room temperature, the mixture was filtered through some anhydrous magnesium sulfate. The solids were washed thoroughly with ethyl acetate and the filtrate and washes were combined and concentrated in vacuo. The residue was flash chromatographed on 200 g of silica gel, eluting with hexane-ethyl acetate (2:1) affording 1.11 g (81%) of the title compound as a white solid, mp 68°-69.5° C.

Anal. Calcd for $C_{36}H_{44}O_9$: C, 69.66; H, 7.14. Found: C, 69.74; H, 7.44.

EXAMPLE 226

Preparation of
7-(Carboxymethoxy)-2-[[5-[(3,4-dihydro-4-oxo-8-propyl-2H-1-benzopyran-7-yl)oxy]pentyl]oxy]-1-naphthalenepropanoic Acid A mixture of 0.86 g (1.39 mmol) of 2-[[5-[(3,4-dihydro-4-oxo-8-propyl-2H-1-benzopyran-7-yl)oxy]pentyl]oxy]-7-(2-ethoxy-2-oxoethoxy)-1-naphthalenepropanoic acid ethyl ester from the preceding example, 0.177 g (4.21 mmol) of lithium hydroxide monohydrate, 10.1 mL of tetrahydrofuran, and 10.1 mL of water was stirred at room temperature for 41.5 hr. A second saponification was carried out with 0.188 g (0.3 mmol) of the starting ester, 38 mg (0.9 mmol) of lithium hydroxide monohydrate, 2.2 mL of tetrahydrofuran and 2.2 mL of water. After combining the two reaction mixtures, 30 mL of 3N aqueous sulfuric acid was added, and the mixture was worked-up with ethyl acetate in the usual manner. The crude product was crystallized from hexane-ethyl acetate to give 0.803 g (84.3%) of the title compound as an off-white solid, mp 175°-177.5° C.

Anal. Calcd for $C_{32}H_{36}O_9$: C, 68.07; H, 6.43. Found: C, 68.09; H, 6.55.

EXAMPLE 227

Preparation of
1,2-Dihydro-8-methoxy-3H-naphtho[2,1-b]pyran-3-one

Starting with a solution of 6.29 g (36.1 mmol) of 6-methoxy-2-naphthalenol, 12.58 g (72.2 mmol) of triethyl orthoacrylate and 1.84 g (18.1 mmol) of trimethylacetic acid in 70 mL of toluene, the title compound (7.12 g; 86.4%) was obtained as a white solid, mp 122°-123° C., using the procedure of example 220.

Anal. Calcd for $C_{14}H_{12}O_3$: C, 73.67; H, 5.30. Found: C, 73.41; H, 5.16.

EXAMPLE 228

Preparation of
1,2-Dihydro-8-hydroxy-3H-naphtho[2,1-b]pyran-3-one

Starting with 4.84 g (21.2 mmol) of 1,2-dihydro-8-methoxy-3H-naphtho[2,1-b]pyran-3-one from the preceding example, the title compound (3.19 g; 70.3%) was obtained as an off-white solid, mp 189°–199° C. (recrystallized from ethanol-ethyl acetate), using the procedure of example 221.

Anal. Calcd for $C_{13}H_{10}O_3$: C, 72.89; H, 4.71. Found: C, 72.81; H, 4.69.

EXAMPLE 229

Preparation of
[(2,3-Dihydro-3-oxo-1H-naphtho[2,1-b]pyran-8-yl)oxy]acetic Acid 1,1-Dimethylethyl Ester A mixture of 2.18 g (10.2 mmol) of 1,2-dihydro-8-hydroxy-3H-naphtho[2,1-b]pyran-3-one from the preceding example, 4.84 g (24.8 mmol) of t-butyl bromoacetate, 5.63 g (40.7 mmol) of anhydrous granular potassium carbonate and 55.5 mL of 2-butanone was heated at 60° C. for 24 hr. A second portion of t-butyl bromoacetate (0.5 mL, 3.1 mmol) was added and the reaction was allowed to proceed for another 17 hr. After being cooled to room temperature, the mixture was filtered and the solids were washed with ethyl acetate and ether. The filtrate and washes were combined and concentrated in vacuo, and the crude product was flash chromatographed on 360 g of silica gel, eluting with hexane-ethyl acetate (7:1 then 6:1) affording 3.04 g (91.0%) of the title compound as a white solid, mp 95°–96° C.

Anal. Calcd for $C_{19}H_{20}O_5$: C, 69.50; H, 6.14. Found: C, 69.66; H, 6.23.

EXAMPLE 230

Preparation of
2-[[5-[(3,4-Dihydro-4-oxo-8-propyl-2H-1-benzopyran-7-yl)oxy]pentyl]oxy]-6-(2-ethoxy-2-oxoethoxy)-1-naphthalenepropanoic Acid Ethyl Ester Starting with [(2,3-dihydro-3-oxo-1H-naphtho[2,1-b]pyran-8-yl)oxy]acetic acid 1,1-dimethylethyl ester from the preceding example, the title compound was obtained as a white solid, mp 100°–102.5° C., using the procedures of examples 223–225.

Anal. Calcd for $C_{36}H_{44}O_9$: C, 69.66; H, 7.15. Found: C, 69.65; H, 7.12.

EXAMPLE 231

Preparation of
6-(Carboxymethoxy)-2-[[5-[(3,4-dihydro-4-oxo-8-propyl-2H-1-benzopyran-7-yl)oxy]pentyl]oxy]-1-naphthalenepropanoic Acid Starting with 0.736 g (1.19 mmol) of 2-[[5-[(3,4-dihydro-4-oxo-8-propyl-2H-1-benzopyran-7-yl)oxy]pentyl]oxy]-6-(2-ethoxy-2-oxoethoxy)-1-naphthalenepropanoic acid ethyl ester from the preceding example, the title compound (0.352 g; 52.6%) was obtained as a white solid, mp 160.5°–163° C. (recrystallized from hexane-ethyl acetate), using the procedure of example 226.

Anal. Calcd for $C_{32}H_{36}O_9$: C, 68.07; H, 6.43. Found: C, 68.03; H, 6.55.

EXAMPLE 232

Preparation of 2-(Bromomethyl)-6-methoxyquinoline

A solution of 10 g (57.7 mmol) of 6-methoxy-2-methylquinoline and 30 drops of pyridine in 40 mL of N,N-dimethylformamide was stirred at 60° C. while a solution of 16.21 g (57.7 mmol) of tribromoacetaldehyde in 20 mL of N,N-dimethylformamide was added over 15 min. The reaction mixture was stirred for another 2 hr and then cooled and poured onto 600 mL of ice-water. Work-up with ethyl acetate was carried out in the usual manner. The crude product was purified by flash chromatography on 800 g of silica gel, eluting with hexane-ethyl acetate (4:1) afforded 4.45 g (30.6%) of the title compound as a violet solid. An analytical sample was obtained by recrystallization from ethanol to give colorless crystals, mp 103° C.

Anal. Calcd for $C_{11}H_{10}BrNO$: C, 52.41; H, 4.00; Br, 31.70; N, 5.56. Found: C, 52.53; H, 3.85; Br, 31.71; N, 5.50.

EXAMPLE 233

Preparation of 6-Methoxy-2-quinolinepropanoic Acid 1,1-Dimethylethyl Ester

To a solution of diisopropylamine (7.4 mL, 52.8 mmol) in 70 mL of tetrahydrofuran cooled to −78° C. was added a solution of 1.6M n-butyllithium in hexanes (31.4 mL, 50.2 mmol). After being stirred for 12 minutes, the resulting solution of lithium diisopropylamide was treated with a solution of t-butyl acetate (4.81 g, 41.4 mmol) in 70 mL of tetrahydrofuran, added slowly through an addition funnel. The reaction mixture was allowed to warm gradually to 10° C. over 3.75 hr, and then recooled to −78° C. whereupon a solution of 2-(bromomethyl)-6-methoxyquinoline from the preceding example (3.46 g, 13.7 mmol) in 40 mL of tetrahydrofuran was added and the reaction was allowed to stir overnight at room temperature. The resulting solution was worked-up with ether in the usual manner. Flash chromatography of the crude product on 360 g of silica gel, eluting with hexane-ethyl acetate (4:1) afforded 1.31 g (33.8%) of the title compound as an orange oil.

Anal. Calcd for $C_{17}H_{21}NO_3$: C, 71.06; H, 7.37; N, 4.87. Found: C, 70.90; H, 7.34; N, 4.75.

EXAMPLE 234

Preparation of 6-Hydroxy-2-quinolinepropanoic Acid Ethyl Ester

A mixture of 1.25 g (4.42 mmol) of 6-methoxy-2-quinolinepropanoic acid 1,1-dimethylethyl ester from the preceding example, and 10 mL of 48% hydrobromic acid solution was heated at reflux for 23 hr then poured onto crushed ice. Concentrated ammonium hydroxide solution was added slowly until the solution became neutral at which point it was concentrated to dryness under reduced pressure. To the residue was added 500 mL of ethanol followed by 20 mL of acetyl chloride and the resulting mixture was stirred at reflux for 17 hr. Most of ethanol was removed under reduced pressure, 150 mL of saturated aqueous sodium bicarbonate and 60 mL of water were added, and the mixture was worked-up with ethyl acetate in the usual manner. The crude product was flash chromatographed on 110 g of silica gel, eluting with hexane-ethyl acetate (3:1) to give 0.819 g (75.5%) of the title compound as a white solid, mp 126.5°–127.5° C.

Anal. Calcd for $C_{14}H_{15}NO_3$: C, 68.56; H, 6.16; N, 5.71. Found: C, 68.54; H, 5.99; N, 5.55.

EXAMPLE 235

Preparation of 6-Hydroxy-2,5-quinolinedipropanoic Acid Diethyl Ester

A solution of 0.779 g (3.17 mmol) of 6-hydroxy-2-quinolinepropanoic acid ethyl ester from the preceding example, 1.11 g (6.38 mmol) of triethyl orthoacrylate and 0.491 g (4.81 mmol) of trimethylacetic acid in 21 mL of toluene was stirred at reflux for 16 hr. A solution of 0.283 g (1.62 mmol) of triethyl orthoacrylate in 3 mL of toluene was added and the reaction was allowed to stir under reflux for another 23 hr. After being cooled to room temperature, the solution was diluted with ether, washed three times with saturated aqueous sodium bicarbonate, and work-up was completed in the usual manner. To the residue was added 25 mL of ether, 25 mL of water and 1.21 g (6.36 mmol) of p-toluenesulfonic acid monohydrate and the resulting mixture was stirred at room temperature for 1.5 hr. Saturated aqueous sodium bicarbonate was added and the mixture was worked-up with ethyl acetate in the usual manner. The crude product was flash chromatographed on 110 g of silica gel, eluting with hexane-ethyl acetate (3:1 and 2:1) affording 0.909 g (82.9%) of the title compound as a white solid, mp 74°–76° C.

Anal. Calcd for $C_{19}H_{23}NO_5$: C, 66.07; H, 6.71; N, 4.06. Found: C, 66.28; H, 6.88; N, 3.93.

EXAMPLE 236

Preparation of 6-[(5-Bromopentyl)oxy]-2,5-quinolinedipropanoic Acid Diethyl Ester A mixture of 0.866 g (2.51 mmol) of 6-hydroxy-2,5-quinolinedipropanoic acid ethyl ester from the preceding example, 2.33 g (10.1 mmol) of 1,5-dibromopentane, 1.75 g (12.7 mmol) of anhydrous granular potassium carbonate and 25 mL of 2-butanone was stirred at 90° C. for 8.25 hr and at room temperature for another 37 hr. The mixture was filtered through anhydrous magnesium sulfate and the solids were washed with ethyl acetate. The filtrate and washes were combined and concentrated under reduced pressure. The residue was dissolved in 200 mL of ethanol, 1.21 g (6.36 mmol) of p-toluenesulfonic acid monohydrate was added and the resulting solution was stirred at room temperature for 22 hr. Most of the ethanol was removed under reduced pressure. The residue was treated with saturated aqueous sodium bicarbonate and worked-up with ethyl acetate in the usual manner. The crude product was partially purified by flash chromatography on 110 g of silica gel, eluting with hexane-ethyl acetate (3:1 and 2:1) giving 1.03 g of the title compound.

EXAMPLE 237

Preparation of 6-[[5-[(3,4-Dihydro-4-oxo-8-propyl-2H-1-benzopyran-7-yl)oxy]pentyl]oxy]-2,5-quinolinedipropanoic Acid Diethyl Ester A mixture of 0.96 g of the partially purified 6-[(5-bromopentyl)oxy]-2,5-quinolinedipropanoic acid diethyl ester from the preceding example, 0.402 g (1.95 mmol) of 2,3-dihydro-7-hydroxy-8-propyl-4H-1-benzopyran-4-one, 1.08 g (7.8 mmol) of anhydrous granular potassium carbonate and 25 mL of 2-butanone was stirred at 90° C. for 18 hr. A second portion of 2,3-dihydro-7-hydroxy-8-propyl-4H-1-benzopyran-4-one (0.117 g, 0.57 mmol) was added and the reaction was continued for another 22.5 hr. The mixture was cooled and filtered through anhydrous magnesium sulfate and the solids were washed with ethyl acetate. The filtrate and washes were combined and concentrated under reduced pressure. The crude product was purified by flash chromatography on 110 g of silica gel, eluting with hexane-ethyl acetate (5:2) to give 0.66 g (54.8%) of the title compound as a white solid, mp 59°–61° C.

Anal. Calcd for $C_{36}H_{45}NO_8$: C, 69.77; H, 7.32; N, 2.26. Found: C, 69.78; H, 7.09; N, 2.39.

EXAMPLE 238

Preparation of 6-[[5-[(3,4-Dihydro-4-oxo-8-propyl-2H-1-benzopyran-7-yl)oxy]pentyl]oxy]-2,5-quinolinedipropanoic Acid To a mixture of 0.126 g (0.2 mmol) of 6-[[5-[(3,4-dihydro-4-oxo-8-propyl-2H-1-benzopyran-7-yl)oxy]pentyl]oxy]-2,5-quinolinedipropanoic acid diethyl ester from the preceding example, 2.5 mL of tetrahydrofuran and 2.5 mL of water was added 25.7 mg (0.61 mmol) of lithium hydroxide monohydrate. The mixture was stirred at room temperature for 28.5 hr, acidified with 7 drops of 3N aqueous sulfuric acid, and worked-up with ethyl acetate in the usual manner. The residue was taken up in small amount of ethyl acetate and methanol and filtered. Most of the solvent in the filtrate was evaporated and hexane was then added to induce crystallization. The title compound (33.4 mg, 29.1%) was thus obtained as a white solid, mp 123°–128° C.

EXAMPLE 239

Preparation of rac-(E)-7-[2-(3-Methoxy-3-oxo-1-propenyl)-3-[6-[(tetrahydro-2H-pyran-2-yl)oxy]-1-hexynyl]phenoxy]heptanoic Acid Ethyl Ester Using the procedure of example 122, rac-(E)-3-[2-hydroxy-6-[6-[(tetrahydro-2H-pyran-2-yl)oxy]-1-hexynyl]phenyl]-2-propenoic acid methyl ester (example 121), was alkylated with ethyl 7-bromoheptanoate giving the title compound as a pale-yellow oil, in 98% yield.

EXAMPLE 240

Preparation of rac-2-[(7-Ethoxy-7-oxoheptyl)oxy]-6-[6-[(tetrahydro-2H-pyran-2-yl)oxy]hexyl]benzenepropanoic Acid Methyl Ester Using the procedure of example 123, rac-(E)-7-[2-(3-methoxy-3-oxo-1-propenyl)-3-[6-[(tetrahydro-2H-pyran-2-yl)oxy]-1-hexynyl]phenoxy]heptanoic acid ethyl ester from the preceding example, was catalytically hydrogenated, giving the title compound as an oil, in quantitative yield.

EXAMPLE 241

Preparation of 2-(6-Hydroxyhexyl)-6-[(7-methoxy-7-oxoheptyl)oxy]-benzenepropanoic Acid Methyl Ester Using the procedure of example 52, rac-2-[(7-ethoxy-7-oxoheptyl)oxy]-6-[6-[(tetrahydro-2H-pyran-2-yl)oxy]hexyl]benzenepropanoic acid methyl ester from the preceding example was converted into the title compound, a colorless oil, in 76% yield.

EXAMPLE 242

Preparation of 2-[(7-Methoxy-7-oxoheptyl)oxy]-6-[6-[(methylsulfonyl)oxy]hexyl]benzenepropanoic Acid Methyl Ester Using the procedure of example 32, 2-(6-hydroxyhexyl)-6-[(7-methoxy-7-oxoheptyl)oxy]benzenepropanoic acid methyl ester from the preceding example, was converted into the title compound, an oil, in quantitative yield.

EXAMPLE 243

Preparation of 2-[(6-Carboxyhexyl)oxy]-6-[6-[(3,4-dihydro-4-oxo-8-propyl-2H-1-benzopyran-7-yl)oxy]hexyl]benzenepropanoic Acid Using the procedure of example 184, 2,3-dihydro-7-hydroxy-8-propyl-4H-1-benzopyran-4-one was converted into the title compound by alkylation with 2-[(7-methoxy-7-oxoheptyl)oxy]-6-[6-(methylsulfonyl)oxyhexyl]benzenepropanoic acid methyl ester from the preceding example, followed by saponification, in 55% overall yield. The product was a colorless solid, mp 91°–93° C., recrystallized from hexane-ethyl acetate.

Anal. Calcd for $C_{34}H_{46}O_8$: C, 70.08, H, 7.96. Found: C, 70.10; H, 7.99.

EXAMPLE 244

Preparation of 2-[(5-Carboxypentyl)oxy]-6-[6-[(3,4-dihydro-4-oxo-8-propyl-2H-1-benzopyran-7-yl)oxy]hexyl]benzenepropanoic Acid Disodium Salt The dicarboxylic acid from example 157 (10 mmol) was neutralized with 20 mL (20 mmol) of 1N aqueous sodium hydroxide. The resulting mixture was diluted with more water and the solution was freeze-dried giving the title salt.

EXAMPLE 245

| WET GRANULATION FORMULATION | | | | |
|---|---|---|---|---|
| Ingredients | mg/tablet | | | |
| 1. Compound A.* | 0.1 | 0.5 | 5.0 | 5.0 |
| 2. Lactose Anhydrous DTG | 106.9 | 106.5 | 102.0 | 118.0 |
| 3. Avicel PH 102 | 15.0 | 15.0 | 15.0 | 25.0 |
| 4. Modified Starch | 7.0 | 7.0 | 7.0 | 10.0 |
| 5. Magnesium Stearate | 1.0 | 1.0 | 1.0 | 2.0 |
| TOTAL | 130.0 | 130.0 | 130.0 | 180.0 |

*Compound A is 2-[(5-Carboxypentyl)oxy]-6-[6-[(3,4-dihydro-4-oxo-8-propyl-2H-1-benzopyran-7-yl)oxy]hexyl]benzenepropanoic Acid.

Manufacturing Procedure:

1) Dissolve Item 1 in a suitable solvent such as alcohol.
2) Spread the solution in Step 1 over Item 2, dry.
3) Add Items 3 and 4 and mix for 10 minutes.
4) Add magnesium stearate and mix for 3 minutes and compress.

EXAMPLE 246

| CAPSULE FORMULATION | | | | |
|---|---|---|---|---|
| Ingredients | mg/capsule | | | |
| 1. Compound A | 0.1 | 0.5 | 0.5 | 25.0 |
| 2. Lactose Hydrous | 168.9 | 168.5 | 159.0 | 123.0 |
| 3. Corn Starch | 20.0 | 20.0 | 25.0 | 35.0 |
| 4. Talc | 10.0 | 10.0 | 10.0 | 15.0 |
| 5. Magnesium Stearate | 1.0 | 1.0 | 1.0 | 2.0 |
| TOTAL | 200.0 | 200.0 | 200.0 | 200.0 |

Manufacturing Procedure:

1) Mix Items 1, 2 and 3 in a suitable mixer for 30 minutes.
2) Add Items 4 and 5 and mix for 3 minutes.
3) Fill into suitable capsule.

EXAMPLE 247

| TABLET FORMULATION (Wet Granulation) | | | |
|---|---|---|---|
| | | mg/tablet | |
| Item | Ingredient | 100 mg | 500 mg |
| 1. | Compound A | 100 | 500 |
| 2. | Lactose | 30 | 150 |
| 3. | Pregelatinized Starch | 6 | 30 |
| 4. | Microcrystalline Cellulose | 30 | 150 |
| 5. | Magnesium Stearate | 1 | 6 |
| TOTAL | | 167 | 836 |

Manufacturing Procedure:

1) Mix Items 1, 2, 3 and 4 and granulate with water.
2) Dry the granulation at 50° C.
3) Pass the granulation through suitable milling equipment.
4) Add Item 5 and mix for three minutes; compress on a suitable press.

EXAMPLE 248

| CAPSULE FORMULATION | | | |
|---|---|---|---|
| | | mg/tablet | |
| Item | Ingredient | 100 mg | 500 mg |
| 1. | Compound A | 100 | 500 |
| 2. | Corn Starch (Pregelatinized) | 8 | 40 |
| 3. | Modified Starch | 4 | 20 |
| 4. | Talc | 4 | 20 |
| 5. | Magnesium Stearate | 1 | 2 |
| TOTAL | | 117 | 582 |

Manufacturing Procedure:

1) Mix Items 1, 2, and 3 and wet granulate with water. Dry at 45° C. overnight.
2) Mill through suitable screen using appropriate milling equipment.
3) Add Items 4 and 5 and mix for five minutes.

EXAMPLE 249

| INHALATION AEROSOL FORMULATION (SUSPENSION) | | |
|---|---|---|
| Item | Ingredients | % w/w |
| 1. | Compound A | 1.0 |
| 2. | Sorbitan Trioleate | 0.5 |
| 3. | Freon 12 | 64.0 |
| 4. | Freon 11 | 18.5 |
| 5. | Freon 114 | 16.0 |
| TOTAL | | 100% |

Manufacturing Procedure:

1) Mix Items 1 and 2 into 4 and homogenize.

2) Fill the concentrate suspension from Step 1 into a suitable can and place in valve and crimp to seal container.

3) Pressure-fill a 80:20 mixture of Items 3 and 5.

NOTE: A suitable valve may be used to deliver 25 to 100 microliters in volume.

We claim:

1. A compound of the formula

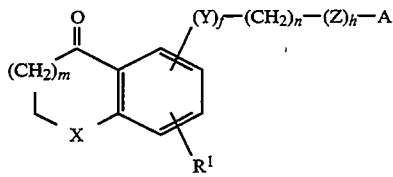

wherein X is $CH_2$;

Y is O, —$CH_2$—$CH_2$—, or —C≡C—;

Z is —$CH_2$—$CH_2$—; f and m are 1 and h, k, and t, independently, are 0 or 1;

n is an integer from 1 to 12;

$R^1$ is hydrogen, lower alkyl, lower alkenyl, cycloalkyl, or aralkyl; and A is B or —O—B, wherein B is a mono-, di- or tricyclic aromatic moiety substituted by the group —$COR^2$, —(O)$_r$—(W)$_s$—$COR^2$ or —(CH=CH)$_p COR^2$ and which may also contain up to 4 additional substituents selected, independently, from the group consisting of halogen, cyano, lower alkyl, lower alkoxy, sulfonamido, alkanoyl, aroyl, —(Q)$_k$—(W)$_{s'}$—E or —(Q)$_k$—(W)$_{s''}$—$C_6H_4$—(W)$_{s'''}$—E, provided that no more than one of said substituents is —(Q)$_k$—(W)$_{s'}$—E or —(Q)$_k$—(W)$_{s''}$—$C_6H_4$—(W)$_{s'''}$—E, and wherein E is $COR^2$ or $R^2$, W is —$CR^3R^4$—, Q is O or carbonyl, p is an integer from 1 to 2, s and s', independently, are an integer from 1-12, s" and s''', independently, are an integer from 0 to 12, $C_6H_4$ is a 1,2-, 1,3-, or 1,4-phenylene moiety, and $R^2$ is hydroxy, lower alkoxy or $NR^3R^4$, wherein $R^3$ and $R^4$, each occurrence, independently, are hydrogen or lower alkyl, a geometric or optical isomer or, when $R^2$ is hydroxy, a pharmaceutically acceptable salt thereof with a base.

2. A compound according to claim 1, wherein Y is O, $R^1$ is lower alkyl and n is 3–8.

3. A compound according to claim 1, wherein Y is O, $R^1$ is lower alkyl, h is O, n is 3–8, and A is B.

4. A compound according to claim 1, wherein Y is O, $R^1$ is lower alkyl or aralkyl, h is O, n is 3–8 and A is B and B is a monocyclic aromatic moiety substituted by —(O)$_r$—(W)$_s$—$COR^2$ and —(Q)$_k$—(W)$_{s'}$—E; wherein Q is O, $R_2$ is hydroxy, t is O, s is 2, k is 1 and s' is 1 to 12.

5. A compound according to claim 1, which is 2-[(5-carboxypentyl)oxy]-6-[6-[5,6,7,8-tetrahydro-5-oxo-1-propyl-2-naphthalenyl)oxy]hexyl]benzenepropanoic acid.

6. A compound according to claim 1, wherein Y are O, $R^1$ is lower alkyl, h is O, k are 1, n is 3–8 and A is B, and B is a monocyclic aromatic moiety substituted by —(O)$_r$—(W)$_s$—$COR^2$ and —(Q)$_k$—(W)$_{s'}$—E, wherein Q is O, $R_2$ is hydroxy, t is O, s is 2, and s' is 1 to 12.

7. A compound according to claim 6, wherein B is phenyl substituted by —(O)$_r$—(W)$_s$—$COR^2$ and —(Q)$_k$—(W)$_{s'}$—$COR^2$, wherein Q is O, $R_2$ is hydroxy, t is O, s is 2, k is 1 and s' is 1–6.

8. A pharmaceutical composition which comprises an effective amount of a compound of formula I

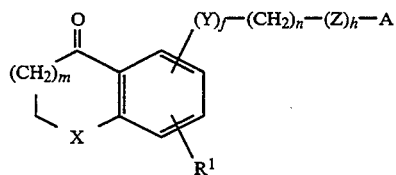

wherein X is $CH_2$;

Y is O, —$CH_2$—$CH_2$—, or —C≡C—;

Z is —$CH_2$—$CH_2$—; f and m are 1 and h, k, and t, independently, are 0 or 1;

n is an integer from 1 to 12;

$R^1$ is hydrogen, lower alkyl, lower alkenyl, cycloalkyl, or aralkyl; and A is B or —O—B, wherein B is a mono-, di- or tricyclic aromatic moiety substituted by the group —$COR^2$, —(O)$_r$—(W)$_s$—$COR^2$ or —(CH=CH)$_p COR^2$ and which may also contain up to 4 additional substituents selected, independently, from the group consisting of halogen, cyano, lower alkyl, lower alkoxy, sulfonamido, alkanoyl, aroyl, —(Q)$_k$—(W)$_{s'}$—E or —(Q)$_k$—(W)$_{s''}$—$C_6H_4$—(W)$_{s'''}$—E, provided that no more than one of said substituents is —(Q)$_k$—(W)$_{s'}$—E or —(Q)$_k$—(W)$_{s''}$—$C_6H_4$—(W)$_{s'''}$—E, and wherein E is $COR^2$ or $R^2$, W is —$CR^3R^4$—, Q is O or carbonyl, p is an integer from 1 to 2, s and s', independently, are an integer from 1-12, s" and s''', independently, are an integer from 0 to 12, $C_6H_4$ is a 1,2-, 1,3-, or 1,4-phenylene moiety, and $R^2$ is hydroxy, lower alkoxy or $NR^3R^4$, wherein $R^3$ and $R^4$, each occurrence, independently, are hydrogen or lower alkyl, a geometric or optical isomer thereof, or when $R^2$ is hydroxy, pharmaceutically acceptable salt thereof with a base, and an inert carrier.

9. A pharmaceutical composition according to claim 8, wherein Y is O, $R^1$ is lower alkyl, n is 3–8.

10. A pharmaceutical composition according to claim 8, wherein Y is O, $R^1$ is lower alkyl, h is O, n is 3–8, n is 1–8 an A is B.

11. A pharmaceutical composition according to claim 8, wherein Y is O, $R^1$ is lower alkyl or aralkyl, h is O, n is 3–8 and A is B, and B is a monocyclic aromatic moiety substituted by —(O)$_r$—(W)$_s$—$COR^2$ and —(Q)$_k$—(W)$_{s'}$—E; wherein Q is O, $R_2$ is hydroxy, t is O, s is 2, k is 1 and s' is 1 to 12.

12. A pharmaceutical composition according to claim 7, wherein the compound of formula I is 2-[(5-carboxypentyl)oxy]-6-[6-[5,6,7,8-tetrahydro-5-oxo-1-propyl-2-naphthalenyl)oxy]hexyl]benzenepropanoic acid.

13. A method of inhibiting the biological activity of leukotriene $B_4$ which comprises administering to a host requiring such inhibitory treatment an effective amount of a compound of formula I

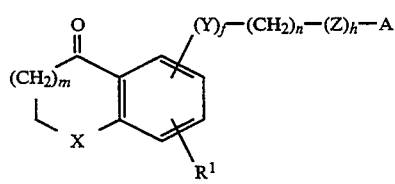

wherein X is $CH_2$;

Y is O, —CH$_2$—CH$_2$—, or —C≡C—;

Z is —CH$_2$—CH$_2$—; f and m are 1 and h, k, and t, independently, are 0 or 1;

n is an integer from 1 to 12;

R$^1$ is hydrogen, lower alkyl, lower alkenyl, cycloalkyl, or aralkyl; and A is B or —O—B, wherein B is a mono-, di- or tricyclic aromatic moiety substituted by the group —COR$^2$, —(O)$_t$—(W)$_s$—COR$^2$ or —(CH=CH)$_p$COR$^2$ and which may also contain up to 4 additional substituents selected, independently, from the group consisting of halogen, cyano, lower alkyl, lower alkoxy, sulfonamido, alkanoyl, aroyl, —(Q)$_k$—(W)$_{s'}$—E or —(Q)$_k$—(W)$_{s''}$—C$_6$H$_4$—(W)$_{s'''}$—E, provided that no more than one of said substituents is —(Q)$_k$—(W)$_{s'}$—E or —(Q)$_k$—(W)$_{s''}$—C$_6$H$_4$—(W)$_{s'''}$—E, and wherein E is COR$^2$ or R$^2$, W is —CR$^3$R$^4$—, Q is O or carbonyl, p is an integer from 1 to 2, s and s', independently, are an integer from 1–12, s'' and s''', independently, are an integer from 0 to 12, C$_6$H$_4$ is a 1,2-, 1,3-, or 1,4-phenylene moiety, and R$^2$ is hydroxy, lower alkoxy or NR$^3$R$^4$, wherein R$^3$ and R$^4$, each occurrence, independently, are hydrogen or lower alkyl, a geometric or optical isomer or, when R$^2$ is hydroxy, a pharmaceutically acceptable salt thereof with a base.

14. A method according to claim 13, wherein Y is O, R$^1$ is lower alkyl, h is O, n is 3–8, and A is B.

15. A method according to claim 13, wherein, Y is O, R$^1$ is lower alkyl or aralkyl, h is O, n is 3–8 and A is B, and B is a monocyclic aromatic moiety substituted by —(O)$_t$—(W)$_s$—COR$^2$ and —(Q)$_k$—(W)$_{s'}$—E, wherein Q is O, R$_2$ is hydroxy, t is O, s is 2, k is 1 and s' is 1 to 12.

16. A method according to claim 13, wherein the compound of formula I is 2-[(5-carboxypentyl)oxy]-6-[6-[5,6,7,8-tetrahydro-5-oxo-1-propyl-2-naphthalenyl)oxy]hexyl]benzenepropanoic acid.

* * * * *